US012698272B2

(12) United States Patent
Li et al.

(10) Patent No.: US 12,698,272 B2
(45) Date of Patent: Aug. 4, 2026

(54) STING ANTAGONISTS AND USES THEREOF

(71) Applicant: Regor Pharmaceuticals, Inc., Cambridge, MA (US)

(72) Inventors: Hailong Li, Shanghai (CN); Wenge Zhong, Thousand Oaks, CA (US); Wei Huang, Shanghai (CN)

(73) Assignee: Regor Pharmaceuticals, Inc., Cambridge, MA (US)

( * ) Notice: Subject to any disclaimer, the term of this patent is extended or adjusted under 35 U.S.C. 154(b) by 536 days.

(21) Appl. No.: 18/037,965

(22) PCT Filed: Nov. 23, 2021

(86) PCT No.: PCT/CN2021/132442

§ 371 (c)(1),
(2) Date: May 19, 2023

(87) PCT Pub. No.: WO2022/105930

PCT Pub. Date: May 27, 2022

(65) Prior Publication Data

US 2024/0002368 A1 Jan. 4, 2024

(30) Foreign Application Priority Data

Nov. 23, 2020 (WO) ................ PCT/CN2020/130793

(51) Int. Cl.

*C07D 403/12* (2006.01)
*C07D 403/14* (2006.01)
*C07D 405/14* (2006.01)
*C07D 413/14* (2006.01)
*C07D 471/04* (2006.01)

(52) U.S. Cl.

CPC ......... *C07D 403/12* (2013.01); *C07D 403/14* (2013.01); *C07D 405/14* (2013.01); *C07D 413/14* (2013.01); *C07D 471/04* (2013.01)

(58) Field of Classification Search

CPC .. C07D 403/12; C07D 403/14; C07D 413/14; C07D 471/04

See application file for complete search history.

(56) References Cited

U.S. PATENT DOCUMENTS

| | | | |
|---|---|---|---|
| 5,998,437 | A | 12/1999 | Nishi et al. |
| 7,482,342 | B2 | 1/2009 | D'Orchymont et al. |
| 7,868,024 | B2 | 1/2011 | Dubois et al. |
| 8,865,734 | B2 | 10/2014 | No et al. |
| 9,029,389 | B2 | 5/2015 | No et al. |
| 10,023,589 | B2 | 7/2018 | Arora et al. |
| 2003/0008832 | A1 | 1/2003 | Pamukcu et al. |
| 2016/0362408 | A1 | 12/2016 | Vakalopoulos et al. |
| 2020/0039976 | A1 | 2/2020 | Huang et al. |

FOREIGN PATENT DOCUMENTS

| | | | | |
|---|---|---|---|---|
| CN | 110963997 A | 4/2020 | | |
| JP | 2858002 B2 | 2/1999 | | |
| WO | 2003/044018 A1 | 5/2003 | | |
| WO | 2004/031158 A1 | 4/2004 | | |
| WO | 2015/127125 A1 | 8/2015 | | |
| WO | 2019/122202 A1 | 6/2019 | | |
| WO | 2019/201939 A1 | 10/2019 | | |
| WO | 2019/219517 A1 | 11/2019 | | |
| WO | 2020/010155 A1 | 1/2020 | | |
| WO | WO-2020010092 A1 * | 1/2020 | ........... | C07D 471/04 |
| WO | 2020/106736 A1 | 5/2020 | | |
| WO | 2020/106741 A1 | 5/2020 | | |
| WO | 2020/132549 A1 | 6/2020 | | |
| WO | 2020/132582 A1 | 6/2020 | | |
| WO | 2020/150439 A1 | 7/2020 | | |
| WO | WO-2020150417 A2 * | 7/2020 | ........... | A61K 31/425 |

(Continued)

OTHER PUBLICATIONS

Liu, Frontiers in Immunology, Sep. 14, 2023 (Year: 2023).*

(Continued)

*Primary Examiner* — Andrew D Kosar
*Assistant Examiner* — Phillip Matthew Rzeczycki
(74) *Attorney, Agent, or Firm* — McCarter & English, LLP; Yu Lu; Wei Song

(57) ABSTRACT

The present disclosure provides compounds of Formula (I) a pharmaceutically acceptable salt, a stereoisomer, or a tautomer thereof, for use in, e.g. treating a condition, disease or disorder in which increased (e.g., excessive) STING activation (e.g., STING signaling) contributes to the pathology and/or symptoms and/or progression of the condition, disease or disorder (e.g., cancer) in a subject (e.g., a human). This disclosure also features compositions containing the same as well as methods of using and making the same.

(I)

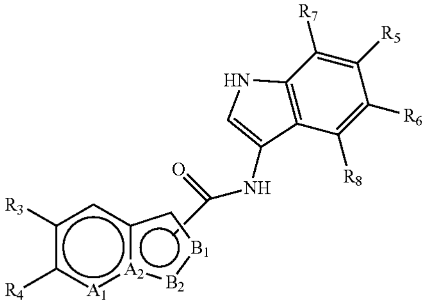

20 Claims, No Drawings

(56) References Cited

FOREIGN PATENT DOCUMENTS

| | | | |
|---|---|---|---|
| WO | 2022/015938 | A1 | 1/2022 |
| WO | 2022/015957 | A1 | 1/2022 |
| WO | 2022/015975 | A1 | 1/2022 |
| WO | 2022/015977 | A1 | 1/2022 |
| WO | 2022/015979 | A1 | 1/2022 |

OTHER PUBLICATIONS

Gan, Frontiers in Immunology, 2022 (Year: 2022).*

Hernandes, Current Drug Targets, Mar. 2010, 11(3): 303-314 (Year: 2010).*

Meanwell, Journal of Medicinal Chemistry, 2018, 61, 5822-5880 (Year: 2018).*

Wang et al., Discovery of novel pyrazolo[1,5-a]pyrimidines as potent pan-Pim inhibitors by structure- and property-based drug design. Bioorg Med Chem Lett. Jun. 1, 2013;23(11):3149-53.

International Search Report and Written Opinion for Application No. PCT/CN2021/132442, dated Feb. 2, 2022, 10 pages.

International Search Report and Written Opinion for Application No. PCT/CN2020/130793, dated Aug. 20, 2021, 16 pages.

* cited by examiner

STING ANTAGONISTS AND USES THEREOF

CROSS REFERENCE TO RELATED APPLICATIONS

This application is a U.S. National Stage Application filed under 35 U.S.C. § 371, based on International Patent Application No. PCT/CN2021/132442, filed on Nov. 23, 2021, which claims the benefit of priority to International Patent Application Number PCT/CN202/130793, filed on Nov. 23, 2020. The entire contents of the aforementioned applications are incorporated herein by reference.

BACKGROUND

STING, also known as transmembrane protein 173 (TMEM173) and MPYS/MITA/ERIS, is a protein that in humans is encoded by the TMEM173 gene. STING has been shown to play a role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner.

The STING pathway is pivotal in mediating the recognition of cytosolic DNA. In this context, STING, a transmembrane protein localized to the endoplasmic reticulum (ER), acts as a second messenger receptor for 2', 3' cyclic GMP-AMP (hereafter cGAMP), which is produced by cGAS after dsDNA binding. In addition, STING can also function as a primary pattern recognition receptor for bacterial cyclic dinucleotides (CDNs) and small molecule agonists. The recognition of endogenous or prokaryotic CDNs proceeds through the carboxy-terminal domain of STING, which faces into the cytosol and creates a V-shaped binding pocket formed by a STING homodimer. Ligand-induced activation of STING triggers its re-localization to the Golgi, a process essential to promote the interaction of STING with TBK1. This protein complex, in turn, signals through the transcription factors IRF-3 to induce type I interferons (IFNs) and other co-regulated antiviral factors. In addition, STING was shown to trigger NF-κB and MAP kinase activation. Following the initiation of signal transduction, STING is rapidly degraded, a step considered important in terminating the inflammatory response.

Excessive activation of STING is associated with a subset of monogenic autoinflammatory conditions, the so-called type I interferonopathies. Examples of these diseases include a clinical syndrome referred to as STING-associated vasculopathy with onset in infancy (SAVI), which is caused by gain-of-function mutations in TMEM173 (the gene name of STING). Moreover, STING is implicated in the pathogenesis of Aicardi-Goutieres Syndrome (AGS) and genetic forms of lupus. As opposed to SAVI, it is the dysregulation of nucleic acid metabolism that underlies continuous innate immune activation in AGS. Apart from these genetic disorders, emerging evidence points to a more general pathogenic role for STING in a range of inflammation-associated disorders such as systemic lupus erythematosus, rheumatoid arthritis and cancer. Thus, small molecule-based pharmacological interventions into the STING signaling pathway hold significant potential for the treatment of a wide spectrum of diseases.

SUMMARY

The present disclosure provides antagonists of STING, for example, inhibitors of structural formula (I), (I-A), (I-B-1), (I-B-2), (I-C-1), or (I-C-2)), pharmaceutically acceptable salts, stereoisomers, tautomers and compositions thereof. It was unexpected to find that the compounds disclosed herein which require the specific bicyclic core structures and a specific combination of substituents at specific positions would effectively inhibit the STING activity.

(I)

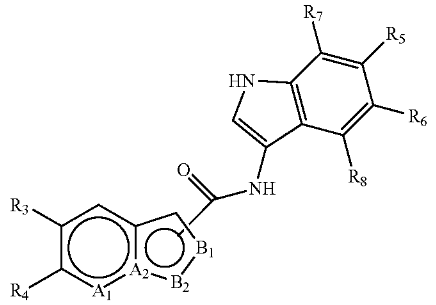

The present disclosure further provides methods of using the compounds disclosed herein (e.g., compounds of structural formula (I), (I-A), (I-B-1), (I-B-2), (I-C-1), or (I-C-2)), and pharmaceutically acceptable salts and compositions thereof, to inhibit the activity of STING. The present disclosure further provides methods for using the compounds disclosed herein (e.g., compounds of structural formula (I), (I-A), (I-B-1), (I-B-2), (I-C-1), or (I-C-2)), pharmaceutically acceptable salts, stereoisomers, tautomers, or compositions thereof, to treat a condition, disease or disorder in which increased (e.g., excessive) STING activation (e.g., STING signaling) contributes to the pathology and/or symptoms and/or progression of the condition, disease or disorder (e.g., an autoimmune disease or a cancer) in a subject (e.g., a human).

An "antagonist" of STING includes compounds that, at the protein level, directly bind or modify STING such that an activity of STING is decreased, e.g., by inhibition, blocking or dampening agonist-mediated responses, altered distribution, or otherwise. STING antagonists include chemical entities, which interfere or inhibit STING signaling.

In one aspect, the present disclosure provides a compound of any one of the formulae described herein (e.g., structural formula (I), (I-A), (I-B-1), (I-B-2), (I-C-1), or (I-C-2)), a pharmaceutically acceptable salt, a stereoisomer, or a tautomer thereof.

In one aspect, the present disclosure provides a pharmaceutical composition comprising a compound of any one of the formulae described herein (e.g., structural formula (I), (I-A), (I-B-1), (I-B-2), (I-C-1), or (I-C-2)), a pharmaceutically acceptable salt, a stereoisomer, or a tautomer thereof, as defined in any one of the embodiments described herein, in a mixture with at least one pharmaceutically acceptable carrier.

In another aspect, the present disclosure provides a compound of any one of the formulae described herein (e.g., structural formula (I), (I-A), (I-B-1), (I-B-2), (I-C-1), or (I-C-2)), a pharmaceutically acceptable salt, a stereoisomer, or a tautomer thereof, as defined in any one of the embodiments described herein, for use as a medicament.

In another aspect, the present disclosure provides a compound of any one of the formulae described herein (e.g., structural formula (I), (I-A), (I-B-1), (I-B-2), (I-C-1), or (I-C-2)), a pharmaceutically acceptable salt, a stereoisomer, or a tautomer thereof, as defined in any one of the embodiments described herein, for use in the treatment of a condition, disease or disorder ameliorated by antagonizing STING are featured, e.g., treating a condition, disease or disorder in which increased (e.g., excessive) STING activation (e.g., STING signaling) contributes to the pathology and/or symptoms and/or progression of the condition, disease or disorder (e.g., an autoimmune disease or a cancer) in a subject (e.g., a human).

In another aspect, the present disclosure provides a method of treating a condition, disease or disorder ameliorated by antagonizing STING are featured, e.g., treating a condition, disease or disorder in which increased (e.g., excessive) STING activation (e.g., STING signaling) contributes to the pathology and/or symptoms and/or progression of the condition, disease or disorder (e.g., an autoimmune disease or a cancer) in a subject (e.g., a human), in a subject in need of such prevention and/or treatment, comprising administering to the subject a therapeutically effective amount of a compound of any one of the formulae described herein (e.g., structural formula (I), (I-A), (I-B-1), (I-B-2), (I-C-1), or (I-C-2)), a pharmaceutically acceptable salt, a stereoisomer, or a tautomer thereof, as defined in any one of the embodiments described herein.

In another aspect, the present disclosure provides a use of a compound of any one of the formulae described herein (e.g., structural formula (I), (I-A), (I-B-1), (I-B-2), (I-C-1), or (I-C-2)), a pharmaceutically acceptable salt, a stereoisomer, or a tautomer thereof, as defined in any one of the embodiments described herein, for the manufacture of a medicament for treating a condition, disease or disorder ameliorated by antagonizing STING are featured, e.g., treating a condition, disease or disorder in which increased (e.g., excessive) STING activation (e.g., STING signaling) contributes to the pathology and/or symptoms and/or progression of the condition, disease or disorder (e.g., an autoimmune disease or a cancer) in a subject (e.g., a human).

In another aspect, the present disclosure provides a compound of any one of the formulae described herein (e.g., structural formula (I), (I-A), (I-B-1), (I-B-2), (I-C-1), or (I-C-2)), a pharmaceutically acceptable salt, a stereoisomer, a tautomer, or a pharmaceutical composition thereof, as defined in any one of the embodiments described herein, for use in the treatment of a condition, disease or disorder for which an antagonist of STING is indicated.

In another aspect, the present disclosure provides a method for inhibiting STING activity in a cell or in a patient. In some embodiments, said method comprises the step of contacting the cell or administering to the patient a compound of structural formula (I) (e.g., (I-A), (I-B-1), (I-B-2), (I-C-1), or (I-C-2)) a pharmaceutically acceptable salt, a stereoisomer, a tautomer or a composition thereof.

DETAILED DESCRIPTION

1. Compounds

In a first embodiment, the present disclosure provides a compound represented by structural formula (I):

(I)

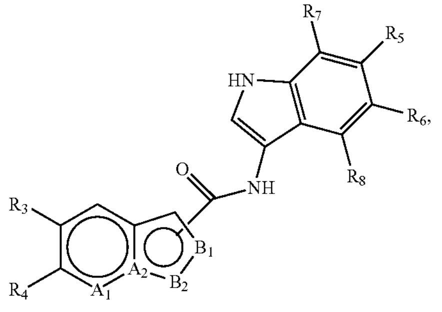

a pharmaceutically acceptable salt, a stereoisomer, or a tautomer thereof, wherein (i) when $A_2$ is C, then $A_1$ is CH or N, $B_2$ is $NR_1$, $B_1$ is Nor CH

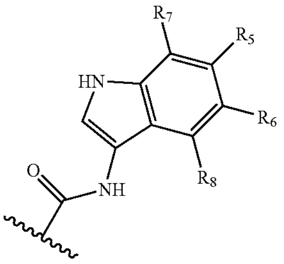

is connected with the carbon atom next to $B_1$; or $B_1$ is C,

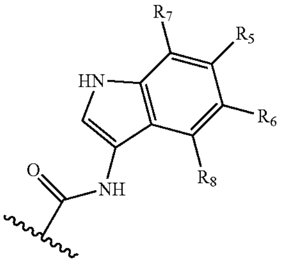

is connected with $B_1$;

(ii) when $A_2$ is N, then $A_1$ is CH, $B_2$ is N, $B_1$ is CH,

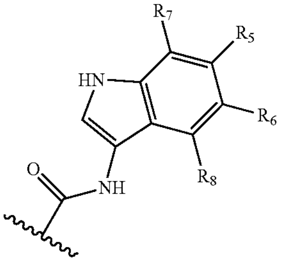

is connected with the carbon atom next to $B_1$; or $B_1$ is C and is connected with

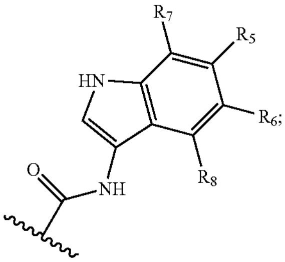

$R_1$ is H, $C_{1-6}$ alkyl, $C_{1-6}$ haloalkyl, —$(CH_2)_{(0\ or\ 1)}$—$C_{3-7}$ cycloalkyl, —$(CH_2)_{(0\ or\ 1)}$—$C_{4-7}$ cycloalkenyl, or —$(CH_2)_{(0\ or\ 1)}$-3-7 membered heterocyclyl, wherein the cycloalkyl, cycloalkenyl, or heterocyclyl represented by $R_1$ is optionally substituted with one or more substituents independently selected from the group consisting of halogen, —OH, oxo, CN, $C_{1-6}$ alkyl, $C_{1-6}$ haloalkyl, $C_{1-6}$alkoxy, $C_{1-6}$ haloalkoxy, and $NR_{11}R_{12}$;

$R_3$ is H, halogen, CN, OH, $C_{1-6}$ alkyl, $C_{2-6}$ alkenyl, $C_{2-6}$ alkynyl, —$C(O)R_{11}$, —$C(O)OR_{11}$, —$C(O)NR_{11}R_{12}$, —$NR_{11}C(O)C_{1-6}$ alkyl, $NR_{11}R_{12}$, —$P({=}O)R_{11}R_{12}$, —$S(O)_2R_{11}$, —$S(O)_2NR_{11}R_{12}$, —$O_{(0\ or\ 1)}$—$C_{3-7}$ cycloalkyl, —$O_{(0\ or\ 1)}$—$C_{4-7}$ cycloalkenyl, —$O_{(0\ or\ 1)}$-3-7 membered heterocyclyl, —$O_{(0\ or\ 1)}$-6-10 membered aryl, —$O_{(0\ or\ 1)}$-5-8 membered heteroaryl, —$(CH_2)_{(0\ or\ 1)}$—$C_{3-7}$ cycloalkyl, —$(CH_2)_{(0\ or\ 1)}$—$C_{4-7}$ cycloalkenyl, —$(CH_2)_{(0\ or\ 1)}$-3-7 membered heterocyclyl, or —$(CH_2)_{(0\ or\ 1)}$aryl, wherein the alkyl, alkenyl, alkynyl, aryl, or heteroaryl represented by $R_3$ or in the group represented by $R_3$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$ haloalkoxy, —$NR_{11}R_{12}$, and —$N(R_{11})C(O)OR_{12}$, wherein the cycloalkyl, cycloalkenyl, or heterocyclyl represented by $R_3$ or in the group represented by $R_3$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$haloalkoxy, —$C(O)OC_{1-6}$ alkyl, and $NR_{11}R_{12}$;

$R_4$, $R_5$, and $R_6$ are independently H, halogen, CN, OH, $C_{1-6}$ alkyl, $C_{1-6}$ alkoxy, $C_{2-6}$ alkenyl, $C_{2-6}$ alkynyl, —$C(O)R_{11}$, —$C(O)OR_{11}$, —$C(O)NR_{11}R_{12}$, —$NR_{11}C(O)C_{1-6}$ alkyl, $NR_{11}R_{12}$, —$P({=}O)R_{11}R_{12}$, —$S(O)_2R_{11}$, —$S(O)_2NR_{11}R_{12}$, —$O_{(0\ or\ 1)}$—$C_{3-7}$ cycloalkyl, —$O_{(0\ or\ 1)}$—$C_{4-7}$ cycloalkenyl, —$O_{(0\ or\ 1)}$-3-7 membered heterocyclyl, —$O_{(0\ or\ 1)}$-6-10 membered aryl, —$O_{(0\ or\ 1)}$-5-8 membered heteroaryl, —$(CH_2)_{(0\ or\ 1)}$—$C_{3-7}$ cycloalkyl, —$(CH_2)_{(0\ or\ 1)}$—$C_{4-7}$ cycloalkenyl, —$(CH_2)_{(0\ or\ 1)}$-3-7 membered heterocyclyl, or —$(CH_2)_{(0\ or\ 1)}$-aryl, wherein the alkyl, alkenyl, alkynyl, alkoxy, aryl, or heteroaryl represented by $R_4$, $R_5$, or $R_6$ or in the group represented by $R_4$, $R_5$, or $R_6$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$haloalkoxy, —$NR_{11}R_{12}$, and —$N(R_{11})C(O)OR_{12}$, wherein the cycloalkyl, cycloalkenyl, or heterocyclyl represented by $R_4$, $R_5$, or $R_6$ or in the group represented by $R_4$, $R_5$, or $R_6$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, —$C(O)OC_{1-6}$alkyl, and $NR_{11}R_{12}$;

wherein at least one of $R_3$, $R_4$, $R_5$, and $R_6$ is not hydrogen;

$R_7$ and $R_8$ are independently H, halogen, $C_{1-6}$ alkyl, $C_{1-6}$ haloalkyl, $C_{1-6}$ alkoxy, or $C_{1-6}$haloalkoxy; and each instance of $R_{11}$ and $R_{12}$ is independently H, $C_{1-6}$alkyl, $C_{1-6}$haloalkyl, or —$C(O)OC_{1-6}$alkyl.

In a second embodiment, the present disclosure provides a compound according to the first embodiment, wherein the compound is represented by structural formula (I-A):

(I-A)

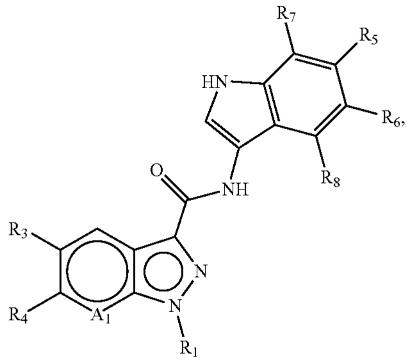

a pharmaceutically acceptable salt, a stereoisomer, or a tautomer thereof, and the definitions of the variables are provided in structural formula (I).

In a third embodiment, the present disclosure provides a compound according to the first embodiment, wherein the compound is represented by structural formula (I-B-1) or (I-B-2):

(I-B-I)

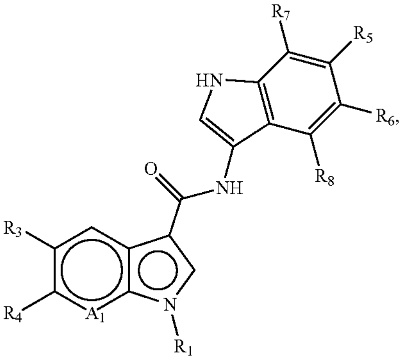

(I-B-2)

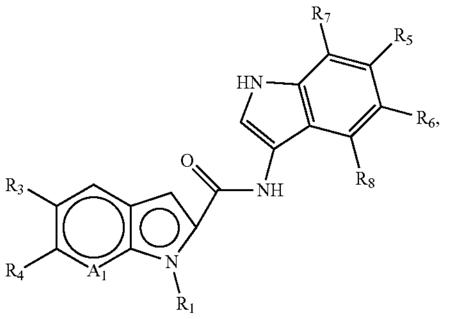

a pharmaceutically acceptable salt, a stereoisomer, or a tautomer thereof, and the definitions of the variables are provided in structural formula (I).

In a fourth embodiment, the present disclosure provides a compound according to the first embodiment, wherein the compound is represented by structural formula (I-C-1) or (I-C-2):

(I-C-1)

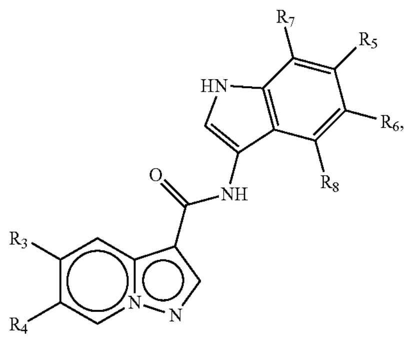

(I-C-2)

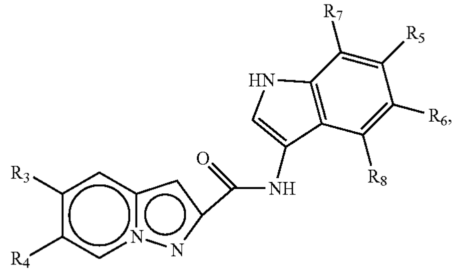

a pharmaceutically acceptable salt, a stereoisomer, or a tautomer thereof, and the definitions of the variables are provided in structural formula (I).

In a fifth embodiment, the present disclosure provides a compound according to the first, second, or third embodiment, a pharmaceutically acceptable salt, a stereoisomer, or a tautomer thereof, wherein each instance of $R_1$ is H, $C_{1-4}$ alkyl, —$(CH_2)_{(0\ or\ 1)}$—$C_{3-4}$ cycloalkyl, or 3-6 membered heterocyclyl, wherein the cycloalkyl or heterocyclyl represented by $R_1$ is optionally substituted with one or more substituents independently selected from the group consisting of halogen, —OH, and $C_{1-4}$ alkyl.

In a sixth embodiment, the present disclosure provides a compound according to the first, second, third, fourth, or fifth embodiment, a pharmaceutically acceptable salt, a stereoisomer, or a tautomer thereof, wherein each instance of $R_7$ and $R_8$ is independently H or halogen.

In a seventh embodiment, the present disclosure provides a compound according to the first, second, third, fourth, fifth, or sixth embodiment, a pharmaceutically acceptable salt, a stereoisomer, or a tautomer thereof, wherein each instance of $R_3$ and $R_5$ is independently H, halogen, $C_{1-6}$ alkyl, or $C_{1-6}$haloalkyl.

In an eighth embodiment, the present disclosure provides a compound according to the first, second, third, fourth, fifth, sixth, or seventh embodiment, a pharmaceutically acceptable salt, a stereoisomer, or a tautomer thereof, wherein each instance of Ra is independently H, halogen, CN, OH, $C_{1-6}$ alkyl, $C_{1-6}$ alkoxy, $C_{2-6}$ alkenyl, $C_{2-6}$ alkynyl, —C(O)$R_{11}$, —C(O)O$R_{11}$, —C(O)N$R_{11}R_{12}$, —N$R_{11}$C(O)$C_{1-6}$ alkyl, N$R_{11}R_{12}$, —S$(O)_2R_{11}$, —S$(O)_2$N$R_{11}R_{12}$, $C_{3-7}$ cycloalkyl, —$(CH_2)_{(0\ or\ 1)}$-3-7 membered heterocyclyl, —$O_{(0\ or\ 1)}$-3-7 membered heterocyclyl, phenyl, —$O_{(0\ or\ 1)}$-5-6 membered heteroaryl, wherein the alkyl, alkoxy, phenyl, or heteroaryl represented by Ra or in the group represented by Ra is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$haloalkoxy, —N$R_{11}R_{12}$, and —N($R_{11}$)C(O)O$R_{12}$, wherein the cycloalkyl or heterocyclyl represented by Ra is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$haloalkoxy, —C(O)O$C_{1-6}$ alkyl, and N$R_{11}R_{12}$.

In a ninth embodiment, the present disclosure provides a compound according to the first, second, third, fourth, fifth, sixth, seventh, or eighth embodiment, a pharmaceutically acceptable salt, a stereoisomer, or a tautomer thereof, wherein each instance of $R_6$ is independently H, halogen, CN, OH, $C_{1-6}$ alkyl, $C_{1-6}$ alkoxy, —C(O)$R_{11}$, —C(O)O$R_{11}$, —C(O)N$R_{11}R_{12}$, —N$R_{11}$C(O)$C_{1-6}$ alkyl, N$R_{11}R_{12}$, —P(═O)$R_{11}R_{12}$, —S$(O)_2R_{11}$, —S$(O)_2$N$R_{11}R_{12}$, $C_{3-7}$ cycloalkyl, 3-7 membered heterocyclyl, phenyl, —$O_{(0\ or\ 1)}$-5-6 membered heteroaryl, wherein the alkyl, alkoxy, phenyl, or heteroaryl represented by $R_6$ or in the group represented by $R_6$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$ haloalkoxy, —N$R_{11}R_{12}$, and —N($R_{11}$)C(O)O$R_{12}$, wherein the cycloalkyl or heterocyclyl represented by $R_6$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, —C(O)O$C_{1-6}$ alkyl, and N$R_{11}R_{12}$.

In a tenth embodiment, the present disclosure provides a compound according to the first, second, third, fifth, sixth, seventh, eighth, or ninth embodiment, a pharmaceutically acceptable salt, a stereoisomer, or a tautomer thereof, wherein each instance of $R_1$ is H, $C_{1-4}$ alkyl, —$(CH_2)_{(0\ or\ 1)}$—$C_{3-4}$ cycloalkyl, or 4-6 membered oxygen-containing heterocyclyl. In one specific embodiment, $R_1$ is H or $C_{1-4}$ alkyl (e.g., methyl).

In an eleventh embodiment, the present disclosure provides a compound according to the first, second, third, fifth, sixth, seventh, eighth, ninth, or tenth embodiment, a pharmaceutically acceptable salt, a stereoisomer, or a tautomer thereof, wherein each instance of $A_1$ is CH.

In a twelfth embodiment, the present disclosure provides a compound according to the first, second, third, fourth, fifth, sixth, seventh, eighth, ninth, tenth, or eleventh embodiment, a pharmaceutically acceptable salt, a stereoisomer, or a tautomer thereof, wherein each instance of $R_7$ and $R_8$ is independently H or F.

In a thirteenth embodiment, the present disclosure provides a compound according to the first, second, third, fourth, fifth, sixth, seventh, eighth, ninth, tenth, eleventh, or twelfth embodiment, a pharmaceutically acceptable salt, a stereoisomer, or a tautomer thereof, wherein each instance of $R_3$ and $R_5$ is independently H, F, Cl, or $CF_3$.

In a fourteenth embodiment, the present disclosure provides a compound according to the first, second, third, fourth, fifth, sixth, seventh, eighth, ninth, tenth, eleventh, twelfth, or thirteenth embodiment, a pharmaceutically acceptable salt, a stereoisomer, or a tautomer thereof, wherein each instance of $R_4$ is independently H, halogen, CN, $C_{1-4}$ alkyl (optionally substituted with OH or —N$R_{11}R_{12}$), $C_{1-4}$ haloalkyl, $C_{1-4}$ alkoxy optionally substituted with $C_{1-4}$ alkoxy, $C_{1-4}$ haloalkoxy, $C_{2-4}$ alkynyl, —C(O)O$R_{11}$, —C(O)N$R_{11}R_{12}$, —S$(O)_2R_{11}$, —

$(CH_2)_{(0\ or\ 1)}$-5-6 membered heterocyclyl, $—O_{(0\ or\ 1)}$-5-6 membered heterocyclyl, —O-5-6 membered heteroaryl, wherein the heteroaryl in the group represented by $R_4$ is optionally substituted with one or more substituents independently selected from the group consisting of halogen, —OH, CN, $C_{1-4}$ alkyl, $C_{1-4}$ haloalkyl, $C_{1-4}$ alkoxy, and $C_{1-4}$ haloalkoxy, wherein the heterocyclyl represented by $R_4$ is optionally substituted with one or more substituents independently selected from the group consisting of halogen, —OH, oxo, CN, $C_{1-4}$ alkyl, $C_{1-4}$ haloalkyl, $C_{1-4}$ alkoxy, $C_{1-4}$ haloalkoxy, $—C(O)OC_{1-4}$ alkyl, and $NR_{11}R_{12}$.

In a fifteenth embodiment, the present disclosure provides a compound according to the first, second, third, fourth, fifth, sixth, seventh, eighth, ninth, tenth, eleventh, twelfth, thirteenth, or fourteenth embodiment, a pharmaceutically acceptable salt, a stereoisomer, or a tautomer thereof, wherein each instance of $R_6$ is independently H, halogen, CN, $C_{1-4}$ alkyl (optionally substituted with $—NR_{11}R_{12}$), $C_{1-4}$ haloalkyl, $C_{1-4}$ alkoxy, $C_{1-4}$ haloalkoxy, $—C(O)OR_{11}$, $—C(O)NR_{11}R_{12}$, $—P(=O)R_{11}R_{12}$, $—S(O)_2R_{11}$, 5-6 membered heterocyclyl, wherein the heterocyclyl represented by $R_6$ is optionally substituted with one or more substituents independently selected from the group consisting of halogen, —OH, oxo, CN, $C_{1-4}$ alkyl, $C_{1-4}$ haloalkyl, $C_{1-4}$ alkoxy, $C_{1-4}$ haloalkoxy, $—C(O)OC_{1-4}$ alkyl, and $NR_{11}R_{12}$.

In a sixteenth embodiment, the present disclosure provides a compound according to the first, second, third, fourth, fifth, sixth, seventh, eighth, ninth, tenth, eleventh, twelfth, thirteenth, fourteenth, or fifteenth embodiment, a pharmaceutically acceptable salt, a stereoisomer, or a tautomer thereof, wherein each instance of $R_4$ is independently H, halogen, CN, $C_{1-4}$ alkyl (optionally substituted with $—NR_{11}R_{12}$), $C_{1-4}$ haloalkyl, $C_{1-4}$ alkoxy, $C_{1-4}$ haloalkoxy, $C_{2-4}$ alkynyl, $—C(O)NR_{11}R_{12}$, or 5-6 membered oxygen containing heterocyclyl. In one specific embodiment, $R_4$ is $C_{1-4}$ alkyl optionally substituted with $—NR_{11}R_{12}$, wherein $R_1$ is H or $C_{1-2}$ alkyl and $R_{12}$ is H, $C_{1-4}$ alkyl, or $C_{1-4}$haloalkyl.

In a seventeenth embodiment, the present disclosure provides a compound according to the first, second, third, fourth, fifth, sixth, seventh, eighth, ninth, tenth, eleventh, twelfth, thirteenth, fourteenth, fifteenth, or sixteenth embodiment, a pharmaceutically acceptable salt, a stereoisomer, or a tautomer thereof, wherein each instance of $R_6$ is independently H, halogen, $C_{1-4}$ alkyl, $C_{1-4}$ haloalkyl, or $—C(O)OC_{1-4}$ alkyl. In one specific embodiment, $R_6$ is H, F, or CN.

In one embodiment, the compound, a pharmaceutically acceptable salt, a stereoisomer, or a tautomer thereof, is selected from the compounds disclosed in examples and Table 1.

2. Definitions

The term "halogen," as used herein, refers to fluoride, chloride, bromide, or iodide.

The term "alkyl" used alone or as part of a larger moiety, such as "alkoxy" or "haloalkyl" and the like, means saturated aliphatic straight-chain or branched monovalent hydrocarbon radical of formula $—C_nH_{(2n+1)}$. Unless otherwise specified, an alkyl group typically has 1-4 carbon atoms, i.e. $(C_1-C_4)$alkyl. As used herein, a "$(C_1-C_4)$alkyl" group means a radical having from 1 to 4 carbon atoms in a linear or branched arrangement. Examples include methyl, ethyl, n-propyl, iso-propyl, and the like.

The term "alkylene" as used herein, means a straight or branched chain divalent hydrocarbon group of formula $—C_nH_{2n}—$. Non-limiting examples include ethylene, and propylene.

The term "alkenyl" means an alkyl group in which one or more carbon/carbon single bond is replaced by a double bond.

The term "alkynyl" means an alkyl group in which one or more carbon/carbon single bond is replaced by a triple bond.

The term "alkoxy" means an alkyl radical attached through an oxygen linking atom, represented by —O-alkyl. For example, "$(C_1-C_4)$alkoxy" includes methoxy, ethoxy, propoxy, and butoxy.

The terms "haloalkyl" and "haloalkoxy" means alkyl or alkoxy, as the case may be, substituted with one or more halogen atoms.

The terms "hydroxyalkyl" and "hydroxyalkoxy" means alkyl or alkoxy, as the case may be, substituted with one or more hydroxy groups.

The term "cycloalkyl" refers to a cyclic, bicyclic, tricyclic, or polycyclic non-aromatic hydrocarbon groups having 3 to 12 ring carbons, preferably, 3 to 7 ring carbons. Any substitutable ring atom can be substituted (e.g., by one or more substituents). Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.0]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro[2.2]pentane, spiro[2.5]octane, spiro[3.5]nonane, spiro[3.5]nonane, spiro[3.5]nonane, spiro[4.4]nonane, spiro[2.6]nonane, spiro[4.5]decane, spiro[3.6]decane, spiro[5.5]undecane, and the like.

The term "cycloalkenyl" refers to partially unsaturated cyclic hydrocarbon groups having 3 to 12 ring carbons, preferably 4 to 7 ring carbons, wherein the cycloalkenyl group may be optionally substituted. Examples of cycloalkenyl groups include, without limitation, cyclopentenyl, cyclohexenyl, cycloheptenyl, and cyclooctenyl. Cycloalkenyl groups may have any degree of saturation provided that none of the rings in the ring system are aromatic; and the cycloalkenyl group is not fully saturated overall. Cycloalkenyl may include multiple fused and/or bridged and/or spirocyclic rings.

The term "heterocyclyl" or "heterocyclic" refers to a radical of a 3- to 12-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone ("3-12 membered heterocyclyl"). In some embodiments, a heterocyclyl group is a 3-7 membered non-aromatic ring system having ring carbon atoms and 1-4 ring heteroatoms, wherein each heteroatom is independently selected from nitrogen, oxygen, and sulfur ("3-7 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a bicyclic system ("bicyclic heterocyclyl") or tricyclic system ("tricyclic heterocyclyl"); polycyclic ring systems include fused, bridged, or spiro ring systems). Exemplary monocyclic heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like. Heterocyclyl polycyclic ring systems can include heteroatoms in one or more rings in the polycyclic ring system. Substituents may be present on one or more rings in the polycyclic ring system.

Generally, the cycloalkyl or the heterocyclyl may be unsubstituted, or be substituted with one or more substituents as valency allows, wherein the substituents can be independently selected from a number of groups such as oxo, —CN, halogen, alkyl and alkoxyl, optionally, the alkyl substitution may be further substituted.

The term "aryl" refers to a 6 to 10 membered all-carbon monocyclic ring or a polycyclic fused ring (a "fused" ring system means that each ring in the system shares an adjacent pair of carbon atoms with other ring in the system) group, and has a completely conjugated π-electron system. Representative examples of aryl are phenyl and naphthyl.

The term "heteroaryl," as used herein, refers to a monocyclic or multicyclic aromatic hydrocarbon in which at least one of the ring carbon atoms has been replaced with a heteroatom independently selected from oxygen, nitrogen and sulfur. Preferably, the heteroaryl is based on a $C_{5-10}$ aryl with one or more of its ring carbon atoms replaced by the heteroatom. A heteroaryl group may be attached through a ring carbon atom or, where valency permits, through a ring nitrogen atom. Generally, the heteroaryl may be unsubstituted, or be substituted with one or more substituents as valency allows with the substituents being independently selected from halogen, OH, alkyl, alkoxyl, and amino (e.g., $NH_2$, NHalkyl, $N(alkyl)_2$), optionally, the alkyl may be further substituted.

Pharmaceutically Acceptable Salts

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in J. Pharm. Sci., 1977, 66, 1-19.

Pharmaceutically acceptable salts of the compounds of any one of the formulae described above include acid addition and base salts.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Pharmaceutically acceptable salts of compounds of any one of the formulae described above may be prepared by one or more of three methods:

(i) by reacting the compound of any one of the formulae described above with the desired acid or base;

(ii) by removing an acid- or base-labile protecting group from a suitable precursor of the compound of any one of the formulae described above or by ring-opening a suitable cyclic precursor, for example, a lactone or lactam, using the desired acid or base; or (iii) by converting one salt of the compound of any one of the formulae described above to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of any one of the formulae described above, and pharmaceutically acceptable salts thereof, may exist in unsolvated and solvated forms.

Solvates and Hydrates

The term "solvate" is used herein to describe a molecular complex comprising the compound of any one of the formulae described above, or a pharmaceutically acceptable salt thereof, and one or more pharmaceutically acceptable solvent molecules, for example, ethanol.

The term "hydrate" is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Stereoisomers and Other Variations

The compounds of any one of the formulae described above may exhibit one or more kinds of isomerism (e.g. optical, geometric or tautomeric isomerism). Such variation is implicit to the compounds of any one of the formulae described above defined as they are by reference to their structural features and therefore within the scope of the present disclosure.

Compounds having one or more chiral centers can exist in various stereoisomeric forms, i.e., each chiral center can have an R or S configuration, or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When a compound is designated by its chemical name (e.g., where the configuration is indicated in the chemical name by "R" or "S") or its structure (e.g., the configuration is indicated by “wedge” bonds) that indicates a single enantiomer, unless indicated otherwise, the compound is at least 60%, 70%, 80%, 90%, 99% or 99.9% optically pure (also referred to as “enantiomerically pure”). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

When two stereoisomers are depicted by their chemical names or structures, and the chemical names or structures are connected by an “and”, a mixture of the two stereoisomers is intended.

When two stereoisomers are depicted by their chemical names or structures, and the names or structures are connected by an “or”, one or the other of the two stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with “S” or “R”, the name is meant to encompass the compound with the S configuration at that chiral center, the compound with the R configuration at that chiral center or the compound with a mixture of the R and S configuration at that chiral center.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

The term “geometric isomer” refers to compounds having at least one double bond, wherein the double bond(s) may exist in cis (also referred to as syn or entgegen (E)) or trans (also referred to as anti or zusammen (Z)) forms as well as mixtures thereof.

Where structural isomers are interconvertible via a low energy barrier, tautomeric isomerism (“tautomerism”) can occur. This can take the form of proton tautomerism in compounds of any one of the formulae described above containing, for example, an imino, keto, or oxime group, or so-called valence tautomerism in compounds which contain an aromatic moiety. It follows that a single compound may exhibit more than one type of isomerism.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

Cis/trans isomers may be separated by conventional techniques well known to those skilled in the art, for example, chromatography and fractional crystallisation.

Conventional techniques for the preparation/isolation of individual enantiomers/diastereomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of any one of the formulae described above contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of any one of the formulae described above (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present disclosure are known in the art (see, for example, Smith, Roger M., Loughborough University, Loughborough, UK; Chromatographic Science Series (1998), 75 (Supercritical Fluid Chromatography with Packed Columns), pp. 223-249 and references cited therein). Columns can be obtained from Chiral Technologies, Inc, West Chester, Pa., USA, a subsidiary of Daicel® Chemical Industries, Ltd., Tokyo, Japan.

It must be emphasized that the compounds of any one of the formulae described above have been drawn herein in a single tautomeric form, all possible tautomeric forms are included within the scope of the present disclosure.

3. Administration and Dosing

Typically, a compound of the present disclosure is administered in an amount effective to treat a condition as described herein. The compounds of the present disclosure can be administered as compound per se, or alternatively, as a pharmaceutically acceptable salt. For administration and dosing purposes, the compound per se or pharmaceutically acceptable salt thereof will simply be referred to as the compounds of the present disclosure.

The compounds of the present disclosure are administered by any suitable route in the form of a pharmaceutical composition adapted to such a route, and in a dose effective for the treatment intended. The compounds of the present disclosure may be administered orally, rectally, vaginally, parenterally, or topically.

The compounds of the present disclosure may be administered orally. Oral administration may involve swallowing, so that the compound enters the gastrointestinal tract, or buccal or sublingual administration may be employed by which the compound enters the bloodstream directly from the mouth.

In another embodiment, the compounds of the present disclosure may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the present disclosure may also be administered topically to the skin or mucosa, that is, dermally or transdermally. In another embodiment, the compounds of the present disclosure can also be administered intranasally or by inhalation. In another embodiment, the compounds of the present disclosure may be administered rectally or vaginally. In another embodiment, the compounds of the present disclosure may also be administered directly to the eye or ear.

The dosage regimen for the compounds of the present disclosure and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the present disclosure is typically from about 0.001 to about 100 mg/kg (i.e., mg compound of the present disclosure per kg body weight) for the treatment of the indicated conditions discussed herein. In another embodiment, total daily dose of the compound of the present disclosure is from about 0.01 to about 30 mg/kg, and in another embodiment, from about 0.03 to about 10 mg/kg, and in yet another embodiment, from about 0.1 to about 3. It is not uncommon that the administration of the compounds of the present disclosure will be repeated a plurality of times in a day (typically no greater than 4 times). Multiple doses per day typically may be used to increase the total daily dose, if desired.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present disclosure include mammalian subjects, including non-human mammal such as primates, rodents (mice, rats, hamsters, rabbits etc).

In one embodiment, humans are suitable subjects. Human subjects may be of either gender and at any stage of development.

4. Pharmaceutical Compositions

In another embodiment, the present disclosure comprises pharmaceutical compositions. Such pharmaceutical compositions comprise a compound of the present disclosure presented with a pharmaceutically acceptable carrier. Other pharmacologically active substances can also be present.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of present disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the present disclosure. In another embodiment, the oral administration may be in a powder or granule form. In another embodiment, the oral dose form is sub-lingual, such as, for example, a lozenge. In such solid dosage forms, the compounds of any one of the formulae described above are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present disclosure comprises a parenteral dose form.

"Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present disclosure comprises a topical dose form.

"Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of present disclosure are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, *J. Pharm. Sci.,* 88:955-958, 1999.

Formulations suitable for topical administration to the eye include, for example, eye drops wherein the compound of present disclosure is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the present disclosure are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present disclosure comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the present disclosure may be prepared by any of the well-known techniques of pharmacy, such as effective formulation and administration procedures.

The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa., 1975; Liberman et al., Eds., *Pharmaceutical Dosage Forms*, Marcel Decker, New York, N.Y., 1980; and Kibbe et al., Eds., *Handbook of Pharmaceutical Excipients* ($3^{rd}$ Ed.), American Pharmaceutical Association, Washington, 1999.

5. Method of Treatment

Various cytosolic pathogen-associated molecular patterns (PAMPs) and damage-associated molecular patterns (DAMPs) can be recognized by intracellular pattern recognition receptors (PRRs), such as cyclic GMP-AMP synthase (cGAS), which recognizes cytosolic nucleic acids including dsDNAs. Recognition of dsDNA by cGAS activates the enzyme, leading to the generation of cyclic GMP-AMP (cGAMP). cGAMP is then recognized by STING, generating type 1 IFNs and NF-κB-mediated generation of proinflammatory cytokines and molecules.

Thus, the cGAS-STING mediated recognition of cytosolic dsDNA plays a crucial role in innate immunity against cytosolic pathogens, PAMPs, and DAMPs. In particular, the cGAS-STING signaling pathway evolved to recognize cytosolic DNA, which can either be the intracellular DNA viruses infecting the host, or host DNA (including mtDNA or nuclear DNA leaked into the cytosol) and bacterial CDNs acting as DAMPs.

Meanwhile, overactivation of this system can lead to the development of autoinflammation and autoimmune diseases. For example, an increased cGAS-STING signaling promotes acute pancreatitis while its blockage by knocking out cGAS or STING decreases the incidence of pancreatitis (Zhao et al., STING signaling promotes inflammation in experimental acute pancreatitis. *Gastroenterology* 154: 1822-1835, e2, 2018). The overactivation of the cGAS-STING signaling also plays a very crucial role in the pathogenesis of autoimmune diseases including SLE. The chronic activation of the pathway causes autoinflammation or autoimmunity (Yang et al., *Proc Natl Acad Sci USA.* 114:E4612-E4620, 2017; Chen et al., *Natl Sci Rev.* 5:308-310, 2018; Dou et al., Nature 550:402-406, 2017; Gluck et al., *Nat Cell Biol.* 19:1061-1070, 2017). Further, the cGAS-STING pathway also activates NLRP3 inflammasome and pro-inflammatory cytokine (IL-1β and IL-18) release by inducing the lysosomal cell death and $K^+$ efflux. Thus, specific targeting of cGAS-STING signaling is of great value for targeting autoimmune diseases including IBD due to the involvement of lysosomal cell death and NLRP3 inflammasome in the pathogenesis. For example, the deletion of STING completely abrogates the enterocolitis and causes a less severe intestinal inflammation in $cGAS^{-/-}$ mice.

Hence, cGAS-STING signaling plays a crucial role in the pathogenesis of inflammation and autoimmune diseases, and thus one aspect of the invention provides a method for treating a disease or condition associated with abnormal STING activity/activation/expression, comprising administering a therapeutically effective amount of a compound of the invention or a pharmaceutical composition thereof to a subject in need of treatment.

In some embodiments, methods for treating a subject having condition, disease or disorder in which increased (e.g., excessive) STING activity (e.g., STING signaling) contributes to the pathology and/or symptoms and/or progression of the condition, disease or disorder (e.g., inflammatory or autoimmune disorders) are provided. In certain embodiments, the condition, disease or disorder is associated with or characterized by activation of the Type I interferon pathway, or type I interferonopathy.

Type I interferons, which are predominantly involved in immune responses against viral infections, include interferon alpha (IFN-$\alpha$), interferon beta (IFN-$\beta$), IFN-kappa, IFN-epsilon and IFN-omega.

In some embodiments, the condition, disease or disorder is STING-associated conditions, e.g., type I interferonopathies (e.g., STING-associated vasculopathy with onset in infancy (SAVI)), Aicardi-Goutieres Syndrome (AGS), Chilblain lupus erythematosus (CHLE), genetic forms of lupus, and inflammation-associated disorders such as systemic lupus erythematosus, and rheumatoid arthritis. In certain embodiments, the condition, disease or disorder is an autoimmune disease (e.g., a cytosolic DNA-triggered autoinflammatory disease). Non-limiting examples of autoimmune disease include rheumatoid arthritis, systemic lupus erythematosus, multiple sclerosis, inflammatory bowel diseases (IBDs) comprising Crohn's disease (CD) and ulcerative colitis (UC), juvenile idiopathic arthritis (JIA), psoriasis, psoriatic arthritis, which are chronic inflammatory conditions with polygenic susceptibility. In certain embodiments, the condition is an inflammatory bowel disease (IBD). In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

For example, TREX1 is a 314 aa protein encoded by a single exon on human chromosome 3p21. It is an exonuclease that digests the cytosolic DNA to prevent the generation of a pathogenic immune response. The loss of TREX1 causes AGS, SLE, familial chilblain lupus (a cutaneous subtype of SLE), and retinal vasculopathy with cerebral leukodystrophy (RVCL) in humans. TREX1 mutations represent the single most common cause of monogenic SLE identified to date. The antimalarial drug hydrochloroquine or the more potent compound X6 given to Trex1$^{-/-}$ mice prevents the development of experimental autoimmune myocarditis by inhibiting the production of cGAMP and the activation of ISGs in spleen and heart tissues, as well as in vitro in peripheral blood monocytes isolated from SLE patients. This data demonstrates that inhibiting the cGAMP-STING pathway can treat autoinflammatory or autoimmune diseases such as SLE (see An et al., Inhibition of cyclic GMP-AMP synthase using a novel antimalarial drug derivative in Trex1-deficient mice. *Arthritis Rheumatol.* 2018; 70:1807-1819), as well as a number of monogenic type I interferonopathies including AGS, STING-associated vasculopathy of infancy (SAVI) and deficiency of DNase II activity.

Indeed, Eli Lilly and Company just recently began a Phase II/III clinical trial to evaluate the efficacy and safety of baricitinib (LY3009104) in adult and pediatric Japanese patients with Nakajo-Nishimura Syndrome/chronic atypical neutrophilic dermatosis with lipodystrophy and elevated temperature (NNS/CANDLE), SAVI, and AGS. See ClinicalTrials.gov Identifier: NCT04517253. Baricitinib is a reversible Janus kinase (JAK) 1 inhibitor. The JAK/STAT pathway is the principal signaling pathway for cytokine and growth factor receptors including the IFN$\alpha$/$\beta$ receptor (IFNAR) and the IFN$\gamma$ receptor (IFNGR). Small molecule inhibitors of JAKs such as baricitinib reduce Type-I and Type-II IFN-induced STAT-1 phosphorylation (pSTAT1) in CANDLE and SAVI patients in vitro, suggesting their utility in reducing the IFN signaling and disease manifestations in CANDLE and SAVI patients. Also see ClinicalTrials.gov Identifier NCT01724580 (Eli Lilly)—compassionate use protocol for the treatment of autoinflammatory syndromes with baricitinib.

Thus direct STING inhibitors, such as the compounds described herein, similarly reduced Type 1 IFN signaling, and can be used to treat diseases such as CANDLE, SAVI, and AGS.

Another example of using STING inhibitor to treat autoinflammatory or autoimmune disease is a natural plant cyclopeptide called astin C (from *Aster tataricus*), which competitively binds to the same pocket of STING in which CDNs (cGAMP) dock. Astin C inhibits the cGAS-STING signaling and the associated pro-inflammatory immune response both in vitro in Trex1$^{-/-}$ bone marrow-derived M$\phi$s, and in vivo in Trex1$^{-/-}$ mice with autoimmune disease. See Li et al., The cyclopeptide astin C specifically inhibits the innate immune CDN sensor STING. *Cell Rep.* 25:3405-3421, e7, 2018.

In some embodiments, modulation of the immune system by STING provides for the treatment of diseases, including diseases caused by foreign agents. Exemplary infections by foreign agents which may be treated and/or prevented by the method of the present disclosure include an infection by a bacterium (e.g., a Gram-positive or Gram-negative bacterium), an infection by a fungus, an infection by a parasite, and an infection by a virus. In one embodiment of the present disclosure, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant enterococcus), or sepsis. In another embodiment, the infection is a fungal infection (e.g. infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma gondiz*).

In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS (including SARS-CoV-2, the pathogen that causes COVID-19), and lower or upper respiratory tract infection (e.g., respiratory syncytial virus)).

A current clinical trial (ClinicalTrials.gov Identifier: NCT04361786) is on-going to study acral cutaneous thrombotic vasculopathy and COVID-19 infection. The interferon pathway is normally involved in anti-viral defense. Thus COVID-19 could cause excessive activation of this pathway, and lead to similar skin involvement as in type I interferonopathies. Indeed, spectrum of skin lesions may arise during COVID-19 virus infection. It includes non-specific urticaria, aphtoids lesions, but also acrosyndromes, in particular suggestive of chilblains. Pathological findings showed thrombocytic lymphocytic vasculitis. Chilblains are sometimes associated with Raynaud's phenomenon or acrocyanosis.

Dermatological features may present pathophysiological similarities with the inflammatory and respiratory vascular disturbances, which makes all the gravity of this disease, or even with other organs. Indeed, genetic conditions such as familial lupus chilblains, linked to a mutation of TREX1 gene, and SAVI (Sting associated vasculopathy with onset on infancy) have similar clinical presentations. In particular, SAVI associates both acral skin and lung damage, and auto-antibodies. They have recently been identified as type I interferonopathies.

In addition, hyperactivation of the type I interferon pathway leads to modulation of the adaptive immune response. Production of autoantibodies, in particular antiphospholipid antibodies, have thrombogenic properties. Thus the compounds of the invention can treat various viral infections, particularly those that trigger IFN response, e.g., COVID-19.

In some embodiments, the condition, disease or disorder is hepatitis B (see, e.g., WO 2015/061294).

In some embodiments, the condition, disease or disorder is selected from cardiovascular diseases (including e.g., myocardial infarction).

In some embodiments, the condition, disease or disorder is age-related macular degeneration.

In some embodiments, the condition, disease or disorder is mucositis, also known as stomatitis, which can occur as a result of chemotherapy or radiation therapy, either alone or in combination as well as damage caused by exposure to radiation outside of the context of radiation therapy.

In some embodiments, the condition, disease or disorder is uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

In some embodiments, the condition, disease or disorder is selected from the group consisting of a cancer, a neurological disorder, an autoimmune disease, hepatitis B, uveitis, a cardiovascular disease, age-related macular degeneration, and mucositis.

In some embodiments, the condition, disease or disorder is cancer. Non-limiting examples of cancer include melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma.

In some embodiments, the condition, disease or disorder is a neurological disorder, which includes disorders that involve the central nervous system (brain, brainstem and cerebellum), the peripheral nervous system (including cranial nerves), and the autonomic nervous system (parts of which are located in both central and peripheral nervous system).

Non-limiting examples of cancer include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia tel egi ectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia;

fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; amyotrophe lateral sclerosis and Zellweger syndrome.

6. Kits

Another aspect of the present disclosure provides kits comprising the compound of any one of the formulae described above or pharmaceutical compositions comprising the compound of any one of the formulae described above of the present disclosure. A kit may include, in addition to the compound of any one of the formulae described above, of the present disclosure or pharmaceutical composition thereof, diagnostic or therapeutic agents. A kit may also include instructions for use in a diagnostic or therapeutic method. In some embodiments, the kit includes the compound of any one of the formulae described above, or a pharmaceutical composition thereof and a diagnostic agent. In other embodiments, the kit includes the compound of any one of the formulae described above, or a pharmaceutical composition thereof.

In yet another embodiment, the present disclosure comprises kits that are suitable for use in performing the methods of treatment described herein. In one embodiment, the kit contains a first dosage form comprising one or more of the compounds of the present disclosure in quantities sufficient to carry out the methods of the present disclosure. In another embodiment, the kit comprises one or more compounds of the present disclosure in quantities sufficient to carry out the methods of the present disclosure and a container for the dosage and a container for the dosage.

7. Preparation

The compounds of any one of the formulae described above, may be prepared by the general and specific methods described below, using the common general knowledge of one skilled in the art of synthetic organic chemistry. Such common general knowledge can be found in standard reference books such as *Comprehensive Organic Chemistry*, Ed. Barton and Ollis, Elsevier; *Comprehensive Organic Transformations: A Guide to Functional Group Preparations*, Larock, John Wiley and Sons; and *Compendium of Organic Synthetic Methods*, Vol. I-XII (published by Wiley-Interscience). The starting materials used herein are commercially available or may be prepared by routine methods known in the art.

In the preparation of the compounds of any one of the formulae described above, it is noted that some of the preparation methods described herein may require protection of remote functionality (e.g., primary amine, secondary amine, carboxyl in any one of the formulae described above precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines, and lower alkyl or benzyl esters for carboxylic acids) which are generally not chemically reactive under the reaction conditions described and can typically be removed without chemically altering other functionality in the any one of the formulae described above compounds.

The Schemes described below are intended to provide a general description of the methodology employed in the preparation of the compounds of the present disclosure. Some of the compounds of the present disclosure may contain single or multiple chiral centers with the stereochemical designation (R) or (S). It will be apparent to one skilled in the art that all of the synthetic transformations can be conducted in a similar manner whether the materials are enantioenriched or racemic. Moreover, the resolution to the desired optically active material may take place at any desired point in the sequence using well known methods such as described herein and in the chemistry literature.

EXAMPLES

General Procedures

All reactions were carried out under a nitrogen atmosphere with dry solvents under anhydrous conditions, unless otherwise noted. Low-resolution mass spectra (LC-MS) was used to monitor progression of reactions and was recorded on Waters ACQUITY UPLC with SQ Detectors using a Waters CORTECS C18 column (2.7 μm, 4.6×30 mm) using a gradient elution method: solvent A: 0.1% formic acid in water; solvent B: 0.1% formic acid in $CH_3CN$; 5% solvent B to 95% solvent B in 1.0 min, hold 1.0 min, equilibration to 5% solvent B in 0.5 min; flow rate: 1.8 mL/min; column temperature 40° C. Purification of final products by Prep-HPLC were carried out on Waters Prep-HPLC with QDA detector, using Xbridge C18 column (5 μm, 150×19 mm) using a gradient elution method.

Abbreviations

AcOH Acetic acid
$Ac_2O$ Acetic anhydride
DCE 1,2-Dichloroethane
DIBAL-H Diisobutylaluminium hydride
DIPEA N-ethyl-N-isopropylpropan-2-amine
DMAP 4-Dimethylaminopyridine
DMF N,N-dimethylformamide
DMSO Dimethyl sulfoxide
Dppf 1,1'-Bis(diphenylphosphino)ferrocene
EDCI N-(3-dimethylaminopropyl)-N'-ethylcarbodiimide hydrochloride
EtOH Ethanol
EtOAc Ethyl acetate
HATU N-[(Dimethylamino)-1H-1,2,3-triazolo-[4,5-b]pyridin-1-ylmethylene]-N methylmethanaminium hexafluorophosphate N-oxide
HOBT 1-Hydroxybenzotriazole
HPLC High-performance liquid chromatography
Prep-HPLC preparative high-performance liquid chromatography
LC-MS Liquid chromatography-mass spectrometry
MeOH Methanol
MsCl Methanesulfonyl chloride
NBS N-bromosuccinimide
$Pd(dppf)Cl_2$ Dichloro[1,1'-bis(diphenylphosphino)ferrocene]palladium
$Pd(PPh_3)_4$ Tetrakis(triphenylphosphine)Palladium
PPTS 4-methylbenzenesulfonic acid
TFA Trifluoroacetic acid
TFAA Trifluoroacetic anhydride
$T_3P$ Propylphosphonic anhydride
Xphos Dicyclohexyl-[2-(2,4,6-triisopropylphenyl)phenyl]phosphane
Xantphos 4,5-Bis(diphenylphosphino)-9,9-dimethylxanthene
tBuXphos 2-Di-t-butylphosphino-2',4',6'-tri-i-propyl-1,1'-biphenyl
% wt. weight percentage
rac racemic

Acid Intermediates

Acid Intermediate 1

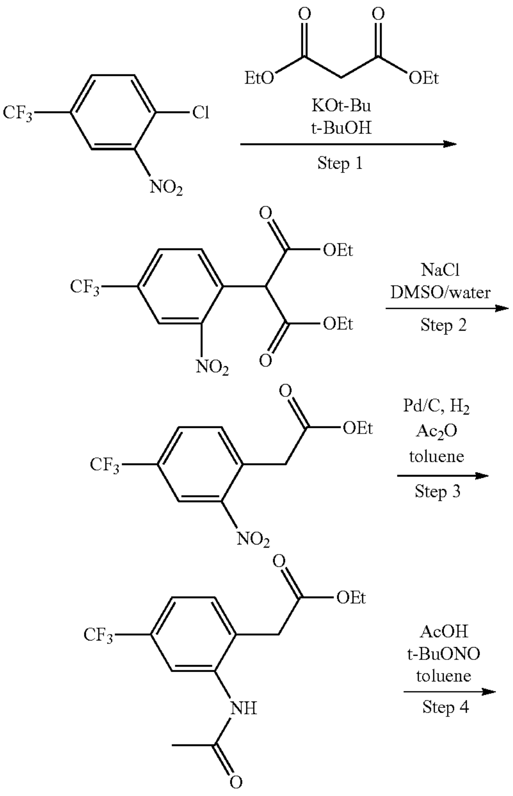

-continued

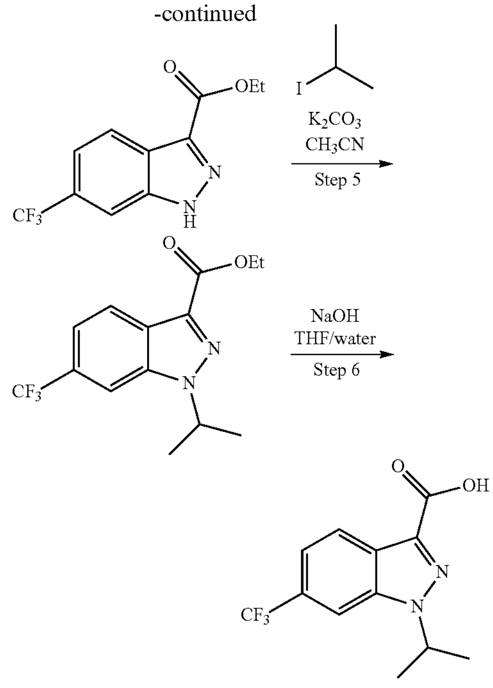

Step 1

To a stirred solution of 1-chloro-2-nitro-4-(trifluoromethyl)benzene (28.0 g, 18.2 mL, 124 mmol) in t-BuOH (30.0 mL) were sequentially added KOt-Bu (27.9 g, 248 mmol) and diethyl propanedioate (39.8 g, 37.5 mL, 248 mmol) at 25° C. The reaction mixture was warmed to 90° C. and stirred at that temperature for 6 h. The reaction mixture was cooled to 25° C., quenched with water (50 mL) and then extracted with EtOAc (200 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 30%) in 20 min to give diethyl 2-[2-nitro-4-(trifluoromethyl)phenyl]propanedioate (28.9 g, 66% yield) as a yellow oil. LC-MS: m/z $[M+H]^+$ 350.1.

Step 2

To a stirred solution of diethyl 2-[2-nitro-4-(trifluoromethyl)phenyl]propanedioate (28.9 g, 82.8 mmol) in DMSO (100 mL) and Water (30.0 mL) was added NaCl (14.5 g, 248 mmol) at 25° C. The reaction mixture was warmed to 120° C. and stirred at that temperature for 16 h. The reaction mixture was cooled to 0° C., quenched with water (200 mL) and stirred at that temperature for 30 min. The precipitates were collected by filtration and dried under vacuum to give ethyl 2-[2-nitro-4 (trifluoromethyl)phenyl]acetate (15.0 g, 65% yield) as a yellow solid which was used in the next step without further purification. LC-MS: m/z $[M+H]^+$ 278.0.

Step 3

To a stirred solution of ethyl 2-[2-nitro-4-(trifluoromethyl)phenyl]acetate (15.0 g, 54.1 mmol) in toluene (50.0 mL) were sequentially added Pd/C (5.76 g, 10% wt., 5.43 mmol) and $Ac_2O$ (27.6 g, 25.6 mL, 271 mmol) at 25° C. The reaction mixture was stirred under hydrogen atmosphere (balloon) at that temperature for 16 h before it was filtered through a pad of Celite. The filtrate was concentrated under reduced pressure. The residue was purified by silica gel chromatography eluting with EtOAc/petroleum ether (with EtOAc from 0 to 30%) in 20 min to give ethyl 2-[2-acetamido-4-(trifluoromethyl)phenyl]acetate (10.0 g, 64% yield) as a white solid. LC-MS: m/z $[M+H]^+$ 290.1.

Step 4

To a stirred solution of ethyl 2-[2-acetamido-4-(trifluoromethyl)phenyl]acetate (10.0 g, 34.6 mmol) in acetic acid (30.0 mL) was added tert-butyl nitrite (7.10 g, 8.20 mL, 69.1 mmol) at 25° C. The reaction mixture was warmed to 90° C. and stirred at that temperature for 16 h. The mixture was cooled to 25° C., poured into ice water (100 mL) and stirred at that temperature for 1 h. The precipitates were collected by filtration and dried under vacuum to give ethyl 6-(trifluoromethyl)-1H-indazole-3-carboxylate (8.40 g, 94% yield) as a white solid which was used in the next step without further purification. LC-MS: m/z $[M+H]^+$ 259.0.

Step 5

To a stirred solution of methyl 6-(trifluoromethyl)-1H-indazole-3-carboxylate (200 mg, 0.819 mmol) in $CH_3CN$ (5.0 mL) were sequentially 2-iodopropane (279 mg, 1.60 mmol) and $K_2CO_3$ (679 mg, 4.91 mmol) at 25° C. The reaction mixture was stirred at that temperature for 16 h before it was quenched with water (10 mL) and then extracted with EtOAc (50 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 30%) in 20 min to give ethyl 1-isopropyl-6-(trifluoromethyl)indazole-3-carboxylate (130 mg, 53% yield) as a colorless oil. LC-MS: m/z $[M+H]^+$ 301.1.

Step 6

To a stirred solution of ethyl 1-isopropyl-6-(trifluoromethyl)indazole-3-carboxylate (130 mg, 0.433 mmol) in THF (3.0 mL) was added aq. NaOH (2.20 mL, 2.0 M, 4.40 mmol) at 25° C. The reaction mixture was warmed to 40° C. and stirred at that temperature for 16 h. The reaction mixture was concentrated under reduced pressure to remove most of THF. The mixture was acidified with aq. HCl (2.0 M) to pH=3 before it was extracted with EtOAc (30 mL×2). The combined organic phases were washed with brine, dried over anhydrous $Na_2SO_4$, and filtered. The filtrate was concentrated under reduced pressure to give 1-isopropyl-6-(trifluoromethyl)indazole-3-carboxylic acid (102 mg, 87% yield) as a white solid which was used in the next step without further purification. LC-MS: m/z $[M+H]^+$ 273.1. Additional intermediates of the present disclosure were prepared using the similar procedure disclosed in acid intermediate 1 from the corresponding materials and their corresponding characterization data are listed in the table below.

| ID | Structure | LC-MS: m/z $[M + H]^+$ |
|---|---|---|
| Acid intermediate 2 | 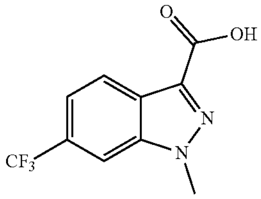 [SMILES: Cn1nc(C(=O)O)c2ccc(C(F)(F)F)cc21] | 245.0 |

-continued

| ID | Structure | LC-MS: m/z $[M + H]^+$ |
|---|---|---|
| Acid intermediate 3 | 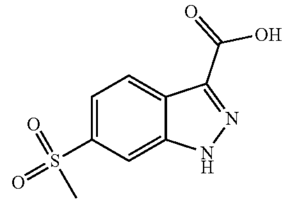 [SMILES: CS(=O)(=O)c1ccc2c(C(=O)O)n[nH]c2c1] | 241.0 |
| Acid intermediate 4 | 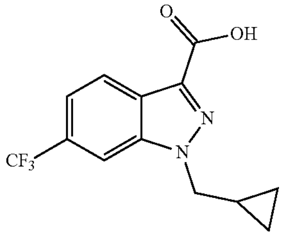 [SMILES: O=C(O)c1nn(CC2CC2)c2cc(C(F)(F)F)ccc12] | 285.0 |

Acid Intermediate 5

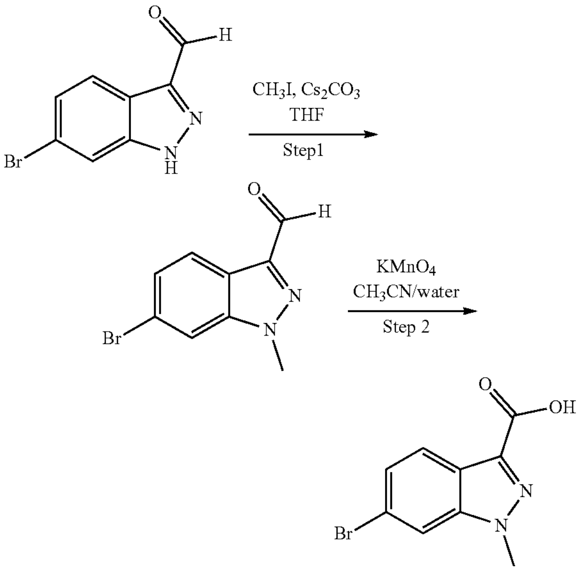

Step 1

To a stirred solution of 6-bromo-1H-indazole-3-carbaldehyde (503 mg, 2.20 mmol) in THF (8.0 mL) were sequentially added $CH_3I$ (381 mg, 167 μL, 2.70 mmol) and $Cs_2CO_3$ (452 mg, 3.27 mmol) at 25° C. The mixture was stirred at that temperature for 16 h before it was quenched with water (20 mL) and then extracted with EtOAc (15 mL×2). The combined organic layers were washed with brine, dried over anhydrous $Na_2SO_4$, and filtered. The filtrate was concentrated under vacuum. The residue was purified by silica gel chromatography eluting with EtOAc/petroleum (with EtOAc from 1% to 82%) in 25 min to give 6-bromo-1-methyl-indazole-3-carbaldehyde (313 mg, 58% yield) as a white solid. LC-MS: m/z $[M+H]^+$ 240.0.

Step 2

To a stirred solution of 6-bromo-1-methyl-indazole-3-carbaldehyde (313 mg, 1.30 mmol) in $CH_3CN$ (10.0 mL) was added aq. $KMnO_4$ (2.0 mL, 1.1 M, 2.2 mmol) at 25° C. The mixture was stirred at that temperature for 4 h before it was poured into ice water (40 mL) and filtered through a pad of Celite. The filtrate was diluted with water (20 mL) and extracted with EtOAc (40 mL×2). The combined organic layers were washed with brine, dried over anhydrous $Na_2SO_4$, and filtered. The filtrate was concentrated under reduced pressure. The residue was purified by silica gel chromatography eluting with EtOAc/petroleum (with EtOAc from 1% to 96%) in 20 min to give afford 6-bromo-1-methyl-indazole-3-carboxylic acid (171 mg, 51% yield) as a white solid. LC-MS: m/z $[M+H]^+$ 255.0.

Acid Intermediate 6

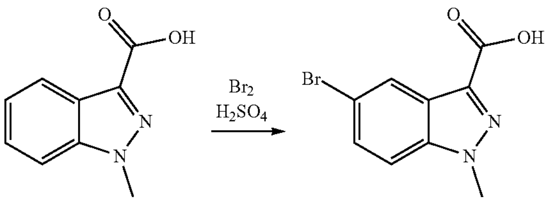

To a stirred solution of 1-methylindazole-3-carboxylic acid (200 mg, 1.14 mmol) in AcOH (5.0 mL) was added molecular bromine (544 mg, 175 μL, 3.40 mmol) at 0° C. The reaction mixture was stirred at that temperature for 3 h before it was quenched with water (50 mL) and then extracted with EtOAc (40 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 1% to 54%) in 30 min to give 5-bromo-1-methyl-indazole-3-carboxylic acid (250 mg, 86% yield) as a white solid. LC-MS: m/z $[M+H]^+$ 255.1.

Acid Intermediate 7

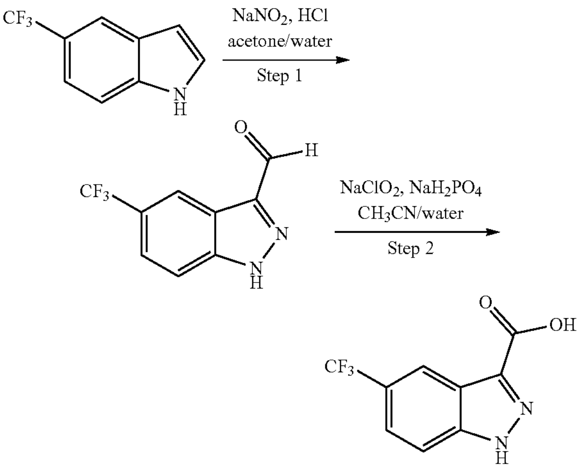

Step 1

To a stirred solution of 5-(trifluoromethyl)-1H-indole (302 mg, 1.60 mmol) in acetone (10.0 mL) were sequentially added aq. $NaNO_2$ (1.5 mL, 8.0 M, 12 mmol) and aq. HCl (1.0 mL, 2.0 M, 2.0 mmol) at 0° C. The resulting mixture was warmed to 25° C. and stirred at that temperature for 2 h. The mixture was diluted with water (20 mL) and extracted with EtOAc (30 mL×3). The combined organic layers were washed with brine, dried over anhydrous $Na_2SO_4$, and filtered. The filtrate was concentrated under reduced pressure to afford 5-(trifluoromethyl)-2H-indazole-3-carbaldehyde (328 mg, 96% yield) as a dark oil which was used directly in the next step without further purification. LC-MS: m/z $[M+H]^+$ 215.0.

Step 2

To a stirred solution of 6-(trifluoromethyl)-1H-indazole-3-carbaldehyde (50.0 mg, 0.233 mmol) in $CH_3CN$ (1.0 mL) were sequentially added aq. $NaH_2PO_4$ (500 μL, 0.7 M, 0.350 mmol) and aq. $NaClO_2$ (500 μL, 1.0 M, 0.500 mmol) at 0° C. The resulting mixture was warmed to 25° C. and stirred at that temperature for 2 h. The reaction mixture was diluted with water (10 mL), treated with aq. NaOH (1.0 mL, 2.0 M) and then extracted with EtOAc (20 mL). The aqueous phase was separated and acidified with aq. HCl (1.0 M) to pH=3 and then extracted with $CH_2Cl_2$ (15 mL×3). The combined organic layers were washed with brine, dried over anhydrous $Na_2SO_4$, and filtered. The filtrate was concentrated under reduced pressure to afford 6-(trifluoromethyl)-1H-indazole-3-carboxylic acid (46.0 mg, 85% yield) as a white solid which was used directly in the next step without further purification. LC-MS: m/z $[M+H]^+$ 231.1.

Acid Intermediate 8

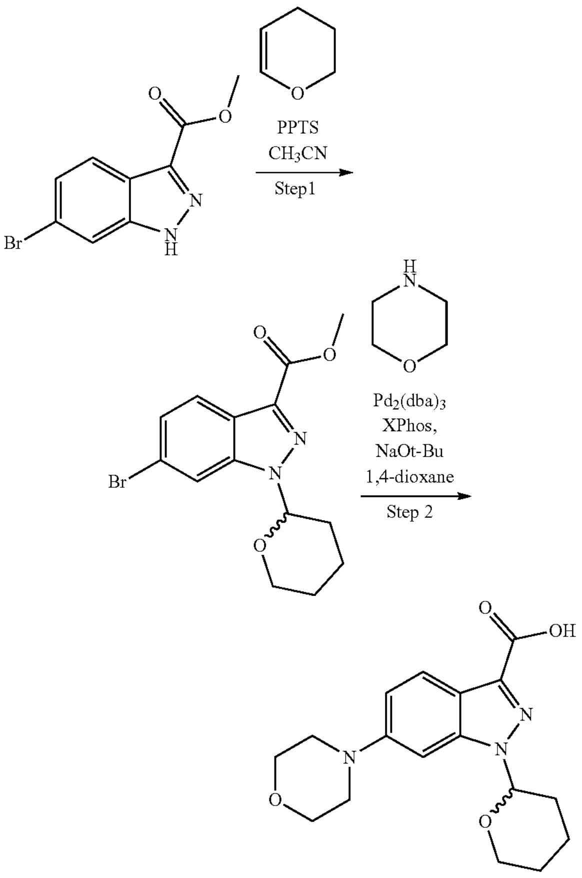

Step 1

To a stirred solution of methyl 6-bromo-1H-indazole-3-carboxylate (500 mg, 2.00 mmol) in $CH_3CN$ (10.0 mL) were sequentially added 3,4-dihydro-2H-pyran (329 mg, 357 μL, 3.90 mmol) and PPTS (33.8 mg, 0.196 mmol) at 25° C. The reaction mixture was warmed to 95° C. and stirred at that temperature for 1 h. The reaction mixture was cooled to 25° C., quenched with water (20 mL) and then extracted with EtOAc (50 mL×2). The combined organic phases were washed with brine, dried over anhydrous $Na_2SO_4$. and filtered. The filtrate was concentrated under reduced pressure. The residue was purified by silica gel chromatography eluting with EtOAc/petroleum ether (with EtOAc from 0 to 30%) in 20 min to give methyl 6-bromo-1-tetrahydropyran-2-yl-indazole-3-carboxylate (600 mg, 90% yield) as a white solid. LC-MS: m/z $[M+Na]^+$ 361.0.

Step 2

To a stirred solution of methyl 6-bromo-1-tetrahydropyran-2-yl-indazole-3-carboxylate (120 mg, 0.354 mmol) in 1,4-dioxane (4.0 mL) were sequentially added morpholine (46.2 mg, 46.2 μL, 0.531 mmol), NaOt-Bu (102 mg, 1.10 mmol), Xphos (33.7 mg, 0.0708 mmol) and $Pd_2(dba)_3$ (32.4 mg, 0.0354 mmol) at 25° C. The reaction mixture was warmed to 110° C. and stirred at that temperature for 3 h. The reaction mixture was cooled to 25° C., treated with water (20 mL) and then washed with EtOAc (10 mL×2). The aqueous layer was separated and acidified with aq. HCl (1.0 M) to pH=3 and then extracted with EtOAc (30 mL×2).

The combined organic phases were washed with brine, dried over anhydrous $Na_2SO_4$, and filtered. The filtrate was concentrated under reduced pressure to give 6-morpholino-1-tetrahydropyran-2-yl-indazole-3-carboxylic acid (60.0 mg, 51% yield) as a yellow solid which was used directly in the next step without further purification. LC-MS: m/z [M+H]+ 332.1.

Acid Intermediate 9

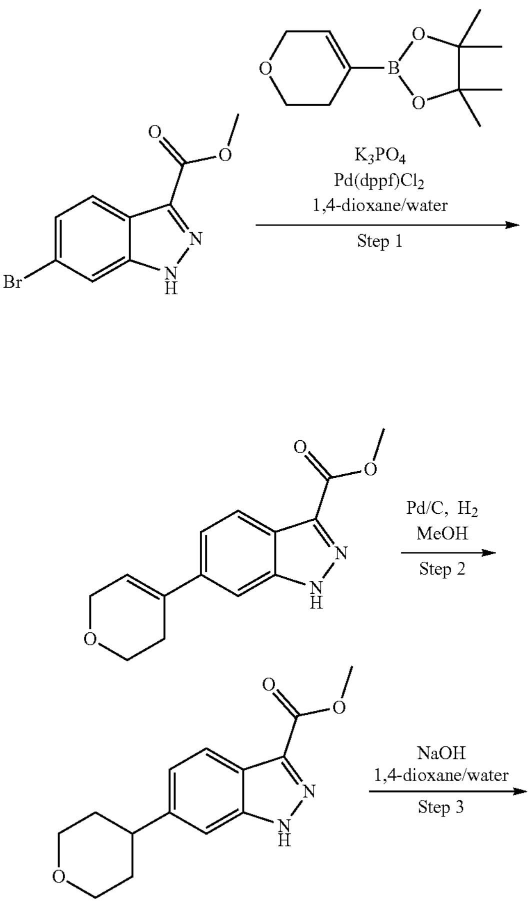

-continued

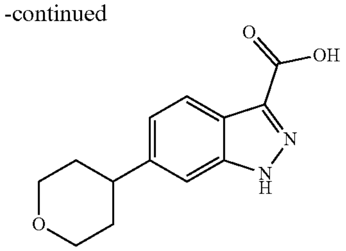

Step 1

To a stirred solution of methyl 6-bromo-2H-indazole-3-carboxylate (300 mg, 1.20 mmol) in 1,4-dioxane (8.0 mL) and water (2.0 mL) were sequentially added 2-(3,6-dihydro-2H-pyran-4-yl)-4,4,5,5-tetramethyl-1,3,2-dioxaborolane (344 mg, 1.60 mmol), Pd(dppf)$Cl_2$ (125 mg, 0.170 mmol) and $K_3PO_4$ (1.60 g, 7.41 mmol) at 25° C. The reaction mixture was warmed to 100° C. and stirred at that temperature for 2 h. The reaction mixture was cooled to 25° C., poured into water (20 mL) and extracted with EtOAc (30 mL×3). The combined organic layers were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 20%) in 25 min to afford methyl 6-(3,6-dihydro-2H-pyran-4-yl)-1H-indazole-3-carboxylate (124 mg, 41% yield) as a white solid. LC-MS: m/z $[M+H]^+$ 259.1.

Step 2

To a stirred solution of methyl 6-(3,6-dihydro-2H-pyran-4-yl)-1H-indazole-3-carboxylate (44.0 mg, 0.170 mmol) in MeOH (25.0 mL) was added Pd/C (9.0 mg, 10% wt., 0.0085 mmol) at 25° C. The reaction mixture was stirred under hydrogen atmosphere (balloon) at that temperature for 12 h. The mixture was filtered through a pad of Celite. The filtrate was concentrated under reduced pressure to afford methyl 6-tetrahydropyran-4-yl-1H-indazole-3-carboxylate (48.0 mg) as a white solid which was used directly in the next step without further purification. LC-MS: m/z $[M+H]^+$ 261.1.

Step 3

To a stirred solution of methyl 6-tetrahydropyran-4-yl-1H-indazole-3-carboxylate (48.0 mg, 0.184 mmol) in 1,4-dioxane (2.0 mL) was added aq. NaOH (2.0 mL, 0.9 M, 1.8 mmol) at 25° C. The reaction mixture was warmed to 100° C. and stirred at that temperature for 4 h. The reaction mixture was cooled to 25° C., diluted with water (15 mL) and extracted with EtOAc (10 mL). The aqueous phase was separated and acidified with aq. HCl (1.0 M) to pH=3 and extracted with EtOAc (15 mL×3). The combined organic layers were washed with brine, dried over anhydrous $Na_2SO_4$, and filtered. The filtrate was concentrated under reduced pressure to afford 6-tetrahydropyran-4-yl-1H-indazole-3-carboxylic acid (31.0 mg, 68% yield) as a white solid which was used directly in the next step without further purification. LC-MS: m/z $[M+H]^+$ 247.1.

Additional intermediates of the present disclosure were prepared using the similar procedure disclosed in acid intermediate 9 from the corresponding materials and their corresponding characterization data are listed in the table below.

| ID | Structure | LC-MS: m/z $[M+H]^+$ |
|---|---|---|
| Acid intermediate 10 | 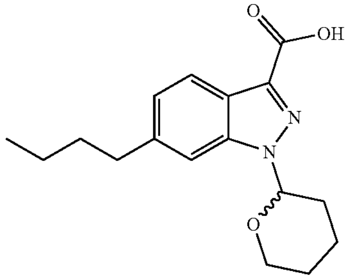 [SMILES: CCCCc1ccc2c(C(=O)O)nn(C3CCCCO3)c2c1] | 303.1 |

Acid Intermediate 11

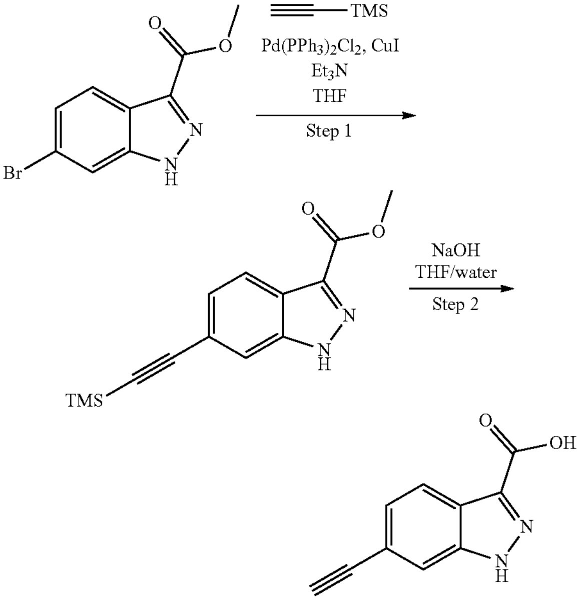

Step 1

To a stirred solution of methyl 6-bromo-1H-indazole-3-carboxylate (150 mg, 0.588 mmol) in THF (10.0 mL) were sequentially added $Et_3N$ (146 mg, 200 μL, 1.44 mmol), CuI (11.2 mg, 0.0588 mmol), $Pd(PPh_3)_2Cl_2$ (41.3 mg, 0.0588 mmol) and ethynyl(trimethyl)silane (86.6 mg, 124 μL, 0.882 mmol) at 25° C. The reaction mixture was warmed to 90° C. and stirred at that temperature for 16 h. The reaction mixture was cooled to 25° C. and filtered through a pad of Celite. The filtrate was quenched with water (100 mL) and extracted with EtOAc (30 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum (with EtOAc from 1% to 56%) in 20 min to give methyl 6-(2-trimethylsilylethynyl)-1H-indazole-3-carboxylate (150 mg, 94% yield) as a brown solid. LC-MS: m/z $[M+H]^+$ 273.1.

Step 2

To a stirred solution of methyl 6-(2-trimethylsilylethynyl)-1H-indazole-3-carboxylate (50.0 mg, 0.184 mmol) in THF (2.0 mL) was added aq. NaOH (0.5 mL, 1.0 M, 0.5 mmol) at 25° C. The reaction mixture was warmed to 50° C.

and stirred at that temperature for 16 h. The reaction mixture was cooled to 25° C., diluted with EtOAc (10 mL) and then extracted with water (10 mL×2). The combined water phases were acidified with aq. HCl (1.0 M) to pH=3 and extracted with EtOAc (20 mL×2). The combined organic phases were washed with brine, dried over anhydrous $Na_2SO_4$, and filtered. The filtrate was concentrated under reduced pressure to give 6-ethynyl-1H-indazole-3-carboxylic acid (34.0 mg, 99% yield) as a white solid which was used directly in the next step without further purification. LC-MS: m/z $[M+H]^+$ 187.1.

Acid Intermediate 12

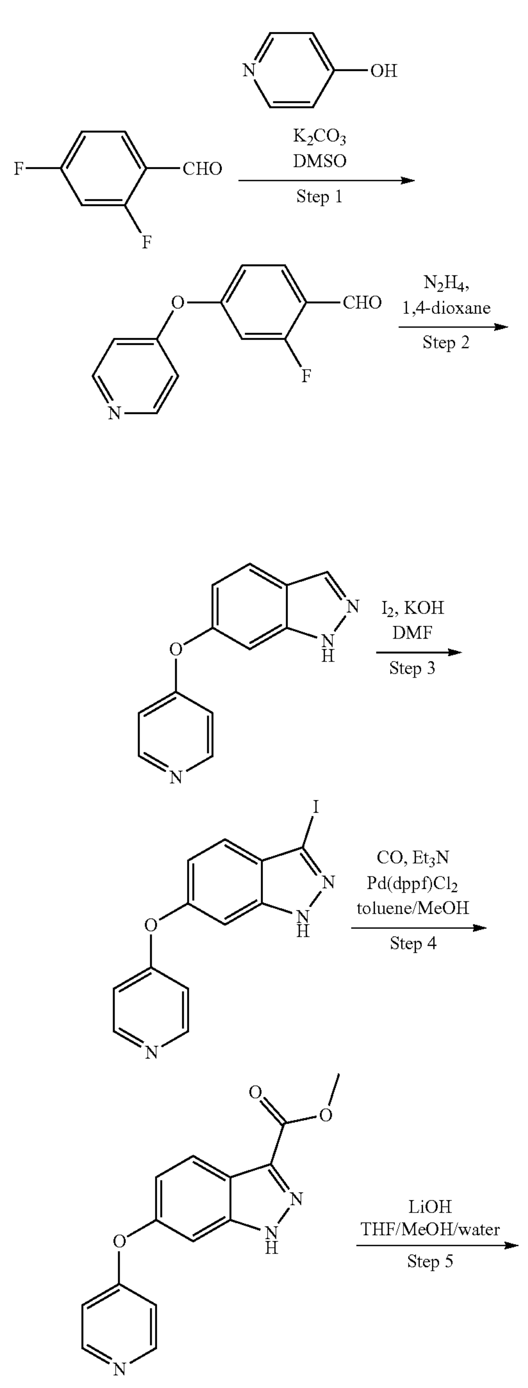

-continued

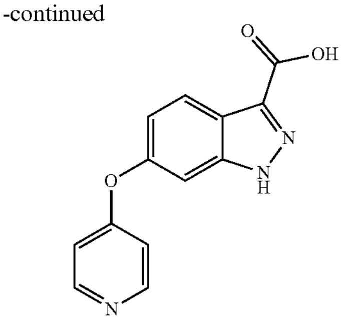

Step 1

To a stirred solution of 2,4-difluorobenzaldehyde (2.00 g, 14.1 mmol) and pyridin-4-ol (1.47 g, 15.4 mmol) in DMSO (10.0 mL) was added $K_2CO_3$ (5.84 g, 42.2 mmol) at 25° C. The reaction mixture was stirred at that temperature for 16 h. The mixture was quenched with water (50 mL) and then extracted with EtOAc (50 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum (with EtOAc from 1% to 75%) in 25 min to give 2-fluoro-4-(4-pyridyloxy)benzaldehyde (1.00 g, 33% yield) as a brown solid.

LC-MS: m/z $[M+H]^+$ 218.1.

Step 2

To a stirred solution of 2-fluoro-4-(4-pyridyloxy)benzaldehyde (1.00 g, 4.60 mmol) in 1,4-dioxane (15.0 mL) was added hydrazine hydrate (690 mg, 670 μL, 78% wt., 10.8 mmol) at 25° C. The reaction mixture was warmed to 115° C. and stirred at that temperature for 48 h. The reaction mixture was cooled to 25° C., quenched with water (100 mL) and then extracted with EtOAc (50 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 1% to 95%) in 20 min to give 6-(4-pyridyloxy)-1H-indazole (260 mg, 27% yield) as a brown solid. LC-MS: m/z $[M+H]^+$ 212.0.

Step 3

To a stirred solution of 6-(4-pyridyloxy)-1H-indazole (250 mg, 1.18 mmol) in DMF (5.0 mL) were sequentially added $I_2$ (449 mg, 1.77 mmol) and KOH (265 mg, 4.72 mmol) at 25° C. The reaction mixture was stirred at that temperature for 2 h. The mixture was quenched with saturated aq. $Na_2S_2O_3$ (20 mL) and extracted with EtOAc (40 mL×2). The combined organic phases were washed with brine, dried over anhydrous $Na_2SO_4$, and filtered. The filtrate was concentrated under reduced pressure. The residue was purified by silica gel chromatography eluting with $MeOH/CH_2Cl_2$ (with MeOH from 1% to 10%) in 20 min to give 3-iodo-6-(4-pyridyloxy)-1H-indazole (180 mg, 45% yield) as a white solid.

LC-MS: m/z $[M+H]^+$ 338.9.

Step 4

To a stirred solution of 3-iodo-6-(4-pyridyloxy)-1H-indazole (180 mg, 0.533 mmol) in toluene (2.0 mL) and MeOH (2.0 mL) was added $Pd(dppf)Cl_2$ (39.1 mg, 0.053 mmol), dppf (29.6 mg, 0.053 mmol) and $Et_3N$ (162 mg, 222 μL, 1.60 mmol) at 25° C. The reaction mixture was warmed to 75° C. and stirred under CO atmosphere (balloon) at that temperature for 14 h. The reaction mixture was cooled to 25° C., quenched with water (100 mL) and then extracted with EtOAc (30 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum (with EtOAc from 1% to 86%) in 20 min to give methyl 6-(4-pyridyloxy)-1H-indazole-3-carboxylate (120 mg, 83% yield) as an off-white solid.

LC-MS: m/z $[M+H]^+$ 270.1.

Step 5

To a stirred solution of methyl 6-(4-pyridyloxy)-1H-indazole-3-carboxylate (120 mg, 0.445 mmol) in THF (2.0 mL), MeOH (2.0 mL) and water (1.0 mL) was added $LiOH \cdot H_2O$ (56.1 mg, 1.34 mmol) at 25° C. The reaction mixture was stirred at that temperature for 16 h. The mixture was acidified with aq. HCl (1.0 M) to pH=5, and then extracted with EtOAc (30 mL×2). The combined organic phases were washed with brine, dried over anhydrous $Na_2SO_4$, and filtered. The filtrate was concentrated under reduced pressure to give 6-(4-pyridyloxy)-1H-indazole-3-carboxylic acid (100 mg, 88% yield) as a brown solid which was used directly in the next step without further purification. LC-MS: m/z $[M+H]^+$ 256.0.

Acid Intermediate 13

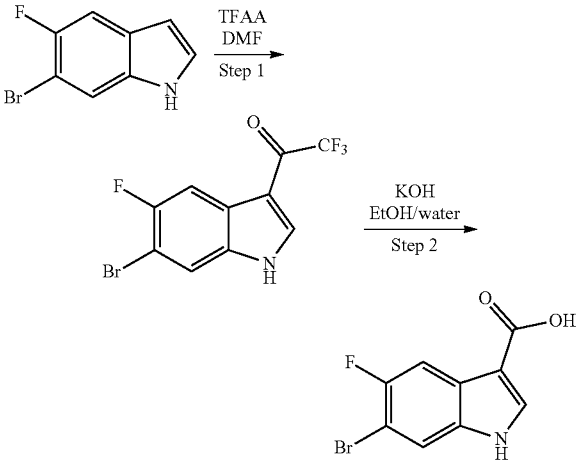

Step 1

To a stirred solution of 6-bromo-5-fluoro-1H-indole (2.00 g, 9.34 mmol) in DMF (15.0 mL) was added TFAA (5.89 g, 3.95 mL, 28.0 mmol) at 0° C. The reaction mixture was warmed to 25° C. and stirred that temperature for 12 h. The reaction mixture was poured into ice-water (200 mL) and the precipitates were collected by filtration to afford 1-(6-bromo-5-fluoro-1H-indol-3-yl)-2,2,2-trifluoro-ethanone (2.89 g, 99% yield) as a yellow solid which was used directly in the next step without further purification. LC-MS: m/z $[M+H]^+$ 310.0.

Step 2

To a stirred solution of 1-(6-bromo-5-fluoro-1H-indol-3-yl)-2,2,2-trifluoro-ethanone (2.60 g, 8.39 mmol) in EtOH (20.0 mL) and water (20.0 mL) was added KOH (2.35 g, 41.9 mmol) at 25° C. The reaction mixture was warmed to 100° C. and stirred that temperature for 16 h. The mixture was cooled 25° C., diluted with water (50 mL) and extracted with EtOAc (50 mL×2). The aqueous phase was separated, acidified with aq. HCl (1.0 M) to pH=3 and extracted with EtOAc (100 mL×3). The combined organic layers were washed with brine, dried over anhydrous $Na_2SO_4$, and filtered. The filtrate was concentrated under reduced pressure to afford 6-bromo-5-fluoro-1H-indole-3-carboxylic acid (1.60 g, 74% yield) as a gray solid which was used directly in the next step without further purification.

LC-MS: m/z $[M+H]^+$ 258.1.

Acid Intermediate 14

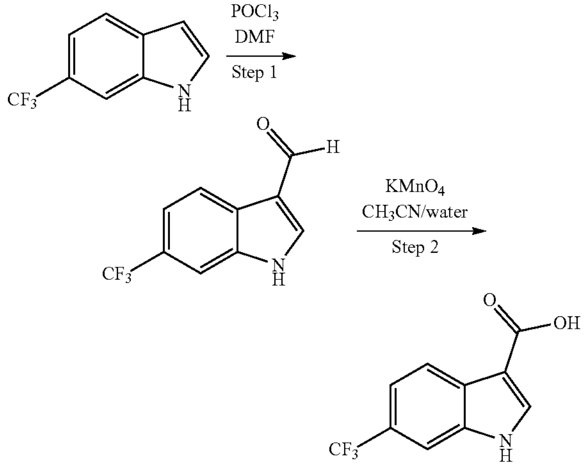

Step 1

To a stirred solution of 6-(trifluoromethyl)-1H-indole (500 mg, 2.70 mmol) in DMF (3.0 mL) was added $POCl_3$ (828 mg, 503 μL, 5.40 mmol) at 0° C. The reaction mixture was stirred at that temperature for 1 h before it was quenched with water (10 mL) and then extracted with EtOAc (10 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 50%) in 20 min to give 6-(trifluoromethyl)-1H-indole-3-carbaldehyde (141 mg, 24% yield) as a white solid. LC-MS: m/z $[M+H]^+$ 214.0.

Step 2

To a stirred solution of 6-(trifluoromethyl)-1H-indole-3-carbaldehyde (141 mg, 0.662 mmol) in $CH_3CN$ (5.0 mL) was added aq. $KMnO_4$ (1.2 mL, 1.0 M, 1.2 mmol) at 25° C. The mixture was stirred at that temperature for 16 h before it was diluted with water (10 mL). The mixture was filtered through a pad of Celite and extracted with EtOAc (20 mL×3). The combined organic phases were washed with brine, dried over anhydrous $Na_2SO_4$, filtered and concentrated under vacuum. The residue was purified by Pre-TLC ($MeOH/CH_2Cl_2$=1:10) to give 6-(trifluoromethyl)-1H-indole-3-carboxylic acid (70.0 mg, 46% yield) as a white solid.

LC-MS: m/z $[M+H]^+$ 230.0.

Acid Intermediate 15

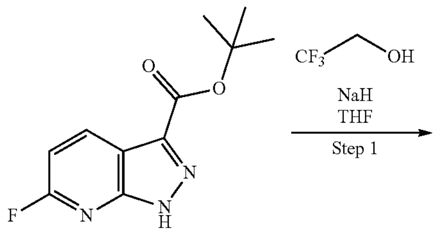

-continued

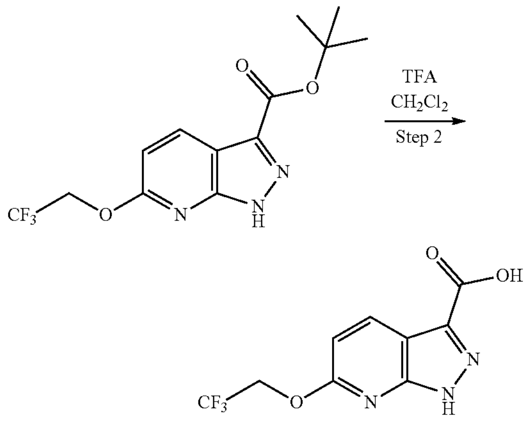

Step 1

To a stirred solution of tert-butyl 6-fluoro-2H-pyrazolo [3,4-b]pyridine-3-carboxylate (550 mg, 2.32 mmol) in THF (10.0 mL) were sequentially added sodium hydride (266 mg, 60% wt., 6.96 mmol) and 2,2,2-trifluoroethanol (695 mg, 500 μL, 6.95 mmol) at 0° C. The reaction mixture was stirred at that temperature for 10 min before it was warmed to 70° C. and stirred at that temperature for 8 h. The reaction mixture was cooled to 25° C., quenched with saturated aq. $NH_4Cl$ (50 mL) and extracted with EtOAc (50 mL×3). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 50%) in 25 min to give tert-butyl 6-(2,2,2-trifluoroethoxy)-2H-pyrazolo[3,4-b]pyridine-3-carboxylate (300 mg, 41% yield) as a yellow oil. LC-MS: m/z $[M+H]^+$ 318.1.

Step 2

To a stirred solution of tert-butyl 6-(2,2,2-trifluoroethoxy)-2H-pyrazolo[3,4-b]pyridine-3-carboxylate (180 mg, 0.567 mmol) in $CH_2Cl_2$ (5.0 mL) was added TFA (323 mg, 210 μL, 2.84 mmol) at 25° C. The reaction mixture was stirred at that temperature for 16 h before it was concentrated under reduced pressure to give 6-(2,2,2-trifluoroethoxy)-2H-pyrazolo[3,4-b]pyridine-3-carboxylic acid (130 mg, 88% yield) as a brown solid which was used directly in the next step without further purification. LC-MS: m/z $[M+H]^+$ 262.1.

Acid Intermediate 16

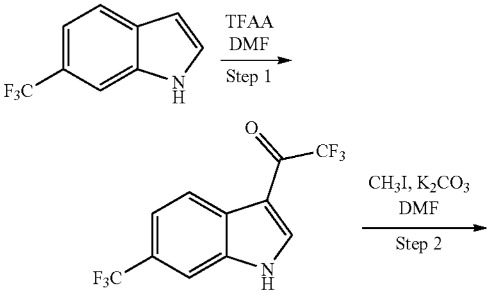

-continued

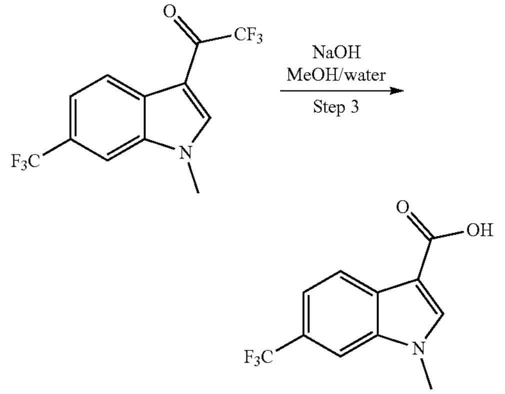

Step 1

To a stirred solution of 6-(trifluoromethyl)-1H-indole (3.00 g, 16.2 mmol) in DMF (20.0 mL) was added TFAA (3.91 g, 2.33 mL, 18.6 mmol) at 0° C. The resulting mixture was stirred at that temperature for 1 h before it was poured into ice water (100 mL). The precipitates were collected by filtration and dried under vacuum to afford 2,2,2-trifluoro-1-[6-(trifluoromethyl)-1H-indol-3-yl]ethanone (4.40 g, 96% yield) as a yellow solid which was used directly in the next step without further purification. LC-MS: m/z $[M+H]^+$ 282.0.

Step 2

To a stirred solution of 2,2,2-trifluoro-1-[6-(trifluoromethyl)-1H-indol-3-yl]ethanone (4.00 g, 14.2 mmol) in DMF (20.0 mL) were sequentially added $K_2CO_3$ (5.90 g, 42.6 mmol) and $CH_3I$ (4.10 g, 1.80 mL, 28.9 mmol) at 25° C. The reaction mixture was warmed to 40° C. and stirred at that temperature for 3 h. The reaction mixture was cooled to 25° C., quenched with water (30 mL) and then extracted with EtOAc (100 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 30%) in 20 min to give 2,2,2-trifluoro-1-[1-methyl-6-(trifluoromethyl)indol-3-yl]ethanone (3.40 g, 80% yield) as an off-white solid. LC-MS: m/z $[M+H]^+$ 296.0.

Step 3

To a stirred solution of 2,2,2-trifluoro-1-[1-methyl-6-(trifluoromethyl)indol-3-yl]ethanone (3.40 g, 11.5 mmol) in MeOH (60.0 mL) was added aq. NaOH (6.0 mL, 3.0 M, 18 mmol) at 25° C. The reaction mixture was warmed to 105° C. and stirred at that temperature for 10 h. The reaction mixture was cooled to 25° C. and extracted with EtOAc (100 mL). The aqueous phase was separated and acidified with aq. HCl (1.0 M) to pH=4 and then extracted with EtOAc (200 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 58%) in 40 min to afford 1-methyl-6-(trifluoromethyl)indole-3-carboxylic acid (2.50 g, 89% yield) as a white solid. LC-MS: m/z [M+Na]+266.0.

Additional intermediates of the present disclosure were prepared using the similar procedure disclosed in acid intermediate 16 from the corresponding materials and their corresponding characterization data are listed in the table below.

| ID | Structure | LC-MS: m/z [M + H]+ |
|---|---|---|
| Acid intermediate 17 | 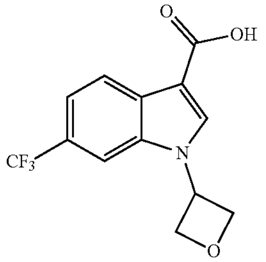 [SMILES: O=C(O)c1cn(C2COC2)c2cc(C(F)(F)F)ccc12] | 286.1 |
| Acid intermediate 18 | 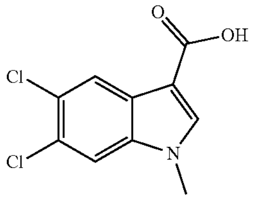 | 244.0 |
| Acid intermediate 19 | 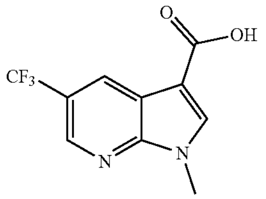 [SMILES: Cn1cc(C(=O)O)c2cc(C(F)(F)F)cnc21] | 245.1 |

Acid Intermediate 20

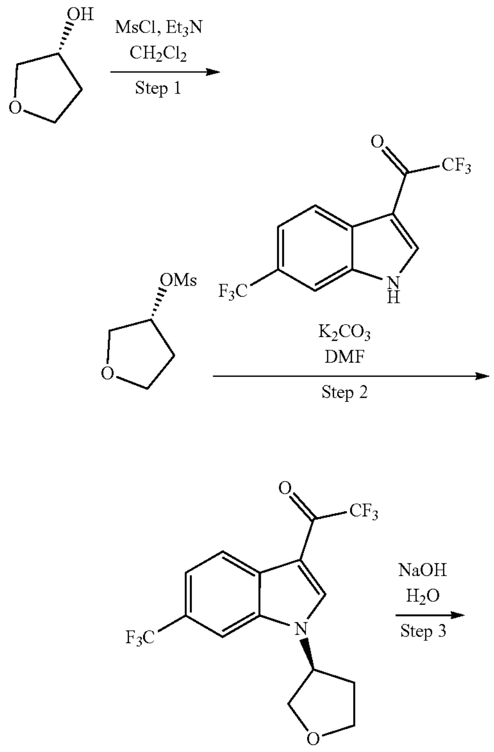

-continued

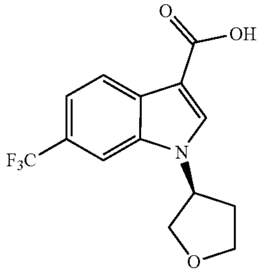

Step 1

To a stirred solution of (3R)-tetrahydrofuran-3-ol (88.0 mg, 0.998 mmol) in $CH_2Cl_2$ (5.0 mL) were sequentially added $Et_3N$ (303 mg, 416 μL, 3.00 mmol) and MsCl (171 mg, 1.50 mmol) at 0° C. The reaction mixture was warmed to 25° C. and stirred at that temperature for 16 h. The reaction mixture was quenched with water (10 mL) and then extracted with $CH_2Cl_2$ (20 mL×2). The combined organic phases were washed with brine, dried over anhydrous $Na_2SO_4$, and filtered. The filtrate was concentrated under reduced pressure. The residue was dried in vacuo to afford [(3R)-tetrahydrofuran-3-yl] methanesulfonate (140 mg, 84% yield) as a yellow oil which was used directly in the next step without further purification.

Step 2

To a Schlenk pressure tube were sequentially added 2,2,2-trifluoro-1-[6-(trifluoromethyl)-1H-indol-3-yl]ethanone (150 mg, 0.533 mmol), [(3R)-tetrahydrofuran-3-yl] methanesulfonate (133 mg, 0.800 mmol), $K_2CO_3$ (221 mg, 1.60 mmol) and DMF (4.0 mL) at 25° C. The mixture was sealed and warmed to 100° C. and stirred at that temperature for 16 h. The mixture was cooled to 25° C. and poured into water (50 mL). The precipitates were collected by filtration to give 2,2,2-trifluoro-1-[1-[(3S)-tetrahydrofuran-3-yl]-6-(trifluoromethyl)indol-3-yl]ethanone (120 mg, 64% yield) as a light brown solid which was used directly in the next step without further purification. LC-MS: m/z $[M+H]^+$ 351.1.

Step 3

To a stirred solution of 2,2,2-trifluoro-1-[1-[(3S)-tetrahydrofuran-3-yl]-6-(trifluoromethyl)indol-3-yl]ethanone (120 mg, 0.341 mmol) in MeOH (6.0 mL) was added aq. NaOH (5.2 mL, 1.0 M, 5.2 mmol) at 25° C. The reaction mixture was warmed to 100° C. and stirred at that temperature for 2 h. The reaction mixture was cooled to 25° C. and extracted with EtOAc (10 mL). The aqueous phase was separated and acidified with aq. HCl (1.0 M) to pH=3. The precipitates were collected by filtration to afford 1-[(3S)-tetrahydrofuran-3-yl]-6-(trifluoromethyl)indole-3-carboxylic acid (85.0 mg, 83% yield) as a light brown solid which was used directly in the next step without further purification. LC-MS: m/z $[M+H]^+$ 300.1.

Additional intermediates of the present disclosure were prepared using the similar procedure disclosed in acid intermediate 20 from the corresponding materials and their corresponding characterization data are listed in the table below.

| ID | Structure | LC-MS: m/z [M + H]$^+$ |
|---|---|---|
| Acid intermediate 21 | 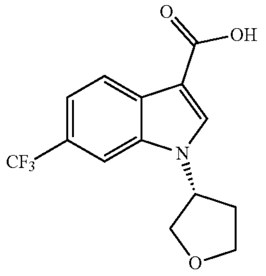 [SMILES: O=C(O)c1cn([C@@H]2CCOC2)c2cc(C(F)(F)F)ccc12] | 300.0 |

Acid Intermediate 22

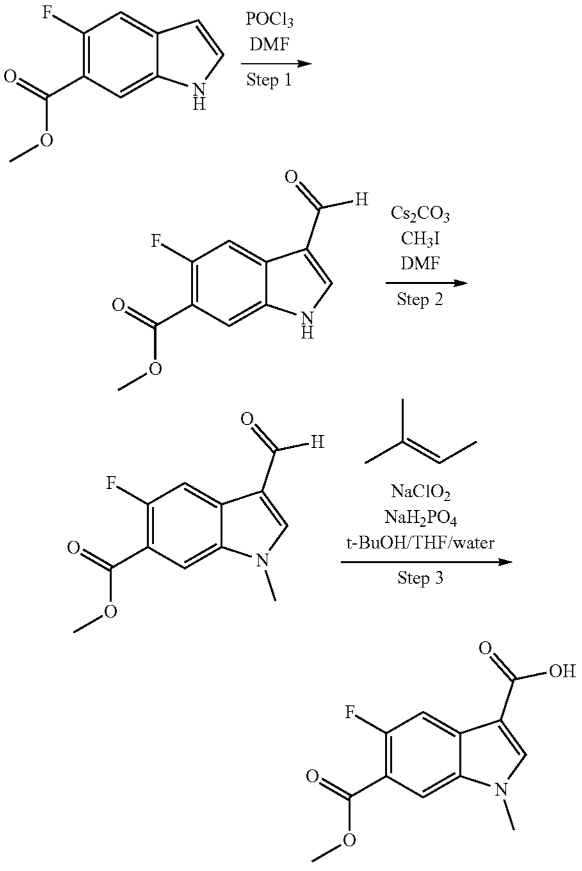

Step 1

To a stirred solution of methyl 5-fluoro-1H-indole-6-carboxylate (800 mg, 4.14 mmol) in DMF (5.0 mL) was added $POCl_3$ (2.22 g, 1.35 mL, 14.5 mmol) at 0° C. The reaction mixture was stirred at that temperature for 1 h before it was poured into saturated aq. $NaHCO_3$ (30 mL) and stirred at 25° C. for 5 h. The precipitates were collected by filtration and dried in vacuo to give methyl 5-fluoro-3-formyl-1H-indole-6-carboxylate (830 mg, 91% yield) as a white solid which was used directly in the next step without further purification.

LC-MS: m/z [M+H]$^+$ 222.1.

Step 2

To a Schlenk pressure tube were sequentially added 5-fluoro-3-formyl-1H-indole-6-carboxylate (250 mg, 1.13 mmol), $CH_3I$ (240 mg, 105 μL, 1.70 mmol), $Cs_2CO_3$ (1.10 g, 3.39 mmol) and DMF (3.0 mL) at 25° C. The mixture was sealed and warmed to 85° C. and stirred at that temperature for 16 h. The mixture was cooled to 25° C. and poured into ice water (50 mL). The precipitates were collected by filtration and dried in vacuo to afford 6-bromo-5-fluoro-1-methyl-indole-3-carbaldehyde (530 mg, 99% yield) as a white solid which was used directly in the next step without further purification.

LC-MS: m/z [M+H]$^+$ 236.1.

Step 3

To a stirred solution of methyl 5-fluoro-3-formyl-1-methyl-indole-6-carboxylate (250 mg, 1.06 mmol) in THF (10.0 mL) and t-BuOH (4.0 mL) were sequentially added 2-methylbut-2-ene (745 mg, 892 μL, 10.6 mmol) and a solution of $NaClO_2$ (481 mg, 5.31 mmol) and $NaH_2PO_4$ (382 mg, 3.19 mmol) in water (4.0 mL) at 0° C. The resulting mixture was warmed to 25° C. and stirred at that temperature for 16 h. The mixture was diluted with water (50 mL) and then extracted with EtOAc (50 mL×2). The combined organic layers were washed with brine (20 mL), dried over anhydrous $Na_2SO_4$. and filtered. The filtrate was concentrated under reduced pressure. The residue was purified by silica gel chromatography eluting with $MeOH/CH_2Cl_2$ (with MeOH from 0 to 10%) in 20 min to give 5-fluoro-6-methoxycarbonyl-1-methyl-indole-3-carboxylic acid (240 mg, 90% yield) as a yellow solid.

LC-MS: m/z [M+H]$^+$ 252.1.

Additional intermediates of the present disclosure were prepared using the similar procedure disclosed in acid intermediate 22 from the corresponding materials and their corresponding characterization data are listed in the table below.

| ID | Structure | LC-MS: m/z [M + H]$^+$ |
|---|---|---|
| Acid intermediate 23 | 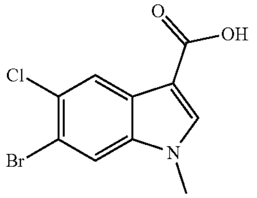 | 287.9 |
| Acid intermediate 24 | 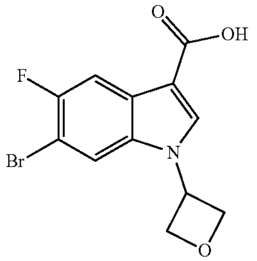 [SMILES: O=C(O)c1cn(C2COC2)c2cc(Br)c(F)cc12] | 314.1 |
| Acid intermediate 25 | 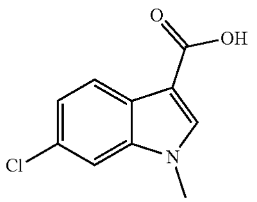 | 210.0 |

Acid Intermediate 26

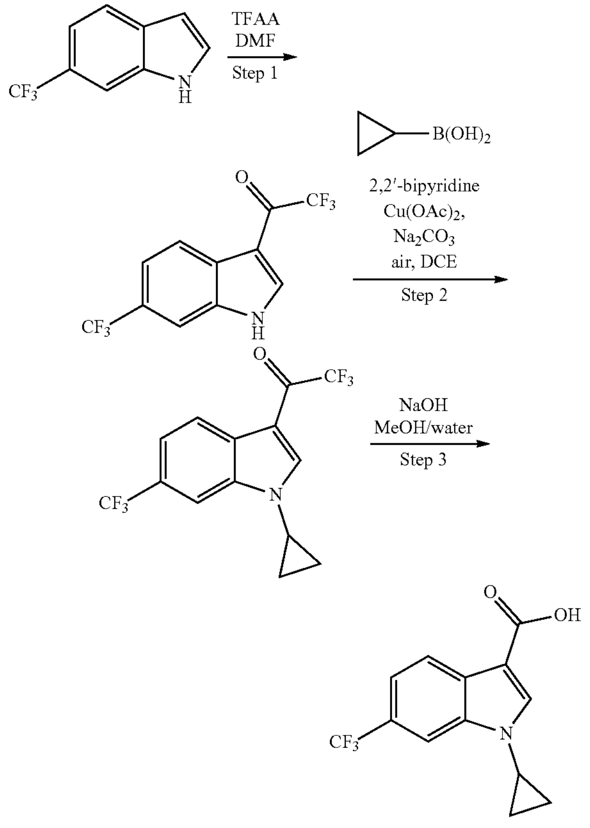

Step 1

To a stirred solution of 6-(trifluoromethyl)-1H-indole (2.00 g, 10.8 mmol) in DMF (15.0 mL) was added TFAA (2.61 g, 1.80 mL, 12.4 mmol) at 0° C. The reaction mixture was warmed to 25° C. and stirred at that temperature for 12 h. The reaction mixture was poured into ice water (200 mL). The precipitates were collected by filtration and dried under vacuum to afford 2,2,2-trifluoro-1-[6-(trifluoromethyl)-1H-indol-3-yl]ethanone (2.53 g, 83% yield) as a pale yellow solid which was used in the next step without further purification.

LC-MS: m/z $[M+H]^+$ 282.0.

Step 2

To a stirred solution of 2,2,2-trifluoro-1-[6-(trifluoromethyl)-1H-indol-3-yl]ethanone (1.00 g, 3.56 mmol) in DCE (25.0 mL) were sequentially added cyclopropylboronic acid (916 mg, 10.7 mmol), 2,2'-bipyridine (611 mg, 3.91 mmol), $Cu(OAc)_2$ (711 mg, 3.91 mmol) and $Na_2CO_3$ (1.13 g, 10.7 mmol) at 25° C. The resulting mixture was warmed to 95° C. and stirred under air (balloon) at that temperature for 6 h. The mixture was cooled to 25° C., quenched with water (80 mL), and extracted with $CH_2Cl_2$ (50 mL×2). The combined organic phases were washed with brine (80 mL), dried over anhydrous $Na_2SO_4$, and filtered. The filtrate was concentrated under reduced pressure. The residue was purified by silica gel chromatography eluting with EtOAc/petroleum ether (with EtOAc from 0 to 50%) in 25 min to give 1-[1-cyclopropyl-6-(trifluoromethyl)indol-3-yl]-2,2,2-trifluoro-ethanone (504 mg, 44% yield) as a pale yellow solid. LC-MS: m/z $[M+H]^+$ 322.0.

Step 3

To a stirred solution of 1-[1-cyclopropyl-6-(trifluoromethyl)indol-3-yl]-2,2,2-trifluoro-ethanone (494 mg, 1.54 mmol) in MeOH (5.0 mL) and water (5.0 mL) was added NaOH (308 mg, 7.69 mmol) at 25° C. The resulting mixture was warmed to 100° C. and stirred at that temperature for 4 h. The mixture was cooled and concentrated under reduced pressure. The residue was diluted with water (30 mL) and extracted with diethyl ether (40 mL×2). The aqueous layer was separated, acidified with aq. HCl (1.0 M) to pH=6, and then extracted with EtOAc (80 mL×3). The combined organic layers were washed with brine (50 mL), dried over anhydrous $Na_2SO_4$, and filtered. The filtrate was concentrated under reduced pressure to give 1-cyclopropyl-6-(trifluoromethyl)indole-3-carboxylic acid (349 mg, 84% yield) as a white solid which was used in the next step without further purification.

LC-MS: m/z $[M+H]^+$ 270.0.

Acid Intermediates 27 and 28

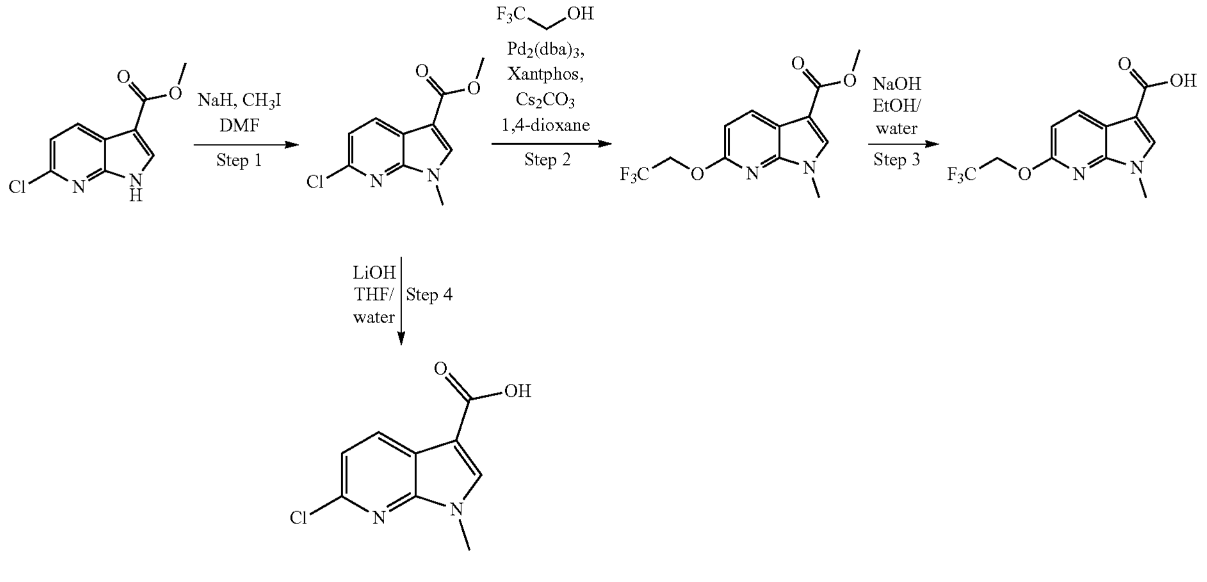

Step 1

To a stirred solution of methyl 6-chloro-1H-pyrrolo[2,3-b]pyridine-3-carboxylate (150 mg, 0.712 mmol) in DMF (6.0 mL) was added NaH (113 mg, 60% wt., 2.85 mmol) at 0° C. The mixture was stirred at that temperature for 10 min before $CH_3I$ (303 mg, 133 μL, 2.14 mmol) was added. The mixture was stirred at 0° C. for 1 h before it was quenched with water (20 mL) and extracted with EtOAc (50 mL×2). The combined organic layers were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0% to 50%) in 25 min to afford methyl 6-chloro-1-methyl-pyrrolo[2,3-b]pyridine-3-carboxylate (157 mg, 98% yield) as a white solid. LC-MS: m/z $[M+H]^+$ 225.0.

Step 2

To a stirred solution of methyl 6-chloro-1-methyl-pyrrolo[2,3-b]pyridine-3-carboxylate (147 mg, 0.654 mmol) in 1,4-dioxane (3.0 mL) were sequentially added 2,2,2-trifluoroethanol (196 mg, 141 μL, 1.96 mmol), $Pd_2(dba)_3$ (119 mg, 0.130 mmol), Xantphos (151 mg, 0.261 mmol) and $Cs_2CO_3$ (852 mg, 2.62 mmol) at 25° C. The resulting mixture was warmed to 110° C. and stirred at that temperature for 6 h. The mixture was cooled to 25° C. and concentrated under reduced pressure. The residue was purified by silica gel chromatography eluting with EtOAc/petroleum ether (with EtOAc from 0 to 35%) in 25 min to afford methyl 1-methyl-6-(2,2,2-trifluoroethoxy)pyrrolo[2,3-b]pyridine-3-carboxylate (115 mg, 61% yield) as a yellow solid. LC-MS: m/z $[M+H]^+$ 289.0.

Step 3

To a stirred solution of methyl 1-methyl-6-(2,2,2-trifluoroethoxy)pyrrolo[2,3-b]pyridine-3-carboxylate (115 mg, 0.399 mmol) in EtOH (10.0 mL) was added aq. NaOH (5.0 mL, 1.2 M, 6.0 mmol) at 25° C. The resulting mixture was warmed to 100° C. and stirred at that temperature for 5 h. The mixture was cooled 25° C., diluted with water (50 mL) and extracted with diethyl ether (50 mL×2). The aqueous phase was separated, acidified with aq. HCl (1.0 M) to pH=6 and extracted with EtOAc (80 mL×3). The combined organic layers were washed with brine, dried over anhydrous $Na_2SO_4$, and filtered. The filtrate was concentrated under reduced pressure to afford 1-methyl-6-(2,2,2-trifluoroethoxy)pyrrolo[2,3-b]pyridine-3-carboxylic acid (103 mg, 94% yield) as a white solid which was used directly in the next step without further purification. LC-MS: m/z $[M+H]^+$ 275.0.

Step 4

To a stirred solution of methyl 6-chloro-1-methyl-pyrrolo[2,3-b]pyridine-3-carboxylate (188 mg, 0.837 mmol) in THF (8.0 mL) was added aq. LiOH (2.0 mL, 6.0 M, 12 mmol) at 25° C. The mixture was stirred at that temperature for 72 h before it was diluted with water (50 mL) and extracted with diethyl ether (50 mL×2). The aqueous phase was separated and acidified with aq. HCl (1.0 M) to pH=6 and then extracted with EtOAc (50 mL×3). The combined organic layers were washed with brine, dried over anhydrous $Na_2SO_4$, and filtered. The filtrate was concentrated under reduced pressure to afford 6-chloro-1-methyl-pyrrolo[2,3-b]pyridine-3-carboxylic acid (175 mg, 99% yield) as a white solid which was used directly in the next step without further purification. LC-MS: m/z $[M+H]^+$ 211.0.

Acid Intermediate 29

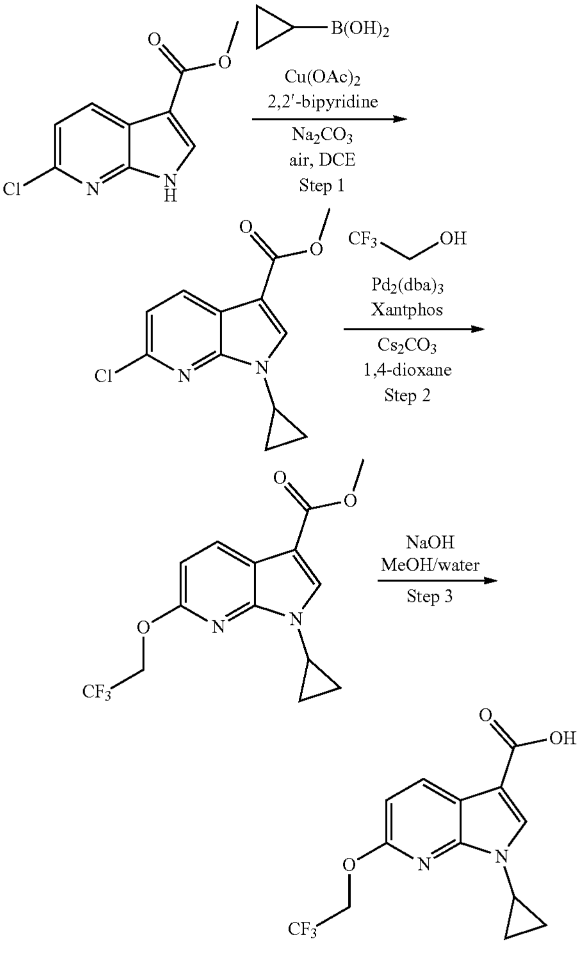

Step 1

To a stirred solution of methyl 6-chloro-1H-pyrrolo[2,3-b]pyridine-3-carboxylate (1.50 g, 7.12 mmol) in DCE (25.0 mL) were sequentially added cyclopropylboronic acid (1.84 g, 21.4 mmol), 2,2'-bipyridine (1.33 g, 8.55 mmol), $Cu(OAc)_2$ (1.55 g, 8.55 mmol) and $Na_2CO_3$ (2.26 g, 21.4 mmol) at 25° C. The reaction mixture was warmed to 95° C. and stirred at that temperature under air (balloon) for 8 h. The mixture was cooled to 25° C., diluted with $CH_2Cl_2$ (100 mL) and then washed with water (80 mL) and brine (80 mL) successively. The organic phase was washed brine, dried over anhydrous $Na_2SO_4$, and filtered. The filtrate was concentrated under reduced pressure. The residue was purified by flash column chromatography eluting with EtOAc/petroleum ether (with EtOAc from 0 to 40%) in 20 min to afford methyl 6-chloro-1-cyclopropyl-pyrrolo[2,3-b]pyridine-3-carboxylate (1.06 g, 60% yield) as a white solid. LC-MS: m/z $[M+H]^+$ 251.0.

Step 2

To a stirred solution of methyl 6-chloro-1-cyclopropyl-pyrrolo[2,3-b]pyridine-3-carboxylate (150 mg, 0.598 mmol) in 1,4-dioxane (4.0 mL) were sequentially added 2,2,2-trifluoroethanol (180 mg, 129 μL, 1.80 mmol), $Pd_2(dba)_3$ (110 mg, 0.120 mmol), Xantphos (138 mg, 0.239 mmol) and $Cs_2CO_3$ (780 mg, 2.39 mmol) at 25° C. The reaction mixture was warmed to 110° C. and stirred at that temperature for 6 h. The reaction mixture was cooled to 25° C., diluted with $CH_2Cl_2$ (100 mL), and filtered. The filtrate was concentrated under reduced pressure. The residue was purified by flash column chromatography eluting with EtOAc/petroleum ether (with EtOAc from 0 to 30%) in 20 min to afford methyl 1-cyclopropyl-6-(2,2,2-trifluoroethoxy)pyrrolo[2,3-b]pyridine-3-carboxylate (156 mg, 83% yield) as a yellow solid. LC-MS: m/z $[M+H]^+$ 315.0.

Step 3

To a stirred solution of methyl 1-cyclopropyl-6-(2,2,2-trifluoroethoxy)pyrrolo[2,3-b]pyridine-3-carboxylate (156 mg, 0.496 mmol) in MeOH (10.0 mL) was added aq. NaOH (5.0 mL, 0.6 M, 3.0 mmol) at 25° C. The resulting mixture was warmed to 100° C. and stirred at that temperature for 5 h. The mixture was cooled 25° C., diluted with water (50 mL) and extracted with diethyl ether (50 mL×2). The aqueous phase was separated, acidified with aq. HCl (1.0 M) to pH=6, and extracted with EtOAc (80 mL×3). The combined organic layers were washed with brine, dried over anhydrous $Na_2SO_4$, and filtered. The filtrate was concentrated under reduced pressure to afford 1-cyclopropyl-6-(2,2,2-trifluoroethoxy)pyrrolo[2,3-b]pyridine-3-carboxylic acid (106 mg, 71% yield) as a pale yellow solid which was used directly in the next step without further purification.

LC-MS: m/z $[M+H]^+$ 301.1.

Additional intermediates of the present disclosure were prepared using the similar procedure disclosed in acid intermediate 29 from the corresponding materials and their corresponding characterization data are listed in the table below.

| ID | Structure | LC-MS: m/z $[M + H]^+$ |
|---|---|---|
| Acid intermediate 30 | 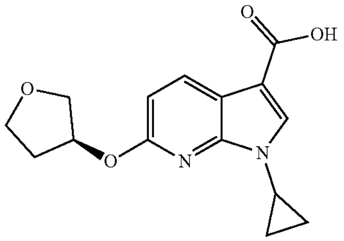 [SMILES: O=C(O)c1cn(C2CC2)c2nc(O[C@H]3CCOC3)ccc12] | 289.0 |
| Acid intermediate 31 | 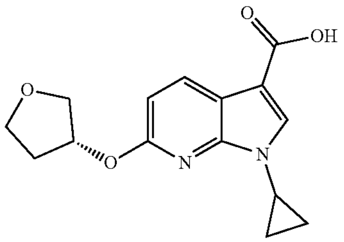 [SMILES: O=C(O)c1cn(C2CC2)c2nc(O[C@@H]3CCOC3)ccc12] | 289.0 |
| Acid intermediate 32 | 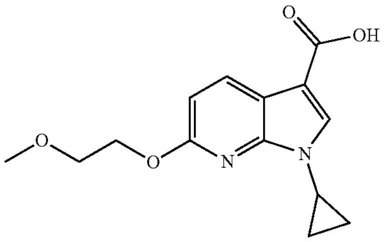 [SMILES: COCCOc1ccc2c(C(=O)O)cn(C3CC3)c2n1] | 277.1 |

Acid Intermediate 33

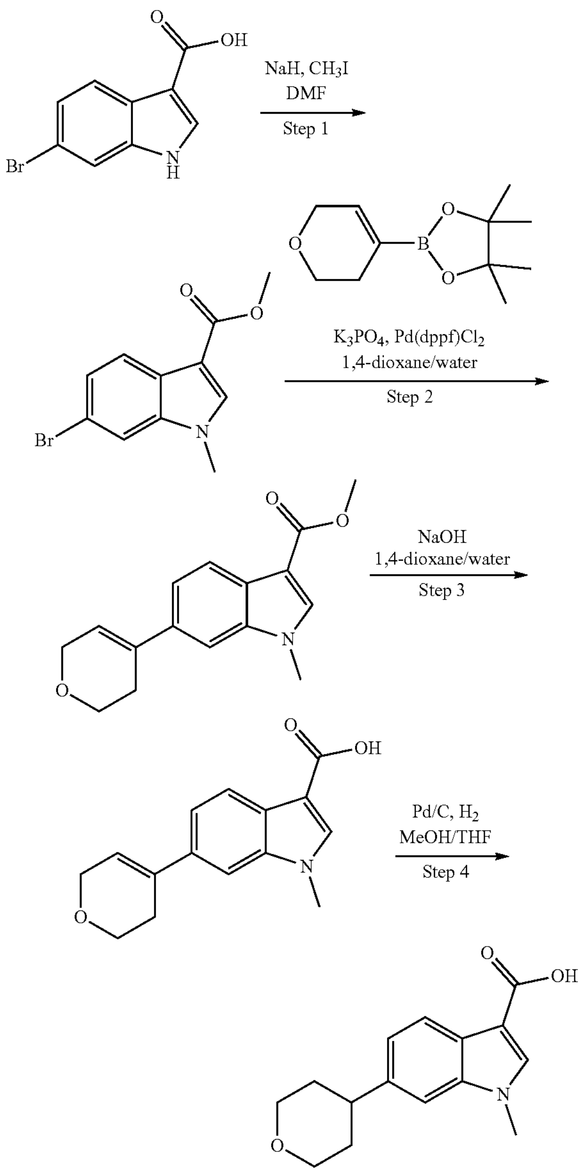

Step 1

To a stirred solution of 6-bromo-1H-indole-3-carboxylic acid (3.00 g, 12.5 mmol) in DMF (20.0 mL) was added NaH (1.50 g, 60% wt., 37.5 mmol) in small batches at 0° C. The resultant mixture was stirred at that temperature for 30 min before $CH_3I$ (5.32 g, 2.33 mL, 37.4 mmol) was added. The resulting mixture was warmed to 25° C. and stirred at that temperature for 16 h. The reaction was poured into ice water (150 mL) and stirred for 30 min. The precipitates were collected by filtration and dried under vacuum to afford methyl 6-bromo-1-methyl-indole-3-carboxylate (2.95 g, 88% yield) as a gray solid which was used directly in the next step without further purification. LC-MS: m/z $[M+H]^+$ 267.1.

Step 2

To a stirred solution of methyl 6-bromo-1-methyl-indole-3-carboxylate (1.30 g, 4.85 mmol) in 1,4-dioxane (20.0 mL) and water (8.0 mL) were sequentially added 2-(3,6-dihydro-2H-pyran-4-yl)-4,4,5,5-tetramethyl-1,3,2-dioxaborolane (1.32 g, 6.30 mmol), $Pd(dppf)Cl_2$ (354 mg, 0.484 mmol) and $K_3PO_4$ (3.09 g, 14.5 mmol) at 25° C. The mixture was warmed to 100° C. and stirred at that temperature for 50 min. The reaction mixture was cooled to 25° C., diluted with water (25 mL) and extracted with EtOAc (50 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 65%) in 25 min to give methyl 6-(3,6-dihydro-2H-pyran-4-yl)-1-methyl-indole-3-carboxylate (1.10 g, 83% yield) as a brown solid. LC-MS: m/z $[M+H]^+$ 272.1.

Step 3

To a stirred solution of methyl 6-(3,6-dihydro-2H-pyran-4-yl)-1-methyl-indole-3-carboxylate (600 mg, 2.21 mmol) in 1,4-dioxane (6.0 mL) was added aq. NaOH (3.0 mL, 3.5 M, 10.5 mmol) at 25° C. The resulting mixture was warmed to 90° C. and stirred at that temperature for 3 h. The mixture was cooled to 25° C., acidified with aq. HCl (1.0 M) to pH=5, and then extracted with EtOAc (30 mL×2). The combined organic phases were washed with brine, dried over anhydrous $Na_2SO_4$, and filtered. The filtrate was concentrated under vacuum to give 6-(3,6-dihydro-2H-pyran-4-yl)-1-methyl-indole-3-carboxylic acid (500 mg, 87% yield) as a white solid which was used directly in the next step without further purification. LC-MS: m/z $[M+H]^+$ 258.1.

Step 4

To a suspension of 6-(3,6-dihydro-2H-pyran-4-yl)-1-methyl-indole-3-carboxylic acid (75.0 mg, 0.291 mmol) in THF (5.0 mL) and MeOH (5.0 mL) was added Pd/C (31.0 mg, 10% wt., 0.0292 mmol) at 25° C. The resultant mixture was stirred under hydrogen atmosphere (balloon) at that temperature for 1 h before it was filtered through a pad of Celite. The filtrate was concentrated under reduced pressure to give 1-methyl-6-tetrahydropyran-4-yl-indole-3-carboxylic acid (70.0 mg, 93% yield) as a white solid which was used directly in the next step without further purification. LC-MS: m/z $[M+H]^+$ 260.1.

Additional intermediates of the present disclosure were prepared using the similar procedure disclosed in acid intermediate 33 from the corresponding materials and their corresponding characterization data are listed in the table below.

| ID | Structure | LC-MS: m/z $[M + H]^+$ |
|---|---|---|
| Acid intermediate 34 | 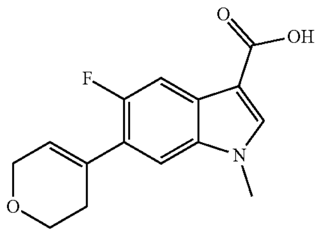 [SMILES: Cn1cc(C(=O)O)c2cc(F)c(C3=CCOCC3)cc21] | 276.0 |

-continued

| ID | Structure | LC-MS: m/z [M + H]+ |
|---|---|---|
| Acid intermediate 35 | 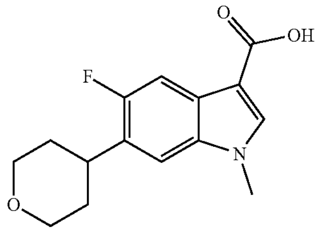 [SMILES: Cn1cc(C(=O)O)c2cc(F)c(C3CCOCC3)cc21] | 278.0 |

Acid Intermediate 36

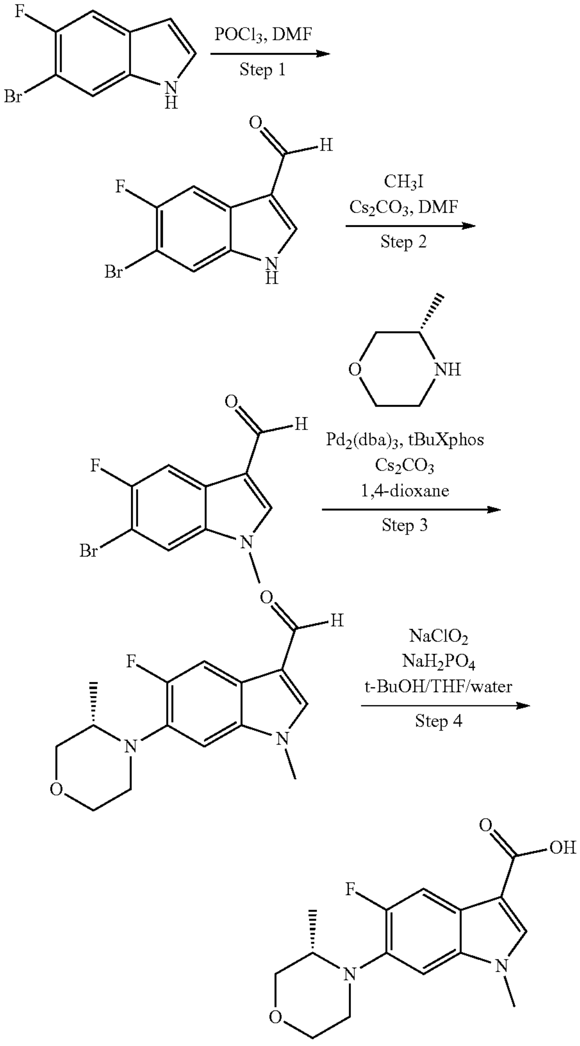

Step 1

To a stirred solution of 6-bromo-5-fluoro-1H-indole (1.00 g, 4.67 mmol) in DMF (6.0 mL) was added $POCl_3$ (2.51 g, 1.52 mL, 16.4 mmol) at 0° C. The resulting mixture was stirred at that temperature for 2 h before it was treated aq. NaOH (2.0 M, 10.0 mL). The mixture was warmed to 25° C. and stirred at that temperature for 1 h. The precipitates were collected by filtration to give 6-bromo-5-fluoro-1H-indole-3-carbaldehyde (1.13 g, 100% yield) as a white solid which was used directly in the next step without further purification. LC-MS: m/z $[M+H]^+$ 241.9.

Step 2

To a Schlenk pressure tube were sequentially added 6-bromo-5-fluoro-1H-indole-3-carbaldehyde (505 mg, 2.09 mmol), $CH_3I$ (444 mg, 195 μL, 3.13 mmol), $Cs_2CO_3$ (2.04 g, 6.26 mmol) and DMF (12.0 mL) at 25° C. The mixture was sealed and warmed to 85° C. and stirred at that temperature for 12 h. The mixture was cooled to 25° C. and poured into ice water (50 mL). The precipitates were collected by filtration to afford 6-bromo-5-fluoro-1-methyl-indole-3-carbaldehyde (530 mg, 99% yield) as a white solid which was used directly in the next step without further purification. LC-MS: m/z $[M+H]^+$ 255.9.

Step 3

To a stirred solution of 6-bromo-5-fluoro-1-methyl-indole-3-carbaldehyde (330 mg, 1.29 mmol) in 1,4-dioxane (6.0 mL) were sequentially added (3S)-3-methylmorpholine (391 mg, 3.87 mmol), $Pd_2(dba)_3$ (236 mg, 0.258 mmol), tBuXphos (219 mg, 0.515 mmol) and $Cs_2CO_3$ (1.26 g, 3.87 mmol) at 25° C. The reaction mixture was warmed to 110° C. and stirred at that temperature for 12 h. The mixture was cooled and concentrated under reduced pressure. The residue was purified by flash column chromatography eluting with EtOAc/petroleum ether (with EtOAc from 0 to 70%) in 25 min to afford 5-fluoro-1-methyl-6-[(3S)-3-methylmorpholin-4-yl]indole-3-carbaldehyde (82.0 mg, 23% yield) as a yellow solid.

LC-MS: m/z $[M+H]^+$ 277.1.

Step 4

To a stirred solution of 5-fluoro-1-methyl-6-[(3S)-3-methylmorpholin-4-yl]indole-3-carbaldehyde (82.0 mg, 0.297 mmol) in THF (5.0 mL) and t-BuOH (1.5 mL) were sequentially added 2-methylbut-2-ene (208 mg, 250 μL, 2.97 mmol) and a solution of $NaClO_2$ (134 mg, 1.48 mmol) and $NaH_2PO_4$ (107 mg, 0.890 mmol) in water (1.5 mL) at 25° C. The reaction mixture was stirred at that temperature for 48 h before it was quenched with saturated aq. $NaHSO_3$ (10 mL). The mixture was concentrated under reduced pressure to remove most of the solvent, diluted with EtOAc (50 mL) and washed with brine (50 mL). The organic layer was separated and dried over anhydrous $Na_2SO_4$, and filtered. The filtrate was concentrated under reduced pressure. The residue was purified by flash column chromatography eluting with EtOAc/petroleum ether (with EtOAc from 0 to 70%) in 25 min to afford 5-fluoro-1-methyl-6-[(3S)-3-methylmorpholin-4-yl]indole-3-carboxylic acid (60.0 mg, 69% yield) as a yellow solid. LC-MS: m/z $[M+H]^+$ 293.1.

Additional intermediates of the present disclosure were prepared using the similar procedure disclosed in acid intermediate 36 from the corresponding materials and their corresponding characterization data are listed in the table below.

| ID | Structure | LC-MS: m/z [M + H]+ |
|---|---|---|
| Acid intermediate 37 | 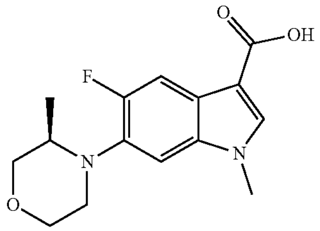 [SMILES: C[C@@H]1COCCN1c1cc2c(cc1F)c(C(=O)O)cn2C] | 293.1 |

Acid Intermediate 38

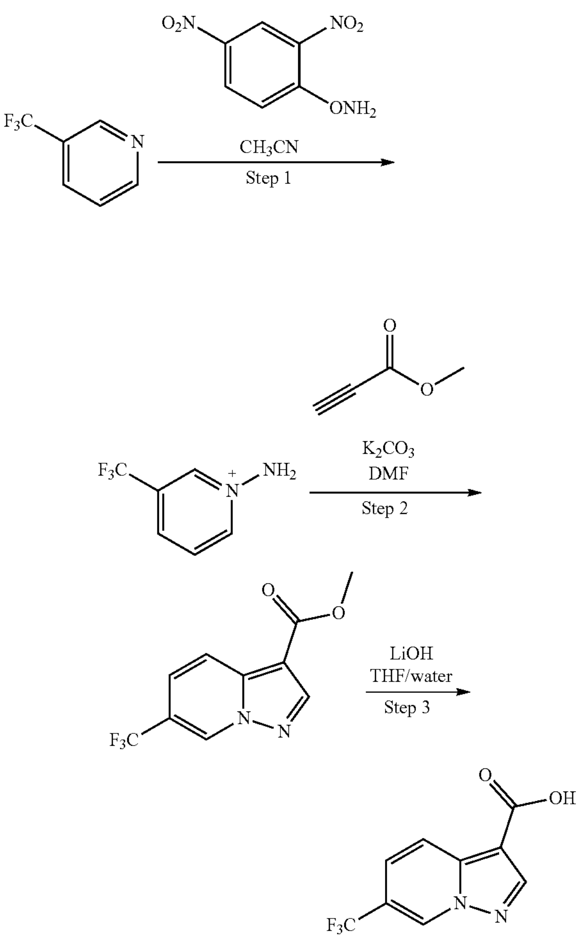

Step 1

To a stirred solution of 3-(trifluoromethyl)pyridine (3.00 g, 20.4 mmol) in $CH_3CN$ (15.0 mL) was added O-(2,4-dinitrophenyl)hydroxylamine (4.90 g, 24.8 mmol) at 25° C. The resultant mixture was warmed to 40° C. and stirred at that temperature for 15 h. The mixture was cooled and concentrated to afford 3-(trifluoromethyl)pyridin-1-ium-1-amine (8.00 g) as a white solid which was used for the next step without further purification. LC-MS: m/z $[M+H]^+$ 163.1.

Step 2

To a stirred suspension of 3-(trifluoromethyl)pyridin-1-ium-1-amine (8.00 g, 49.0 mmol) in DMF (35.0 mL) were sequentially added methyl propiolate (1.80 g, 1.90 mL, 20.8 mmol) and $K_2CO_3$ (10.1 g, 73.0 mmol) at 25° C. The resultant mixture was stirred at that temperature for 2 h before it was quenched with $H_2O$ (100 mL) and then extracted with EtOAc (150 mL×2). The combined organic layers were washed with brine, dried over anhydrous $Na_2SO_4$, and filtered. The filtrate was concentrated under reduced pressure. The residue was purified by flash column chromatography eluting with EtOAc/petroleum ether (with EtOAc from 0 to 30%) in 20 min to afford methyl 6-(trifluoromethyl)pyrazolo[1,5-a]pyridine-3-carboxylate (423 mg, 8% yield) as a yellow solid. LC-MS: m/z $[M+H]^+$ 245.1.

Step 3

To a stirred solution of methyl 6-(trifluoromethyl)pyrazolo[1,5-a]pyridine-3-carboxylate (310 mg, 1.30 mol) in THF (5.0 mL) was added aq. LiOH (2.0 mL, 9.5 M, 19 mmol) at 25° C. The resulting mixture was stirred at that temperature for 72 h before it was diluted with water (50 mL) and then extracted with diethyl ether (50 mL×2). The aqueous phase was separated, acidified with aq. HCl (1.0 M) to pH=6 and then extracted with EtOAc (50 mL×2). The combined organic layers were washed with brine, dried over anhydrous $Na_2SO_4$, and filtered. The filtrate was concentrated under reduced pressure to afford 6-(trifluoromethyl)pyrazolo[1,5-a]pyridine-3-carboxylic acid (290 mg, 99% yield) as a yellow solid which was used in the next step without further purification. LC-MS: m/z $[M+H]^+$ 231.1.

Acid Intermediate 39

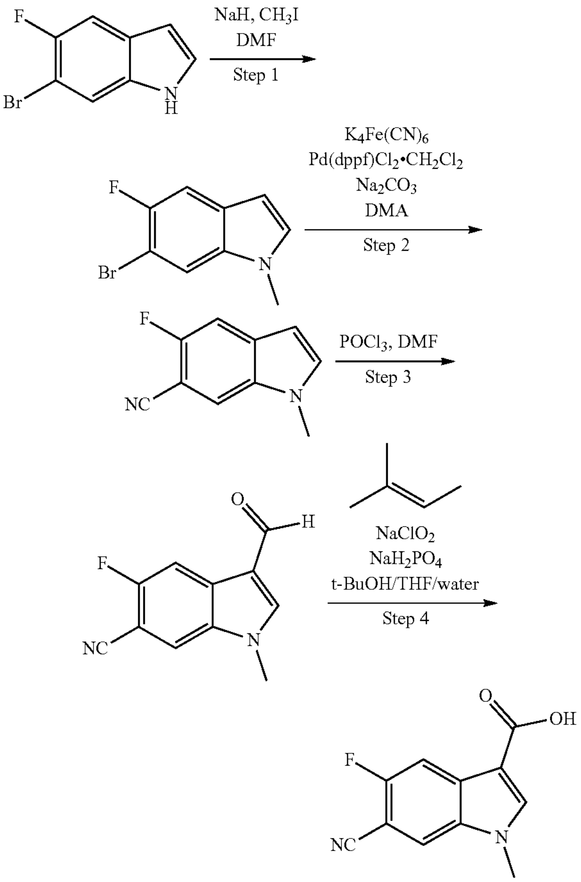

Step 1

To a stirred solution of 6-bromo-5-fluoro-1H-indole (5.00 g, 23.4 mmol) in DMF (25.0 mL) was added NaH (1.32 g, 60% wt., 30.4 mmol) at 0° C. The mixture was stirred at that temperature for 10 min before iodomethane (3.65 g, 25.7 mmol, 1.60 mL) was added. The mixture was stirred at 0° C. for 2 h before it was quenched with water (20 mL) and extracted with EtOAc (50 mL×3). The combined organic layers were washed with brine, dried over anhydrous $Na_2SO_4$, and filtered. The filtrate was concentrated under reduced pressure. The residue was slurried with EtOAc/petroleum ether (v/v=2:1, 20 mL) for 2 h and filtered to afford 6-bromo-5-fluoro-1-methyl-indole (4.80 g, 90% yield) as a brown solid. LC-MS: m/z $[M+H]^+$ 227.0.

Step 2

To a stirred solution of 6-bromo-5-fluoro-1-methyl-indole (2.20 g, 9.65 mmol) in DMA (25.0 mL) were sequentially added $K_4Fe(CN)_6$ (2.04 g, 4.82 mmol), $Pd(dppf)Cl_2$—$CH_2Cl_2$ (197 mg, 0.241 mmol) and $Na_2CO_3$ (1.12 g, 10.6 mmol) at 25° C. The resulting mixture was warmed to 120° C. and stirred at that temperature for 2 h. The reaction mixture was cooled to 25° C. and filtered through a pad of Celite. The filtrate was diluted with water (20 mL) and extracted with EtOAc (50 mL×3). The combined organic phases were washed with brine (50 mL), dried over anhydrous $Na_2SO_4$, and filtered. The solvent was evaporated under vacuum. The residue was purified by silica gel chromatography eluting with EtOAc/petroleum ether (with EtOAc from 0 to 50%) in 25 min to give 5-fluoro-1-methyl-indole-6-carbonitrile (1.20 g, 71% yield) as a brown solid. LC-MS: m/z $[M+H]^+$ 175.1.

Step 3

A solution of phosphoryl trichloride (1.10 g, 7.20 mmol) in DMF (5.0 mL) was stirred at 0° C. for 30 min before a solution of 5-fluoro-1-methyl-indole-6-carbonitrile (1.14 g, 6.55 mmol) in DMF (15.0 mL) was added. The reaction mixture was warmed to 25° C. and stirred at that temperature for 1 h before it was poured into saturated aq. $NaHCO_3$ (20 mL) and stirred at that temperature for 2 h. The precipitates were collected by filtration and dried in vacuo to give 5-fluoro-3-formyl-1-methyl-indole-6-carbonitrile (1.00 g, 76% yield) as a white solid which was used directly in the next step without further purification. LC-MS: m/z $[M+H]^+$ 203.1.

Step 4

To a stirred suspension of 5-fluoro-3-formyl-1H-indole-6-carbonitrile (2.50 g, 13.3 mmol) in THF (40.0 mL) and t-BuOH (10.0 mL) were sequentially added 2-methylbut-2-ene (7.45 g, 106 mmol, 11.3 mL) and a solution of $NaClO_2$ (4.81 g, 53.2 mmol) and $NaH_2PO_4$ (8.29 g, 53.2 mmol) in water (40.0 mL) at 0° C. The resulting mixture was warmed to 25° C. and stirred at that temperature for 48 h. The mixture was diluted with water (50 mL) and then extracted with EtOAc (50 mL×3). The combined organic layers were washed with brine (50 mL), dried over anhydrous $Na_2SO_4$. and filtered. The filtrate was concentrated under reduced pressure to give 6-cyano-5-fluoro-1H-indole-3-carboxylic acid (2.00 g, 74% yield) as a yellow solid which was used in the next step without further purification. LC-MS: m/z $[M+H]^+$ 219.1.

Acid Intermediate 40

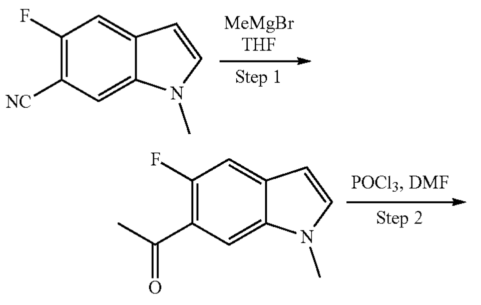

-continued

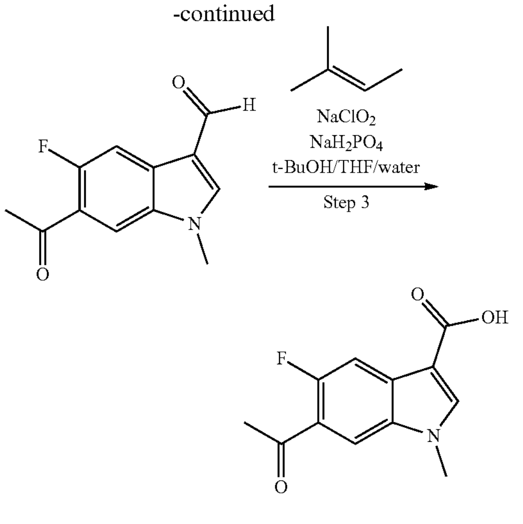

Step 1

To a stirred solution of 5-fluoro-1-methyl-indole-6-carbonitrile (500 mg, 2.87 mmol) in THF (5.0 mL) was added MeMgBr (3.83 mL, 3.0 M in THF2-MeTHF, 11.5 mmol) at 25° C. The resulting mixture was warmed to 40° C. and stirred at that temperature for 12 h. The mixture was quenched with saturated aq. $NH_4Cl$ (20 mL), and extracted with EtOAc (50 mL×3). The combined organic phases were washed with brine (30 mL), dried over anhydrous $Na_2SO_4$, and filtered. The filtrate was concentrated under reduced pressure. The residue was purified by silica gel chromatography eluting with EtOAc/petroleum ether (with EtOAc from 0 to 50%) in 20 min to give 1-(5-fluoro-1-methyl-indol-6-yl)ethanone (482 mg, 89% yield) as a pale yellow solid. LC-MS: m/z $[M+H]^+$ 192.1.

Step 2

A solution of phosphoryl trichloride (425 mg, 2.77 mmol) in DMF (2.0 mL) was stirred at 0° C. for 30 min before a solution of 1-(5-fluoro-1-methyl-indol-6-yl)ethanone (482 mg, 2.52 mmol) in DMF (10.0 mL) was added. The reaction mixture was warmed to 25° C. and stirred at that temperature for 3 h before it was poured into saturated aq. $NaHCO_3$ (20 mL) and stirred at 25° C. for 2 h. The precipitates were collected by filtration and dried in vacuo to give 6-acetyl-5-fluoro-1-methyl-indole-3-carbaldehyde (480 mg, 87% yield) as a white solid which was used directly in the next step without further purification. LC-MS: m/z $[M+H]^+$ 220.1.

Step 3

To a stirred suspension of 6-acetyl-5-fluoro-1-methyl-indole-3-carbaldehyde (480 mg, 2.19 mmol) in THF (8.0 mL) and t-BuOH (2.0 mL) were sequentially added 2-methylbut-2-ene (1.23 g, 17.5 mmol, 1.80 mL) and a solution of $NaClO_2$ (792 mg, 8.76 mmol) and $NaH_2PO_4$ (1.37 g, 8.76 mmol) in water (8.0 mL) at 0° C. The resulting mixture was warmed to 25° C. and stirred at that temperature for 48 h. The mixture was diluted with water (50 mL) and then extracted with EtOAc (50 mL×3). The combined organic layers were washed with brine (20 mL), dried over anhydrous $Na_2SO_4$, and filtered. The filtrate was concentrated under reduced pressure. The residue was purified by silica gel chromatography eluting with $MeOH/CH_2Cl_2$ (with MeOH from 0 to 10%) in 20 min to give 6-acetyl-5-fluoro-1-methyl-indole-3-carboxylic acid (410 mg, 80% yield) as a yellow solid. LC-MS: m/z $[M+H]^+$ 236.1.

Amine Intermediates

Amine Intermediate 1

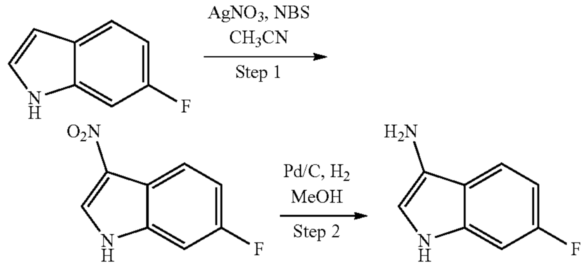

Step 1

To a stirred solution of $AgNO_3$ (1.70 g, 10.0 mmol) in $CH_3CN$ (50.0 mL) were sequentially added NBS (1.78 g, 10.0 mmol) and a solution of 6-fluoro-1H-indole (1.35 g, 10.0 mmol) in $CH_3CN$ (10.0 mL) at 80° C. The mixture was stirred at that temperature for 2 h before it was cooled to 25° C. and filtered through a pad of Celite. The filtrate was concentrated under reduced pressure. The residue was purified by silica gel chromatography eluting with EtOAc/petroleum ether (with EtOAc from 1% to 26%) in 25 min to give 6-fluoro-3-nitro-1H-indole (440 mg, 24% yield) as a brown solid. LC-MS: m/z $[M+H]^+$ 181.0.

Step 2

To a stirred solution of 6-fluoro-3-nitro-1H-indole (35.0 mg, 0.194 mmol) in MeOH (6.0 mL) was added Pd/C (20.6 mg, 10% wt., 0.0194 mmol) at 25° C. The reaction mixture was stirred under hydrogen atmosphere (balloon) at that temperature for 2 h before it was filtered through a pad of Celite. The filtrate was concentrated under reduced pressure to afford 6-fluoro-1H-indol-3-amine (23.3 mg, 80% yield) as a brown solid which was used directly in the next step without further purification. LC-MS: m/z $[M+H]^+$ 151.1.

Additional intermediates of the present disclosure were prepared using the similar procedure disclosed in amine intermediate 1 from the corresponding materials and their corresponding characterization data are listed in the table below.

| ID | Structure | LC-MS: m/z $[M + H]^+$ |
|---|---|---|
| Amine intermediate 2 | 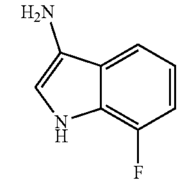 [SMILES: Nc1c[nH]c2c(F)cccc12] | 151.1 |
| Amine intermediate 3 | 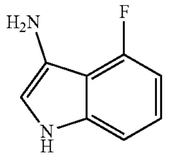 [SMILES: Nc1c[nH]c2cccc(F)c12] | 151.1 |
| Amine intermediate 4 | 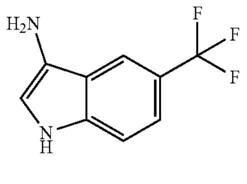 [SMILES: Nc1c[nH]c2ccc(C(F)(F)F)cc12] | 201.1 |

-continued

| ID | Structure | LC-MS: m/z $[M + H]^+$ |
|---|---|---|
| Amine intermediate 5 | 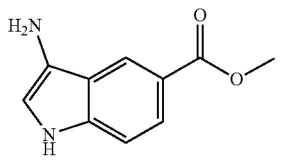 | 191.1 |

Amine Intermediate 6

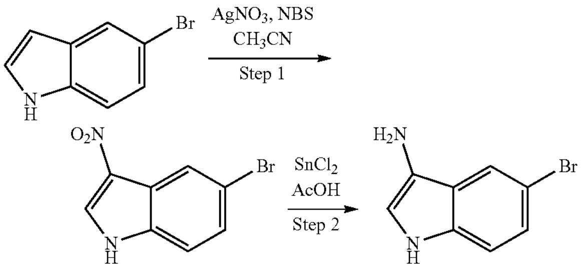

Step 1

To a stirred solution of NBS (1.40 g, 7.60 mmol) in $CH_3CN$ (50.0 mL) were sequentially added $AgNO_3$ (1.30 g, 7.60 mmol) and a solution of 5-bromo-1H-indole (1.50 g, 7.60 mmol) in $CH_3CN$ (5.0 mL) at 80° C. The reaction mixture was stirred at that temperature for 3 h before it was cooled to 25° C. and filtered through a pad of Celite. The filtrate was concentrated under reduced pressure. The residue was purified by silica gel chromatography eluting with EtOAc/petroleum ether (with EtOAc from 1% to 56%) in 20 min to give 5-bromo-3-nitro-1H-indole (700 mg, 38% yield) as a brown solid. LC-MS: m/z $[M+H]^+$ 241.1.

Step 2

To a stirred solution of 5-bromo-3-nitro-1H-indole (100 mg, 0.414 mmol) in AcOH (2.0 mL) was added $SnCl_2$ (78.7 mg, 0.415 mmol) at 25° C. The resulting mixture was warmed to 85° C. and stirred at that temperature for 2 h. The mixture was cooled to 25° C. and concentrated under reduced pressure to give 5-bromo-1H-indol-3-amine (80.0 mg, 92% yield) as a yellow solid which was used directly in the next step without further purification. LC-MS: m/z $[M+H]^+$ 211.1.

Amine Intermediate 7

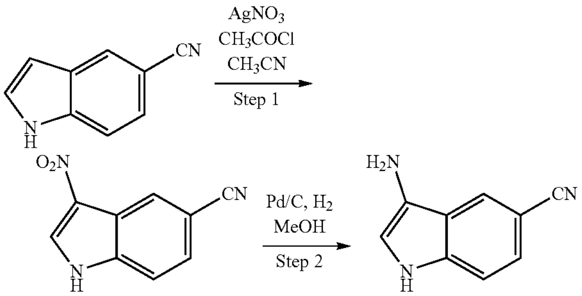

Step 1

To a stirred solution of 1H-indole-5-carbonitrile (2.00 g, 14.1 mmol) and $AgNO_3$ (2.63 g, 15.5 mmol) in $CH_3CN$ (40.0 mL) was slowly added a solution of acetyl chloride (1.21 g, 0.942 mL, 15.5 mmol) in $CH_3CN$ (10.0 mL) at −10° C. The reaction mixture was stirred at that temperature for 1 h before it was quenched with saturated aq. $NaHCO_3$ solution (50 mL). The mixture was extracted with EtOAc (150 mL×2). The combined organic layers were washed with brine, dried over anhydrous $Na_2SO_4$, and filtered. The filtrate was concentrated under reduced pressure. The residue was slurried with petrol ether/EtOAc=1.5:1 (30 mL) and filtered to afford 3-nitro-1H-indole-5-carbonitrile (2.20 g, 84% yield) as an orange solid.

LC-MS: m/z $[M+H]^+$ 188.0.

Step 2

To a solution of 3-nitro-1H-indole-5-carbonitrile (60.0 mg, 0.321 mmol) in MeOH (5.0 mL) was added Pd/C (13.0 mg, 10% wt., 0.012 mmol) at 25° C. The reaction mixture was stirred under hydrogen atmosphere (balloon) at that temperature for 2 h before it was filtered through a pad of Celite. The filtrate was treated with HCl (2.0 M in EtOAc, 10 mL) at 25° C., stirred at that temperature for 10 min and concentrated under reduced pressure to afford 3-amino-1H-indole-5-carbonitrile hydrochloride (61.4 mg, 99% yield) as a brown solid which was used directly in the next step without further purification. LC-MS: m/z $[M+H]^+$ 158.1.

Additional intermediates of the present disclosure were prepared using the similar procedure disclosed in amine intermediate 7 from the corresponding materials and their corresponding characterization data are listed in the table below.

| ID | Structure | LC-MS: m/z [M+H]+ |
|---|---|---|
| Amine intermediate 8 | 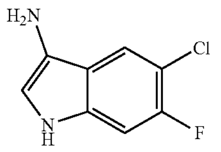 [SMILES: Nc1c[nH]c2cc(F)c(Cl)cc12] | 185.0 |
| Amine intermediate 9 | 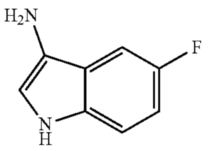 [SMILES: Nc1c[nH]c2ccc(F)cc12] | 151.1 |
| Amine intermediate 10 | 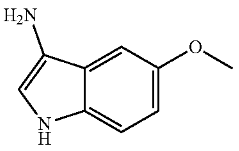 | 163.1 |
| Amine intermediate 11 | 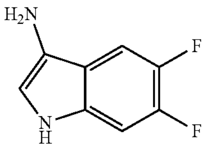 [SMILES: Nc1c[nH]c2cc(F)c(F)cc12] | 169.0 |
| Amine intermediate 12 | 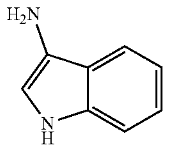 | 133.0 |

Amine Intermediate 13

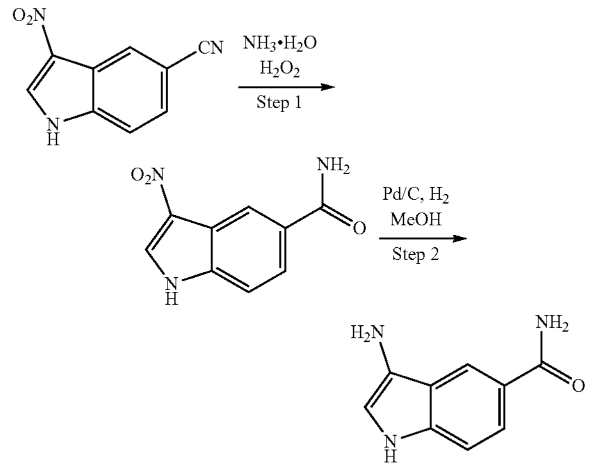

Step 1

To a stirred solution of 3-nitro-1H-indole-5-carbonitrile (190 mg, 1.00 mmol) in $NH_3{\cdot}H_2O$ (3.0 mL) was added hydrogen peroxide (653 mg, 30% wt., 5.70 mmol) at 25° C. The resultant mixture was stirred at that temperature for 16 h before it was quenched with saturated aq. $Na_2S_2O_3$ (20 mL). The mixture was extracted with EtOAc (50 mL×2). The combined organic layers were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 100%) in 25 min to give 3-nitro-1H-indole-5-carboxamide (200 mg, 96% yield) as a white solid. LC-MS: m/z $[M+H]^+$ 206.1.

Step 2

To a stirred solution of 3-nitro-1H-indole-5-carboxamide (200 mg, 0.974 mmol) in MeOH (10.0 mL) was added Pd/C (50.0 mg, 10% wt., 0.0472) at 25° C. The resulting mixture was stirred under hydrogen atmosphere (balloon) at that temperature for 16 h before it was filtered through a pad of Celite. The filtrate was treated with HCl (1.0 mL, 4.0 M in 1,4-dioxane) and concentrated under reduced pressure to give 3-amino-1H-indole-5-carboxamide hydrochloride (150 mg, 88%) as a black solid which was used directly in the next step without further purification. LC-MS: m/z $[M+H]^+$ 176.1.

Amine Intermediate 14

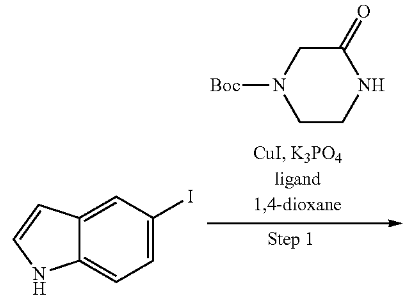

-continued

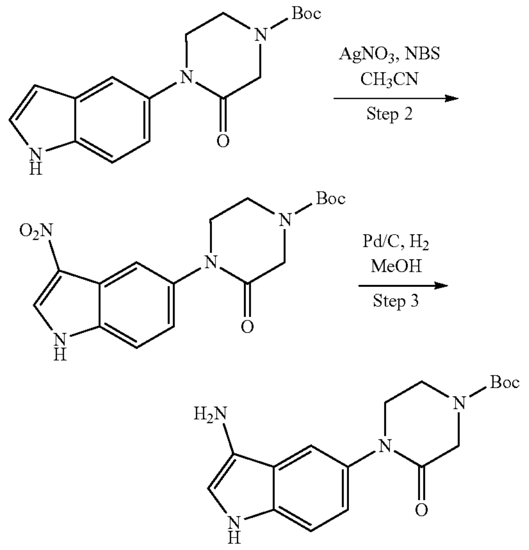

Step 1

To a stirred solution of 5-iodo-1H-indole (1.00 g, 4.11 mmol) in 1,4-dioxane (20.0 mL) were sequentially added tert-butyl 3-oxopiperazine-1-carboxylate (1.24 g, 6.17 mmol), (1R,2R)—N,N'-Dimethyl-1,2-cyclohexanediamine (234 mg, 1.65 mmol), CuI (156 mg, 0.822 mmol) and $K_3PO_4$ (2.62 g, 12.3 mmol) at 25° C. The resulting mixture was warmed to 110° C. and stirred at that temperature for 4 h. The mixture was cooled to 25° C. and filtered through a pad of Celite. The filtrate was concentrated under reduced pressure. The residue was purified by silica gel chromatography eluting with EtOAc/petroleum ether (with EtOAc from 0 to 100%) in 25 min to give tert-butyl 4-(1H-indol-5-yl)-3-oxo-piperazine-1-carboxylate (230 mg, 17% yield) as a white solid. LC-MS: m/z $[M+H]^+$ 316.1.

Step 2

To a stirred solution of NBS (129 mg, 0.729 mmol) in $CH_3CN$ (5.0 mL) were sequentially added $AgNO_3$ (123 mg, 0.729 mmol) and a solution of tert-butyl 4-(1H-indol-5-yl)-3-oxo-piperazine-1-carboxylate (230 mg, 0.729 mmol) in $CH_3CN$ (3.0 mL) at 80° C. The resulting mixture was stirred at that temperature for 3 h before it was cooled to 25° C., filtered, and concentrated under reduced pressure. The residue was purified by silica gel chromatography eluting with EtOAc/petroleum ether (with EtOAc from 0 to 100%) in 25 min to give tert-butyl 4-(3-nitro-1H-indol-5-yl)-3-oxo-piperazine-1-carboxylate (50.0 mg, 19% yield) as a yellow solid. LC-MS: m/z $[M+H]^+$ 305.0.

Step 3

To a suspension of tert-butyl 4-(3-nitro-1H-indol-5-yl)-3-oxo-piperazine-1-carboxylate (50.0 mg, 0.138 mmol) in MeOH (5.0 mL) was added Pd/C (14.7 mg, 10% wt., 0.0139 mmol) at 25° C. The mixture was stirred at that temperature under hydrogen atmosphere (balloon) for 8 h before it was filtered through a pad of Celite. The filtrate was concentrated under reduced pressure to give tert-butyl 4-(3-amino-1H-indol-5-yl)-3-oxo-piperazine-1-carboxylate (45.0 mg) as a black solid which was used directly in the next step without further purification. LC-MS: m/z $[M+H]^+$ 331.2.

Amine Intermediate 15

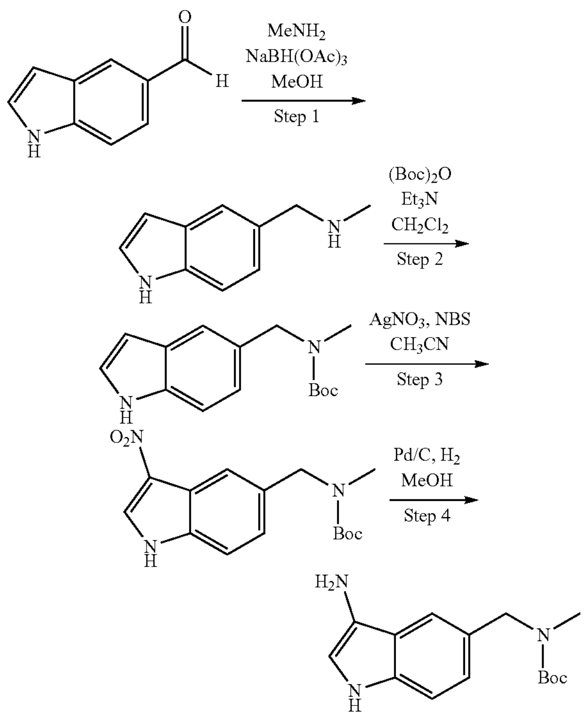

Step 1

To a stirred solution of 1H-indole-5-carbaldehyde (1.00 g, 6.89 mmol) in MeOH (10.0 mL) was added $MeNH_2$ (1.43 g, 30% wt. in MeOH, 13.8 mmol) at 25° C. The resultant mixture was stirred at that temperature for 30 min before $NaBH(OAc)_3$ (1.59 g, 7.50 mmol) was added. The reaction mixture was stirred at 25° C. for 3 h before it was quenched with saturated aq. $NaHCO_3$ (20 mL). The resultant mixture was extracted with EtOAc (50 mL×3). The combined organic phases were washed with brine (50 mL), dried over anhydrous $Na_2SO_4$, and filtered. The solvent was evaporated under vacuum to give 1-(1H-indol-5-yl)-N-methylmethanamine (1.01 g, 91% yield) as a brown solid which was used in the next step without further purification. LC-MS: m/z $[M+H]^+$ 161.0.

Step 2

To a stirred solution of 1-(1H-indol-5-yl)-N-methylmethanamine (1.00 g, 6.25 mmol) in $CH_2Cl_2$ (20.0 mL) were sequentially added $(Boc)_{2O}$ (1.36 g, 1.44 mL, 6.25 mmol) and $Et_3N$ (632 mg, 869 μL, 6.25 mmol) at 0° C. The resultant mixture was stirred at that temperature for 1 h before it was quenched with saturated aq. $NaHCO_3$ (20 mL). The resultant mixture was extracted with EtOAc (50 mL×3). The combined organic phases were washed with brine (50 mL), dried over anhydrous $Na_2SO_4$, and filtered. The solvent was evaporated under vacuum. The residue was purified by silica gel chromatography eluting with EtOAc/petroleum ether (with EtOAc from 0 to 60%) in 20 min to give tert-butyl ((1H-indol-5-yl)methyl)(methyl)carbamate (1.30 g, 80% yield) as a white solid. LC-MS: m/z $[M+H]^+$ 205.0.

Step 3

To a stirred solution of NBS (822 mg, 4.62 mmol) in $CH_3CN$ (20.0 mL) were sequentially added $AgNO_3$ (785 mg, 4.62 mmol) and a solution of tert-butyl ((1H-indol-5-yl)methyl) (methyl)carbamate (1.20 g, 4.62 mmol) in $CH_3CN$ (5.0 mL) at 80° C. The resulting mixture was stirred at that temperature for 2 h. The mixture was cooled to 25°

C., filtered, and concentrated under reduced pressure. The residue was purified by silica gel chromatography eluting with EtOAc/petroleum ether (with EtOAc from 0 to 50%) in 25 min to give tert-butyl methyl((3-nitro-1H-indol-5-yl)methyl)carbamate (276 mg, 20% yield) as a yellow solid.

LC-MS: m/z $[M+H]^+$ 250.9.

Step 4

To a suspension of tert-butyl 4-(3-nitro-1H-indol-5-yl)-3-oxo-piperazine-1-carboxylate (250 mg, 0.820 mmol) in MeOH (10.0 mL) was added Pd/C (43.5 mg, 10% wt., 0.041 mmol) at 25° C. The mixture was stirred at that temperature under hydrogen atmosphere (balloon) for 8 h before it was filtered through a pad of Celite. The filtrate was concentrated under reduced pressure to give tert-butyl ((3-amino-1H-indol-5-yl)methyl)(methyl)carbamate (145 mg, 64% yield) as a black solid which was used directly in the next step without further purification. LC-MS: m/z $[M+H]^+$ 276.9.

Amine Intermediate 16

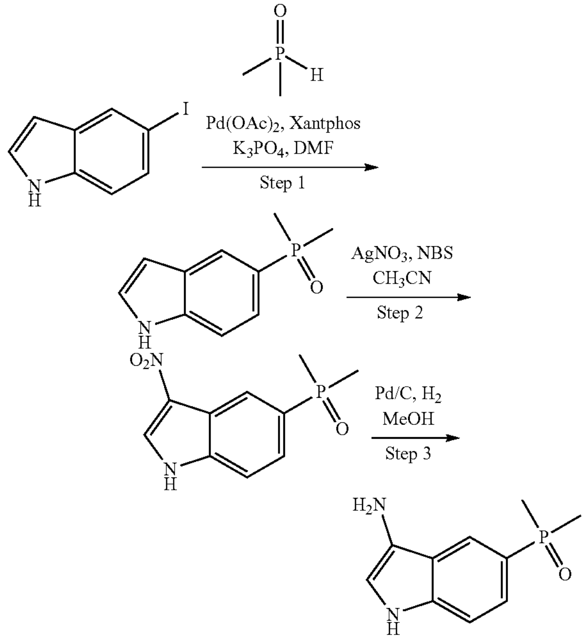

Step 1

To a stirred solution of 5-iodo-1H-indole (500 mg, 2.00 mmol) in DMF (10.0 mL) were sequentially added dimethylphosphine oxide (176 mg, 2.20 mmol), $Pd(OAc)_2$ (92.3 mg, 0.411 mmol), Xantphos (476 mg, 0.822 mmol) and $K_3PO_4$ (1.30 g, 6.10 mmol) at 25° C. The resulting mixture was warmed to 120° C. and stirred at that temperature for 12 h. The mixture was cooled to 25° C. and filtered through a pad of Celite. The filtrate was concentrated under reduced pressure. The residue was purified by silica gel chromatography eluting with $MeOH/CH_2Cl_2$ (with MeOH from 0 to 5%) in 15 min to give 5-dimethylphosphoryl-1H-indole (200 mg, 50% yield) as a yellow solid. LC-MS: m/z $[M+H]^+$ 194.1.

Step 2

To a stirred solution of NBS (184 mg, 1.04 mmol) in $CH_3CN$ (5.0 mL) were sequentially added $AgNO_3$ (175 mg, 1.00 mmol) and a solution of 5-dimethylphosphoryl-1H-indole (200 mg, 1.40 mmol) in $CH_3CN$ (2.0 mL) at 80° C. The reaction mixture was stirred at 80° C. for 3 h before it was cooled to 25° C. and filtered through a pad of Celite. The filtrate was diluted water (30 mL) and then extracted with EtOAc (20 mL×2). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 56%) in 20 min to give 5-dimethylphosphoryl-3-nitro-1H-indole (35.0 mg, 14% yield) as a yellow solid.

LC-MS: m/z $[M+H]^+$ 239.1.

Step 3

To a stirred solution of 5-dimethylphosphoryl-3-nitro-1H-indole (65.0 mg, 0.272 mmol) in MeOH (5.0 mL) was added Pd/C (50.0 mg, 10% wt., 0.0472 mmol). The reaction mixture was stirred under hydrogen atmosphere (balloon) at 25° C. for 16 h before it was filtered. The filtrate was concentrated under reduced pressure to give 5-dimethylphosphoryl-1H-indol-3-amine (40.0 mg, 71% yield) as a brown solid which was used in the next step without further purification. LC-MS: m/z $[M+H]^+$ 209.1.

Amine Intermediate 17

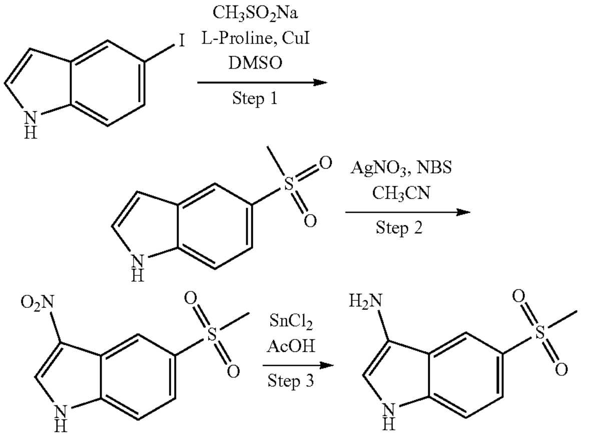

Step 1

To a stirred solution of 5-iodo-1H-indole (1.50 g, 6.17 mmol) in DMSO (10.0 mL) were sequentially added sodium methanesulfinate (819 mg, 8.02 mmol), CuI (235 mg, 1.23 mmol) and L-Proline (284 mg, 2.47 mmol) at 25° C. The resulting mixture was warmed to 110° C. and stirred at that temperature for 24 h. The mixture was cooled to 25° C., quenched with $NH_4Cl$ (35 mL) and extracted with EtOAc (50 mL×3). The combined organic phases were washed with brine, dried over anhydrous $Na_2SO_4$, and filtered. The filtrate was concentrated under reduced pressure. The residue was purified by silica gel chromatography eluting with EtOAc/petroleum ether (with EtOAc from 0 to 30%) in 20 min to give 5-methylsulfonyl-1H-indole (550 mg, 46% yield) as a yellow solid. LC-MS: m/z $[M+H]^+$ 196.0.

Step 2

To a stirred solution of NBS (638 mg, 3.59 mmol) in $CH_3CN$ (20.0 mL) were sequentially added $AgNO_3$ (609 mg, 3.59 mmol) and a solution of 5-methylsulfonyl-1H-indole (700 mg, 3.59 mmol) in $CH_3CN$ (5.0 mL) at 80° C. The reaction mixture was stirred at 80° C. for 3 h before it was cooled to 25° C. and filtered through a pad of Celite. The filtrate as concentrated under reduced pressure. The residue was purified by silica gel chromatography eluting with EtOAc/petroleum ether (with EtOAc from 1% to 16%) in 20 min to give 5-methylsulfonyl-3-nitro-1H-indole (550 mg, 63% yield) as a yellow solid. LC-MS: m/z $[M+H]^+$ 241.0.

Step 3

To a stirred solution of 5-methylsulfonyl-3-nitro-1H-indole (99.6 mg, 0.414 mmol) in HOAc (2.0 mL) was added $SnCl_2$ (78.7 mg, 0.414 mmol) at 25° C. The resulting mixture was warmed to 85° C. and stirred at that temperature for 2 h. The mixture was cooled to 25° C. and concentrated under reduced pressure to give 5-methylsulfonyl-1H-indol-3-amine (50.0 mg, 58%) as a yellow solid which was used directly in the next step without further purification. LC-MS: m/z $[M+H]^+$ 211.0.

SYNTHETIC EXAMPLES

Example 1

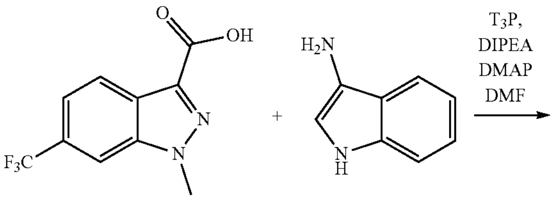

-continued

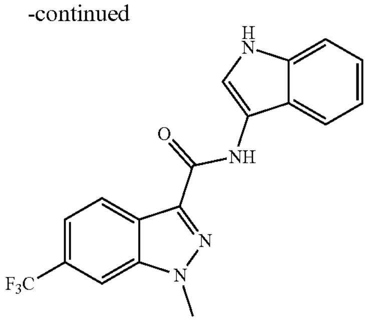

To a stirred solution of 1-methyl-6-(trifluoromethyl)indazole-3-carboxylic acid (22.0 mg, 0.0901 mmol) in DMF (3.0 mL) were sequentially added T3P (115 mg, 50% wt. in EtOAc, 0.180 mmol), DMAP (2.2 mg, 0.018 mmol), DIPEA (35 mg, 48 μL, 0.27 mmol) and 1H-indol-3-amine (13.1 mg, 0.0991 mmol) at 25° C. The resulting mixture was warmed to 40° C. and stirred at that temperature for 2 h. The mixture was cooled to 25° C. and concentrated under reduced pressure. The residue was purified by Prep-HPLC eluting with $CH_3CN$/water (with $CH_3CN$ from 45% to 75%) in 8 min to give N-(1H-indol-3-yl)-1-methyl-6-(trifluoromethyl)indazole-3-carboxamide (9.0 mg, 28% yield) as a white solid.

LC-MS: m/z $[M+H]^+$ 359.1.

The following compounds were prepared using the similar procedure disclosed in synthetic example 1 and their corresponding characterization data are presented in the table below.

| Synthetic Example | Structure | LC-MS: m/z $[M + H]^+$ |
|---|---|---|
| 2 | 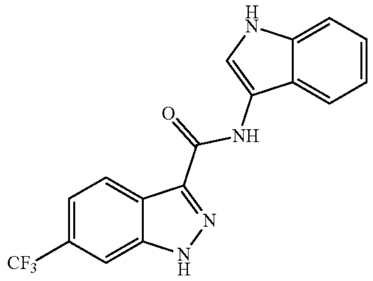 [SMILES: O=C(Nc1c[nH]c2ccccc12)c1n[nH]c2cc(C(F)(F)F)ccc12] | 345.1 |
| 3 | 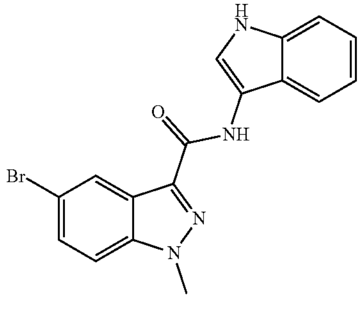 [SMILES: Cn1nc(C(=O)Nc2c[nH]c3ccccc23)c2cc(Br)ccc21] | 369.0 |

-continued
| Synthetic Example | Structure | LC-MS: m/z $[M + H]^+$ |
|---|---|---|
| 4 | 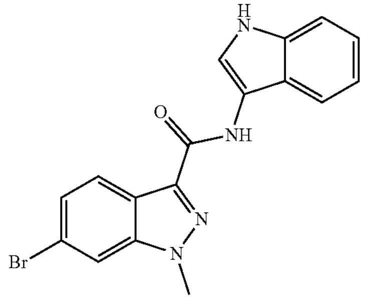 [SMILES: Cn1nc(C(=O)Nc2c[nH]c3ccccc23)c2ccc(Br)cc21] | 369.0 |
| 5 | 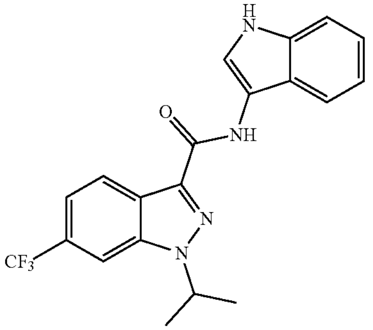 [SMILES: CC(C)n1nc(C(=O)Nc2c[nH]c3ccccc23)c2ccc(C(F)(F)F)cc21] | 387.1 |
| 6 | 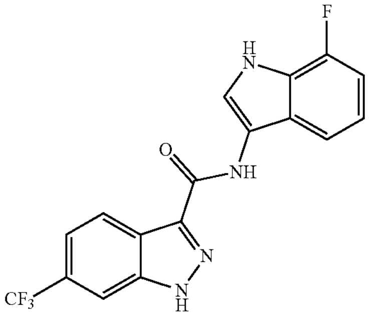 [SMILES: O=C(Nc1c[nH]c2c(F)cccc12)c1n[nH]c2cc(C(F)(F)F)ccc12] | 363.7 |
| 7 | 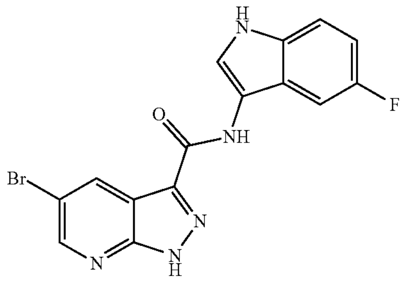 [SMILES: O=C(Nc1c[nH]c2ccc(F)cc12)c1n[nH]c2ncc(Br)cc12] | 374.7 |
| 8 | 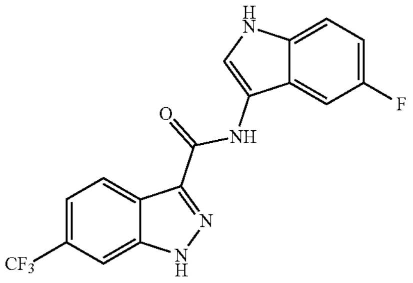 | 363.1 |

-continued
| Synthetic Example | Structure | LC-MS: m/z $[M + H]^+$ |
|---|---|---|
| 9 | 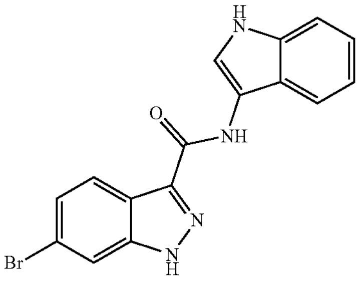 [SMILES: O=C(Nc1c[nH]c2ccccc12)c1n[nH]c2cc(Br)ccc12] | 355.7 |
| 10 | 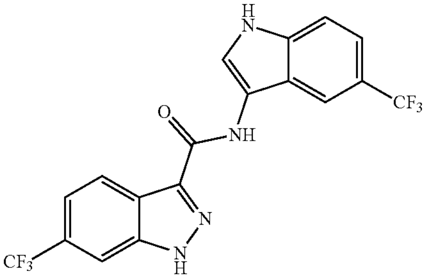 [SMILES: O=C(Nc1c[nH]c2ccc(C(F)(F)F)cc12)c1n[nH]c2cc(C(F)(F)F)ccc12] | 413.1 |
| 11 | 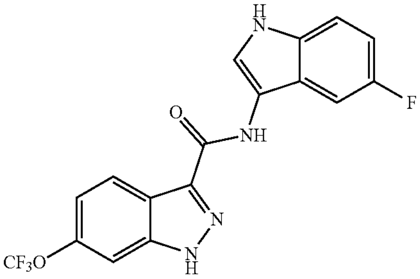 | 379.0 |
| 12 | 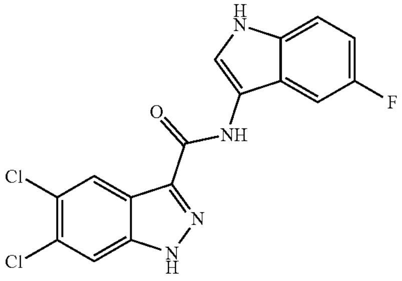 [SMILES: O=C(Nc1c[nH]c2ccc(F)cc12)c1n[nH]c2cc(Cl)c(Cl)cc12] | 363.0 |
| 13 | 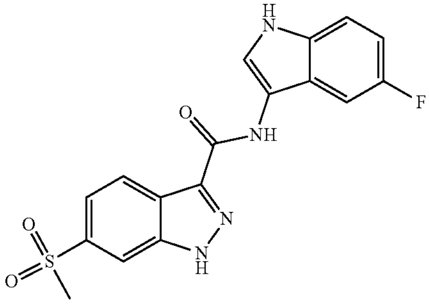 [SMILES: CS(=O)(=O)c1ccc2c(C(=O)Nc3c[nH]c4ccc(F)cc34)n[nH]c2c1] | 373.1 |

-continued
| Synthetic Example | Structure | LC-MS: m/z $[M + H]^+$ |
|---|---|---|
| 14 | 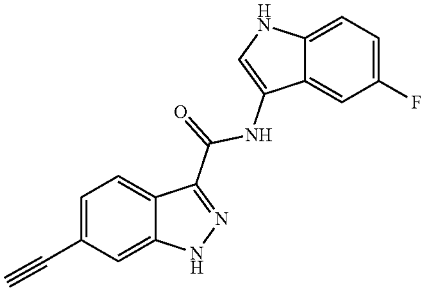 [SMILES: C#Cc1ccc2c(C(=O)Nc3c[nH]c4ccc(F)cc34)n[nH]c2c1] | 319.0 |
| 15 | 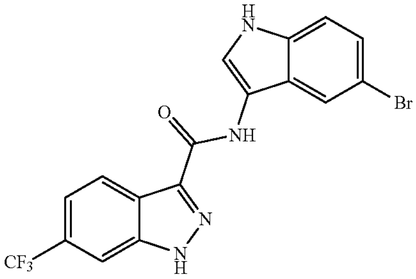 [SMILES: O=C(Nc1c[nH]c2ccc(Br)cc12)c1n[nH]c2cc(C(F)(F)F)ccc12] | 423.1 |
| 16 | 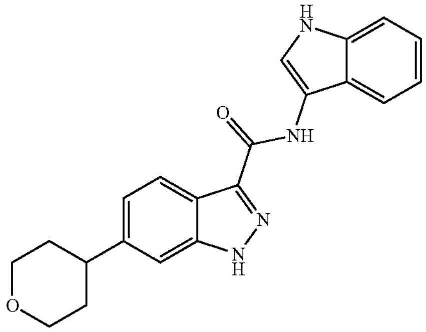 [SMILES: O=C(Nc1c[nH]c2ccccc12)c1n[nH]c2cc(C3CCOCC3)ccc12] | 361.1 |
| 17 | 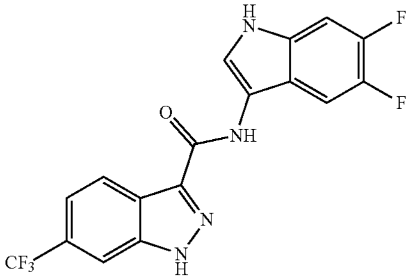 [SMILES: O=C(Nc1c[nH]c2cc(F)c(F)cc12)c1n[nH]c2cc(C(F)(F)F)ccc12] | 381.7 |
| 18 | 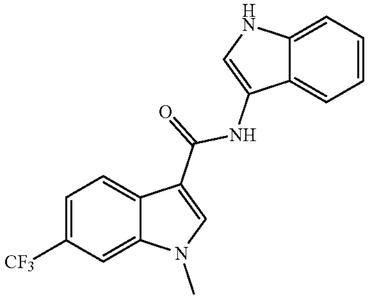 [SMILES: Cn1cc(C(=O)Nc2c[nH]c3ccccc23)c2ccc(C(F)(F)F)cc21] | 358.1 |

-continued
| Synthetic Example | Structure | LC-MS: m/z [M + H]$^+$ |
|---|---|---|
| 19 | 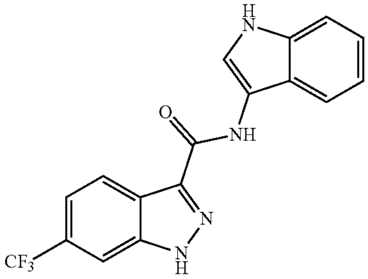 [SMILES: O=C(Nc1c[nH]c2ccccc12)c1n[nH]c2cc(C(F)(F)F)ccc12] | 344.0 |
| 20 | 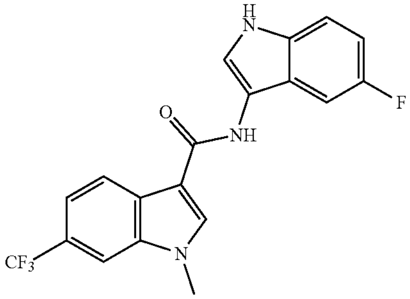 [SMILES: Cn1cc(C(=O)Nc2c[nH]c3ccc(F)cc23)c2ccc(C(F)(F)F)cc21] | 376.0 |
| 21 | 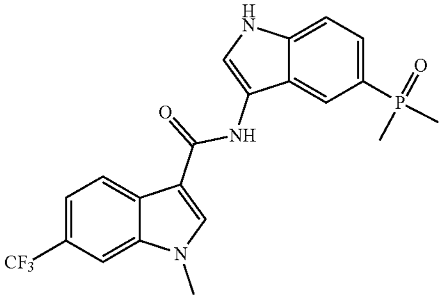 [SMILES: Cn1cc(C(=O)Nc2c[nH]c3ccc(P(C)(C)=O)cc23)c2ccc(C(F)(F)F)cc21] | 434.1 |
| 22 | 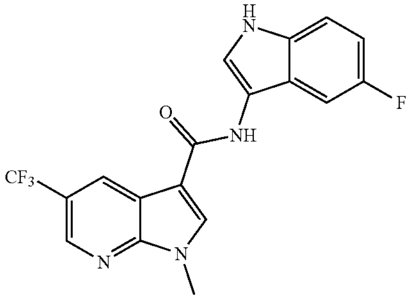 [SMILES: Cn1cc(C(=O)Nc2c[nH]c3ccc(F)cc23)c2cc(C(F)(F)F)cnc21] | 377.1 |
| 23 | 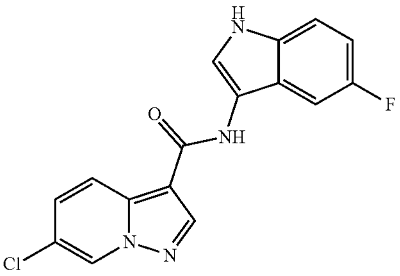 [SMILES: O=C(Nc1c[nH]c2ccc(F)cc12)c1cnn2cc(Cl)ccc12] | 329.0 |

-continued

| Synthetic Example | Structure | LC-MS: m/z [M + H]+ |
|---|---|---|
| 24 | 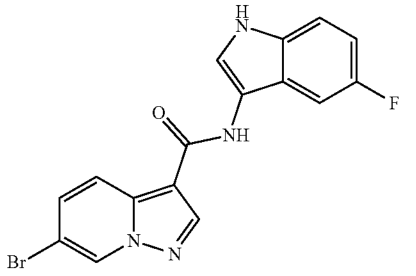 | 373.0 |

Example 25

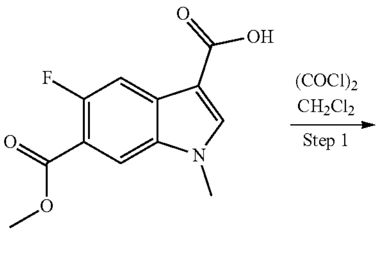

-continued

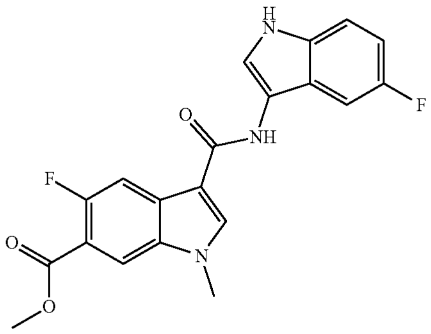

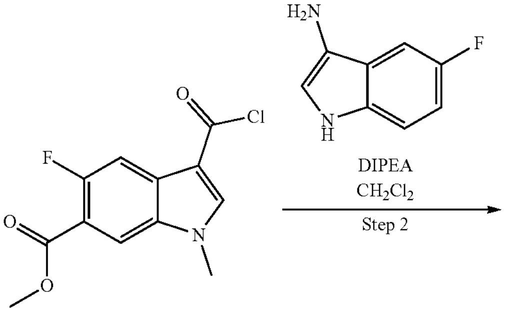

To a stirred suspension of 5-fluoro-6-methoxycarbonyl-1-methyl-indole-3-carboxylic acid (150 mg, 0.597 mmol) in $CH_2Cl_2$ (5.0 mL) were sequentially added oxalyl dichloride (227 mg, 151 μL, 1.79 mmol) and DMF (19.0 mg, 20.0 μL, 0.260 mmol) at 25° C. The resulting mixture was stirred at that temperature for 1 h before it was concentrated under vacuum to obtain the crude acid chloride. To a stirred solution of 5-fluoro-1H-indol-3-amine (100 mg, 0.667 mmol) in $CH_2Cl_2$ (5.0 mL) were sequentially added DIPEA (287 mg, 367 μL, 2.23 mmol) and the above prepared acid chloride at 25° C. The reaction mixture was stirred at that temperature for 16 h before it was quenched with water (30 mL) and then extracted with $CH_2Cl_2$ (30 mL×2). The combined organic layers were washed with brine, dried over anhydrous $Na_2SO_4$, and filtered. The filtrate was concentrated under vacuum. The residue was purified by silica gel chromatography eluting with EtOAc/petroleum ether (with EtOAc from 0 to 50%) in 25 min to give methyl 5-fluoro-3-[(5-fluoro-1H-indol-3-yl)carbamoyl]-1-methyl-indole-6-carboxylate (200 mg, 94% yield) as a light yellow solid. LC-MS: m/z $[M+H]^+$ 384.1.

The following compounds were prepared using the similar procedure disclosed in synthetic example 25 and their corresponding characterization data are presented in the table below.

| Synthetic Example | Structure | LC-MS: m/z [M + H]+ |
|---|---|---|
| 26 | 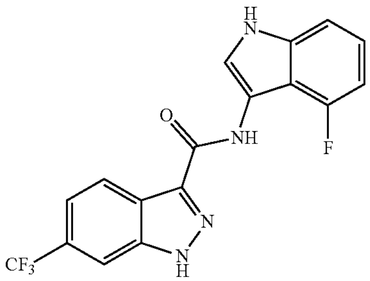 [SMILES: O=C(Nc1c[nH]c2cccc(F)c12)c1n[nH]c2cc(C(F)(F)F)ccc12] | 363.0 |
| 27 | 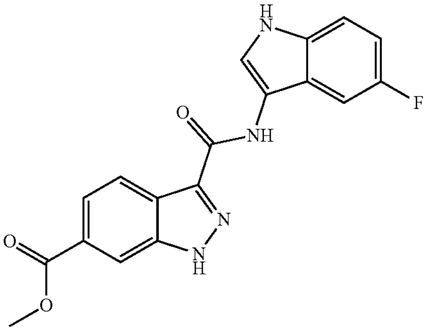 [SMILES: COC(=O)c1ccc2c(C(=O)Nc3c[nH]c4ccc(F)cc34)n[nH]c2c1] | 353.1 |
| 28 | 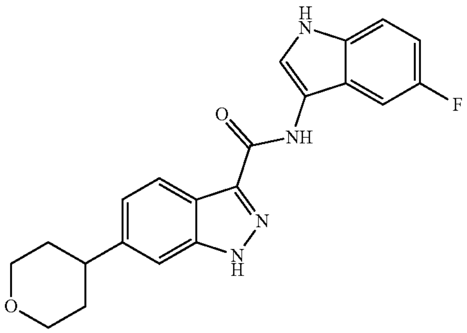 | 379.1 |
| 29 | 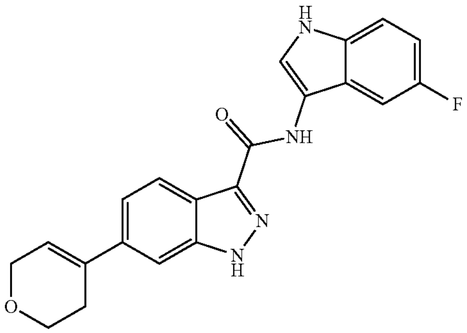 [SMILES: O=C(Nc1c[nH]c2ccc(F)cc12)c1n[nH]c2cc(C3=CCOCC3)ccc12] | 377.1 |

-continued
| Synthetic Example | Structure | LC-MS: m/z [M + H]$^+$ |
| --- | --- | --- |
| 30 | 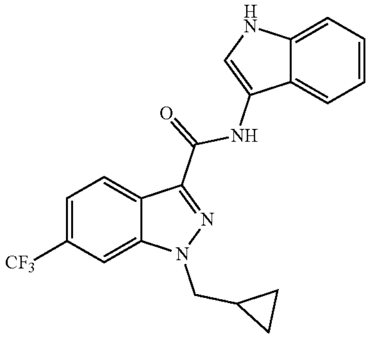 [SMILES: O=C(Nc1c[nH]c2ccccc12)c1nn(CC2CC2)c2cc(C(F)(F)F)ccc12] | 399.4 |
| 31 | 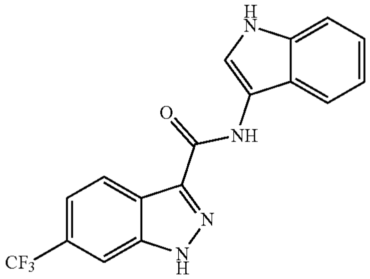 [SMILES: O=C(Nc1c[nH]c2ccccc12)c1n[nH]c2cc(C(F)(F)F)ccc12] | 345.1 |
| 32 | 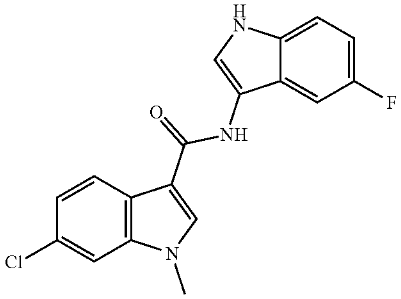 [SMILES: Cn1cc(C(=O)Nc2c[nH]c3ccc(F)cc23)c2ccc(Cl)cc21] | 342.0 |
| 33 | 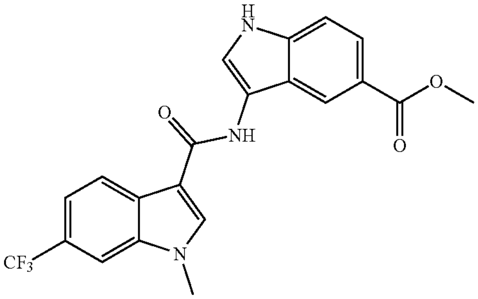 [SMILES: COC(=O)c1ccc2[nH]cc(NC(=O)c3cn(C)c4cc(C(F)(F)F)ccc34)c2c1] | 416.1 |
| 34 | 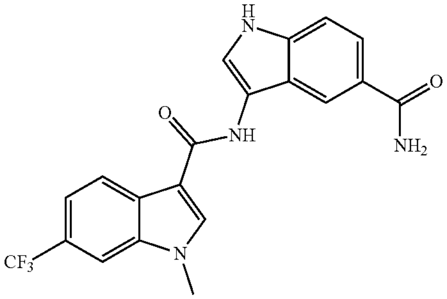 [SMILES: Cn1cc(C(=O)Nc2c[nH]c3ccc(C(N)=O)cc23)c2ccc(C(F)(F)F)cc21] | 401.1 |

-continued
| Synthetic Example | Structure | LC-MS: m/z $[M + H]^+$ |
|---|---|---|
| 35 | 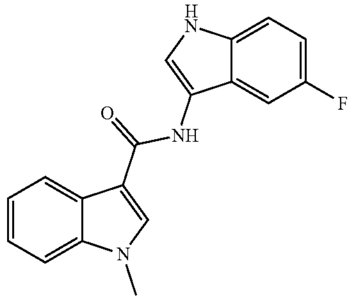 [SMILES: Cn1cc(C(=O)Nc2c[nH]c3ccc(F)cc23)c2ccccc21] | 308.3 |
| 36 | 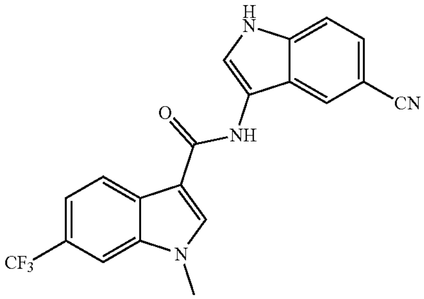 [SMILES: Cn1cc(C(=O)Nc2c[nH]c3ccc(C#N)cc23)c2ccc(C(F)(F)F)cc21] | 383.0 |
| 37 | 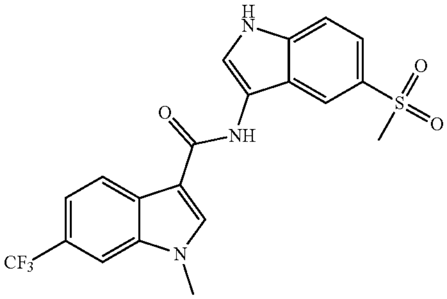 [SMILES: Cn1cc(C(=O)Nc2c[nH]c3ccc(S(C)(=O)=O)cc23)c2ccc(C(F)(F)F)cc21] | 436.0 |
| 38 | 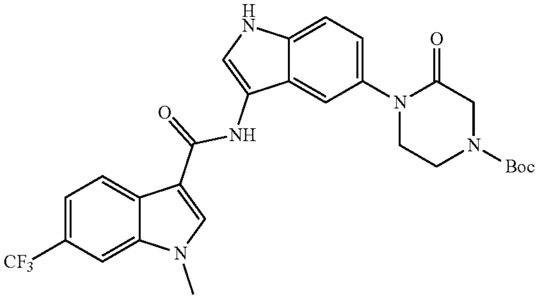 [SMILES: Cn1cc(C(=O)Nc2c[nH]c3ccc(N4CCN(C(=O)OC(C)(C)C)CC4=O)cc23)c2ccc(C(F)(F)F)cc21] | 500.0 |
| 39 | 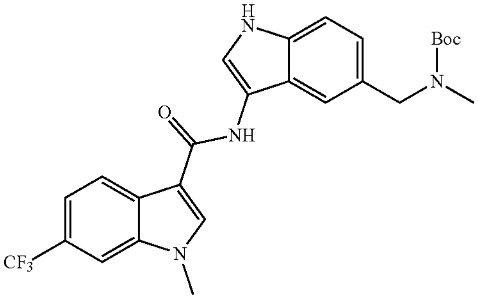 [SMILES: CN(Cc1ccc2[nH]cc(NC(=O)c3cn(C)c4cc(C(F)(F)F)ccc34)c2c1)C(=O)OC(C)(C)C] | 445.8 |

-continued
| Synthetic Example | Structure | LC-MS: m/z $[M + H]^+$ |
|---|---|---|
| 40 | 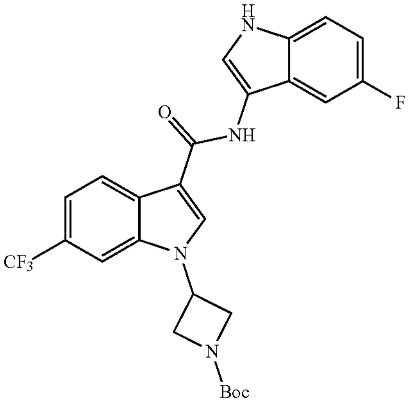 [SMILES: CC(C)(C)OC(=O)N1CC(n2cc(C(=O)Nc3c[nH]c4ccc(F)cc34)c3ccc(C(F)(F)F)cc32)C1] | 517.0 |
| 41 | 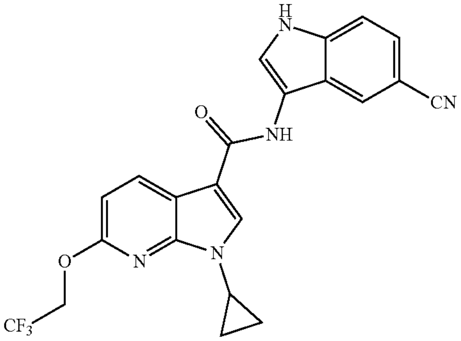 [SMILES: N#Cc1ccc2[nH]cc(NC(=O)c3cn(C4CC4)c4nc(OCC(F)(F)F)ccc34)c2c1] | 440.0 |
| 42 | 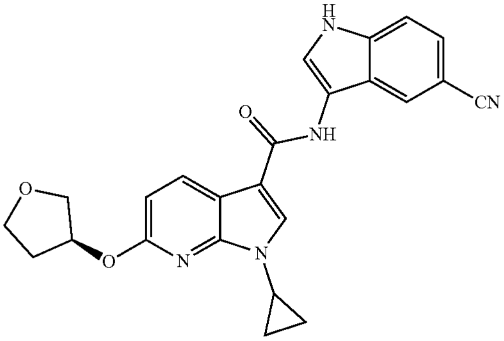 [SMILES: N#Cc1ccc2[nH]cc(NC(=O)c3cn(C4CC4)c4nc(O[C@H]5CCOC5)ccc34)c2c1] | 428.1 |
| 43 | 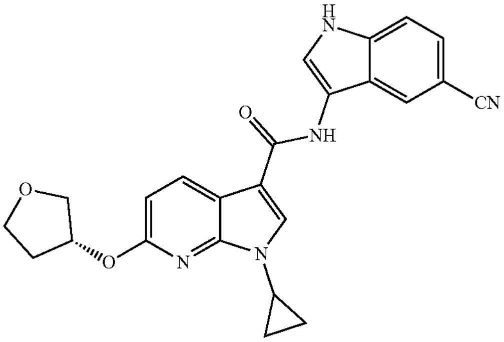 [SMILES: N#Cc1ccc2[nH]cc(NC(=O)c3cn(C4CC4)c4nc(O[C@@H]5CCOC5)ccc34)c2c1] | 428.1 |

-continued
| Synthetic Example | Structure | LC-MS: m/z [M + H]$^+$ |
|---|---|---|
| 44 | 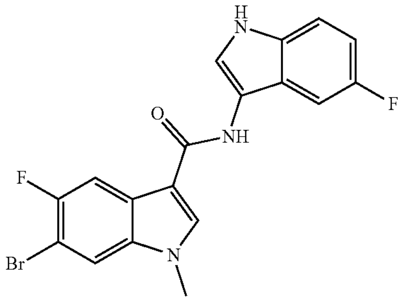 [SMILES: Cn1cc(C(=O)Nc2c[nH]c3ccc(F)cc23)c2cc(F)c(Br)cc21] | 404.1 |
| 45 | 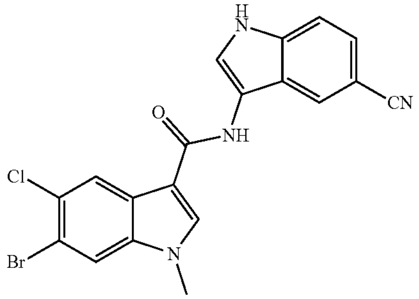 [SMILES: Cn1cc(C(=O)Nc2c[nH]c3ccc(C#N)cc23)c2cc(Cl)c(Br)cc21] | 427.0 |
| 46 | 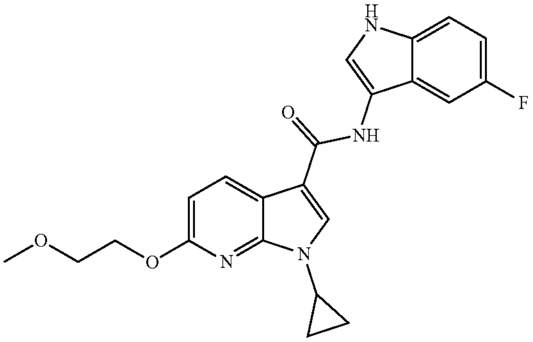 [SMILES: COCCOc1ccc2c(C(=O)Nc3c[nH]c4ccc(F)cc34)cn(C3CC3)c2n1] | 409.1 |
| 47 | 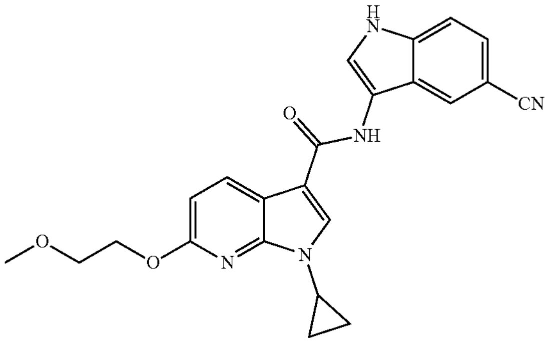 [SMILES: COCCOc1ccc2c(C(=O)Nc3c[nH]c4ccc(C#N)cc34)cn(C3CC3)c2n1] | 416.1 |

-continued
| Synthetic Example | Structure | LC-MS: m/z $[M + H]^+$ |
|---|---|---|
| 48 | 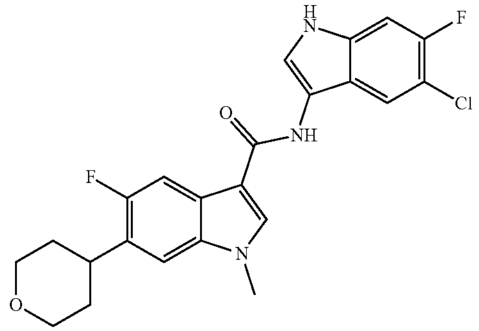 [SMILES: Cn1cc(C(=O)Nc2c[nH]c3cc(F)c(Cl)cc23)c2cc(F)c(C3CCOCC3)cc21] | 444.1 |
| 49 | 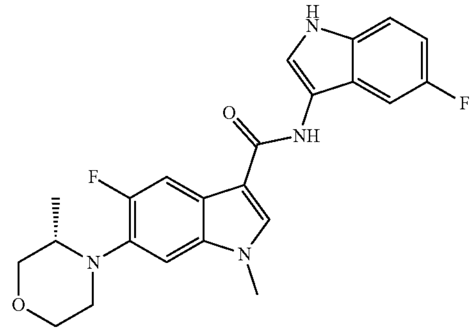 [SMILES: C[C@H]1COCCN1c1cc2c(cc1F)c(C(=O)Nc1c[nH]c3ccc(F)cc13)cn2C] | 425.1 |
| 50 | 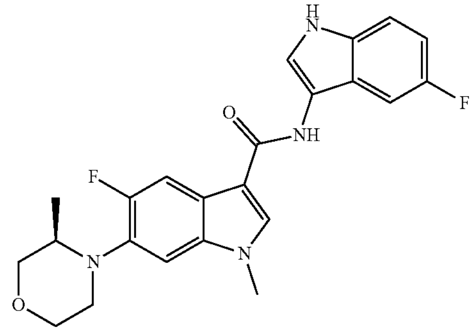 [SMILES: C[C@@H]1COCCN1c1cc2c(cc1F)c(C(=O)Nc1c[nH]c3ccc(F)cc13)cn2C] | 425.1 |
| 51 | 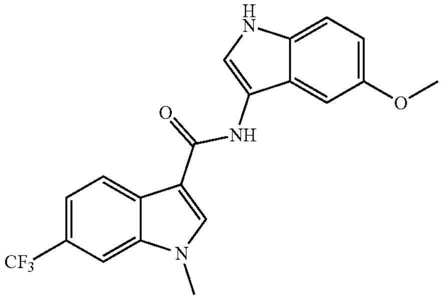 [SMILES: COc1ccc2[nH]cc(NC(=O)c3cn(C)c4cc(C(F)(F)F)ccc34)c2c1] | 388.1 |

-continued
| Synthetic Example | Structure | LC-MS: m/z [M + H]$^+$ |
|---|---|---|
| 52 | 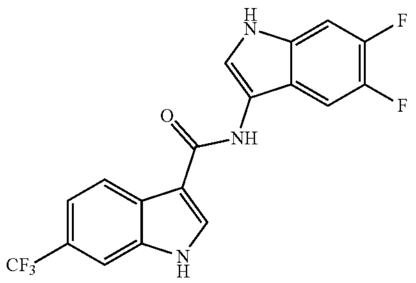 [SMILES: O=C(Nc1c[nH]c2cc(F)c(F)cc12)c1c[nH]c2cc(C(F)(F)F)ccc12] | 380.0 |
| 53 | 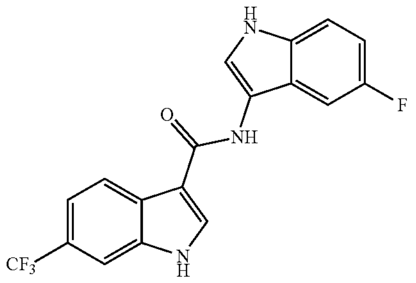 [SMILES: O=C(Nc1c[nH]c2ccc(F)cc12)c1c[nH]c2cc(C(F)(F)F)ccc12] | 362.1 |
| 54 | 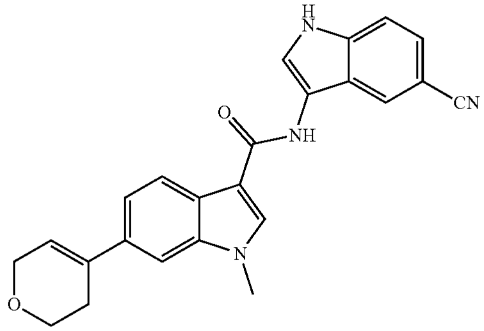 [SMILES: Cn1cc(C(=O)Nc2c[nH]c3ccc(C#N)cc23)c2ccc(C3=CCOCC3)cc21] | 397.1 |
| 55 | 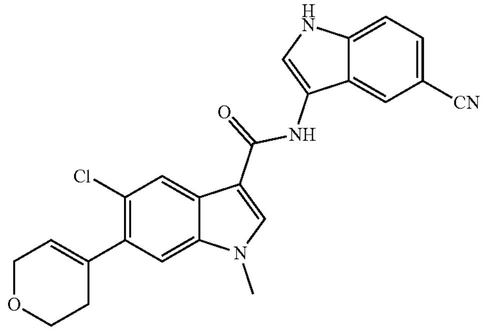 [SMILES: Cn1cc(C(=O)Nc2c[nH]c3ccc(C#N)cc23)c2cc(Cl)c(C3=CCOCC3)cc21] | 431.0 |
| 56 | 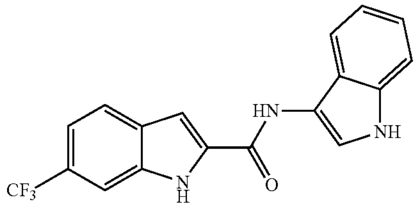 [SMILES: O=C(Nc1c[nH]c2ccccc12)c1cc2ccc(C(F)(F)F)cc2[nH]1] | 344.0 |

-continued

| Synthetic Example | Structure | LC-MS: m/z [M + H]$^+$ |
|---|---|---|
| 57 | 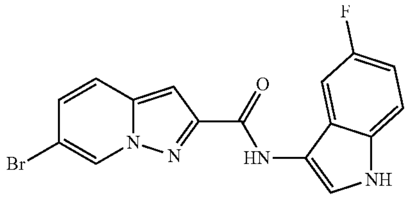 [SMILES: O=C(Nc1c[nH]c2ccc(F)cc12)c1cc2ccc(Br)cn2n1] | 373.1 |
| 58 | 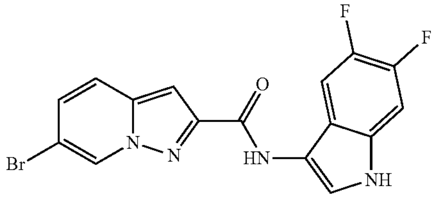 [SMILES: O=C(Nc1c[nH]c2cc(F)c(F)cc12)c1cc2ccc(Br)cn2n1] | 391.0 |
| 59 | 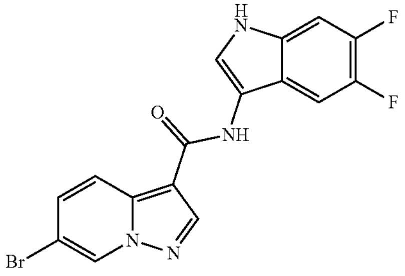 [SMILES: O=C(Nc1c[nH]c2cc(F)c(F)cc12)c1cnn2cc(Br)ccc12] | 391.0 |

Example 60

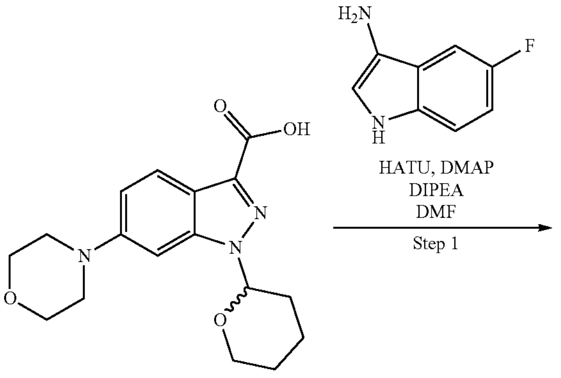

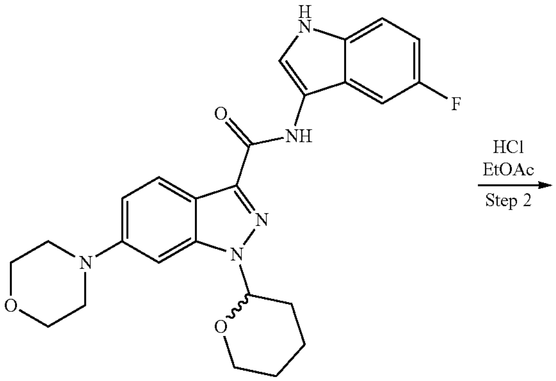

-continued

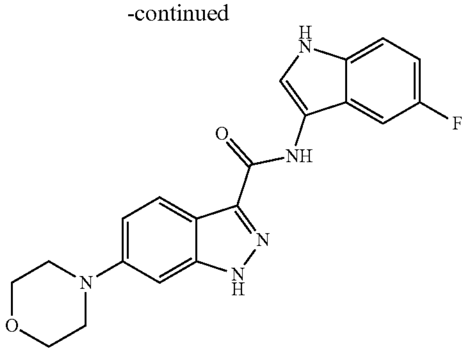

Step 1

To a stirred solution of 6-morpholino-1-tetrahydropyran-2-yl-indazole-3-carboxylic acid (60.0 mg, 0.181 mmol) in DMF (3.0 mL) was added DMAP (2.2 mg, 0.018 mmol), DIPEA (94.1 mg, 120 µL, 0.728 mmol), HATU (208 mg, 0.543 mmol) and 5-fluoro-1H-indol-3-amine (32.6 mg, 0.217 mmol) at 25° C. The reaction mixture was stirred at that temperature for 1 h before it was quenched with water (10 mL) and then extracted with EtOAc (15 mL×2). The combined organic phases were washed with brine, dried over anhydrous $Na_2SO_4$, and filtered. The filtrate was concentrated under reduced pressure. The residue was purified by Pre-TLC (EtOAc/petroleum ether=1:2) to give N-(5-fluoro-1H-indol-3-yl)-6-morpholino-1-tetrahydropyran-2-yl-indazole-3-carboxamide (40.0 mg, 48% yield) as a yellow solid. LC-MS: m/z [M+H]$^+$ 464.1.

Step 2

To a stirred solution of N-(5-fluoro-1H-indol-3-yl)-6-morpholino-1-tetrahydropyran-2-yl-indazole-3-carboxamide (40.0 mg, 0.0863 mmol) in EtOAc (2.0 mL) was added HCl (1.0 mL, 1.0 M in EtOAc, 1.0 mmol) at 25° C. The reaction mixture was stirred at that temperature for 36 h before it was concentrated under reduced pressure. The residue was purified by Prep-HPLC eluting with $CH_3CN$/water (with $CH_3CN$ from 25% to 55%) in 8 min to give N-(5-fluoro-1H-indol-3-yl)-6-morpholino-1H-indazole-3-carboxamide (7.0 mg, 19% yield) as a yellow solid. LC-MS: m/z $[M+H]^+$ 380.1.

The following compounds were prepared using the similar procedure disclosed in synthetic example 60 and their corresponding characterization data are presented in the table below.

| Synthetic Example | Structure | LC-MS: m/z [M+H]+ |
|---|---|---|
| 61 | 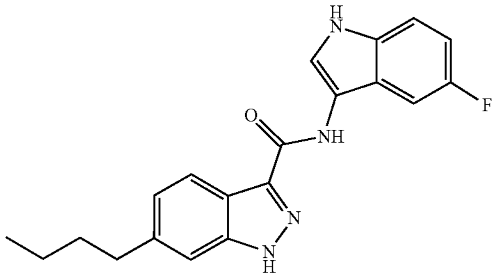 [SMILES: CCCCc1ccc2c(C(=O)Nc3c[nH]c4ccc(F)cc34)n[nH]c2c1] | 351.1 |
| 62 | 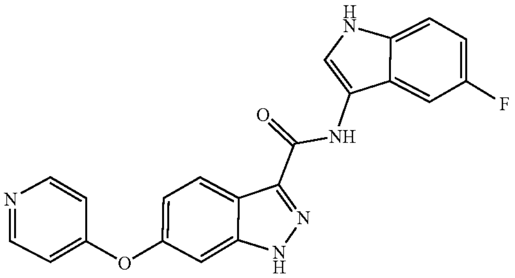 [SMILES: O=C(Nc1c[nH]c2ccc(F)cc12)c1n[nH]c2cc(Oc3ccncc3)ccc12] | 388.1 |
| 63 | 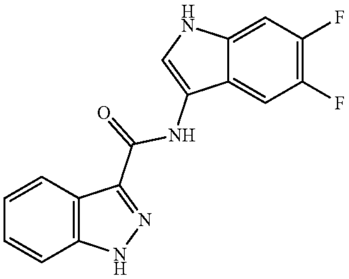 [SMILES: O=C(Nc1c[nH]c2cc(F)c(F)cc12)c1n[nH]c2ccccc12] | 313.8 |
| 64 | 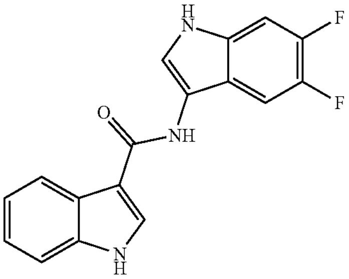 [SMILES: O=C(Nc1c[nH]c2cc(F)c(F)cc12)c1c[nH]c2ccccc12] | 312.8 |

-continued

| Synthetic Example | Structure | LC-MS: m/z [M+H]+ |
|---|---|---|
| 65 | 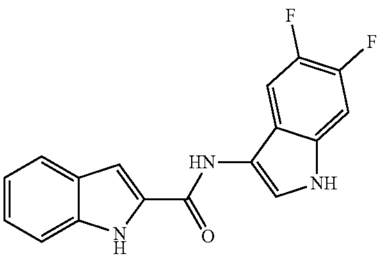 [SMILES: O=C(Nc1c[nH]c2cc(F)c(F)cc12)c1cc2ccccc2[nH]1] | 312.8 |
| 66 | 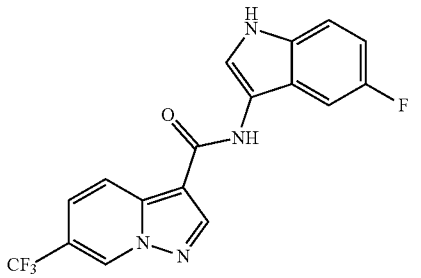 [SMILES: O=C(Nc1c[nH]c2ccc(F)cc12)c1cnn2cc(C(F)(F)F)ccc12] | 363.1 |

Example 67

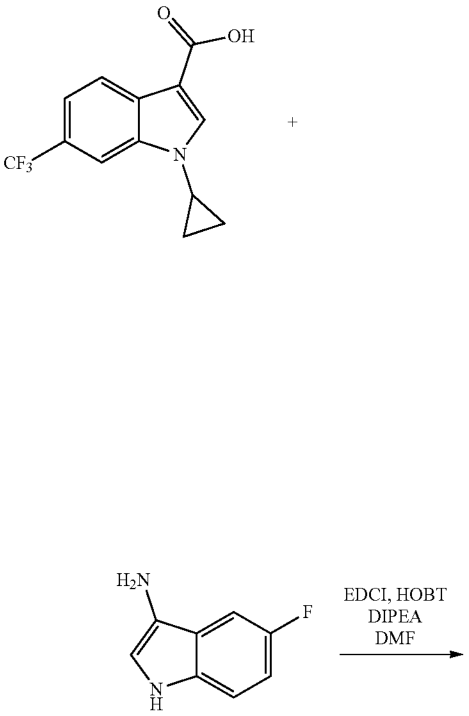

-continued

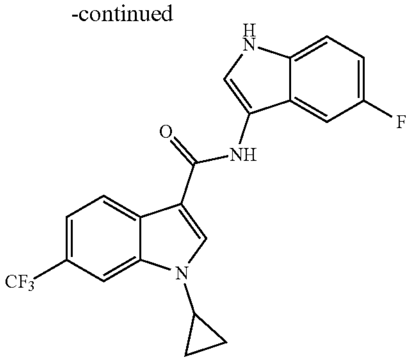

To a stirred solution of 1-cyclopropyl-6-(trifluoromethyl) indole-3-carboxylic acid (120 mg, 0.446 mmol) in DMF (5.0 mL) were sequentially added and 5-fluoro-1H-indol-3-amine hydrochloride (108 mg, 0.579 mmol), EDCI (256 mg, 1.34 mmol), HOBT (181 mg, 1.34 mmol) and DIPEA (461 mg, 590 μL, 3.57 mmol) at 25° C. The reaction mixture was stirred at that temperature for 12 h before it was quenched with water (30 mL) and extracted with EtOAc (50 mL×2). The combined organic layers were washed with brine (100 mL), dried over anhydrous $Na_2SO_4$, and filtered. The filtrate was concentrated under reduced pressure. The residue was purified by silica gel chromatography eluting with EtOAc/petroleum ether (with EtOAc from 0 to 50%) in 25 min to afford a crude product which was further purified by Prep-HPLC eluting with $CH_3CN$/water (with $CH_3CN$ from 50% to 80%) in 8 min to give 1-cyclopropyl-N-(5-fluoro-1H- indol-3-yl)-6-(trifluoromethyl)indole-3-carboxamide (90.0 mg, 50% yield) as a white solid. LC-MS: m/z $[M+H]^+$ 402.0.
The following compounds were prepared using the similar procedure disclosed in synthetic example 67 and their corresponding characterization data are presented in the table below.
| Synthetic Example | Structure | LC-MS: m/z $[M + H]^+$ |
| --- | --- | --- |
| 68 | 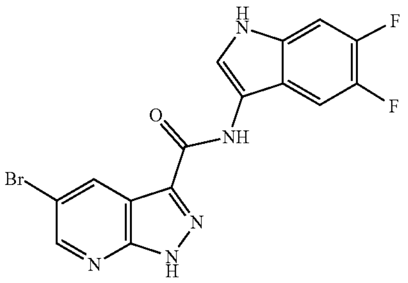 [SMILES: O=C(Nc1c[nH]c2cc(F)c(F)cc12)c1n[nH]c2ncc(Br)cc12] | 392.1 |
| 69 | 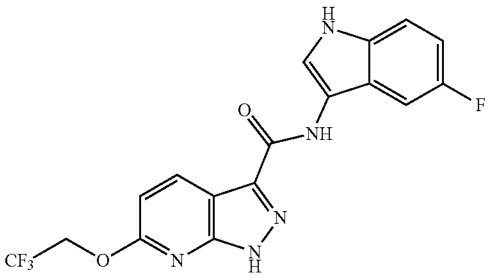 [SMILES: O=C(Nc1c[nH]c2ccc(F)cc12)c1n[nH]c2nc(OCC(F)(F)F)ccc12] | 394.0 |
| 70 | 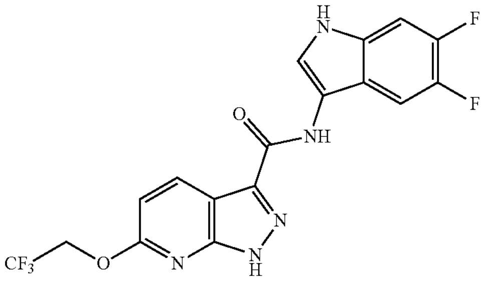 [SMILES: O=C(Nc1c[nH]c2cc(F)c(F)cc12)c1n[nH]c2nc(OCC(F)(F)F)ccc12] | 412.0 |
| 71 | 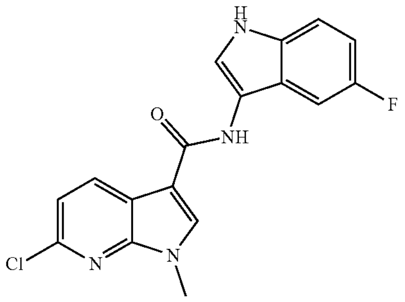 [SMILES: Cn1cc(C(=O)Nc2c[nH]c3ccc(F)cc23)c2ccc(Cl)nc21] | 343.0 |

-continued
| Synthetic Example | Structure | LC-MS: m/z [M + H]$^+$ |
|---|---|---|
| 72 | 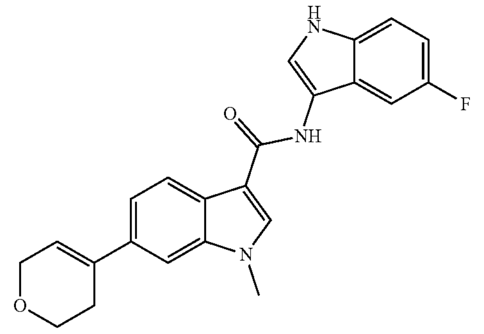 [SMILES: Cn1cc(C(=O)Nc2c[nH]c3ccc(F)cc23)c2ccc(C3=CCOCC3)cc21] | 390.1 |
| 73 | 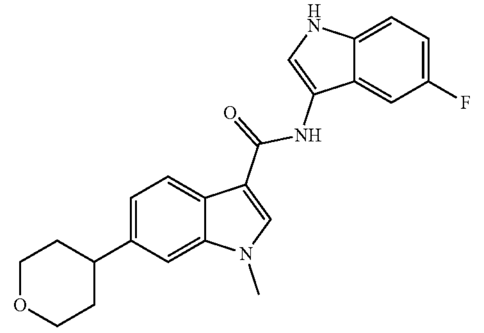 [SMILES: Cn1cc(C(=O)Nc2c[nH]c3ccc(F)cc23)c2ccc(C3CCOCC3)cc21] | 392.1 |
| 74 | 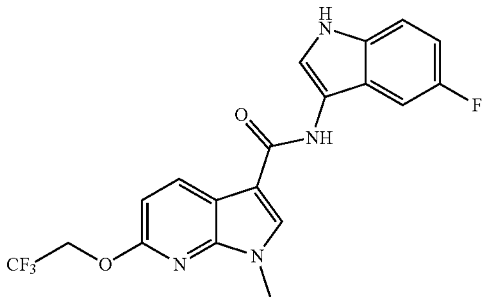 [SMILES: Cn1cc(C(=O)Nc2c[nH]c3ccc(F)cc23)c2ccc(OCC(F)(F)F)nc21] | 407.0 |
| 75 | 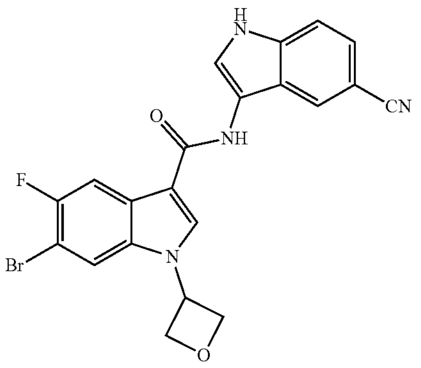 [SMILES: N#Cc1ccc2[nH]cc(NC(=O)c3cn(C4COC4)c4cc(Br)c(F)cc34)c2c1] | 453.1 |

-continued
| Synthetic Example | Structure | LC-MS: m/z $[M + H]^+$ |
| --- | --- | --- |
| 76 | 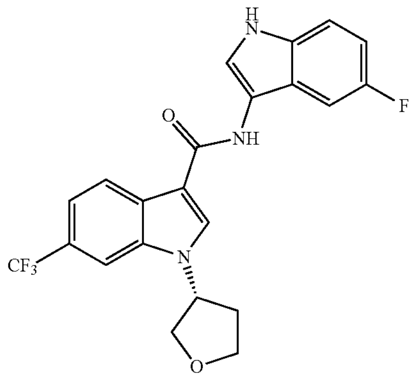 [SMILES: O=C(Nc1c[nH]c2ccc(F)cc12)c1cn([C@@H]2CCOC2)c2cc(C(F)(F)F)ccc12] | 432.0 |
| 77 | 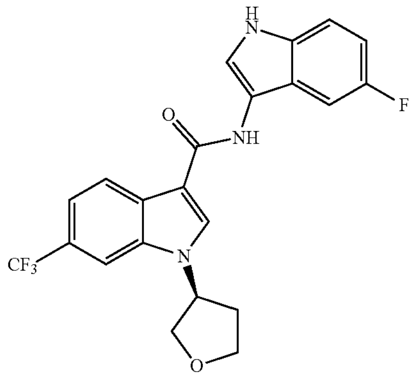 [SMILES: O=C(Nc1c[nH]c2ccc(F)cc12)c1cn([C@H]2CCOC2)c2cc(C(F)(F)F)ccc12] | 432.0 |
| 78 | 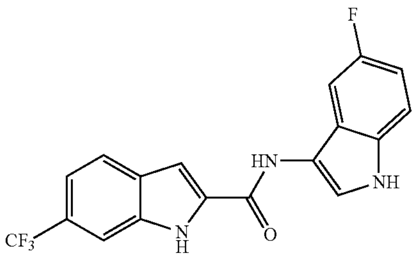 [SMILES: O=C(Nc1c[nH]c2ccc(F)cc12)c1cc2ccc(C(F)(F)F)cc2[nH]1] | 362.0 |
| 79 | 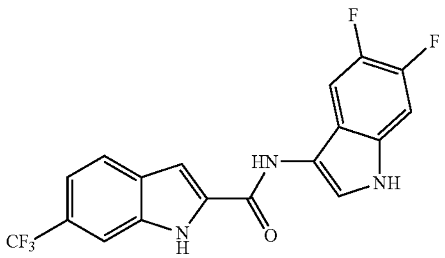 [SMILES: O=C(Nc1c[nH]c2cc(F)c(F)cc12)c1cc2ccc(C(F)(F)F)cc2[nH]1] | 380.0 |

-continued
| Synthetic Example | Structure | LC-MS: m/z $[M + H]^+$ |
|---|---|---|
| 80 | 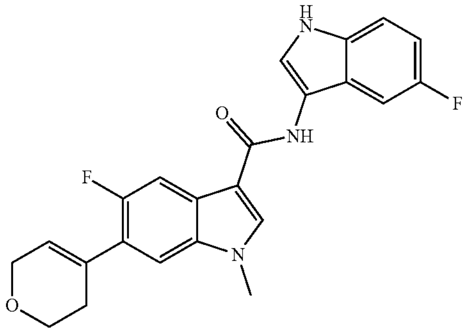 [SMILES: Cn1cc(C(=O)Nc2c[nH]c3ccc(F)cc23)c2cc(F)c(C3=CCOCC3)cc21] | 408.0 |
| 81 | 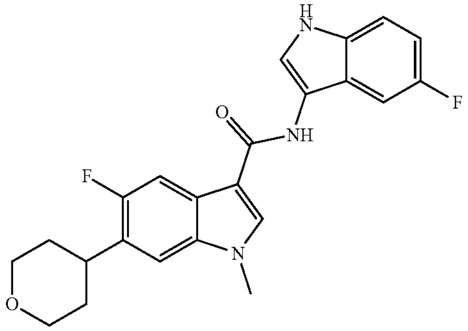 [SMILES: Cn1cc(C(=O)Nc2c[nH]c3ccc(F)cc23)c2cc(F)c(C3CCOCC3)cc21] | 410.1 |
| 82 | 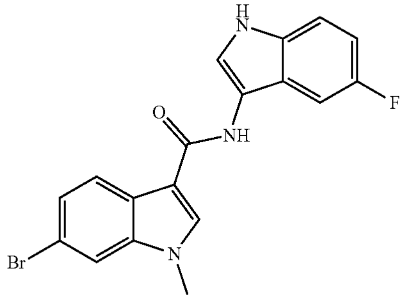 | 386.0 |
| 83 | 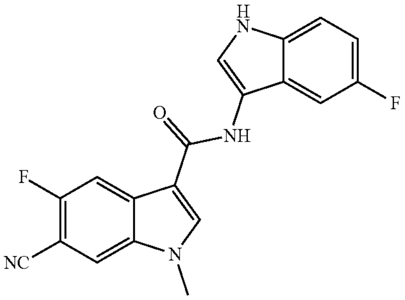 [SMILES: Cn1cc(C(=O)Nc2c[nH]c3ccc(F)cc23)c2cc(F)c(C#N)cc21] | 351.1 |

-continued

| Synthetic Example | Structure | LC-MS: m/z $[M + H]^+$ |
|---|---|---|
| 84 | 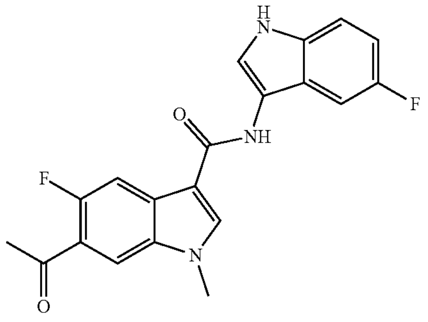 [SMILES: CC(=O)c1cc2c(cc1F)c(C(=O)Nc1c[nH]c3ccc(F)cc13)cn2C] | 368.1 |
| 85 | 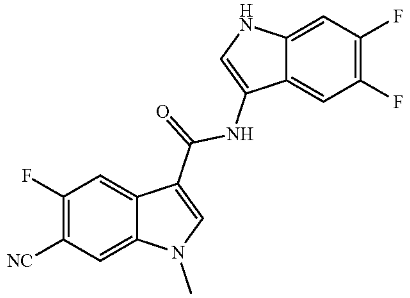 [SMILES: Cn1cc(C(=O)Nc2c[nH]c3cc(F)c(F)cc23)c2cc(F)c(C#N)cc21] | 369.1 |

Post-Amidation Transformations

Example 86

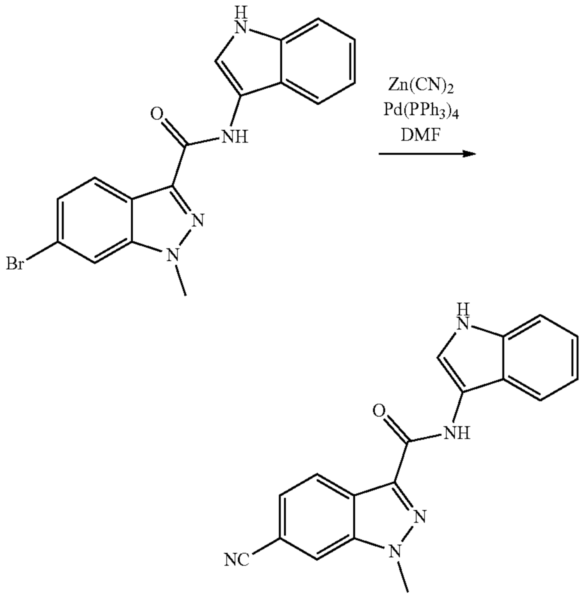

To a stirred solution of 6-bromo-N-(1H-indol-3-yl)-1-methyl-indazole-3-carboxamide (27.0 mg, 0.0731 mmol) in DMF (3.0 mL) were added $Zn(CN)_2$ (20.0 mg, 0.170 mmol) and $Pd(PPh_3)_4$ (10.0 mg, 0.00865 mmol) at 25° C. The resulting mixture was warmed to 110° C. and stirred at that temperature for 12 h. The mixture was cooled to 25° C., poured into water (30 mL) and then extracted with EtOAc (20 mL×3). The combined organic phases were washed with brine, dried over anhydrous $Na_2SO_4$, and filtered. The filtrate was concentrated under reduced pressure. The residue was purified by Prep-HPLC eluting with $CH_3CN$/water (with $CH_3CN$ from 45% to 75%) in 8 min to give 6-cyano-N-(1H-indol-3-yl)-1-methyl-indazole-3-carboxamide (5.8 mg, 23% yield) as a yellow solid. LC-MS: m/z $[M+H]^+$ 316.1.

Example 87

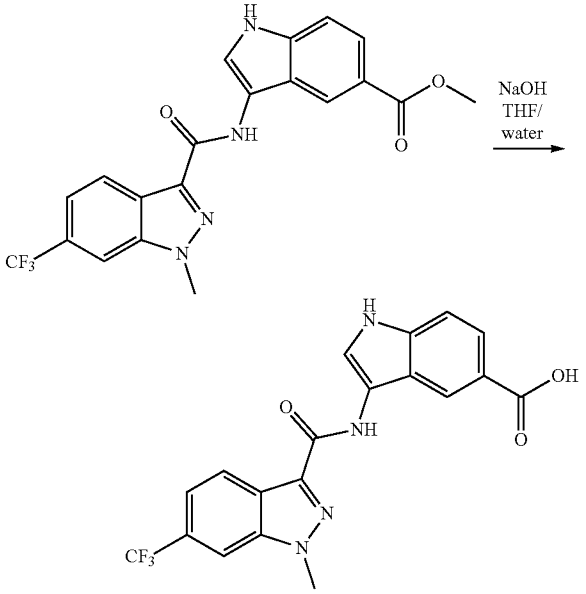

To a stirred solution of methyl 3-[[1-methyl-6-(trifluoromethyl)indole-3-carbonyl]amino]-1H-indole-5-carboxylate (50.0 mg, 0.120 mmol) in THF (2.0 mL) was added aq. NaOH (1.0 mL, 0.6 M, 0.60 mmol) at 25° C. The reaction mixture was stirred at that temperature for 16 h before it was acidified with aq. HCl (1.0 M) to pH=4 and then concentrated under reduced pressure. The residue was purified by Prep-HPLC eluting with $CH_3CN$/water (with $CH_3CN$ from 35% to 65%) in 8 min to give 3-[[1-methyl-6-(trifluoromethyl)indole-3-carbonyl]amino]-1H-indole-5-carboxylic acid (14.4 mg, 29% yield) as an white solid.

LC-MS: m/z $[M+H]^+$ 402.1.

Examples 88-89

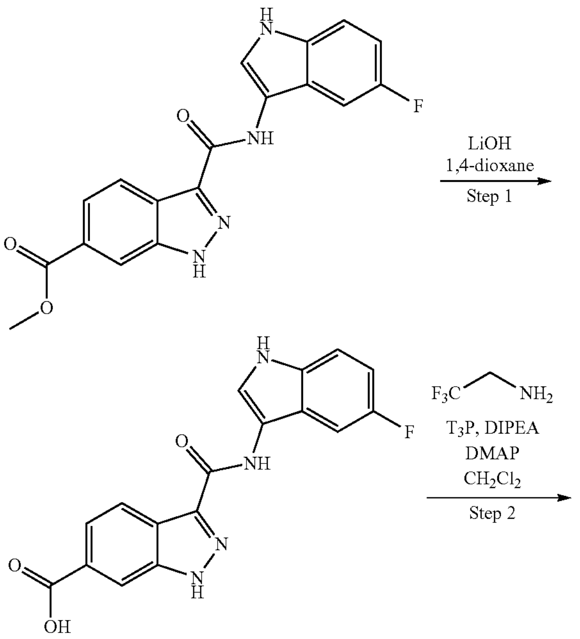

Example 88

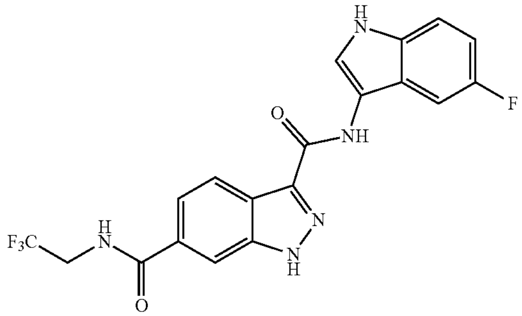

Example 89

Step 1, Example 88

To a stirred solution of methyl 3-[(5-fluoro-1H-indol-3-yl)carbamoyl]-1H-indazole-6-carboxylate (41.0 mg, 0.116 mmol) in 1,4-dioxane (1.0 mL) was added a solution of aq. LiOH (700 μL, 1.0 M, 0.700 mmol) at 25° C. The resulting mixture was warmed to 50° C. and stirred at that temperature for 30 min. The mixture was cooled and concentrated under reduced pressure. The residue was diluted with water (20 mL) and extracted EtOAc (20 mL). The aqueous phase was separated and acidified with aq. HCl (1.0 M) to pH=3 and extracted with EtOAc (15 mL×3). The combined organic layers were washed with brine, dried over anhydrous $Na_2SO_4$, and filtered. The filtrate was concentrated under vacuum to afford 3-[(5-fluoro-1H-indol-3-yl)carbamoyl]-1H-indazole-6-carboxylic acid (32 mg, 81% yield) as a white solid which was used in the next step without further purification.

LC-MS: m/z $[M+H]^+$ 339.0.

Step 2, Example 89

To a stirred solution of 3-[(5-fluoro-1H-indol-3-yl)carbamoyl]-1H-indazole-6-carboxylic acid (28.0 mg, 0.0828 mmol) in $CH_2Cl_2$ (4.0 mL) were sequentially added DIPEA (49.0 mg, 62.7 μL, 0.379 mmol), DMAP (3.0 mg, 0.025 mmol), T3P (124 mg, 50% wt. in EtOAc, 0.195 mmol) and 2,2,2-trifluoroethanamine (13.0 mg, 0.131 mmol) at 25° C. The resulting mixture was warmed to 40° C. and stirred at that temperature for 2 h. The mixture was cooled to 25° C., quenched with water (10 mL) and extracted with $CH_2Cl_2$ (10 mL×3). The combined organic layers were washed with brine, dried over anhydrous $Na_2SO_4$, and filtered. The filtrate was concentrated under reduced pressure. The residue was purified by Pre-TLC (EtOAc/petroleum ether=1:2) to afford N-(6-fluoro-1H-indol-3-yl)-N-(2,2,2-trifluoroethyl)-1H-indazole-3,6-dicarboxamide (10.4 mg, 30% yield) as a gray solid.

LC-MS: m/z $[M+H]^+$ 420.0.

Examples 90-92

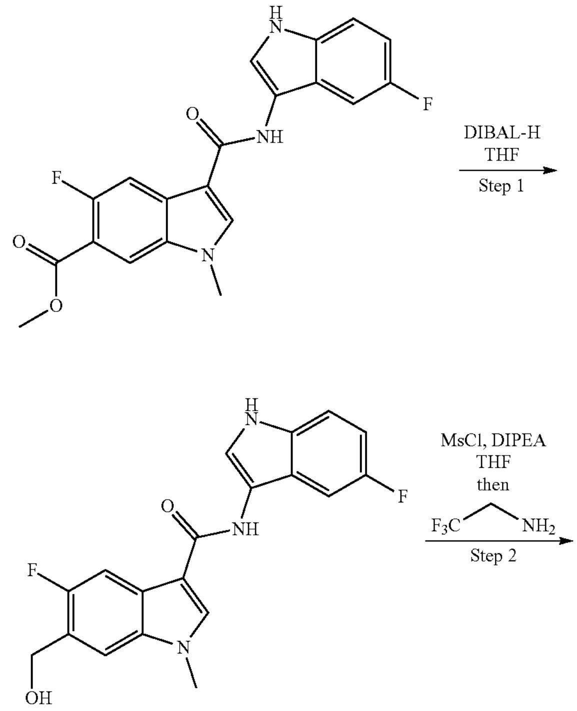

Example 90

-continued

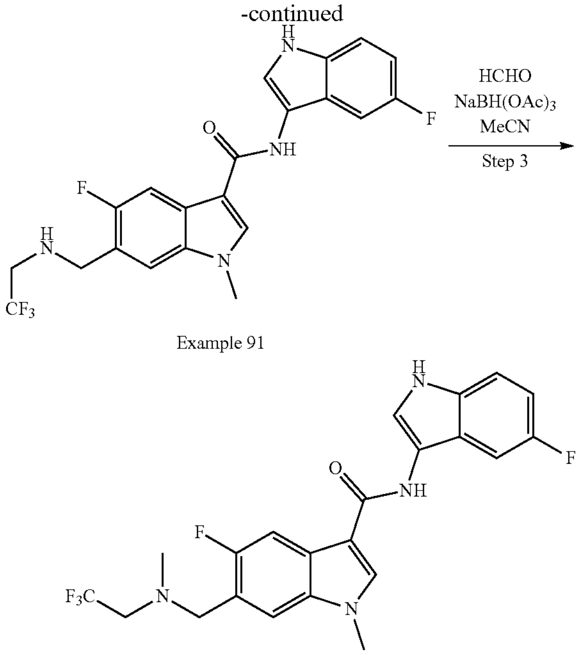

Example 91

Example 92

Step 1, Example 90

To a stirred solution of methyl 5-fluoro-3-[(5-fluoro-1H-indol-3-yl)carbamoyl]-1-methyl-indole-6-carboxylate (200 mg, 0.0521 mmol) in THF (8.0 mL) was added DIBAL-H (2.09 mL, 1.0 M in THF, 2.09 mmol) at 25° C. The resulting mixture was stirred at that temperature for 16 h before it was quenched with saturated aq. potassium sodium tartrate (10.0 mL), diluted with EtOAc (20 mL), and stirred at 25° C. for 30 min. The aqueous layer was extracted with EtOAc (30 mL×2). The combined organic layers were washed with brine, dried over anhydrous $Na_2SO_4$, and filtered. The filtrate was concentrated under vacuum. The residue was purified by silica gel chromatography eluting with MeOH/$CH_2Cl_2$ (with MeOH from 0 to 15%) in 20 min to give 5-fluoro-N-(5-fluoro-1H-indol-3-yl)-6-(hydroxymethyl)-1-methyl-indole-3-carboxamide (60.0 mg, 33% yield) as a light yellow solid. LC-MS: m/z $[M+H]^+$ 356.1.

Step 2, Example 91

To a stirred solution of 5-fluoro-N-(5-fluoro-1H-indol-3-yl)-6-(hydroxymethyl)-1-methyl-indole-3-carboxamide (50.0 mg, 0.140 mmol) in THF (2.0 mL) were sequentially added DIPEA (42.7 mg, 54.6 μL, 0.422 mmol) and MsCl (24.2 mg, 16.3 μL, 0.211 mmol) at 0° C. The resulting mixture was warmed to 25° C. and stirred at that temperature for 1 h. The mixture was concentrated under vacuum to obtain the crude methanesulfonate as a yellow oil. To the above prepared methanesulfonate was added 2,2,2-trifluoroethan-1-amine (177 mg, 140 μL, 1.79 mmol) at 25° C. The resulting mixture was stirred at that temperature for 16 h before it was quenched with water (10 mL) and extracted with EtOAc (20 mL×3). The combined organic layers were washed with brine, dried over anhydrous $Na_2SO_4$, and filtered. The filtrate was concentrated under vacuum. The residue was purified by Prep-HPLC eluting with $CH_3CN$/water (with $CH_3CN$ from 18% to 28%) in 6 min to give 5-fluoro-N-(5-fluoro-1H-indol-3-yl)-1-methyl-6-[(2,2,2-trifluoroethylamino)methyl]indole-3-carboxamide (7.4 mg, 19% yield) as a white solid. LC-MS: m/z $[M+H]^+$ 437.1.

Step 3, Example 92

To a stirred solution of 5-fluoro-N-(5-fluoro-1H-indol-3-yl)-1-methyl-6-[(2,2,2-trifluoroethylamino)methyl]indole-3-carboxamide (10.0 mg, 0.0223 mmol) in MeCN (5.0 mL) were sequentially added formaldehyde (69 mg, 2.3 mmol, 0.063 mL) and $NaBH(OAc)_3$ (14.6 mg, 0.0688 mmol) at 25° C. The reaction mixture was stirred at that temperature for 12 h before it was quenched with saturated aq. $NaHCO_3$ (10 mL) and extracted with EtOAc (10 mL×3). The combined organic layers were washed with brine (10 mL), dried over anhydrous $Na_2SO_4$, and filtered. The filtrate was concentrated under reduced pressure. The residue was firstly purified by silica gel chromatography eluting with EtOAc/petroleum ether (with EtOAc from 0 to 100%) in 20 min, and then by PrepPrep-HPLC eluting with $CH_3CN$/water (with $CH_3CN$ from 5% to 95%) in 10 min to give 5-fluoro-N-(5-fluoro-1H-indol-3-yl)-1-methyl-6-[[methyl(2,2,2-trifluoroethyl)amino]methyl]indole-3-carboxamide (3.0 mg, 29% yield) as a white solid. LC-MS: m/z $[M+H]^+$ 451.7.

The following compounds were prepared using the similar procedure disclosed in synthetic example 91 and their corresponding characterization data are presented in the table below.

| Synthetic Example | Structure | LC-MS: m/z $[M + H]^+$ |
|---|---|---|
| 93 | 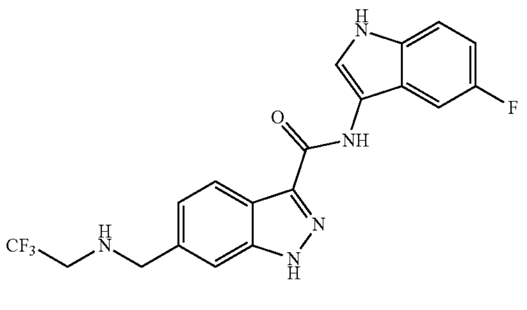 [SMILES: O=C(Nc1c[nH]c2ccc(F)cc12)c1n[nH]c2cc(CNCC(F)(F)F)ccc12] | 406.0 |

-continued
| Synthetic Example | Structure | LC-MS: m/z $[M + H]^+$ |
|---|---|---|
| 94 | 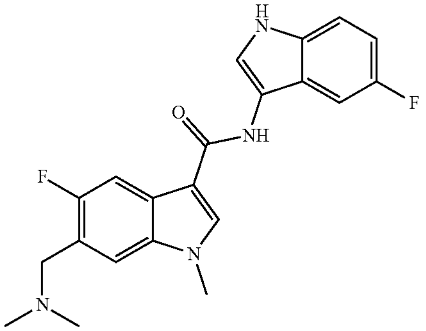 [SMILES: CN(C)Cc1cc2c(cc1F)c(C(=O)Nc1c[nH]c3ccc(F)cc13)cn2C] | 383.1 |
| 95 | 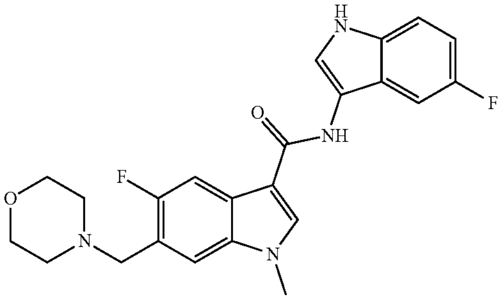 [SMILES: Cn1cc(C(=O)Nc2c[nH]c3ccc(F)cc23)c2cc(F)c(CN3CCOCC3)cc21] | 425.1 |
| 96 | 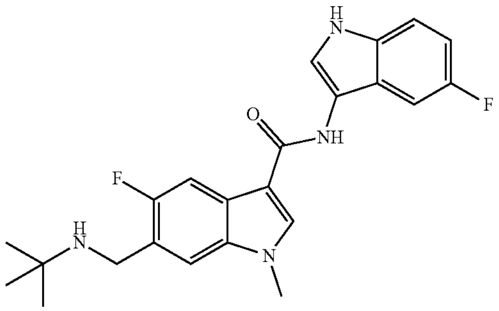 [SMILES: Cn1cc(C(=O)Nc2c[nH]c3ccc(F)cc23)c2cc(F)c(CNC(C)(C)C)cc21] | 411.1 |

Example 97

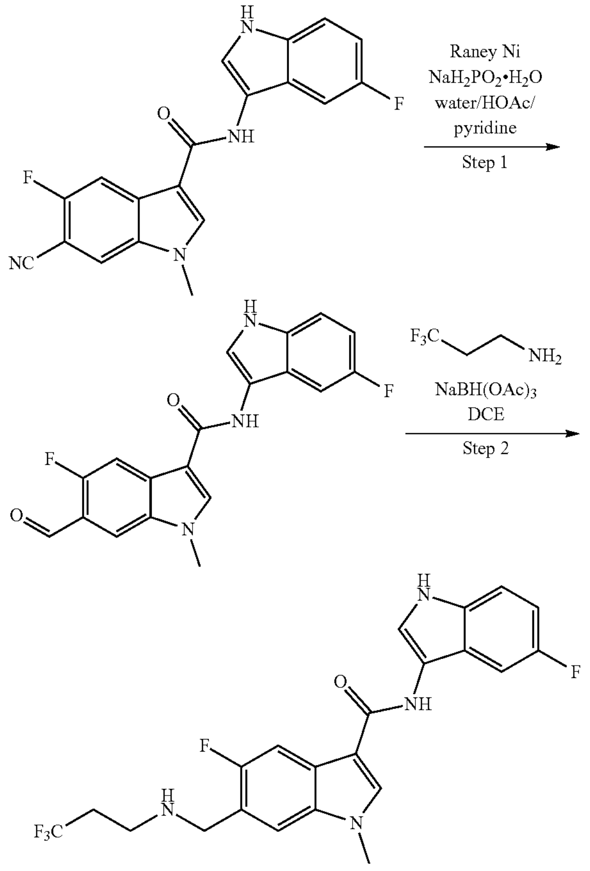

Step 1

To a stirred suspension of 6-cyano-5-fluoro-N-(5-fluoro-1H-indol-3-yl)-1-methyl-indole-3-carboxamide (25.0 mg, 0.0714 mmol) in water (3.0 mL), HOAc (3.0 mL) and pyridine (6.0 mL) were sequentially added $NaH_2PO_2 \cdot H_2O$ (14.8 mg, 143 mmol) and Raney nickel (30 mg, 0.36 mmol) at 25° C. The mixture was warmed to 45° C. and stirred at that temperature for 3 h. The reaction mixture was filtered through a pad of Celite and extracted with EtOAc (20 mL×3). The combined organic layers were washed with brine (30 mL), dried over anhydrous $Na_2SO_4$, and filtered. The filtrate was concentrated under reduced pressure. The residue was purified by silica gel chromatography eluting with EtOAc/petroleum ether (with EtOAc from 0 to 100%) in 20 min to give 5-fluoro-N-(5-fluoro-1H-indol-3-yl)-6-formyl-1-methyl-indole-3-carboxamide (15 mg, 59% yield) as a yellow solid. LC-MS: m/z [M+H]+ 354.1.

Step 2

To a stirred solution of 5-fluoro-N-(5-fluoro-1H-indol-3-yl)-6-formyl-1-methyl-indole-3-carboxamide (5.0 mg, 0.014 mmol) in DCE (2.0 mL) were sequentially added 3,3,3-trifluoropropan-1-amine (25.0 mg, 0.221 mmol) and $NaBH(OAc)_3$ (28.1 mg, 0.133 mmol) at 25° C. The reaction mixture was stirred at that temperature for 12 h before it was quenched with saturated aq. $NaHCO_3$ (10 mL) and extracted with EtOAc (10 mL×3). The combined organic layers were washed with brine (10 mL), dried over anhydrous $Na_2SO_4$, and filtered. The filtrate was concentrated under reduced pressure. The residue was purified by PrepPrep-HPLC eluting with $CH_3CN$/water (with $CH_3CN$ from 5% to 95%) in 10 min to give 5-fluoro-N-(5-fluoro-1H-indol-3-yl)-1-methyl-6-[(3,3,3-trifluoropropylamino)methyl]indole-3-carboxamide (2.0 mg, 10% yield) as a white solid. LC-MS: m/z $[M+H]^+$ 451.7.

The following compounds were prepared using the similar procedure disclosed in synthetic example 97.

| Synthetic Example | Structure | LC-MS: m/z $[M + H]^+$ |
|---|---|---|
| 98 | 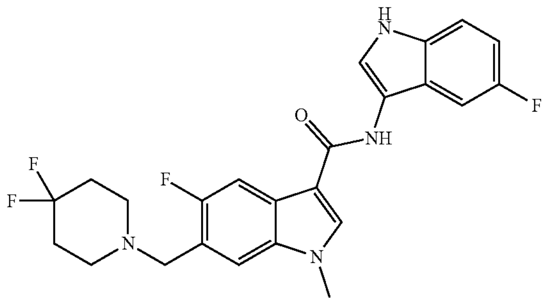 [SMILES: Cn1cc(C(=O)Nc2c[nH]c3ccc(F)cc23)c2cc(F)c(CN3CCC(F)(F)CC3)cc21] | 459.7 |
| 99 | 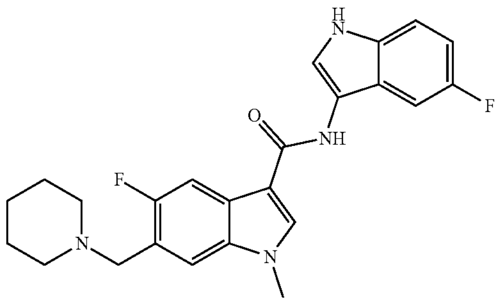 [SMILES: Cn1cc(C(=O)Nc2c[nH]c3ccc(F)cc23)c2cc(F)c(CN3CCCCC3)cc21] | 423.8 |

-continued
| Synthetic Example | Structure | LC-MS: m/z $[M + H]^+$ |
| --- | --- | --- |
| 100 | 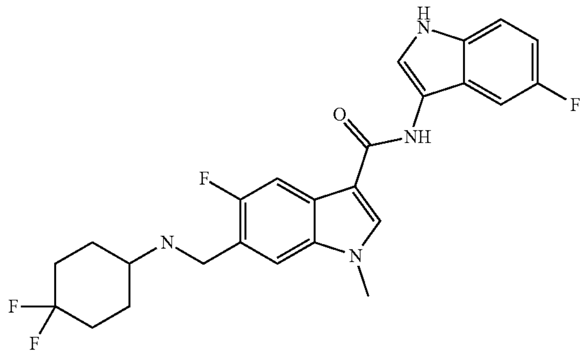 [SMILES: Cn1cc(C(=O)Nc2c[nH]c3ccc(F)cc23)c2cc(F)c(CNC3CCC(F)(F)CC3)cc21] | 473.7 |
| 101 | 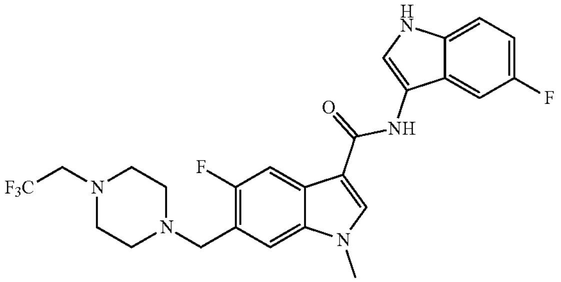 [SMILES: Cn1cc(C(=O)Nc2c[nH]c3ccc(F)cc23)c2cc(F)c(CN3CCN(CC(F)(F)F)CC3)cc21] | 506.7 |
| 102 | 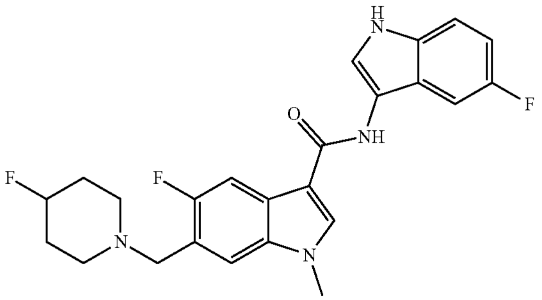 [SMILES: Cn1cc(C(=O)Nc2c[nH]c3ccc(F)cc23)c2cc(F)c(CN3CCC(F)CC3)cc21] | 441.8 |
| 103 | 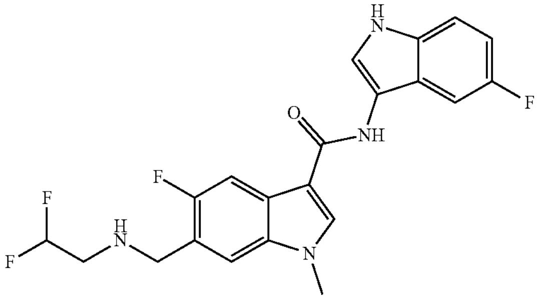 [SMILES: Cn1cc(C(=O)Nc2c[nH]c3ccc(F)cc23)c2cc(F)c(CNCC(F)F)cc21] | 419.7 |
| 104 | 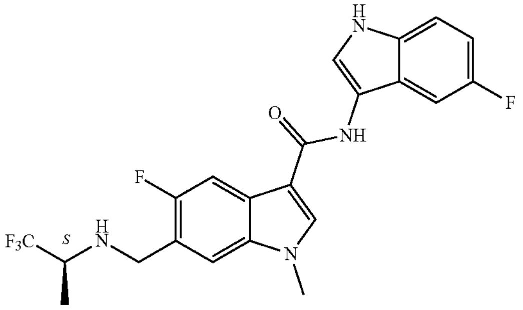 | 451.7 |

-continued

| Synthetic Example | Structure | LC-MS: m/z $[M + H]^+$ |
| --- | --- | --- |
| 105 | 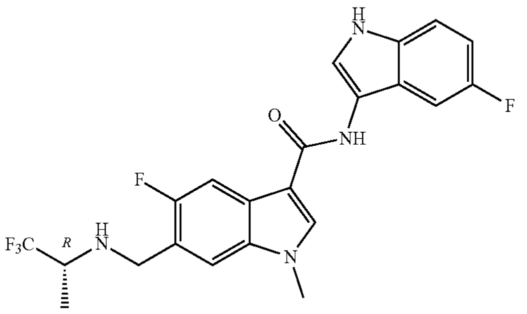 | 451.7 |
| 106 | 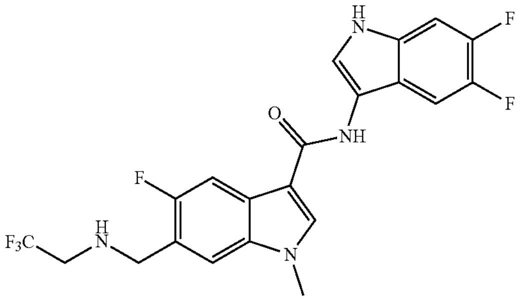 [SMILES: Cn1cc(C(=O)Nc2c[nH]c3cc(F)c(F)cc23)c2cc(F)c(CNCC(F)(F)F)cc21] | 455.7 |

Example 107

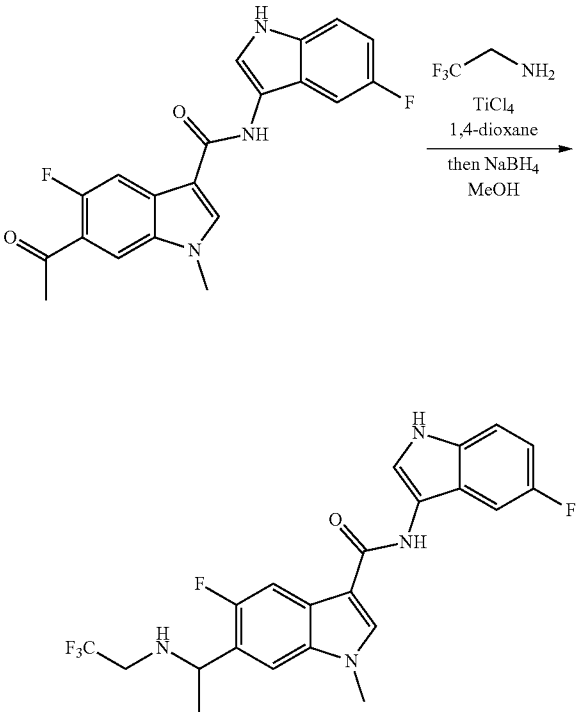

rac

To a stirred solution of 6-acetyl-5-fluoro-N-(5-fluoro-1H-indol-3-yl)-1-methyl-indole-3-carboxamide (5.0 mg, 0.014 mmol) in 1,4-dioxane (2.0 mL) were sequentially added 2,2,2-trifluoroethanamine (6.7 mg, 0.068 mmol, 5.4 μL) and $TiCl_4$ (27 μL, 1.0 M in $CH_2Cl_2$, 0.027 mmol) at 25° C. The resulting mixture was stirred at that temperature for 3 h before it was filtered. The filtrate was diluted with Methanol (2.0 mL) before $NaBH_4$ (5.0 mg, 0.13 mmol) was added at 25° C. The resulting mixture was stirred at that temperature for 5 min before it was quenched with saturated aq. $NaHCO_3$ (5.0 mL). The mixture was extracted with EtOAc (10 mL×3). The combined organic phases were washed with brine, dried over anhydrous $Na_2SO_4$, and filtered. The filtrate was concentrated under reduced pressure. The residue was purified by Prep-HPLC eluting with $CH_3CN$/water (with $CH_3CN$ from 5% to 95%) in 10 min to give rac-5-fluoro-N-(5-fluoro-1H-indol-3-yl)-1-methyl-6-[1-(2,2,2-trifluoroethylamino)ethyl]indole-3-carboxamide (1.6 mg, 26% yield) as a white solid. LC-MS: m/z $[M+H]^+$ 451.7.

Examples 108 and 109

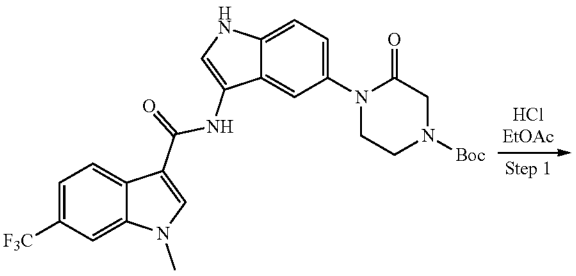

-continued

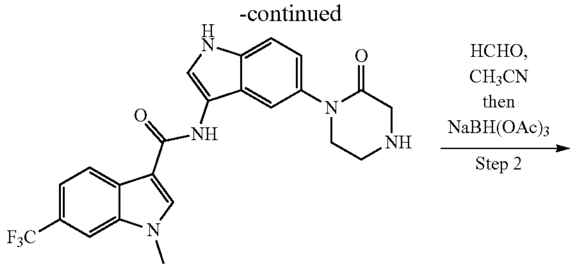

Example 108

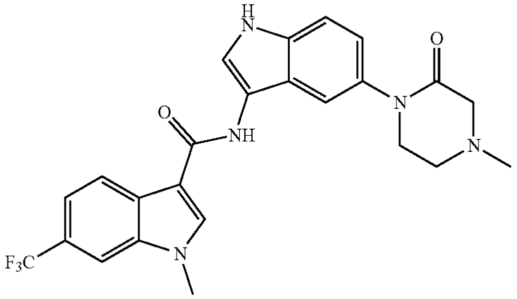

Example 109

Step 1, Example 108

To a stirred solution of tert-butyl 4-[3-[[1-methyl-6-(trifluoromethyl)indole-3-carbonyl]amino]-1H-indol-5-yl]-3-oxo-piperazine-1-carboxylate (20.0 mg, 0.0360 mmol) in EtOAc (2.0 mL) was added HCl (2.0 mL, 4.0 M in EtOAc, 8.0 mmol) at 25° C. The mixture was stirred at that temperature for 2 h before it was concentrated under reduced pressure. The residue was purified by Prep-HPLC eluting with $CH_3CN$/water (with $CH_3CN$ from 35% to 65%) in 8 min to give 1-methyl-N-[5-(2-oxopiperazin-1-yl)-1H-indol-3-yl]-6-(trifluoromethyl)indole-3-carboxamide (13.0 mg, 79% yield) as a yellow solid.

LC-MS: m/z $[M+H]^+$ 456.0.

Step 2, Example 109

To a stirred solution of 1-methyl-N-[5-(2-oxopiperazin-1-yl)-1H-indol-3-yl]-6-(trifluoromethyl)indole-3-carboxamide (5.0 mg, 0.011 mmol) in $CH_3CN$ (1.0 mL) was added aq. formaldehyde (200 μL, 37% wt., 2.71 mmol) at 25° C. The mixture was stirred at that temperature for 2 h before $NaBH(OAc)_3$ (7.0 mg, 0.033 mmol) was added. The resultant mixture was stirred at 25° C. for 3 h before it was quenched with saturated aq. $NaHCO_3$ (5 mL) and extracted with EtOAc (10 mL×3). The combined organic phases were washed with brine (10 mL), dried over anhydrous $Na_2SO_4$, and filtered. The filtrate was concentrated under vacuum. The residue was purified by Prep-HPLC eluting with $CH_3CN$/water (with $CH_3CN$ from 5% to 95%) in 10 min to afford N-(5-fluoro-1H-indol-3-yl)-6-[(2,2,2-trifluoroethylamino)methyl]-1H-indazole-3-carboxamide (2.3 mg, 45% yield) as a white solid.

LC-MS: m/z $[M+H]^+$ 470.8.

Examples 110 and 111

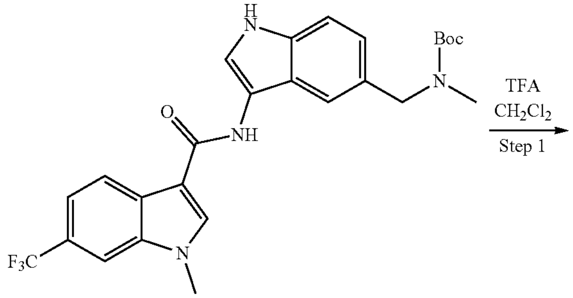

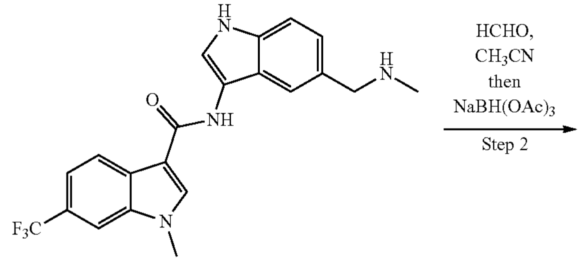

Example 110

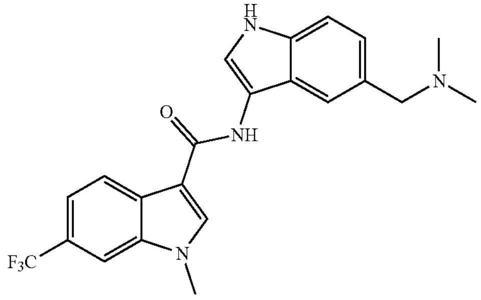

Example 111

Step 1, Example 110

To a stirred solution of tert-butyl methyl((3-(1-methyl-6-(trifluoromethyl)-1H-indole-3-carboxamido)-1H-indol-5-yl)methyl)carbamate (17.0 mg, 0.0340 mmol) in $CH_2Cl_2$ (2.0 mL) was added TFA (307 mg, 200 μL, 2.69 mmol) at 25° C. The mixture was stirred at that temperature for 2 h before it was concentrated under reduced pressure. The residue was purified by Prep-HPLC eluting with $CH_3CN$/water (with $CH_3CN$ from 5% to 95%) in 10 min to give 1-methyl-N-(5-((methylamino)methyl)-1H-indol-3-yl)-6-(trifluoromethyl)-1H-indole-3-carboxamide (10.0 mg, 77% yield) as a yellow solid. LC-MS: m/z $[M+H]^+$ 401.8.

Step 2, Example 111

To a stirred solution of 1-methyl-N-(5-((methylamino)methyl)-1H-indol-3-yl)-6-(trifluoromethyl)-1H-indole-3-carboxamide (5.0 mg, 0.013 mmol) in $CH_3CN$ (1.0 mL) was added aq. formaldehyde (200 μL, 37% wt., 2.71 mmol) at 25° C. The mixture was stirred at that temperature for 2 h before $NaBH(OAc)_3$ (8.0 mg, 0.0377 mmol) was added. The resultant mixture was stirred at 25° C. for 3 h before it was quenched with saturated aq. $NaHCO_3$ (5 mL) and extracted with EtOAc (10 mL×3). The combined organic phases were washed with brine (10 mL), dried over anhydrous $Na_2SO_4$, and filtered. The filtrate was concentrated under vacuum. The residue was purified by Prep-HPLC eluting with $CH_3CN$/water (with $CH_3CN$ from 5% to 95%) in 10 min to afford N-(5-((dimethylamino)methyl)-1H-indol-3-yl)-1-methyl-6-(trifluoromethyl)-1H-indole-3-carboxamide (2.1 mg, 41% yield) as a white solid. LC-MS: m/z $[M+H]^+$ 415.8.

Example 112

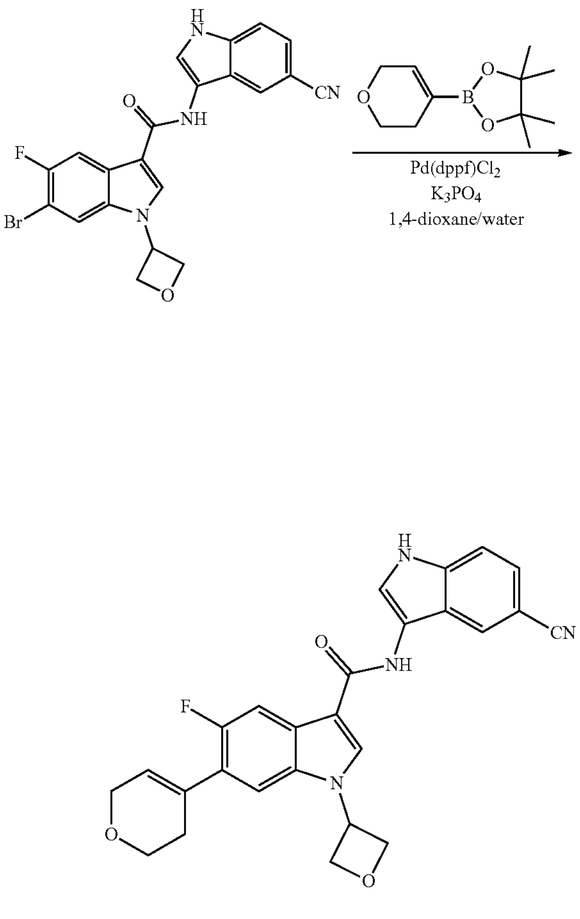

To a stirred solution of 6-bromo-N-(5-cyano-1H-indol-3-yl)-5-fluoro-1-(oxetan-3-yl)indole-3-carboxamide (160 mg, 0.353 mmol) in 1,4-dioxane (5.0 mL) and water (3.0 mL) were sequentially added 2-(3,6-dihydro-2H-pyran-4-yl)-4,4,5,5-tetramethyl-1,3,2-dioxaborolane (96.4 mg, 0.458 mmol), $Pd(dppf)Cl_2$ (25.8 mg, 0.0353 mmol) and $K_3PO_4$ (224 mg, 1.06 mmol) at 25° C. The resulting mixture was warmed to 100° C. and stirred at that temperature for 50 min. The mixture was cooled to 25° C., diluted with water (25 mL) and extracted with EtOAc (50 mL×2). The combined organic phases were washed with brine, dried over anhydrous $Na_2SO_4$, and filtered. The filtrate was concentrated under reduced pressure. The residue was purified by Prep-HPLC eluting with $CH_3CN$/water (with $CH_3CN$ from 35% to 65%) in 8 min to give N-(5-cyano-1H-indol-3-yl)-6-(3,6-dihydro-2H-pyran-4-yl)-5-fluoro-1-(oxetan-3-yl)indole-3-carboxamide (22.0 mg, 14% yield) as a light brown solid. LC-MS: m/z $[M+H]^+$ 457.1.

Examples 113 and 114

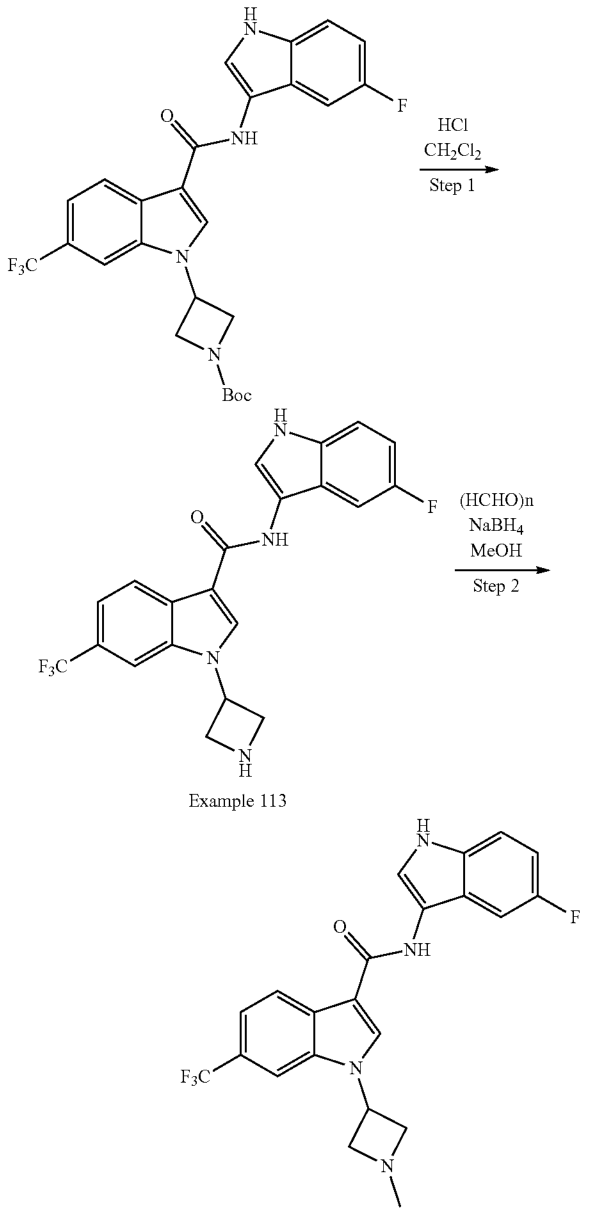

Example 113

Example 114

Step 1, Example 113

To a stirred solution of tert-butyl 3-[3-[(5-fluoro-1H-indol-3-yl)carbamoyl]-6-(trifluoromethyl)indol-1-yl]azetidine-1-carboxylate (170 mg, 0.329 mmol) in $CH_2Cl_2$ (5.0 mL) was added HCl (1.00 mL, 2.0 M in EtOAc, 2.00 mmol) at 25° C. The reaction mixture was stirred at that temperature for 2 h before it was concentrated under reduced pressure. The residue was purified Prep-HPLC eluting with $CH_3CN$/water (with $CH_3CN$ from 20% to 50%) in 8 min to give 1-(azetidin-3-yl)-N-(5-fluoro-1H-indol-3-yl)-6-(trifluoromethyl)indole-3-carboxamide (135 mg, 90% yield) as a white solid. LC-MS: m/z $[M+H]^+$ 417.1.

Step 2, Example 114

To a stirred solution of 1-(azetidin-3-yl)-N-(5-fluoro-1H-indol-3-yl)-6-(trifluoromethyl) indole-3-carboxamide (100 mg, 0.240 mmol) in MeOH (10.0 mL) were sequentially added formaldehyde (43.3 mg, 1.44 mmol) and $NaBH_4$ (109 mg, 2.88 mmol) at 25° C. The mixture was stirred at that temperature for 48 h before it was quenched with water (30 mL) and extracted with EtOAc (50 mL×3). The combined organic layers were washed with brine, dried over anhydrous $Na_2SO_4$, and filtered. The filtrate was concentrated under reduced pressure. The residue was purified by silica gel chromatography eluting with $MeOH/CH_2Cl_2$ (with MeOH from 0 to 10%) in 20 min to afford a crude product which was further purified by Pre-TLC (EtOAc 100%) to afford N-(5-fluoro-1H-indol-3-yl)-1-(1-methylazetidin-3-yl)-6-(trifluoromethyl)indole-3-carboxamide (16.0 mg, 15% yield) as a white solid. LC-MS: m/z $[M+H]^+$ 431.1.

Examples 115 and 116

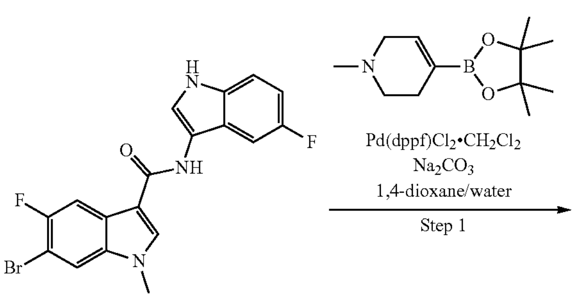

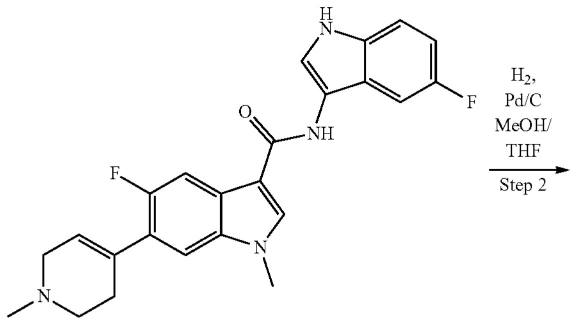

Example 115

-continued

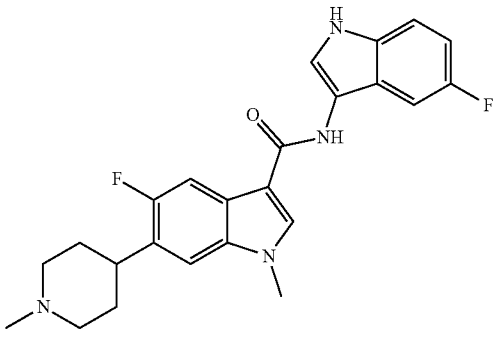

Example 116

Step 1, Example 115

To a stirred solution of 6-bromo-5-fluoro-N-(5-fluoro-1H-indol-3-yl)-1-methyl-indole-3-carboxamide (175 mg, 0.435 mmol) in 1,4-dioxane (4.0 mL) and water (1.0 mL) were sequentially added 1-methyl-4-(4,4,5,5-tetramethyl-1,3,2-dioxaborolan-2-yl)-3,6-dihydro-2H-pyridine (173 mg, 0.779 mmol), $Na_2CO_3$ (137 mg, 1.30 mmol) and Pd(dppf) $Cl_2$—$CH_2Cl_2$ (70.7 mg, 0.086 mmol) at 25° C. The resulting mixture was warmed to 100° C. and stirred at that temperature for 6 h. The reaction mixture was cooled to 25° C., quenched with water (15 mL). The precipitates were collected by filtration and further purified by Prep-HPLC eluting with $CH_3CN$/water (with $CH_3CN$ from 10% to 40%) in 8 min to give 5-fluoro-N-(5-fluoro-1H-indol-3-yl)-1-methyl-6-(1-methyl-3,6-dihydro-2H-pyridin-4-yl)indole-3-carboxamide (65.0 mg, 36% yield) as a yellow solid. LC-MS: m/z $[M+H]^+$ 421.1.

Step 2, Example 116

To a solution of 5-fluoro-N-(5-fluoro-1H-indol-3-yl)-1-methyl-6-(1-methyl-3,6-dihydro-2H-pyridin-4-yl)indole-3-carboxamide (50.0 mg, 0.118 mmol) in MeOH (2.0 mL) and THF (2.0 mL) was added Pd/C (5.0 mg, 10% wt., 0.0047 mmol) at 25° C. The reaction mixture was stirred under hydrogen atmosphere (balloon) at that temperature for 50 min before it was filtered through a pad of Celite. The filtrate was concentrated under reduced pressure. The residue was purified by Prep-HPLC eluting with $CH_3CN$/water (with $CH_3CN$ from 15% to 45%) in 8 min to give 5-fluoro-N-(5-fluoro-1H-indol-3-yl)-1-methyl-6-(1-methyl-4-piperidyl)indole-3-carboxamide (10.2 mg, 20% yield) as a yellow solid. LC-MS: m/z $[M+H]^+$ 423.1.

The following compounds were prepared using the similar procedure disclosed in synthetic example 116 and their corresponding characterization data are presented in the table below.

| Synthetic Example | Structure | LC-MS: m/z $[M + H]^+$ |
|---|---|---|
| 117 | 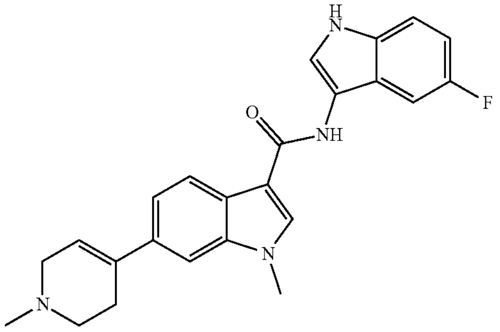 [SMILES: CN1CC=C(c2ccc3c(C(=O)Nc4c[nH]c5ccc(F)cc45)cn(C)c3c2)CC1] | 403.0 |
| 118 | 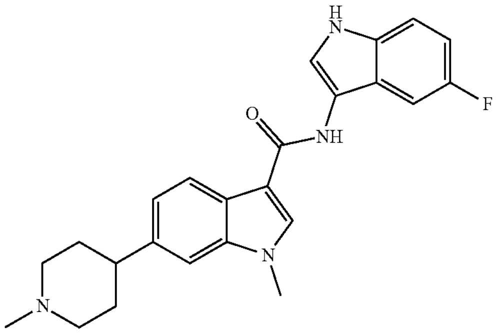 [SMILES: CN1CCC(c2ccc3c(C(=O)Nc4c[nH]c5ccc(F)cc45)cn(C)c3c2)CC1] | 405.1 |

Examples 119 and 120

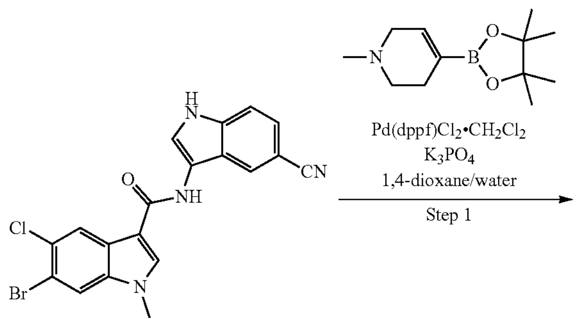

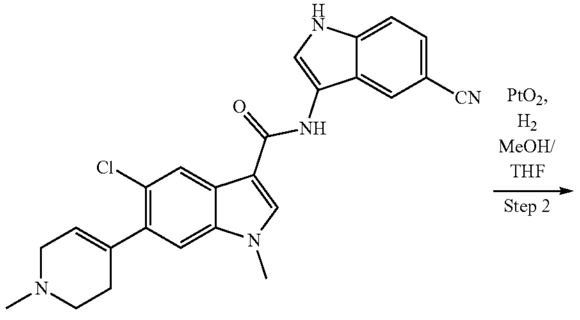

Example 119

-continued

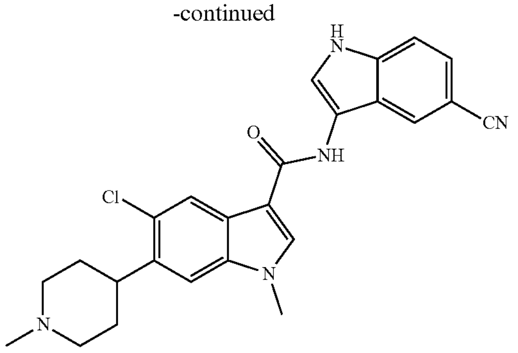

Example 120

Step 1, Example 119

To a stirred solution of 6-bromo-5-chloro-N-(5-cyano-1H-indol-3-yl)-1-methyl-indole-3-carboxamide (140 mg, 0.327 mmol) in 1,4-dioxane (8.0 mL) and water (2.0 mL) were sequentially added 1-methyl-4-(4,4,5,5-tetramethyl-1,3,2-dioxaborolan-2-yl)-3,6-dihydro-2H-pyridine (131 mg, 0.589 mmol), $Pd(dppf)Cl_2—CH_2Cl_2$ (53.4 mg, 0.0655 mmol), $K_3PO_4$ (208 mg, 0.982 mmol) at 25° C. The resulting mixture was warmed up to 100° C. and stirred at that temperature for 1 h. The reaction mixture was cooled to 25° C., diluted with water (15 mL). The precipitates were collected by filtration and further purified by Prep-HPLC eluting with $CH_3CN$/water (with $CH_3CN$ from 15% to 45%) in 8 min to give 5-chloro-N-(5-cyano-1H-indol-3-yl)-1-methyl-6-(1-methyl-3,6-dihydro-2H-pyridin-4-yl)indole-3-carboxamide (93.1 mg, 64% yield) as a yellow solid. LC-MS: m/z $[M+H]^+$ 444.1.

Step 2, Example 120

To a solution of 5-chloro-N-(5-cyano-1H-indol-3-yl)-1-methyl-6-(1-methyl-3,6-dihydro-2H-pyridin-4-yl)indole-3-carboxamide (70.0 mg, 0.157 mmol) in MeOH (2.0 mL) and THF (2.0 mL) was added $PtO_2$ (3.6 mg, 0.016 mmol) at 25° C. The reaction mixture was stirred under hydrogen atmosphere (balloon) at that temperature for 20 h before it was filtered through a pad of Celite. The filtrate was concentrated under reduced pressure. The residue was purified by Prep-HPLC eluting with $CH_3CN$/water with ($CH_3CN$ from 22% to 32%) in 8 min to give 5-chloro-N-(5-cyano-1H-indol-3-yl)-1-methyl-6-(1-methyl-4-piperidyl)indole-3-carboxamide (1.5 mg, 2% yield) as a yellow solid. LC-MS: m/z $[M+H]^+$ 446.1.

Biological Example 1

STING pathway deactivation by the compounds described herein was measured using THP1 cells. The THP1 Cells (obtained from ATCC, Cat #TIB-202) were maintained in RPMI-1640 (Gibco, Cat #22400105), 10% FBS, 1% Pen-Strep, 0.05 mM 2-mercaptoethanol. For STING activation, 2'3'-cGAMP (MW 718.38, obtained from Invivogen) was used and prepared in serum-free RPMI-1640 media. Growth media: RPMI-1640 (HEPES, glutamine), 10% FBS, 1% Pen-Strep, 0.05 mM 2-mercaptoethanol. Assay media: RPMI-1640 (HEPES, glutamine), 0.5% FBS. 2'3'-cGAMP: Dissolve 2'3'-cGAMP to 10 mM stock in $H_2O$.

IFN β Reporter Assay:

The cells were prepared and seeded at 100K, 90 μL/well with assay media in cell culture plate (Greiner 655180). The compounds were added in 96-well tissue culture plates by Tecan D300e for a final concentration of 0.00137-3 μM.

Lipo2000/3000 and 2'3'-cGAMP stock solutions were diluted respectively in serum-free RPMI-1640 media. The diluted 2'3'-cGAMP and Lipo (V/V=1:1) were mixed and stood for 15 min at room temperature. 10 μL 2,3-cGAMP/Lipofectamine (10×) was transferred to the 96-well assay plate with a final 2'3'-cGAMP concentration of 5 μM. The cell plates were centrifuged at 1000 rpm for 5 min after incubating at 37° C., 5% $CO_2$ overnight.

All reagents (human IFN beta kit, Cisbio 62HIFNBPEG) were warmed to room temperature for at least 30 min before the assay. The instructions of the kit were followed to prepare the detection media. 14 μL of cell supernatants was transferred into their dedicated wells in 384-well plate. Then 2 μL of the activation reagent solution and 4 μL of the mixed antibody solution were added to all wells. The plate was sealed and incubated for 3 h at room temperature.

The HTRF signal was read in Envision (PerkinElmer). IFN β reporter activity was then measured. The calculated ratio is the signal at 665 nm/signal at 615 nm. $IC_{50}$ values are calculated by using standard methods known in the art.

The following table shows the IFN β secretion inhibition activity of compounds in IFN β reporter assay: <0.05 μM="++++"; >0.05 and <0.2 μM="+++"; >0.2 and <1.0 μM="++"; >1.0 μM="+". "–"=not available.

TABLE 1

| Synthetic Example | structure | IFN β reporter activity $IC_{50}$ (μM) |
|---|---|---|
| 1 | 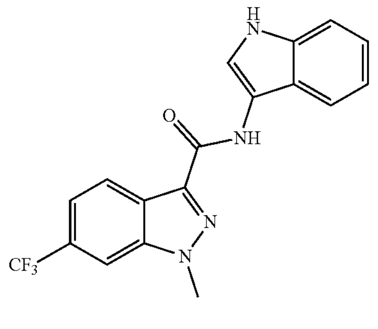 [SMILES: Cn1nc(C(=O)Nc2c[nH]c3ccccc23)c2ccc(C(F)(F)F)cc21] | +++ |
| 2 | 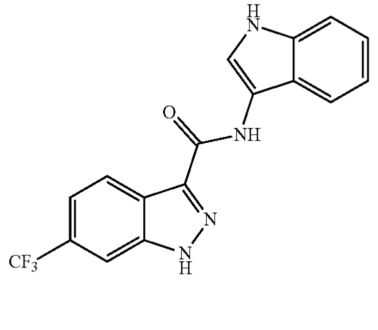 [SMILES: O=C(Nc1c[nH]c2ccccc12)c1n[nH]c2cc(C(F)(F)F)ccc12] | +++ |

TABLE 1-continued
| Synthetic Example | structure | IFN β reporter activity $IC_{50}$ (μM) |
|---|---|---|
| 3 | 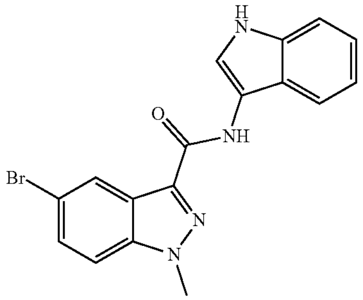 [SMILES: Cn1nc(C(=O)Nc2c[nH]c3ccccc23)c2cc(Br)ccc21] | +++ |
| 4 | 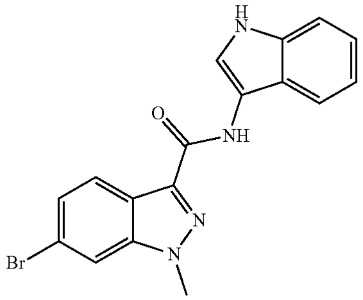 [SMILES: Cn1nc(C(=O)Nc2c[nH]c3ccccc23)c2ccc(Br)cc21] | +++ |
| 5 | 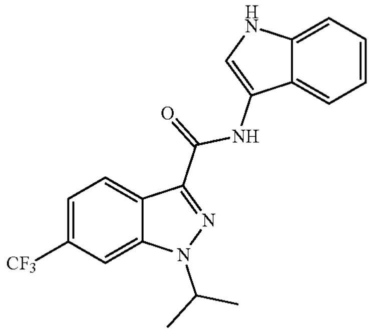 [SMILES: CC(C)n1nc(C(=O)Nc2c[nH]c3ccccc23)c2ccc(C(F)(F)F)cc21] | ++ |
| 6 | 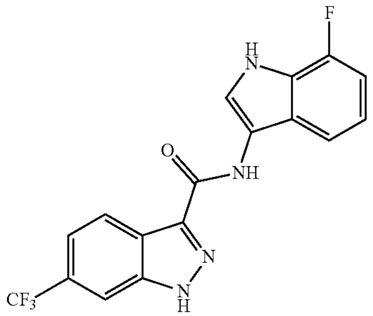 [SMILES: O=C(Nc1c[nH]c2c(F)cccc12)c1n[nH]c2cc(C(F)(F)F)ccc12] | ++ |
| 7 | 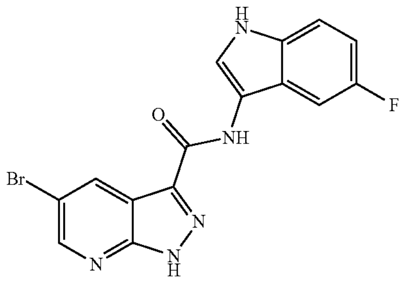 [SMILES: O=C(Nc1c[nH]c2ccc(F)cc12)c1n[nH]c2ncc(Br)cc12] | +++ |

TABLE 1-continued
| Synthetic Example | structure | IFN β reporter activity $IC_{50}$ (μM) |
|---|---|---|
| 8 | 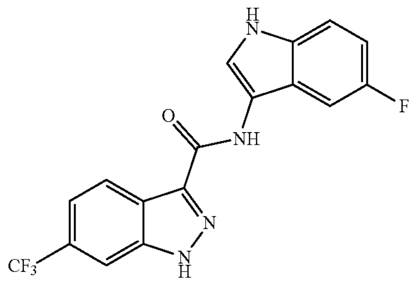 [SMILES: O=C(Nc1c[nH]c2ccc(F)cc12)c1n[nH]c2cc(C(F)(F)F)ccc12] | ++++ |
| 9 | 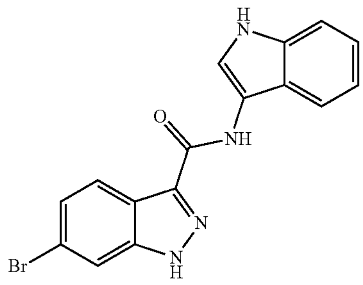 [SMILES: O=C(Nc1c[nH]c2ccccc12)c1n[nH]c2cc(Br)ccc12] | ++++ |
| 10 | 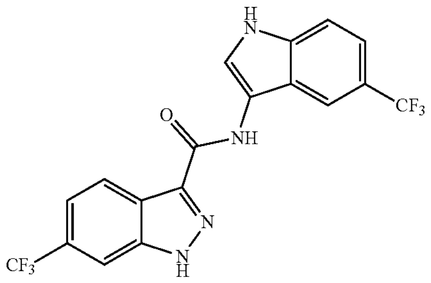 [SMILES: O=C(Nc1c[nH]c2ccc(C(F)(F)F)cc12)c1n[nH]c2cc(C(F)(F)F)ccc12] | +++ |
| 11 | 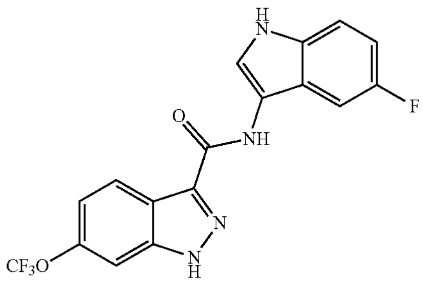 | ++ |
| 12 | 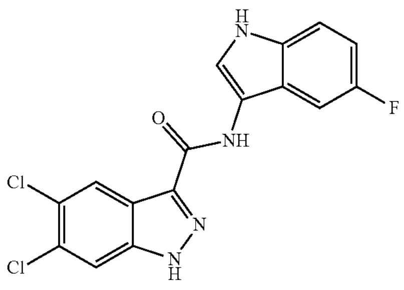 [SMILES: O=C(Nc1c[nH]c2ccc(F)cc12)c1n[nH]c2cc(Cl)c(Cl)cc12] | ++++ |

TABLE 1-continued
| Synthetic Example | structure | IFN β reporter activity $IC_{50}$ (μM) |
|---|---|---|
| 13 | 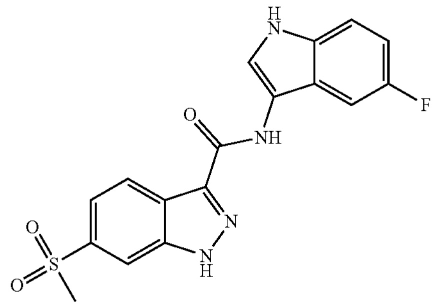 [SMILES: CS(=O)(=O)c1ccc2c(C(=O)Nc3c[nH]c4ccc(F)cc34)n[nH]c2c1] | + |
| 14 | 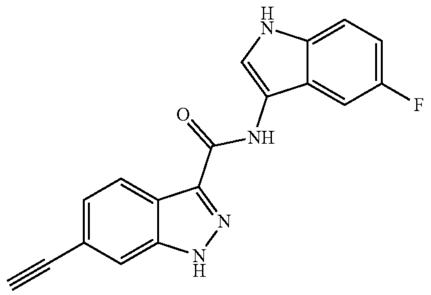 [SMILES: C#Cc1ccc2c(C(=O)Nc3c[nH]c4ccc(F)cc34)n[nH]c2c1] | +++ |
| 15 | 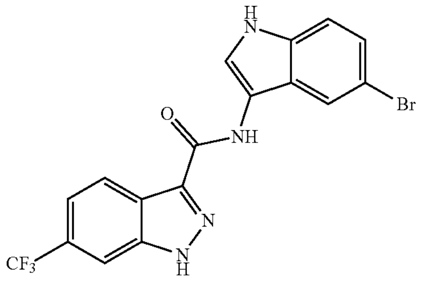 [SMILES: O=C(Nc1c[nH]c2ccc(Br)cc12)c1n[nH]c2cc(C(F)(F)F)ccc12] | ++++ |
| 16 | 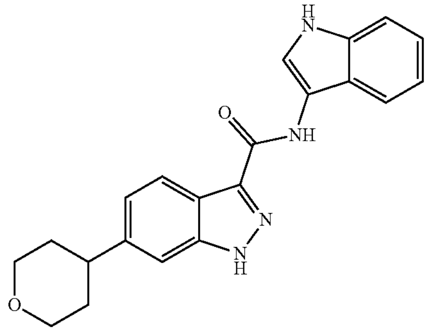 [SMILES: O=C(Nc1c[nH]c2ccccc12)c1n[nH]c2cc(C3CCOCC3)ccc12] | +++ |
| 17 | 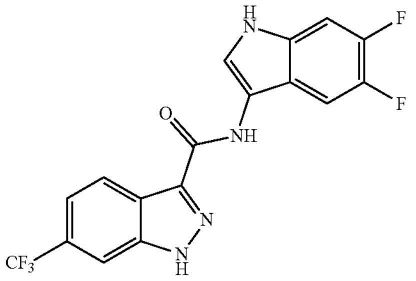 [SMILES: O=C(Nc1c[nH]c2cc(F)c(F)cc12)c1n[nH]c2cc(C(F)(F)F)ccc12] | ++++ |

TABLE 1-continued
| Synthetic Example | structure | IFN β reporter activity $IC_{50}$ (μM) |
|---|---|---|
| 18 | 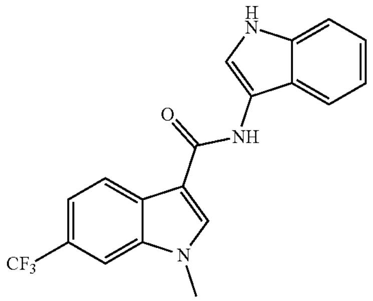 [SMILES: Cn1cc(C(=O)Nc2c[nH]c3ccccc23)c2ccc(C(F)(F)F)cc21] | +++ |
| 19 | 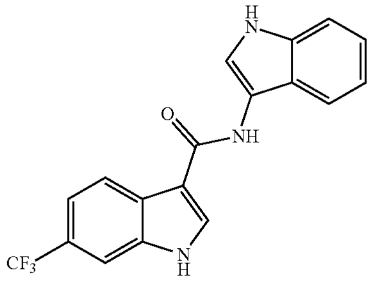 [SMILES: O=C(Nc1c[nH]c2ccccc12)c1c[nH]c2cc(C(F)(F)F)ccc12] | +++ |
| 20 | 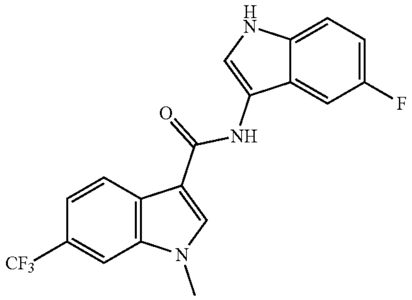 [SMILES: Cn1cc(C(=O)Nc2c[nH]c3ccc(F)cc23)c2ccc(C(F)(F)F)cc21] | ++++ |
| 21 | 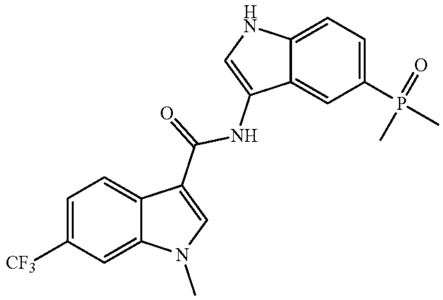 [SMILES: Cn1cc(C(=O)Nc2c[nH]c3ccc(P(C)(C)=O)cc23)c2ccc(C(F)(F)F)cc21] | + |
| 22 | 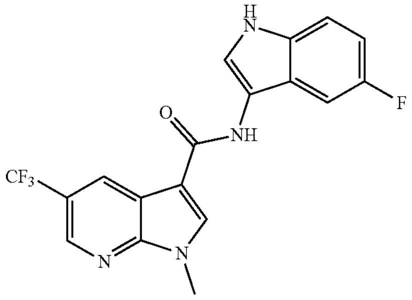 [SMILES: Cn1cc(C(=O)Nc2c[nH]c3ccc(F)cc23)c2cc(C(F)(F)F)cnc21] | ++ |

TABLE 1-continued
| Synthetic Example | structure | IFN β reporter activity $IC_{50}$ (μM) |
|---|---|---|
| 23 | 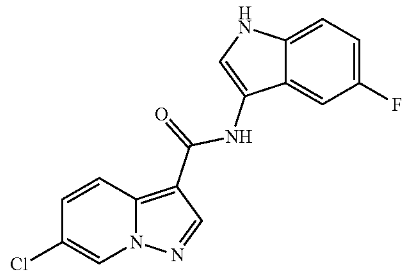 [SMILES: O=C(Nc1c[nH]c2ccc(F)cc12)c1cnn2cc(Cl)ccc12] | ++ |
| 24 | 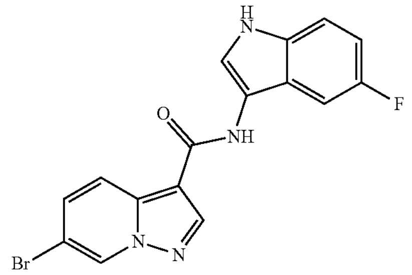 | ++++ |
| 25 | 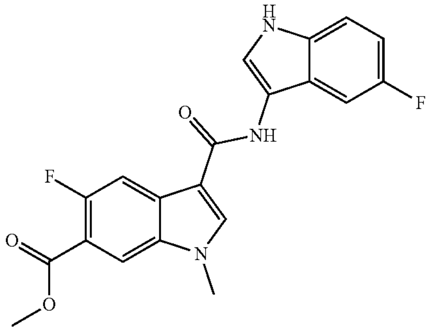 [SMILES: COC(=O)c1cc2c(cc1F)c(C(=O)Nc1c[nH]c3ccc(F)cc13)cn2C] | − |
| 26 | 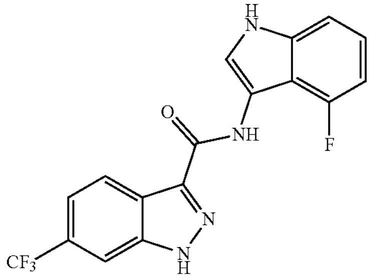 [SMILES: O=C(Nc1c[nH]c2cccc(F)c12)c1n[nH]c2cc(C(F)(F)F)ccc12] | +++ |
| 27 | 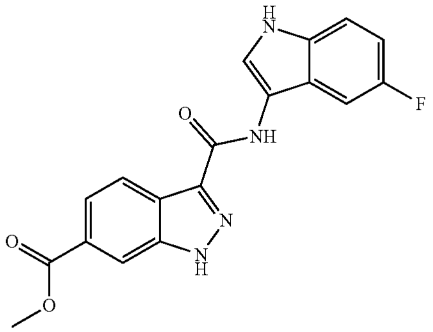 [SMILES: COC(=O)c1ccc2c(C(=O)Nc3c[nH]c4ccc(F)cc34)n[nH]c2c1] | + |

TABLE 1-continued
| Synthetic Example | structure | IFN β reporter activity $IC_{50}$ (μM) |
|---|---|---|
| 28 | 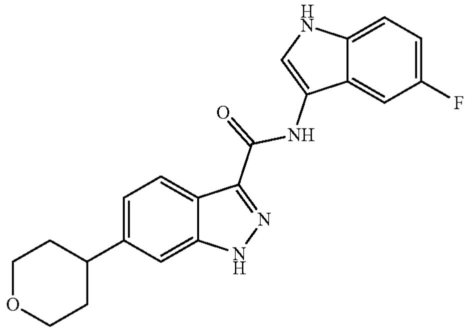 | +++ |
| 29 | 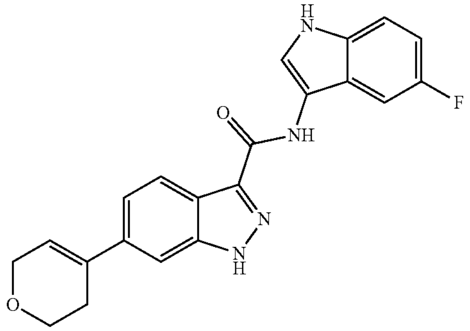 [SMILES: O=C(Nc1c[nH]c2ccc(F)cc12)c1n[nH]c2cc(C3=CCOCC3)ccc12] | +++ |
| 30 | 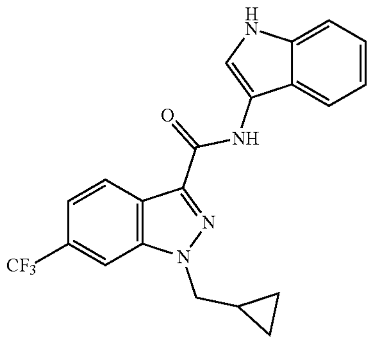 [SMILES: O=C(Nc1c[nH]c2ccccc12)c1nn(CC2CC2)c2cc(C(F)(F)F)ccc12] | +++ |
| 31 | 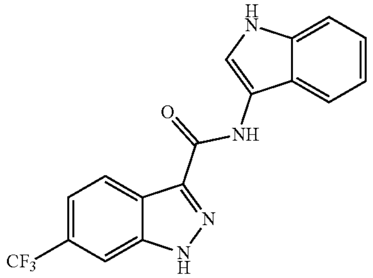 [SMILES: O=C(Nc1c[nH]c2ccccc12)c1n[nH]c2cc(C(F)(F)F)ccc12] | ++++ |

TABLE 1-continued
| Synthetic Example | structure | IFN β reporter activity $IC_{50}$ (μM) |
|---|---|---|
| 32 | 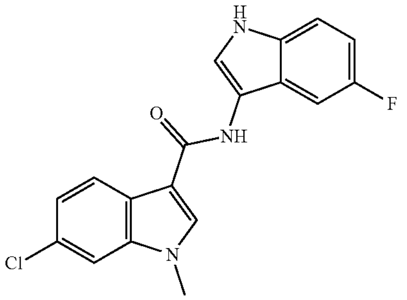 [SMILES: Cn1cc(C(=O)Nc2c[nH]c3ccc(F)cc23)c2ccc(Cl)cc21] | ++++ |
| 33 | 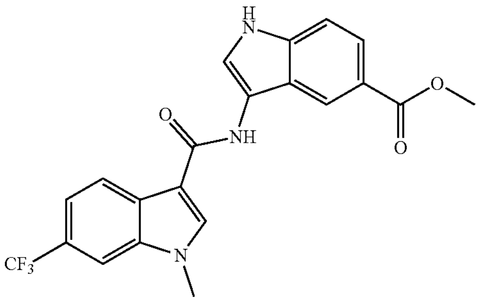 [SMILES: COC(=O)c1ccc2[nH]cc(NC(=O)c3cn(C)c4cc(C(F)(F)F)ccc34)c2c1] | +++ |
| 34 | 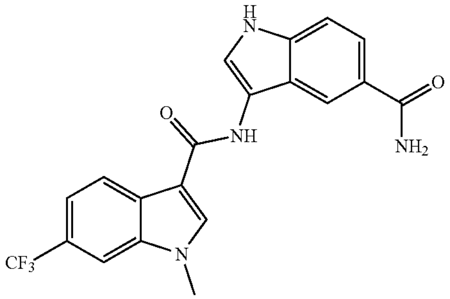 [SMILES: Cn1cc(C(=O)Nc2c[nH]c3ccc(C(N)=O)cc23)c2ccc(C(F)(F)F)cc21] | + |
| 35 | 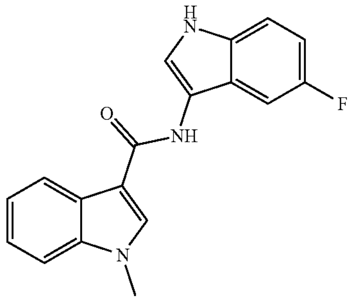 [SMILES: Cn1cc(C(=O)Nc2c[nH]c3ccc(F)cc23)c2ccccc21] | ++ |
| 36 | 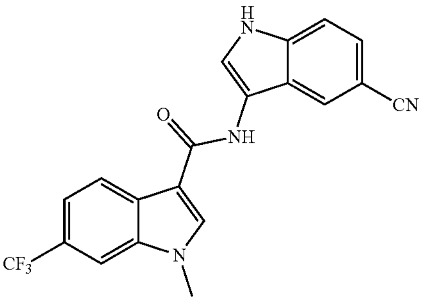 [SMILES: Cn1cc(C(=O)Nc2c[nH]c3ccc(C#N)cc23)c2ccc(C(F)(F)F)cc21] | ++++ |

TABLE 1-continued
| Synthetic Example | structure | IFN β reporter activity $IC_{50}$ (μM) |
|---|---|---|
| 37 | 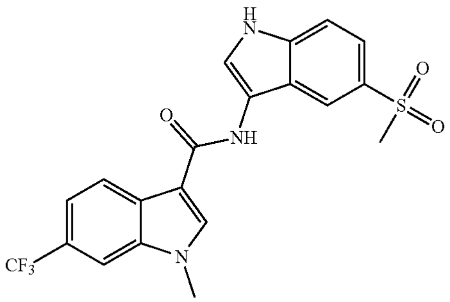 [SMILES: Cn1cc(C(=O)Nc2c[nH]c3ccc(S(C)(=O)=O)cc23)c2ccc(C(F)(F)F)cc21] | + |
| 38 | 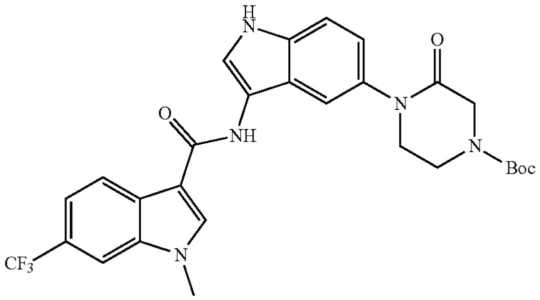 [SMILES: Cn1cc(C(=O)Nc2c[nH]c3ccc(N4CCN(C(=O)OC(C)(C)C)CC4=O)cc23)c2ccc(C(F)(F)F)cc21] | +++ |
| 39 | 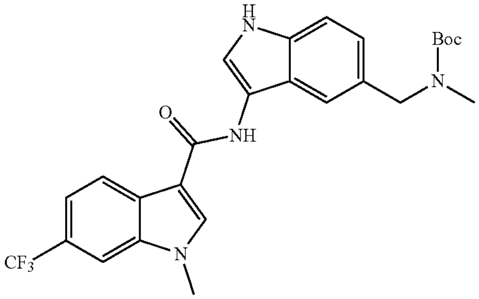 [SMILES: CN(Cc1ccc2[nH]cc(NC(=O)c3cn(C)c4cc(C(F)(F)F)ccc34)c2c1)C(=O)OC(C)(C)C] | +++ |
| 40 | 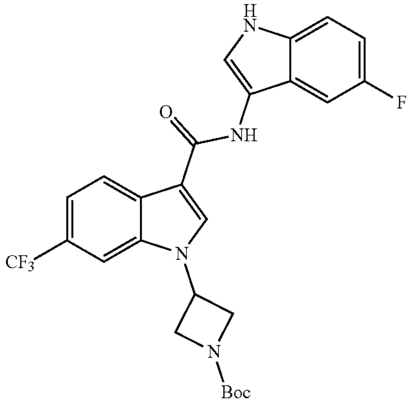 [SMILES: CC(C)(C)OC(=O)N1CC(n2cc(C(=O)Nc3c[nH]c4ccc(F)cc34)c3ccc(C(F)(F)F)cc32)C1] | – |

TABLE 1-continued
| Synthetic Example | structure | IFN β reporter activity $IC_{50}$ (μM) |
|---|---|---|
| 41 | 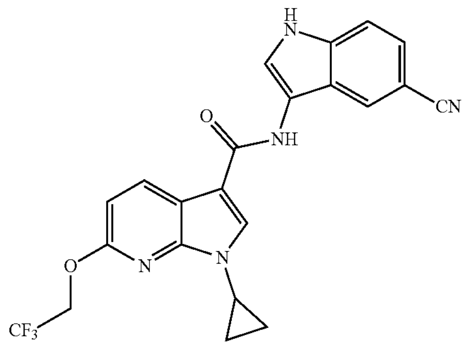 [SMILES: N#Cc1ccc2[nH]cc(NC(=O)c3cn(C4CC4)c4nc(OCC(F)(F)F)ccc34)c2c1] | +++ |
| 42 | 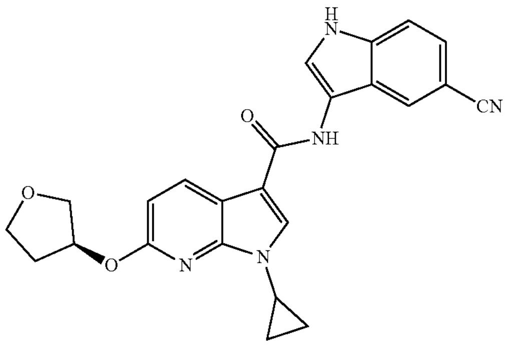 [SMILES: N#Cc1ccc2[nH]cc(NC(=O)c3cn(C4CC4)c4nc(O[C@H]5CCOC5)ccc34)c2c1] | ++ |
| 43 | 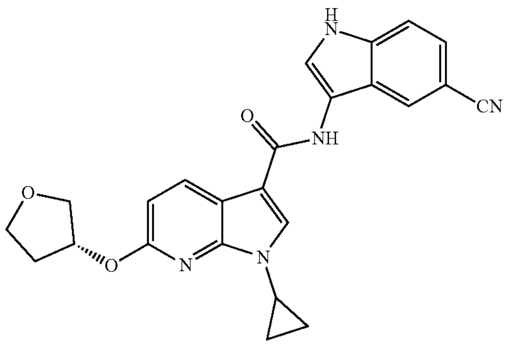 [SMILES: N#Cc1ccc2[nH]cc(NC(=O)c3cn(C4CC4)c4nc(O[C@@H]5CCOC5)ccc34)c2c1] | ++ |
| 44 | 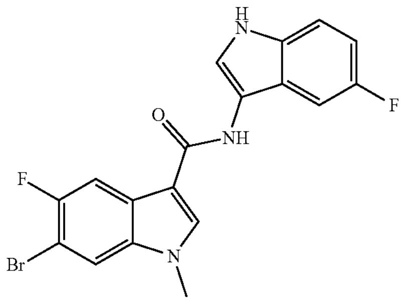 [SMILES: Cn1cc(C(=O)Nc2c[nH]c3ccc(F)cc23)c2cc(F)c(Br)cc21] | – |

TABLE 1-continued
| Synthetic Example | structure | IFN β reporter activity $IC_{50}$ (μM) |
|---|---|---|
| 45 | 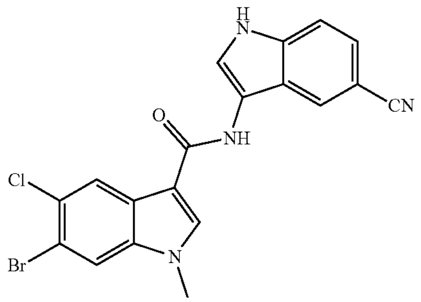 [SMILES: Cn1cc(C(=O)Nc2c[nH]c3ccc(C#N)cc23)c2cc(Cl)c(Br)cc21] | – |
| 46 | 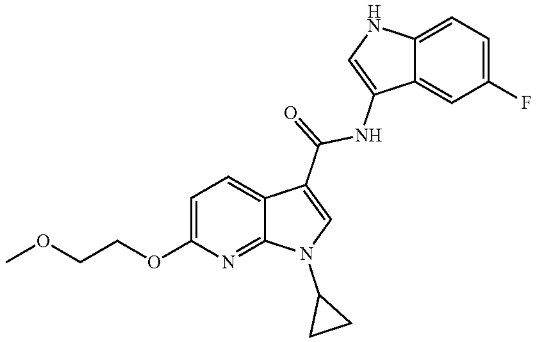 [SMILES: COCCOc1ccc2c(C(=O)Nc3c[nH]c4ccc(F)cc34)cn(C3CC3)c2n1] | +++ |
| 47 | 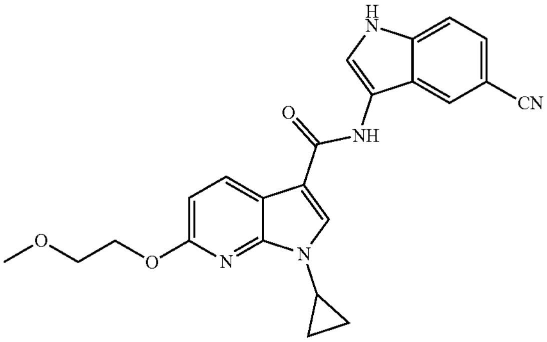 [SMILES: COCCOc1ccc2c(C(=O)Nc3c[nH]c4ccc(C#N)cc34)cn(C3CC3)c2n1] | ++ |
| 48 | 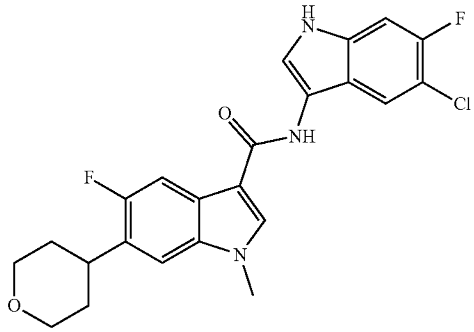 [SMILES: Cn1cc(C(=O)Nc2c[nH]c3cc(F)c(Cl)cc23)c2cc(F)c(C3CCOCC3)cc21] | +++ |

TABLE 1-continued
| Synthetic Example | structure | IFN β reporter activity $IC_{50}$ (μM) |
| --- | --- | --- |
| 49 | 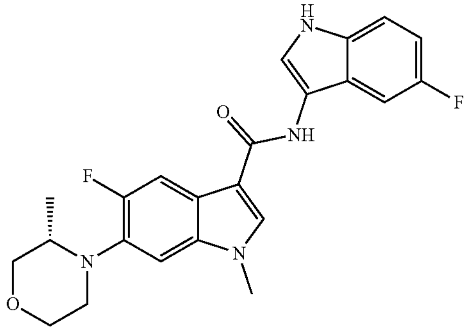 [SMILES: C[C@H]1COCCN1c1cc2c(cc1F)c(C(=O)Nc1c[nH]c3ccc(F)cc13)cn2C] | ++ |
| 50 | 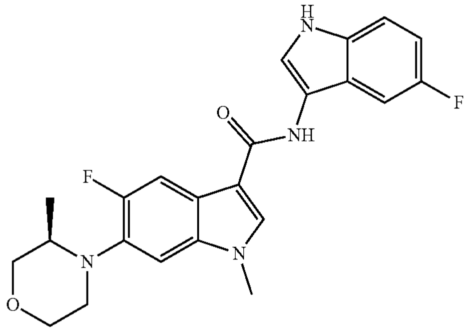 [SMILES: C[C@@H]1COCCN1c1cc2c(cc1F)c(C(=O)Nc1c[nH]c3ccc(F)cc13)cn2C] | ++ |
| 51 | 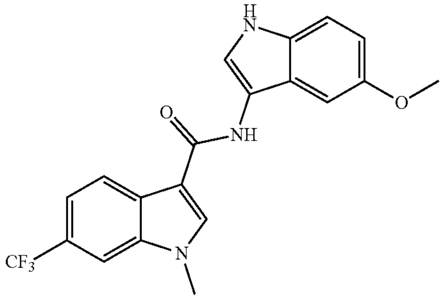 [SMILES: COc1ccc2[nH]cc(NC(=O)c3cn(C)c4cc(C(F)(F)F)ccc34)c2c1] | +++ |
| 52 | 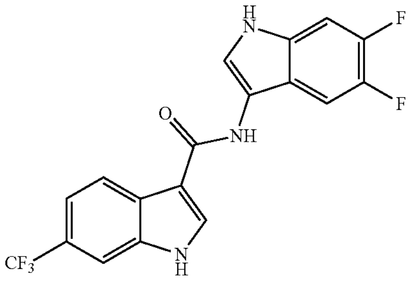 [SMILES: O=C(Nc1c[nH]c2cc(F)c(F)cc12)c1c[nH]c2cc(C(F)(F)F)ccc12] | ++++ |
| 53 | 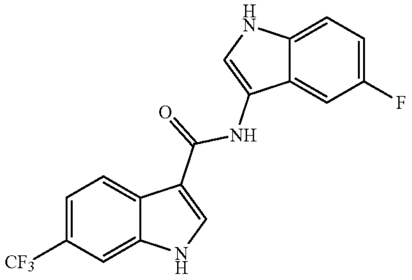 [SMILES: O=C(Nc1c[nH]c2ccc(F)cc12)c1c[nH]c2cc(C(F)(F)F)ccc12] | ++++ |

TABLE 1-continued
| Synthetic Example | structure | IFN β reporter activity $IC_{50}$ (μM) |
|---|---|---|
| 54 | 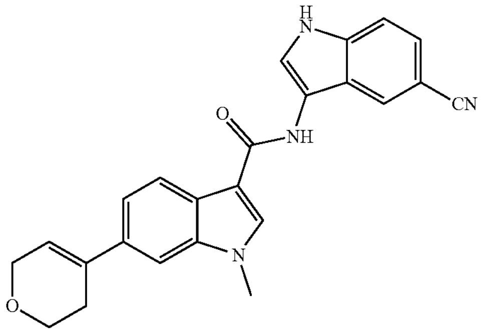 [SMILES: Cn1cc(C(=O)Nc2c[nH]c3ccc(C#N)cc23)c2ccc(C3=CCOCC3)cc21] | ++ |
| 55 | 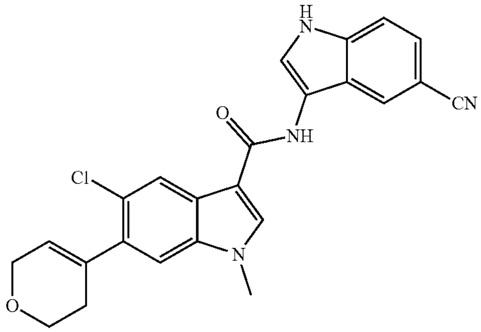 [SMILES: Cn1cc(C(=O)Nc2c[nH]c3ccc(C#N)cc23)c2cc(Cl)c(C3=CCOCC3)cc21] | +++ |
| 56 | 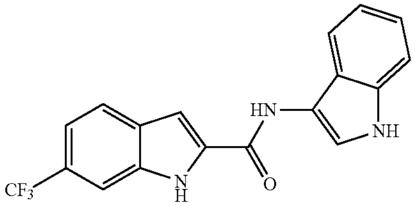 [SMILES: O=C(Nc1c[nH]c2ccccc12)c1cc2ccc(C(F)(F)F)cc2[nH]1] | +++ |
| 57 | 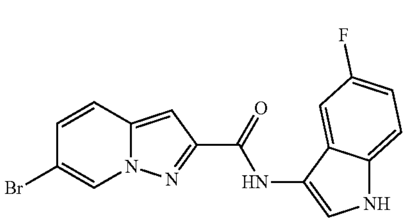 [SMILES: O=C(Nc1c[nH]c2ccc(F)cc12)c1cc2ccc(Br)cn2n1] | ++++ |
| 58 | 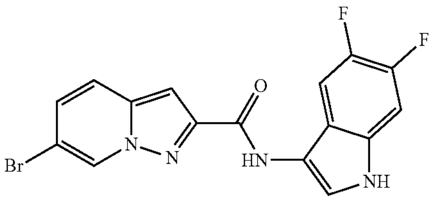 [SMILES: O=C(Nc1c[nH]c2cc(F)c(F)cc12)c1cc2ccc(Br)cn2n1] | ++ |

TABLE 1-continued
| Synthetic Example | structure | IFN β reporter activity $IC_{50}$ (μM) |
|---|---|---|
| 59 | 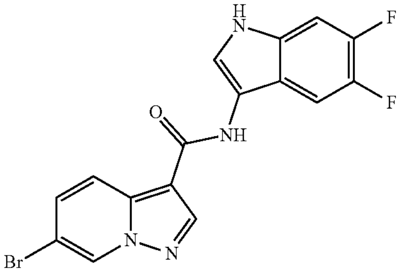 [SMILES: O=C(Nc1c[nH]c2cc(F)c(F)cc12)c1cnn2cc(Br)ccc12] | ++ |
| 60 | 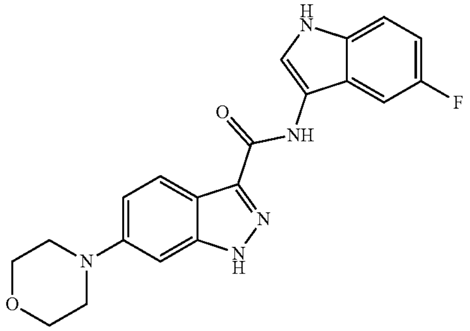 | ++ |
| 61 | 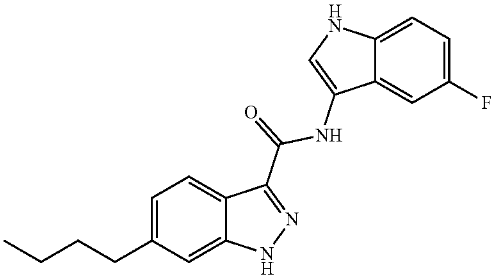 [SMILES: CCCCc1ccc2c(C(=O)Nc3c[nH]c4ccc(F)cc34)n[nH]c2c1] | +++ |
| 62 | 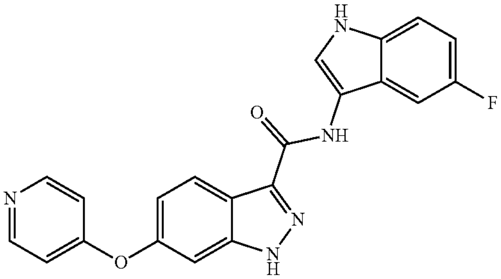 [SMILES: O=C(Nc1c[nH]c2ccc(F)cc12)c1n[nH]c2cc(Oc3ccncc3)ccc12] | + |
| 63 | 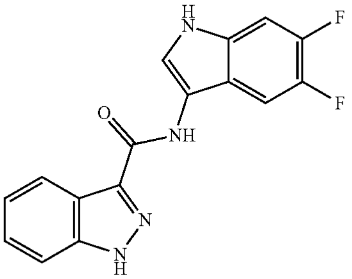 [SMILES: O=C(Nc1c[nH]c2cc(F)c(F)cc12)c1n[nH]c2ccccc12] | +++ |

TABLE 1-continued
| Synthetic Example | structure | IFN β reporter activity $IC_{50}$ (μM) |
|---|---|---|
| 64 | 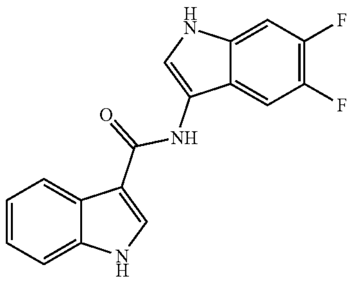 [SMILES: O=C(Nc1c[nH]c2cc(F)c(F)cc12)c1c[nH]c2ccccc12] | +++ |
| 65 | 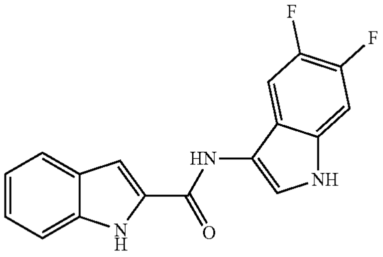 [SMILES: O=C(Nc1c[nH]c2cc(F)c(F)cc12)c1cc2ccccc2[nH]1] | ++++ |
| 66 | 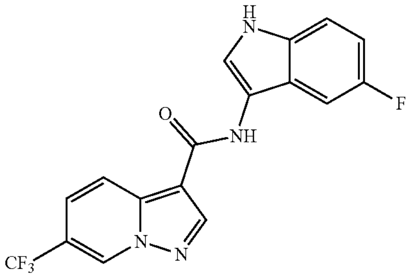 [SMILES: O=C(Nc1c[nH]c2ccc(F)cc12)c1cnn2cc(C(F)(F)F)ccc12] | ++ |
| 67 | 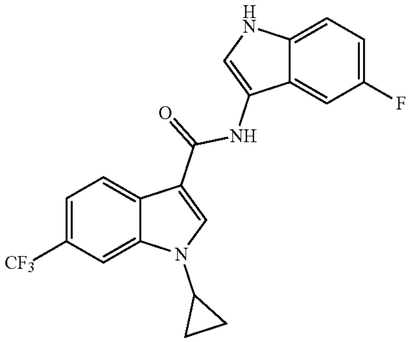 [SMILES: O=C(Nc1c[nH]c2ccc(F)cc12)c1cn(C2CC2)c2cc(C(F)(F)F)ccc12] | ++++ |
| 68 | 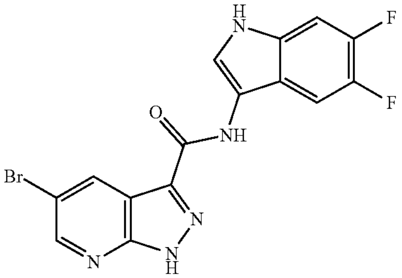 [SMILES: O=C(Nc1c[nH]c2cc(F)c(F)cc12)c1n[nH]c2ncc(Br)cc12] | +++ |

TABLE 1-continued
| Synthetic Example | structure | IFN β reporter activity $IC_{50}$ (μM) |
|---|---|---|
| 69 | 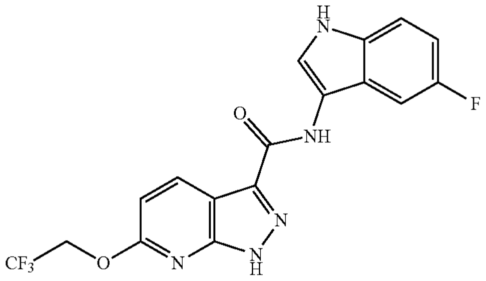 [SMILES: O=C(Nc1c[nH]c2ccc(F)cc12)c1n[nH]c2nc(OCC(F)(F)F)ccc12] | +++ |
| 70 | 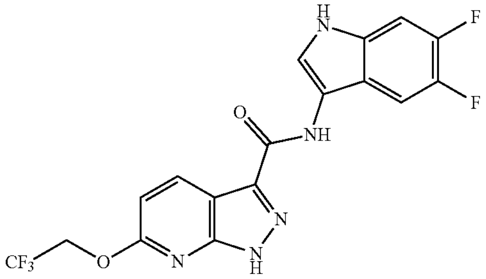 [SMILES: O=C(Nc1c[nH]c2cc(F)c(F)cc12)c1n[nH]c2nc(OCC(F)(F)F)ccc12] | +++ |
| 71 | 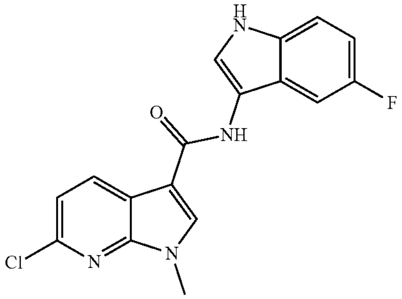 [SMILES: Cn1cc(C(=O)Nc2c[nH]c3ccc(F)cc23)c2ccc(Cl)nc21] | +++ |
| 72 | 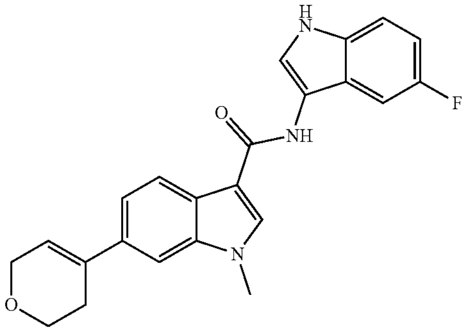 [SMILES: Cn1cc(C(=O)Nc2c[nH]c3ccc(F)cc23)c2ccc(C3=CCOCC3)cc21] | +++ |
| 73 | 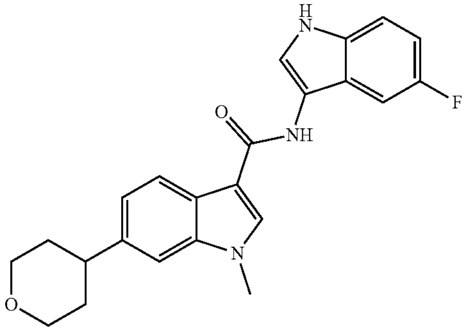 [SMILES: Cn1cc(C(=O)Nc2c[nH]c3ccc(F)cc23)c2ccc(C3CCOCC3)cc21] | +++ |

TABLE 1-continued
| Synthetic Example | structure | IFN β reporter activity $IC_{50}$ (μM) |
|---|---|---|
| 74 | 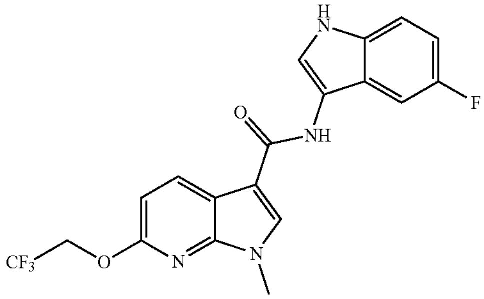 [SMILES: Cn1cc(C(=O)Nc2c[nH]c3ccc(F)cc23)c2ccc(OCC(F)(F)F)nc21] | +++ |
| 75 | 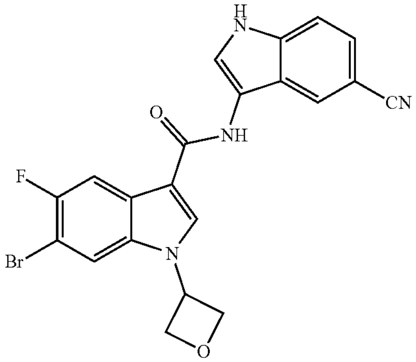 [SMILES: N#Cc1ccc2[nH]cc(NC(=O)c3cn(C4COC4)c4cc(Br)c(F)cc34)c2c1] | – |
| 76 | 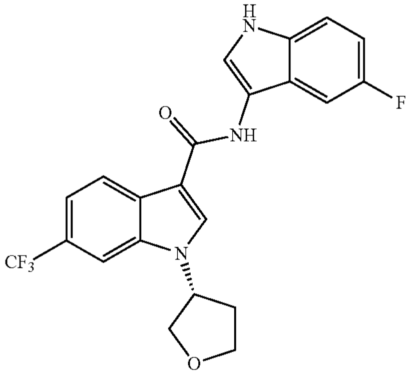 [SMILES: O=C(Nc1c[nH]c2ccc(F)cc12)c1cn([C@@H]2CCOC2)c2cc(C(F)(F)F)ccc12] | ++ |
| 77 | 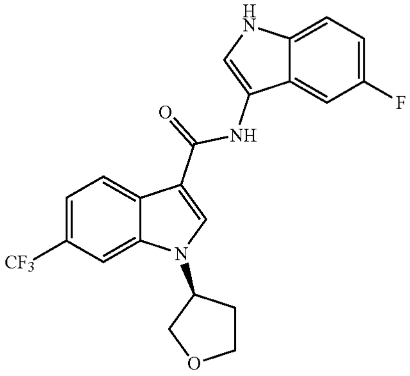 [SMILES: O=C(Nc1c[nH]c2ccc(F)cc12)c1cn([C@H]2CCOC2)c2cc(C(F)(F)F)ccc12] | +++ |

TABLE 1-continued
| Synthetic Example | structure | IFN β reporter activity $IC_{50}$ (μM) |
|---|---|---|
| 78 | 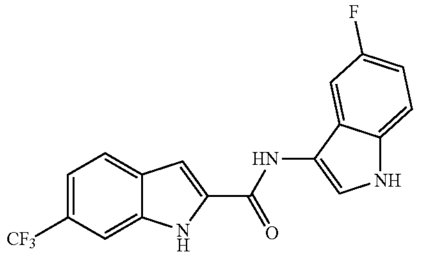 [SMILES: O=C(Nc1c[nH]c2ccc(F)cc12)c1cc2ccc(C(F)(F)F)cc2[nH]1] | +++ |
| 79 | 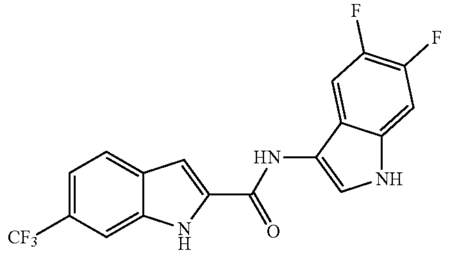 [SMILES: O=C(Nc1c[nH]c2cc(F)c(F)cc12)c1cc2ccc(C(F)(F)F)cc2[nH]1] | +++ |
| 80 | 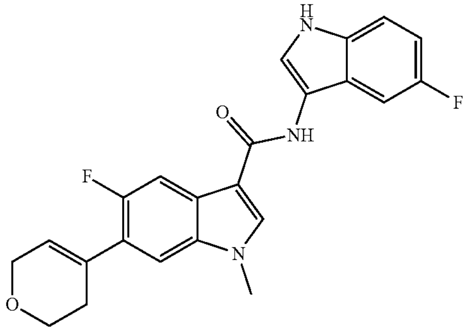 [SMILES: Cn1cc(C(=O)Nc2c[nH]c3ccc(F)cc23)c2cc(F)c(C3=CCOCC3)cc21] | +++ |
| 81 | 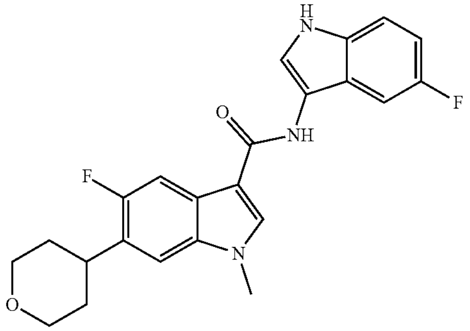 [SMILES: Cn1cc(C(=O)Nc2c[nH]c3ccc(F)cc23)c2cc(F)c(C3CCOCC3)cc21] | ++++ |
| 82 | 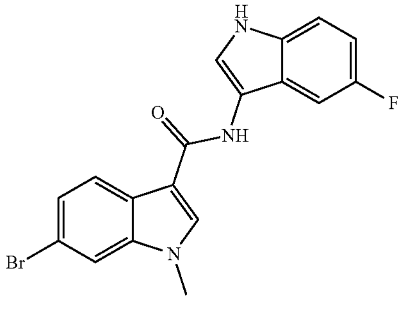 [SMILES: Cn1cc(C(=O)Nc2c[nH]c3ccc(F)cc23)c2ccc(Br)cc21] | − |

TABLE 1-continued
| Synthetic Example | structure | IFN β reporter activity $IC_{50}$ (μM) |
|---|---|---|
| 83 | 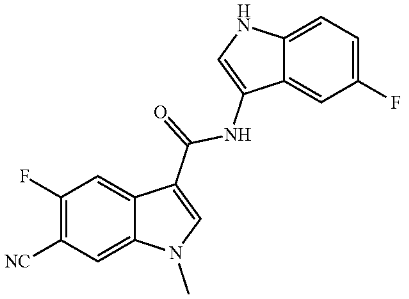 [SMILES: Cn1cc(C(=O)Nc2c[nH]c3ccc(F)cc23)c2cc(F)c(C#N)cc21] | − |
| 84 | 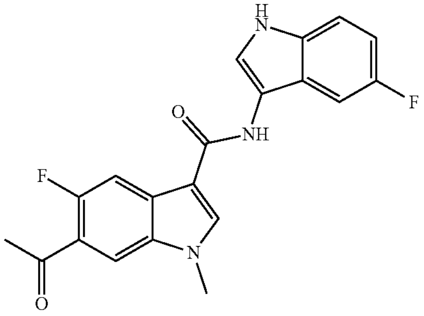 [SMILES: CC(=O)c1cc2c(cc1F)c(C(=O)Nc1c[nH]c3ccc(F)cc13)cn2C] | − |
| 85 | 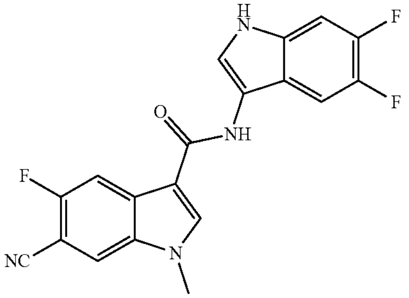 [SMILES: Cn1cc(C(=O)Nc2c[nH]c3cc(F)c(F)cc23)c2cc(F)c(C#N)cc21] | − |
| 86 | 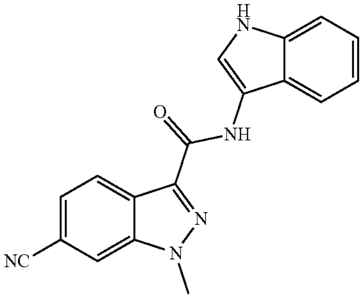 [SMILES: Cn1nc(C(=O)Nc2c[nH]c3ccccc23)c2ccc(C#N)cc21] | + |
| 87 | 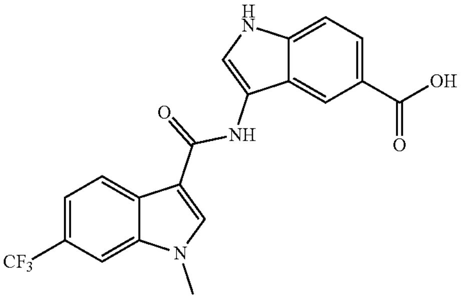 [SMILES: Cn1cc(C(=O)Nc2c[nH]c3ccc(C(=O)O)cc23)c2ccc(C(F)(F)F)cc21] | + |

TABLE 1-continued
| Synthetic Example | structure | IFN β reporter activity $IC_{50}$ (μM) |
|---|---|---|
| 88 | 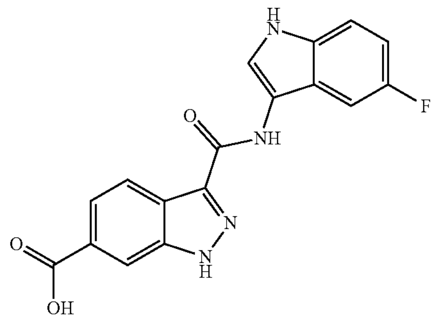 [SMILES: O=C(O)c1ccc2c(C(=O)Nc3c[nH]c4ccc(F)cc34)n[nH]c2c1] | + |
| 89 | 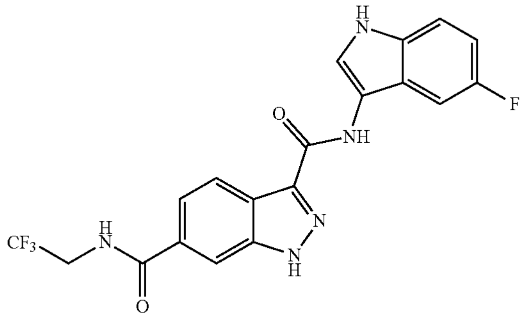 [SMILES: O=C(NCC(F)(F)F)c1ccc2c(C(=O)Nc3c[nH]c4ccc(F)cc34)n[nH]c2c1] | ++ |
| 90 | 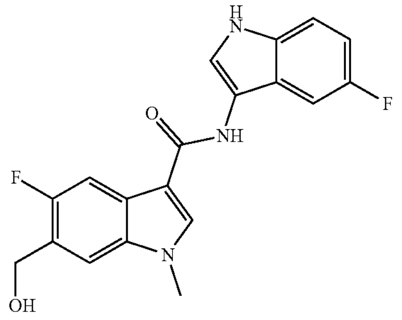 [SMILES: Cn1cc(C(=O)Nc2c[nH]c3ccc(F)cc23)c2cc(F)c(CO)cc21] | − |
| 91 | 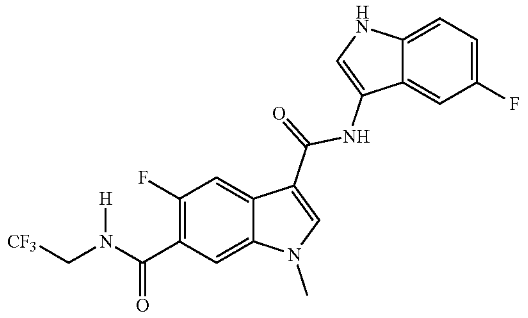 [SMILES: Cn1cc(C(=O)Nc2c[nH]c3ccc(F)cc23)c2cc(F)c(C(=O)NCC(F)(F)F)cc21] | +++ |

TABLE 1-continued
| Synthetic Example | structure | IFN β reporter activity $IC_{50}$ (μM) |
|---|---|---|
| 92 | 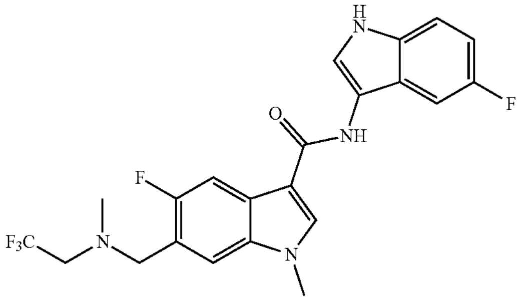 [SMILES: CN(Cc1cc2c(cc1F)c(C(=O)Nc1c[nH]c3ccc(F)cc13)cn2C)CC(F)(F)F] | +++ |
| 93 | 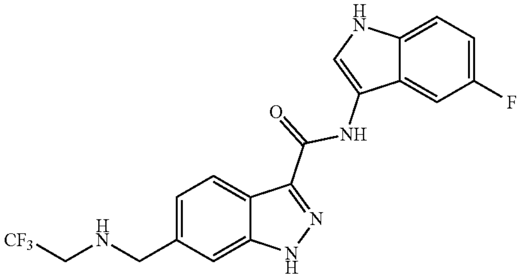 [SMILES: O=C(Nc1c[nH]c2ccc(F)cc12)c1n[nH]c2cc(CNCC(F)(F)F)ccc12] | +++ |
| 94 | 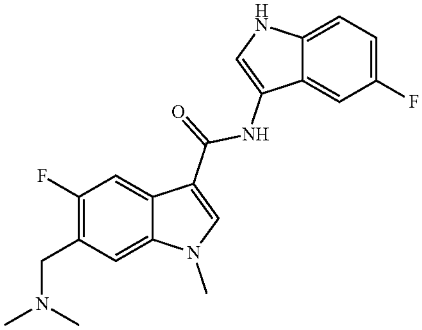 [SMILES: CN(C)Cc1cc2c(cc1F)c(C(=O)Nc1c[nH]c3ccc(F)cc13)cn2C] | + |
| 95 | 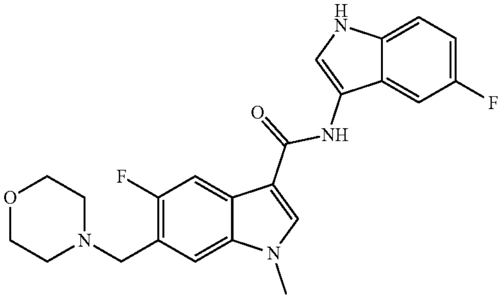 [SMILES: Cn1cc(C(=O)Nc2c[nH]c3ccc(F)cc23)c2cc(F)c(CN3CCOCC3)cc21] | ++ |
| 96 | 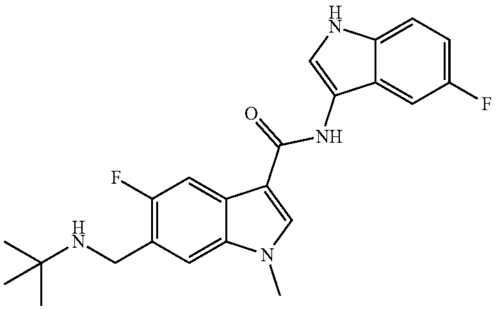 [SMILES: Cn1cc(C(=O)Nc2c[nH]c3ccc(F)cc23)c2cc(F)c(CNC(C)(C)C)cc21] | + |

TABLE 1-continued
| Synthetic Example | structure | IFN β reporter activity $IC_{50}$ (μM) |
|---|---|---|
| 97 | 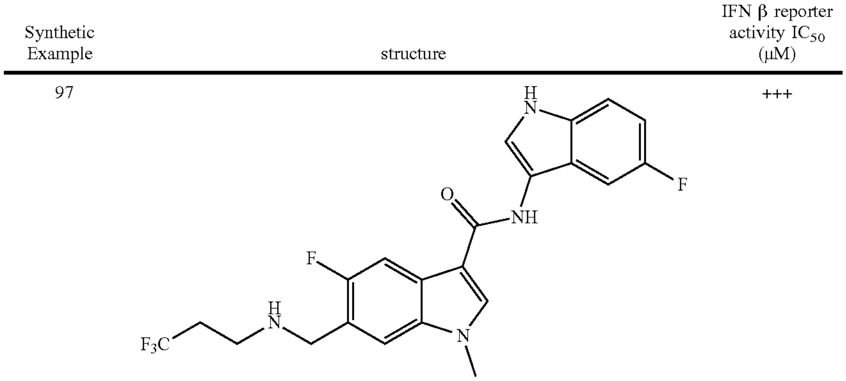 | +++ |
| 98 | 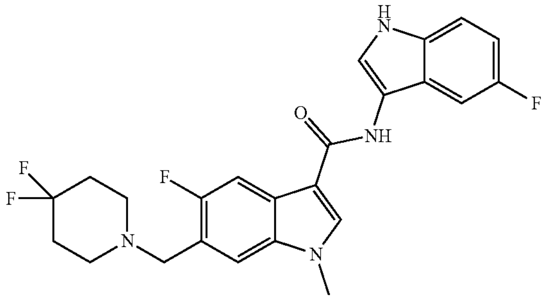 [SMILES: Cn1cc(C(=O)Nc2c[nH]c3ccc(F)cc23)c2cc(F)c(CN3CCC(F)(F)CC3)cc21] | ++++ |
| 99 | 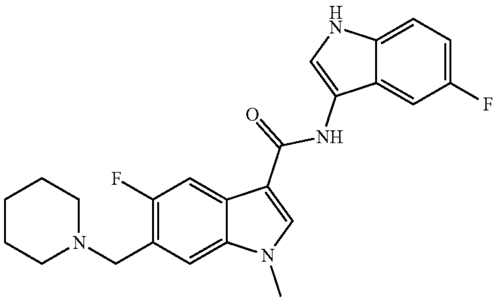 [SMILES: Cn1cc(C(=O)Nc2c[nH]c3ccc(F)cc23)c2cc(F)c(CN3CCCCC3)cc21] | + |
| 100 | 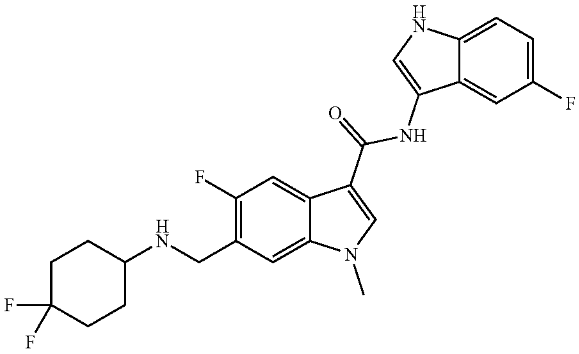 [SMILES: Cn1cc(C(=O)Nc2c[nH]c3ccc(F)cc23)c2cc(F)c(CNC3CCC(F)(F)CC3)cc21] | +++ |
| 101 | 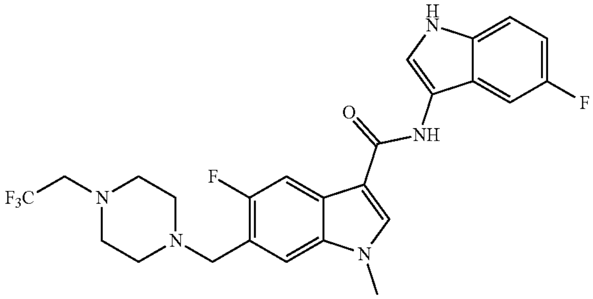 [SMILES: Cn1cc(C(=O)Nc2c[nH]c3ccc(F)cc23)c2cc(F)c(CN3CCN(CC(F)(F)F)CC3)cc21] | +++ |

TABLE 1-continued
| Synthetic Example | structure | IFN β reporter activity $IC_{50}$ (μM) |
|---|---|---|
| 102 | 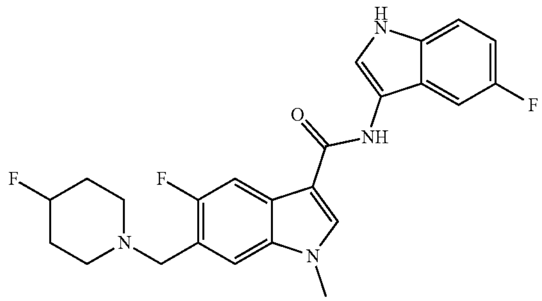 [SMILES: Cn1cc(C(=O)Nc2c[nH]c3ccc(F)cc23)c2cc(F)c(CN3CCC(F)CC3)cc21] | ++ |
| 103 | 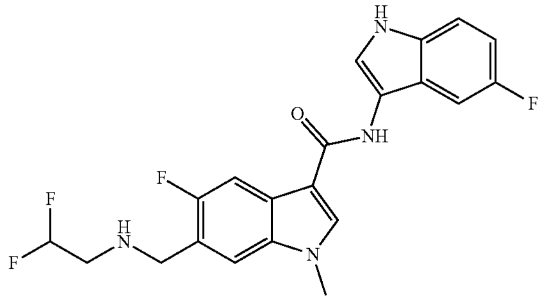 [SMILES: Cn1cc(C(=O)Nc2c[nH]c3ccc(F)cc23)c2cc(F)c(CNCC(F)F)cc21] | +++ |
| 104 | 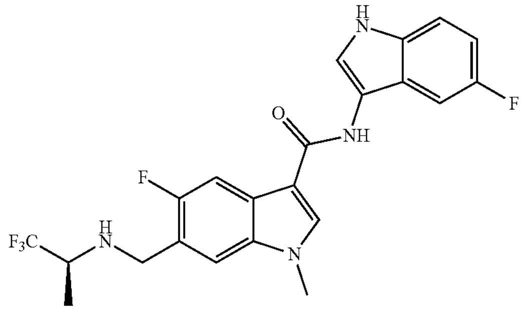 [SMILES: C[C@H](NCc1cc2c(cc1F)c(C(=O)Nc1c[nH]c3ccc(F)cc13)cn2C)C(F)(F)F] | ++++ |
| 105 | 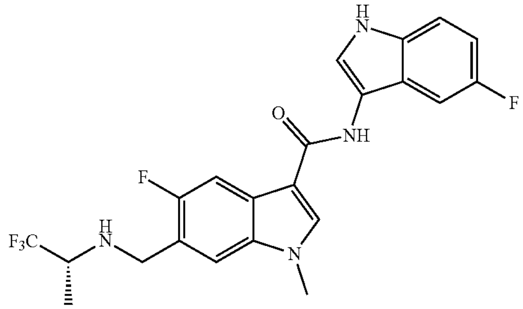 [SMILES: C[C@@H](NCc1cc2c(cc1F)c(C(=O)Nc1c[nH]c3ccc(F)cc13)cn2C)C(F)(F)F] | ++++ |
| 106 | 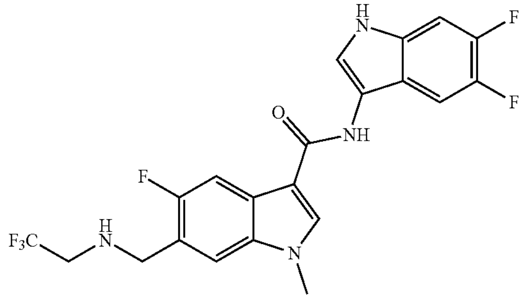 [SMILES: Cn1cc(C(=O)Nc2c[nH]c3cc(F)c(F)cc23)c2cc(F)c(CNCC(F)(F)F)cc21] | ++++ |

TABLE 1-continued
| Synthetic Example | structure | IFN β reporter activity $IC_{50}$ (μM) |
|---|---|---|
| 107 | 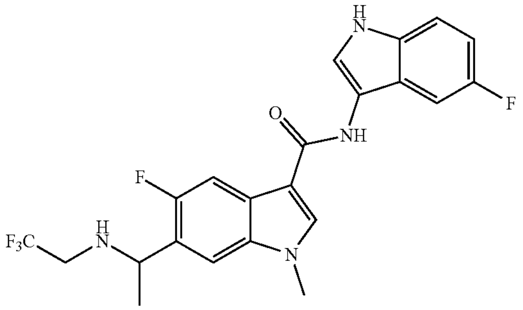 [SMILES: CC(NCC(F)(F)F)c1cc2c(cc1F)c(C(=O)Nc1c[nH]c3ccc(F)cc13)cn2C] | +++ |
| 108 | 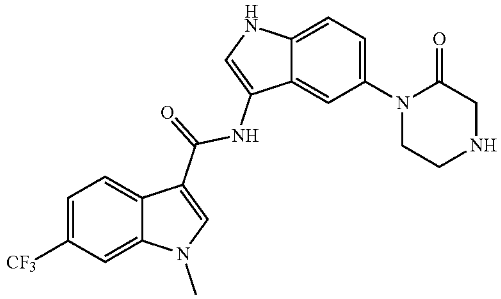 [SMILES: Cn1cc(C(=O)Nc2c[nH]c3ccc(N4CCNCC4=O)cc23)c2ccc(C(F)(F)F)cc21] | + |
| 109 | 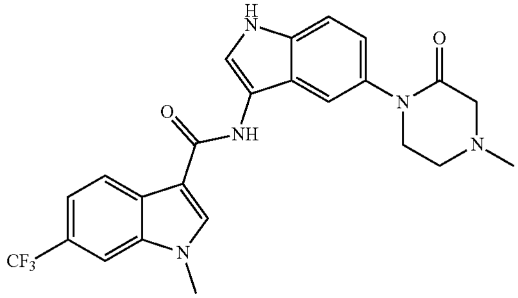 [SMILES: CN1CCN(c2ccc3[nH]cc(NC(=O)c4cn(C)c5cc(C(F)(F)F)ccc45)c3c2)C(=O)C1] | + |
| 110 | 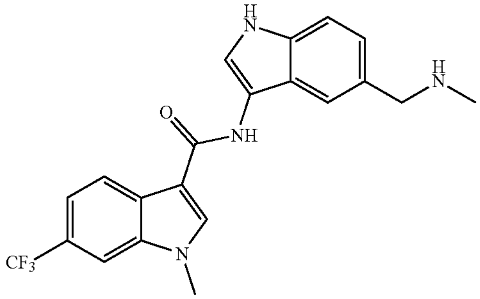 [SMILES: CNCc1ccc2[nH]cc(NC(=O)c3cn(C)c4cc(C(F)(F)F)ccc34)c2c1] | + |
| 111 | 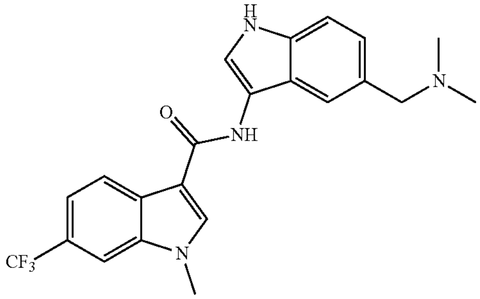 [SMILES: CN(C)Cc1ccc2[nH]cc(NC(=O)c3cn(C)c4cc(C(F)(F)F)ccc34)c2c1] | + |

TABLE 1-continued
| Synthetic Example | structure | IFN β reporter activity $IC_{50}$ (μM) |
|---|---|---|
| 112 | 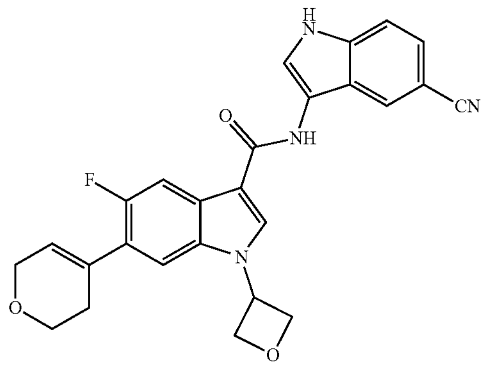 [SMILES: N#Cc1ccc2[nH]cc(NC(=O)c3cn(C4COC4)c4cc(C5=CCOCC5)c(F)cc34)c2c1] | +++ |
| 113 | 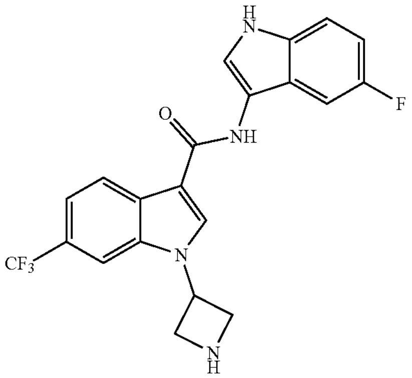 [SMILES: O=C(Nc1c[nH]c2ccc(F)cc12)c1cn(C2CNC2)c2cc(C(F)(F)F)ccc12] | + |
| 114 | 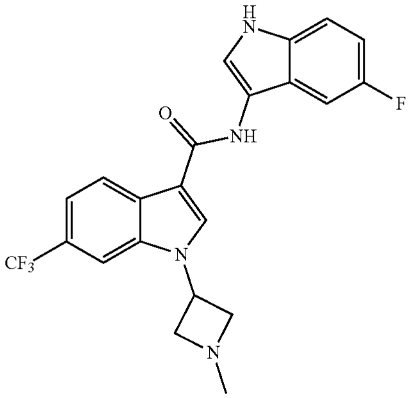 [SMILES: CN1CC(n2cc(C(=O)Nc3c[nH]c4ccc(F)cc34)c3ccc(C(F)(F)F)cc32)C1] | + |
| 115 | 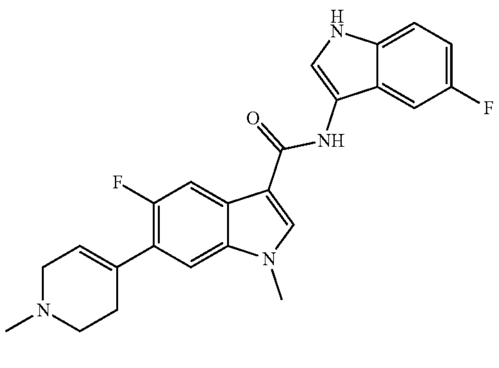 [SMILES: CN1CC=C(c2cc3c(cc2F)c(C(=O)Nc2c[nH]c4ccc(F)cc24)cn3C)CC1] | + |

TABLE 1-continued
| Synthetic Example | structure | IFN β reporter activity $IC_{50}$ (μM) |
|---|---|---|
| 116 | 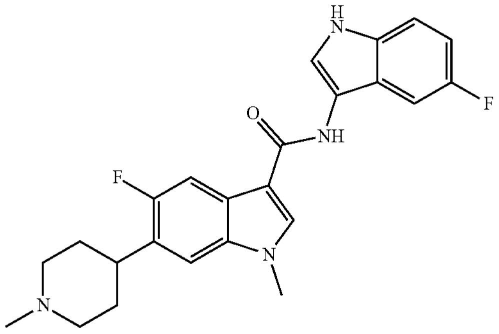 [SMILES: CN1CCC(c2cc3c(cc2F)c(C(=O)Nc2c[nH]c4ccc(F)cc24)cn3C)CC1] | + |
| 117 | 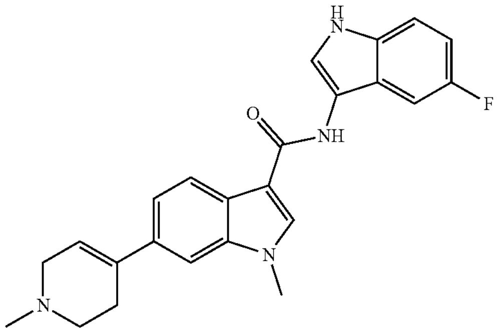 [SMILES: CN1CC=C(c2ccc3c(C(=O)Nc4c[nH]c5ccc(F)cc45)cn(C)c3c2)CC1] | + |
| 118 | 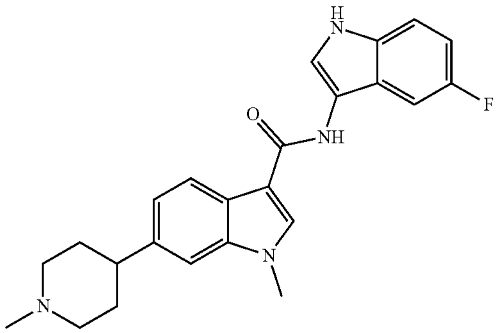 [SMILES: CN1CCC(c2ccc3c(C(=O)Nc4c[nH]c5ccc(F)cc45)cn(C)c3c2)CC1] | + |
| 119 | 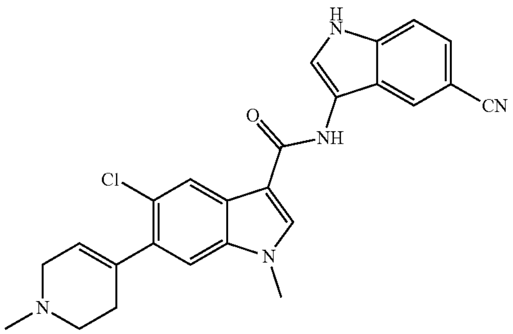 [SMILES: CN1CC=C(c2cc3c(cc2Cl)c(C(=O)Nc2c[nH]c4ccc(C#N)cc24)cn3C)CC1] | + |

TABLE 1-continued
| Synthetic Example | structure | IFN β reporter activity $IC_{50}$ (μM) |
|---|---|---|
| 120 | 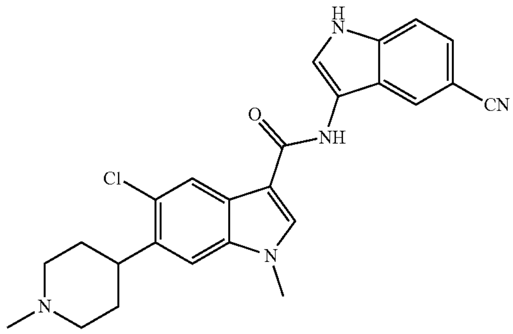 [SMILES: CN1CCC(c2cc3c(cc2Cl)c(C(=O)Nc2c[nH]c4ccc(C#N)cc24)cn3C)CC1] | + |
| Comparator A | 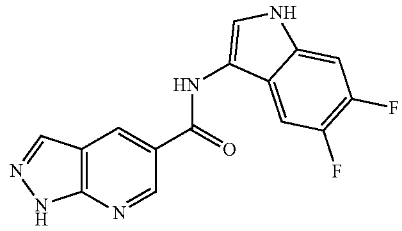 [SMILES: O=C(Nc1c[nH]c2cc(F)c(F)cc12)c1cnc2[nH]ncc2c1] | >30 |
| Comparator B | 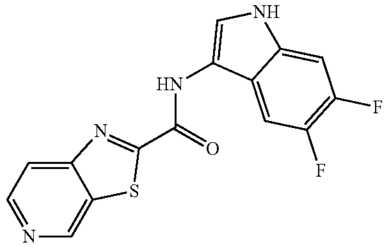 [SMILES: O=C(Nc1c[nH]c2cc(F)c(F)cc12)c1nc2ccncc2s1] | >3.0 |
| Comparator C | 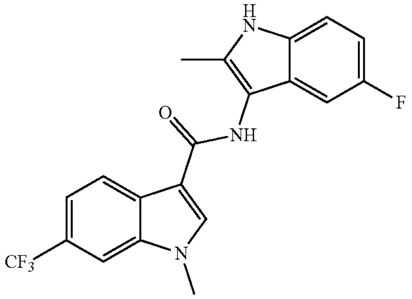 [SMILES: Cc1[nH]c2ccc(F)cc2c1NC(=O)c1cn(C)c2cc(C(F)(F)F)ccc12] | 11 |
| Comparator D | 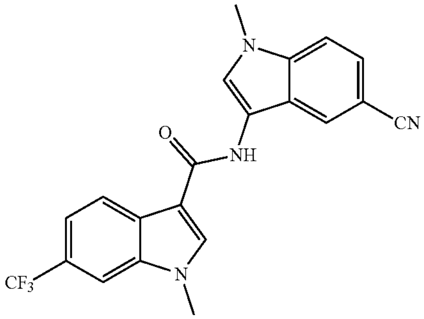 [SMILES: Cn1cc(NC(=O)c2cn(C)c3cc(C(F)(F)F)ccc23)c2cc(C#N)ccc21] | 10 |

TABLE 1-continued

| Synthetic Example | structure | IFN β reporter activity $IC_{50}$ (μM) |
|---|---|---|
| Comparator E | 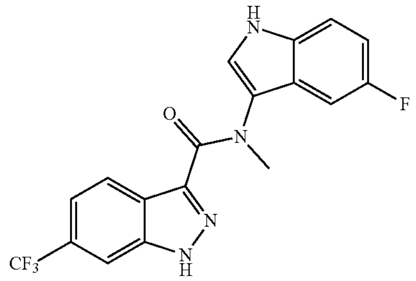 [SMILES: CN(C(=O)c1n[nH]c2cc(C(F)(F)F)ccc12)c1c[nH]c2ccc(F)cc12] | 12 |

The invention claimed is:

1. A compound represented by structural formula (I-B-1) or (I-B-2):

(I-B-1)

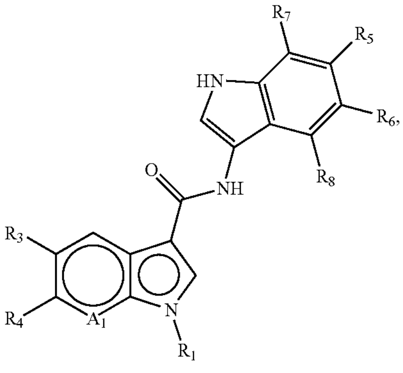

(I-B-2)

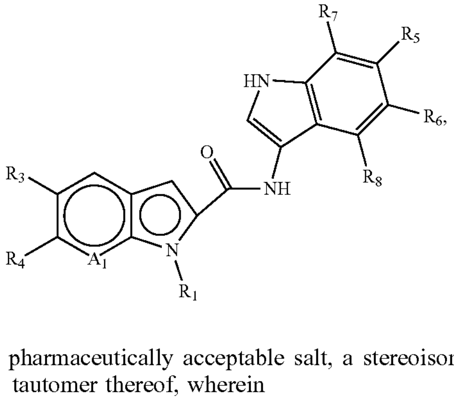

a pharmaceutically acceptable salt, a stereoisomer, or a tautomer thereof, wherein $A_1$ is CH or N;

$R_1$ is H, $C_{1-6}$ alkyl, $C_{1-6}$ haloalkyl, —$(CH_2)_{(0\ or\ 1)}$—$C_{3-7}$ cycloalkyl, —$(CH_2)_{(0\ or\ 1)}$—$C_{4-7}$ cycloalkenyl, or —$(CH_2)_{(0\ or\ 1)}$-3-7 membered heterocyclyl, wherein the cycloalkyl, cycloalkenyl, or heterocyclyl represented by $R_1$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, and $NR_{11}R_{12}$;

$R_3$ is H, halogen, CN, OH, $C_{1-6}$ alkyl, $C_{2-6}$ alkenyl, $C_{2-6}$ alkynyl, —$C(O)R_{11}$, —$C(O)OR_{11}$, —$C(O)NR_{11}R_{12}$, —$NR_{11}C(O)C_{1-6}$ alkyl, $NR_{11}R_{12}$, —$P(=O)R_{11}R_{12}$, —$S(O)_2R_{11}$, —$S(O)_2NR_{11}R_{12}$, —$O_{(0\ or\ 1)}$—$C_{3-7}$ cycloalkyl, —$O_{(0\ or\ 1)}$—$C_{4-7}$ cycloalkenyl, —$O_{(0\ or\ 1)}$-3-7 membered heterocyclyl, —$O_{(0\ or\ 1)}$-6-10 membered aryl, —$O_{(0\ or\ 1)}$-5-8 membered heteroaryl, —$(CH_2)_{(0\ or\ 1)}$—$C_{3-7}$ cycloalkyl, —$(CH_2)_{(0\ or\ 1)}$—$C_{4-7}$ cycloalkenyl, —$(CH_2)_{(0\ or\ 1)}$-3-7 membered heterocyclyl, or —$(CH_2)_{(0\ or\ 1)}$-aryl, wherein the alkyl, alkenyl, alkynyl, aryl, or heteroaryl represented by $R_3$ or in the group represented by $R_3$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$ haloalkoxy, —$NR_{11}R_{12}$, and —$N(R_{11})C(O)OR_{12}$, wherein the cycloalkyl, cycloalkenyl, or heterocyclyl represented by $R_3$ or in the group represented by $R_3$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, —$C(O)OC_{1-6}$ alkyl, and $NR_{11}R_{12}$;

$R_4$, $R_5$, and $R_6$ are independently H, halogen, CN, OH, $C_{1-6}$ alkyl, $C_{1-6}$ alkoxy, $C_{2-6}$ alkenyl, $C_{2-6}$ alkynyl, —$C(O)R_{11}$, —$C(O)OR_{11}$, —$C(O)NR_{11}R_{12}$, —$NR_{11}C(O)C_{1-6}$ alkyl, $NR_{11}R_{12}$, —$P(=O)R_{11}R_{12}$, —$S(O)_2R_{11}$, —$S(O)_2NR_{11}R_{12}$, —$O_{(0\ or\ 1)}$—$C_{3-7}$ cycloalkyl, —$O_{(0\ or\ 1)}$—$C_{4-7}$ cycloalkenyl, —$O_{(0\ or\ 1)}$-3-7 membered heterocyclyl, —$O_{(0\ or\ 1)}$-6-10 membered aryl, —$O_{(0\ or\ 1)}$-5-8 membered heteroaryl, —$(CH_2)_{(0\ or\ 1)}$—$C_{3-7}$ cycloalkyl, —$(CH_2)_{(0\ or\ 1)}$—$C_{4-7}$ cycloalkenyl, $(CH_2)_{(0\ or\ 1)}$-3-7 membered heterocyclyl, or —$(CH_2)_{(0\ or\ 1)}$-aryl, wherein the alkyl, alkenyl, alkynyl, alkoxy, aryl, or heteroaryl represented by $R_4$, $R_5$, or $R_6$ or in the group represented by $R_4$, $R_5$, or $R_6$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$ haloalkoxy, —$NR_{11}R_{12}$, and —$N(R_{11})C(O)OR_{12}$, wherein the cycloalkyl, cycloalkenyl, or heterocyclyl represented by $R_4$, $R_5$, or $R_6$ or in the group represented by $R_4$, $R_5$, or $R_6$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, —$C(O)OC_{1-6}$ alkyl, and $NR_{11}R_{12}$;

wherein at least one of $R_3$, $R_4$, $R_5$, and $R_6$ is not hydrogen;

$R_7$ and $R_8$ are independently H, halogen, $C_{1-6}$ alkyl, $C_{1-6}$ haloalkyl, $C_{1-6}$ alkoxy, or $C_{1-6}$ haloalkoxy; and each instance of $R_{11}$ and $R_{12}$ is independently H, $C_{1-6}$ alkyl, $C_{1-6}$ haloalkyl, or —$C(O)OC_{1-6}$ alkyl.

2. The compound of claim 1, a pharmaceutically acceptable salt, a stereoisomer, or a tautomer thereof, wherein each instance of $R_1$ is H, $C_{1-4}$ alkyl, —$(CH_2)_{(0\ or\ 1)}$—$C_{3-4}$ cycloalkyl, or 3-6 membered heterocyclyl, wherein the cycloalkyl or heterocyclyl represented by $R_1$ is optionally substituted with one or more substituents independently selected from the group consisting of halogen, —OH, and $C_{1-4}$ alkyl.

3. The compound of claim 2, a pharmaceutically acceptable salt, a stereoisomer, or a tautomer thereof, wherein each instance of $R_7$ and $R_8$ is independently H or halogen.

4. The compound of claim 3, a pharmaceutically acceptable salt, a stereoisomer, or a tautomer thereof, wherein each instance of $R_3$ and $R_5$ is independently H, halogen, $C_{1-6}$ alkyl, or $C_{1-6}$ haloalkyl.

5. The compound of claim 4, a pharmaceutically acceptable salt, a stereoisomer, or a tautomer thereof, wherein each instance of $R_4$ is independently H, halogen, CN, OH, $C_{1-6}$ alkyl, $C_{1-6}$ alkoxy, $C_{2-6}$ alkenyl, $C_{2-6}$ alkynyl, —C(O) $R_{11}$, —C(O)$OR_{11}$, —C(O)$NR_{11}R_{12}$, —$NR_{11}C(O)C_{1-6}$ alkyl, $NR_{11}R_{12}$, —$S(O)_2R_{11}$, —$S(O)_2NR_{11}R_{12}$, $C_{3-7}$ cycloalkyl, $(CH_2)_{(0\ or\ 1)}$-3-7 membered heterocyclyl, —$O_{(0\ or\ 1)}$-3-7 membered heterocyclyl, phenyl, or —$O_{(0\ or\ 1)}$-5-6 membered heteroaryl, wherein the alkyl, alkoxy, phenyl, or heteroaryl represented by $R_4$ or in the group represented by $R_4$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$ haloalkoxy, —$NR_{11}R_{12}$, and —$N(R_{11})$ C(O)$OR_{12}$, wherein the cycloalkyl or heterocyclyl represented by $R_4$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, —C(O)$OC_{1-6}$ alkyl, and $NR_{11}R_{12}$.

6. The compound of claim 5, a pharmaceutically acceptable salt, a stereoisomer, or a tautomer thereof, wherein each instance of $R_6$ is independently H, halogen, CN, OH, $C_{1-6}$ alkyl, $C_{1-6}$ alkoxy, —C(O) $R_{11}$, —C(O)$OR_{11}$, —C(O) $NR_{11}R_{12}$, —$NR_{11}C(O)C_{1-6}$ alkyl, $NR_{11}R_{12}$, —P(=O) $R_{11}R_{12}$, —$S(O)_2R_{11}$, —$S(O)_2NR_{11}R_{12}$, $C_{3-7}$ cycloalkyl, 3-7 membered heterocyclyl, phenyl, or —$O_{(0\ or\ 1)}$-5-6 membered heteroaryl, wherein the alkyl, alkoxy, phenyl, or heteroaryl represented by $R_6$ or in the group represented by $R_6$ is optionally substituted with one or more substituents independently selected from the group consisting of halogen, —OH, CN, $C_{1-6}$ alkyl, $C_{1-6}$ haloalkyl, $C_{1-6}$ alkoxy, $C_{1-6}$ haloalkoxy, —$NR_{11}R_{12}$, and —$N(R_{11})C(O)OR_{12}$, wherein the cycloalkyl or heterocyclyl represented by $R_6$ is optionally substituted with one or more substituents independently selected from the group consisting of halogen, —OH, oxo, CN, $C_{1-6}$ alkyl, $C_{1-6}$ haloalkyl, $C_{1-6}$ alkoxy, $C_{1-6}$ haloalkoxy, —C(O)$OC_{1-6}$ alkyl, and $NR_{11}R_{12}$.

7. The compound of claim 1, a pharmaceutically acceptable salt, a stereoisomer, or a tautomer thereof, wherein each instance of $R_1$ is H, $C_{1-4}$ alkyl, $(CH_2)_{(0\ or\ 1)}$—$C_{3-4}$ cycloalkyl, or 4-6 membered oxygen-containing heterocyclyl.

8. The compound of claim 7, a pharmaceutically acceptable salt, a stereoisomer, or a tautomer thereof, wherein each instance of $A_1$ is CH.

9. The compound of claim 8, a pharmaceutically acceptable salt, a stereoisomer, or a tautomer thereof, wherein each instance of $R_7$ and $R_8$ is independently H or F.

10. The compound of claim 9, a pharmaceutically acceptable salt, a stereoisomer, or a tautomer thereof, wherein each instance of $R_3$ and $R_5$ is independently H, F, $C_1$, or $CF_3$.

11. The compound of claim 10, a pharmaceutically acceptable salt, a stereoisomer, or a tautomer thereof, wherein each instance of $R_4$ is independently H, halogen, CN, $C_{1-4}$ alkyl (optionally substituted with OH or —$NR_{11}R_{12}$), $C_{1-4}$ haloalkyl, $C_{1-4}$ alkoxy optionally substituted with $C_{1-4}$ alkoxy, $C_{1-4}$ haloalkoxy, $C_{2-4}$ alkynyl, —C(O)$OR_{11}$, —C(O)$NR_{11}R_{12}$, —$S(O)_2R_{11}$, —$(CH_2)_{(0\ or\ 1)}$-5-6 membered heterocyclyl, —$O_{(0\ or\ 1)}$-5-6 membered heterocyclyl, or —O-5-6 membered heteroaryl, wherein the heteroaryl in the group represented by $R_4$ is optionally substituted with one or more substituents independently selected from the group consisting of halogen, —OH, CN, $C_{1-4}$ alkyl, $C_{1-4}$ haloalkyl, $C_{1-4}$ alkoxy, and $C_{1-4}$ haloalkoxy, wherein the heterocyclyl represented by $R_4$ is optionally substituted with one or more substituents independently selected from the group consisting of halogen, —OH, oxo, CN, $C_{1-4}$ alkyl, $C_{1-4}$ haloalkyl, $C_{1-4}$ alkoxy, $C_{1-4}$ haloalkoxy, —C(O)$OC_{1-4}$ alkyl, and $NR_{11}R_{12}$.

12. The compound of claim 11, a pharmaceutically acceptable salt, a stereoisomer, or a tautomer thereof, wherein each instance of $R_6$ is independently H, halogen, CN, $C_{1-4}$ alkyl (optionally substituted with —$NR_{11}R_{12}$), $C_{1-4}$ haloalkyl, $C_{1-4}$ alkoxy, $C_{1-4}$ haloalkoxy, —C(O)$OR_{11}$, —C(O)$NR_{11}R_{12}$, —P(=O) $R_{11}R_{12}$, —S(O) $2R_{11}$, or 5-6 membered heterocyclyl, wherein the heterocyclyl represented by $R_6$ is optionally substituted with one or more substituents independently selected from the group consisting of halogen, —OH, oxo, CN, $C_{1-4}$ alkyl, $C_{1-4}$ haloalkyl, $C_{1-4}$ alkoxy, $C_{1-4}$ haloalkoxy, —C(O)$OC_{1-4}$ alkyl, and $NR_{11}R_{12}$.

13. The compound of claim 12, a pharmaceutically acceptable salt, a stereoisomer, or a tautomer thereof, wherein each instance of $R_4$ is independently H, halogen, CN, $C_{1-4}$ alkyl (optionally substituted with —$NR_{11}R_{12}$), $C_{1-4}$ haloalkyl, $C_{1-4}$ alkoxy, $C_{1-4}$ haloalkoxy, $C_{2-4}$ alkynyl, —C(O)$NR_{11}R_{12}$, or 5-6 membered oxygen containing heterocyclyl.

14. The compound of claim 13, a pharmaceutically acceptable salt, a stereoisomer, or a tautomer thereof, wherein each instance of $R_6$ is independently H, halogen, $C_{1-4}$ alkyl, $C_{1-4}$ haloalkyl, or —C(O)$OC_{1-4}$ alkyl.

15. The compound of claim 1, wherein the compound is represented by the following structural formula:

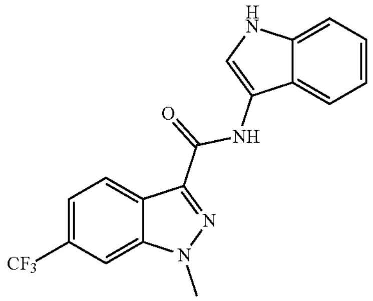

,

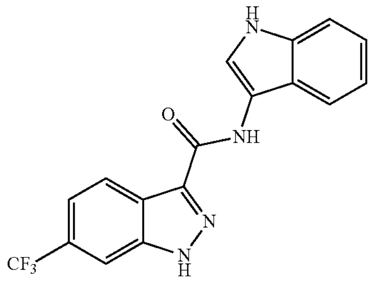

,

-continued
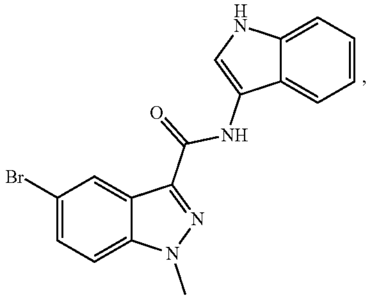
,
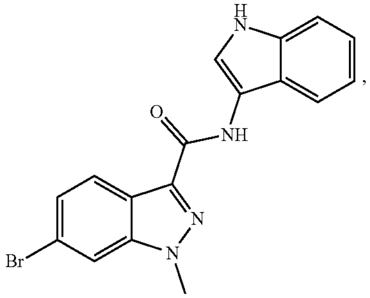
,
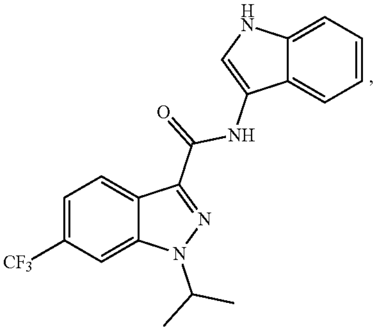
,
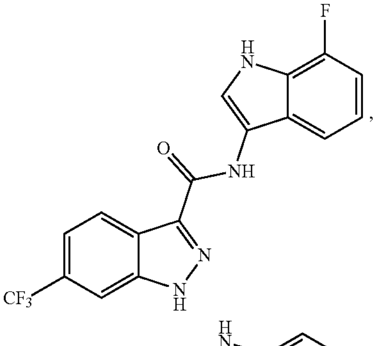
,
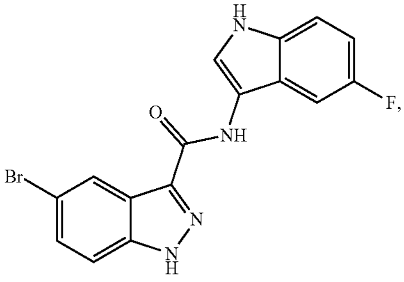
,
-continued
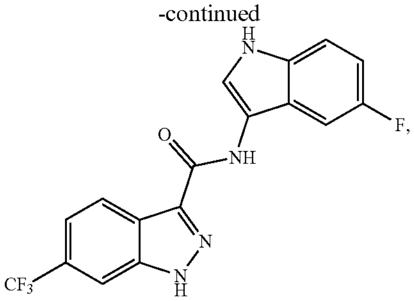
,
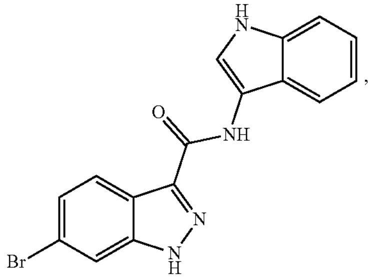
,
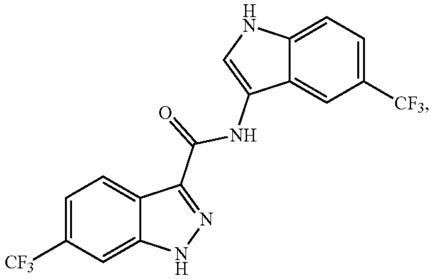
,
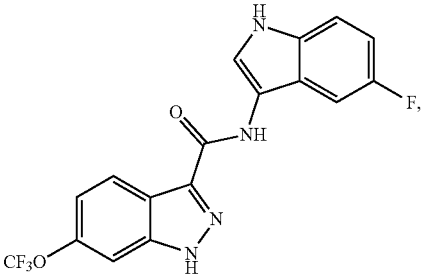
,
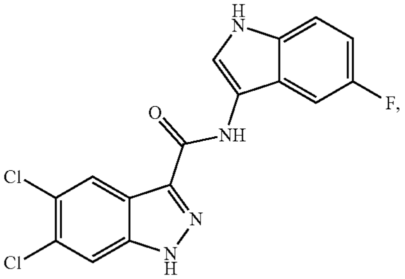
,
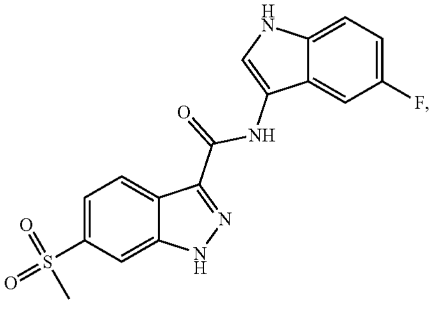
, -continued
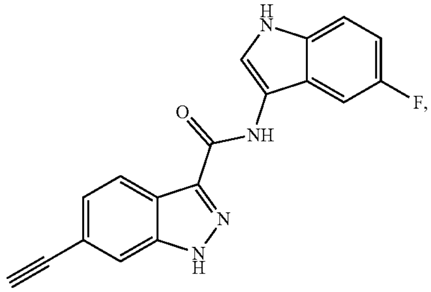
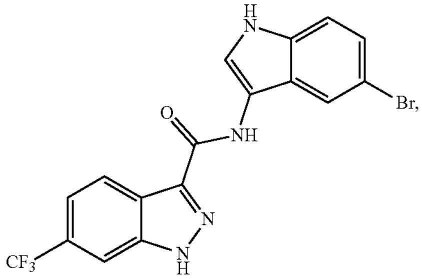
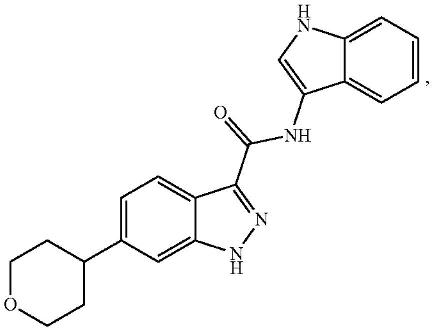
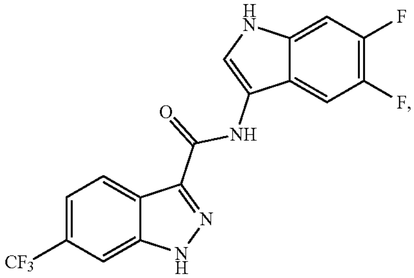
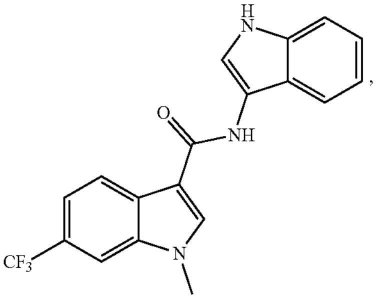
-continued
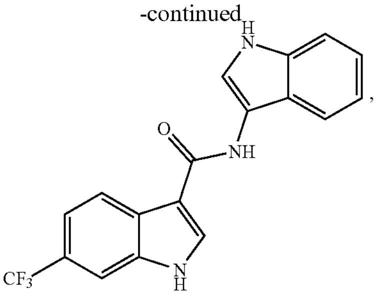
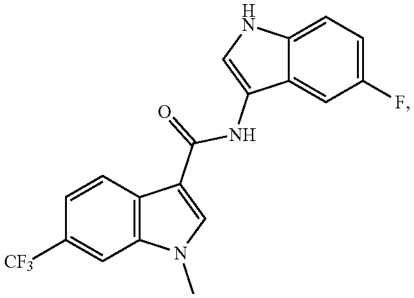
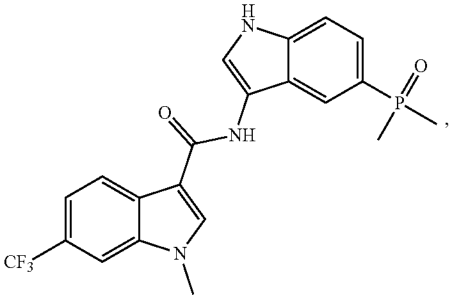
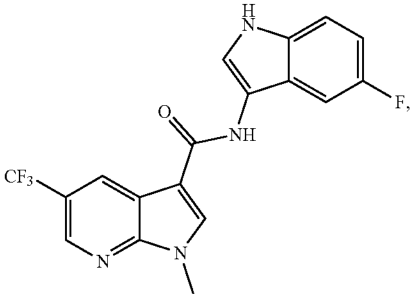
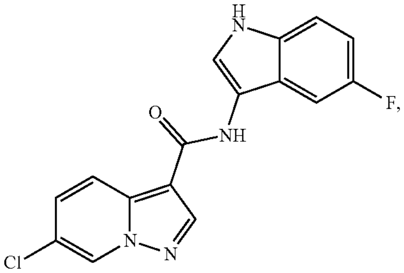
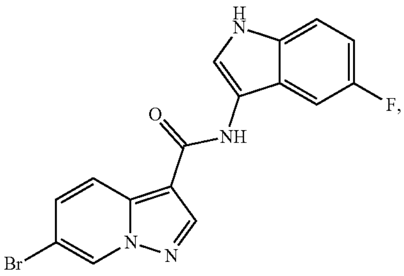

-continued
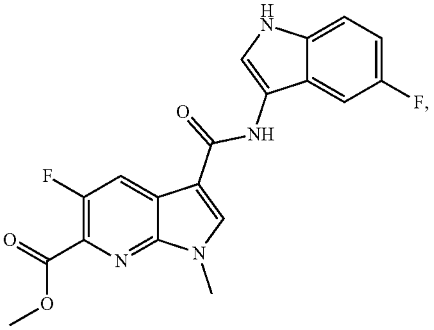
,
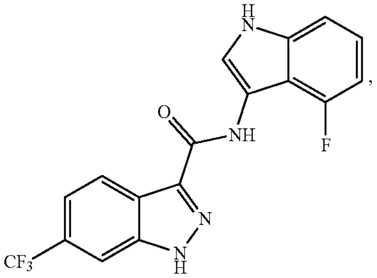
,
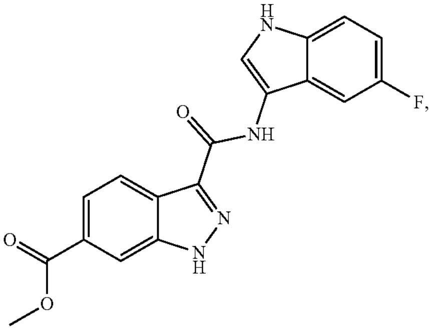
,
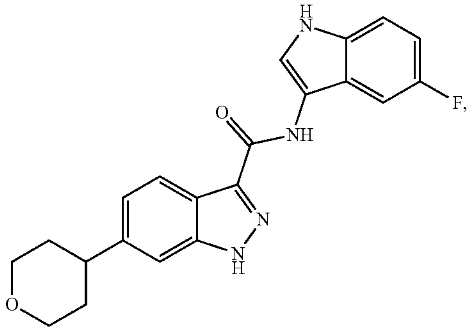
,
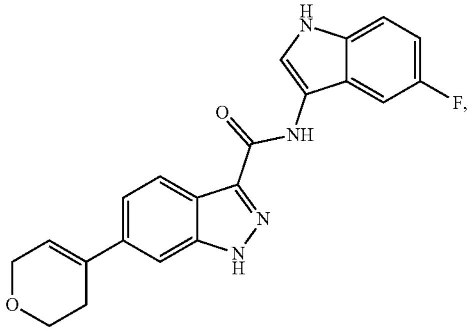
,
-continued
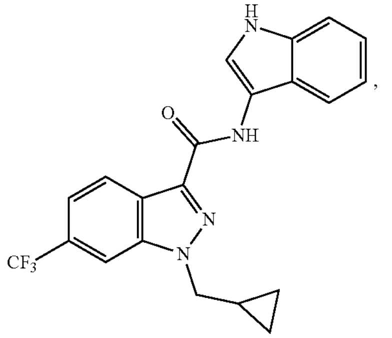
,
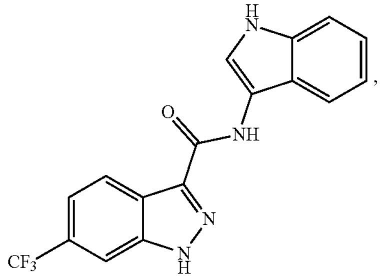
,
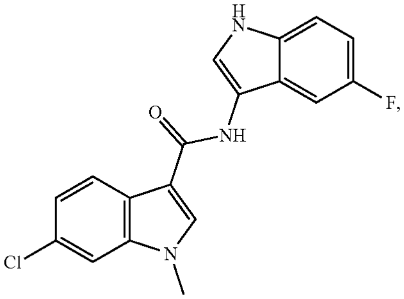
,
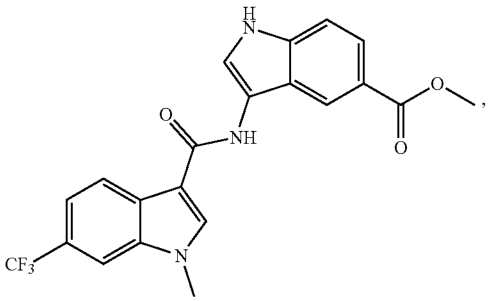
,
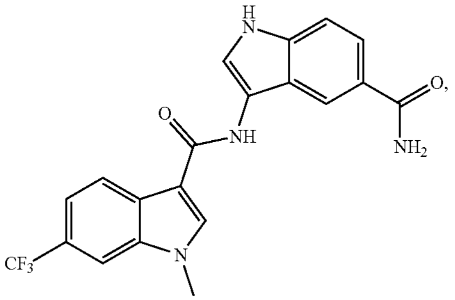
, -continued
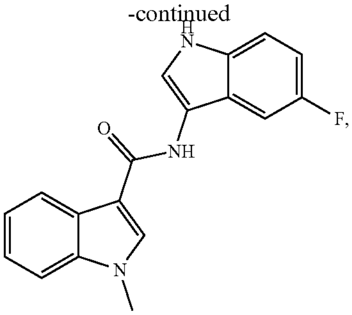
,
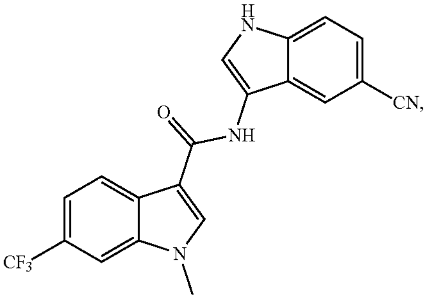
,
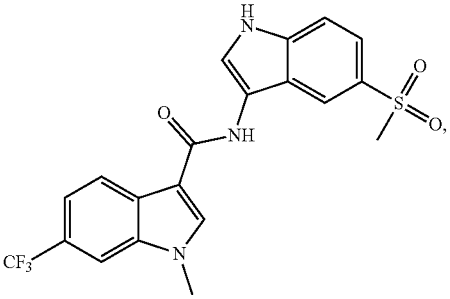
,
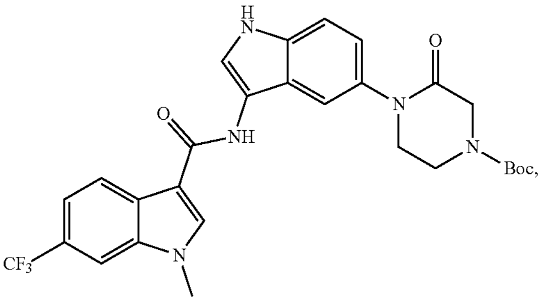
,
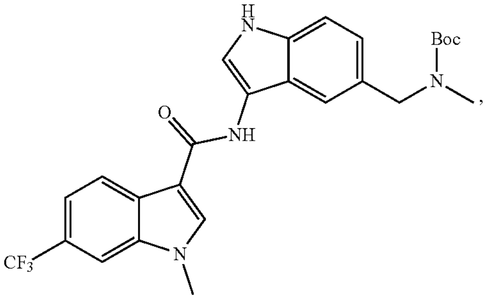
,
-continued
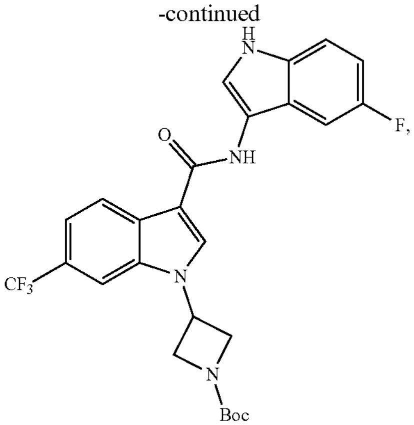
,
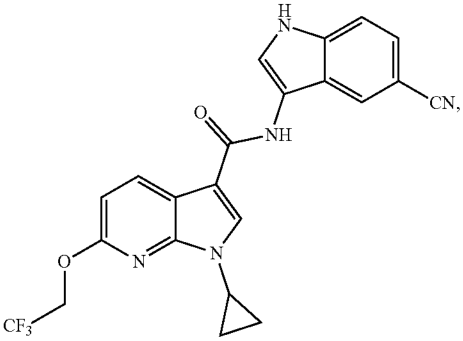
,
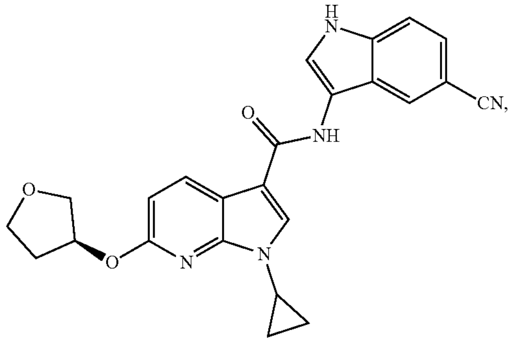
,
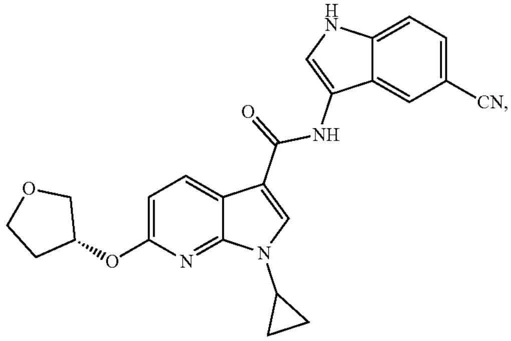
,
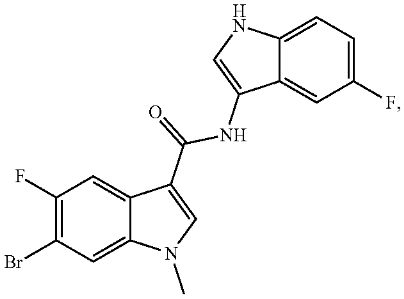
, -continued
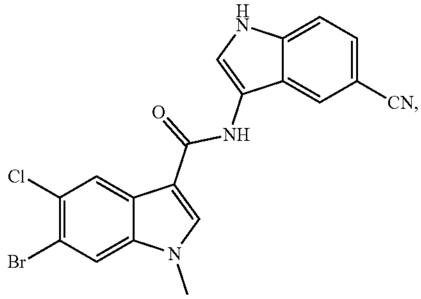
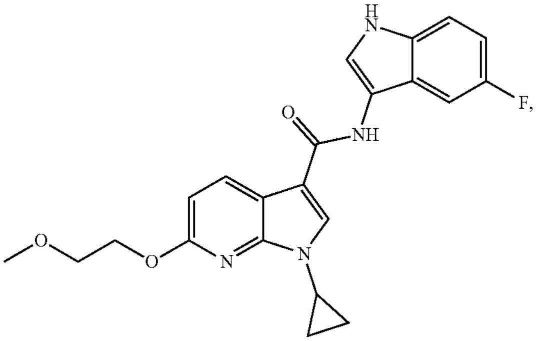
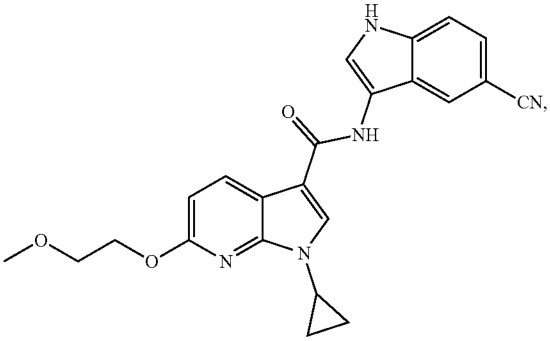
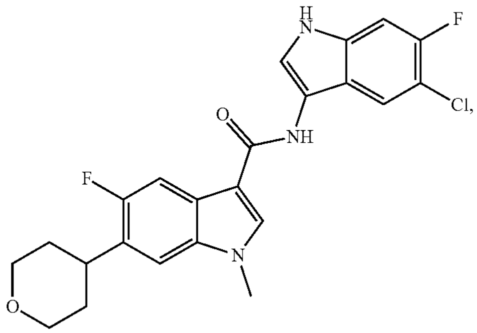
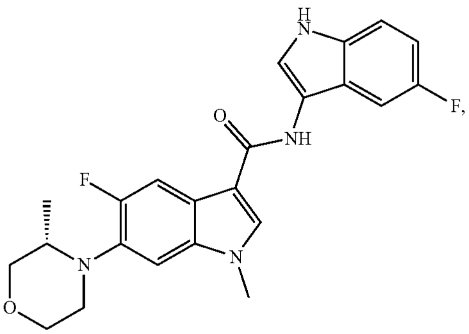
-continued
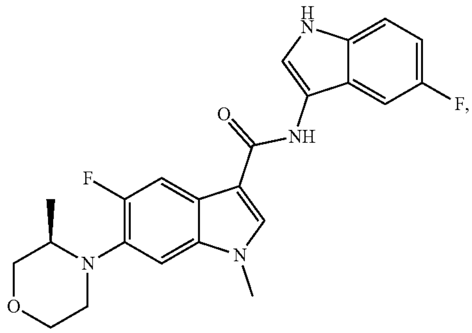
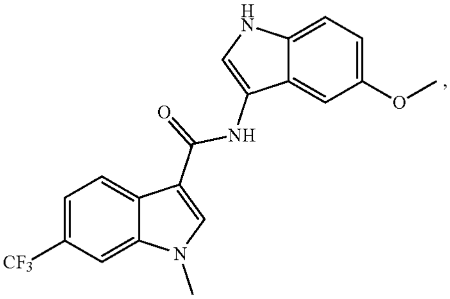
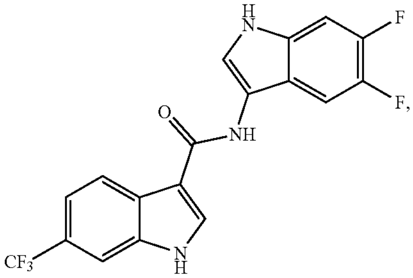
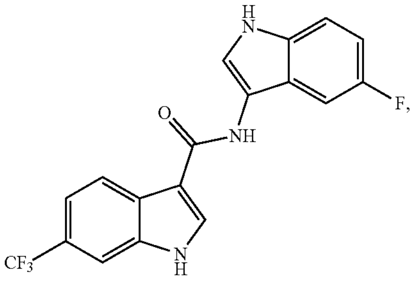
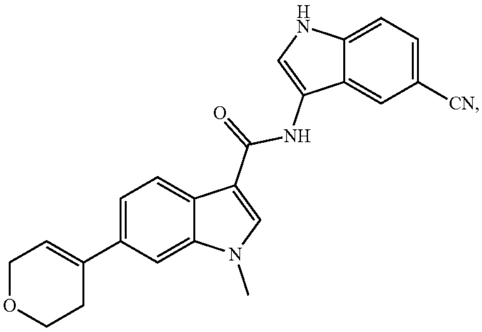

-continued
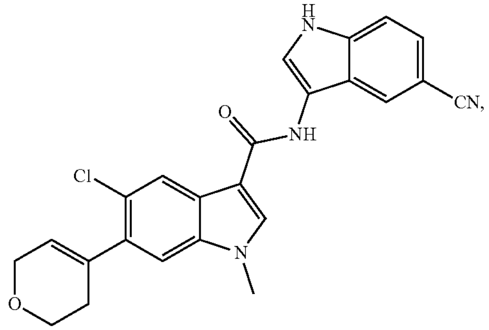
,
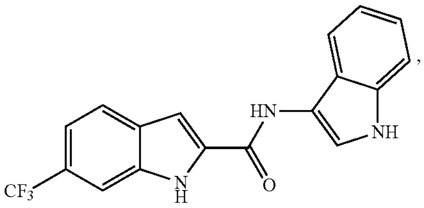
,
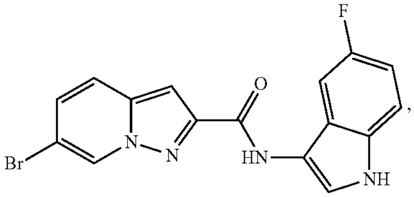
,
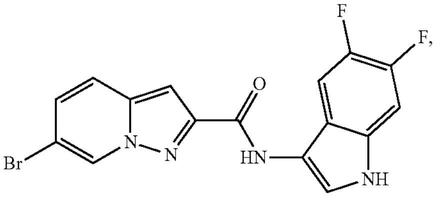
,
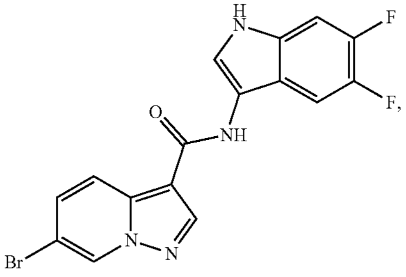
,
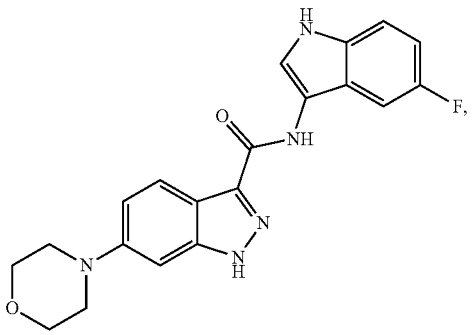
,
-continued
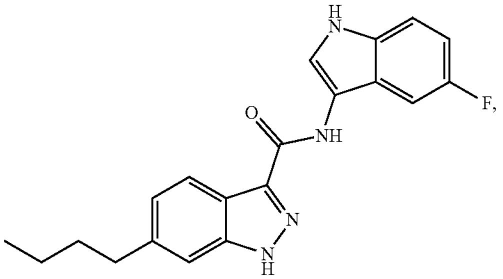
,
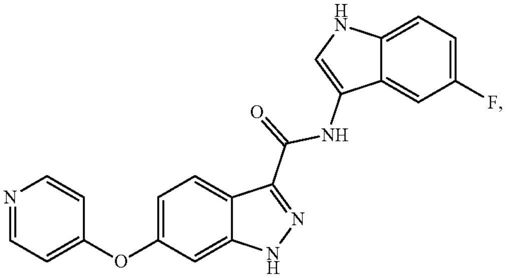
,
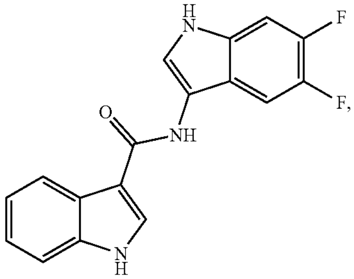
,
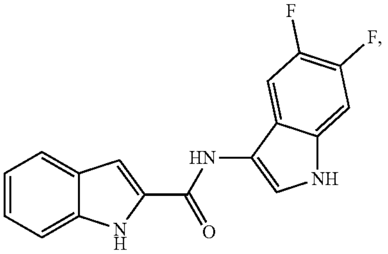
,
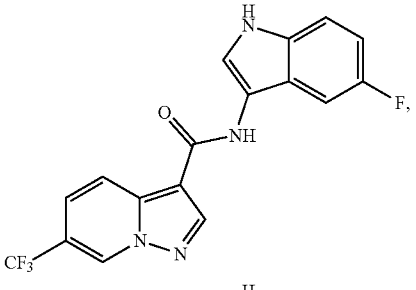
,
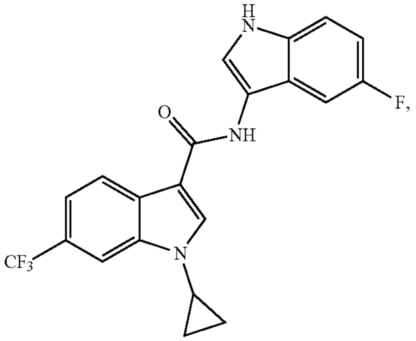
, -continued
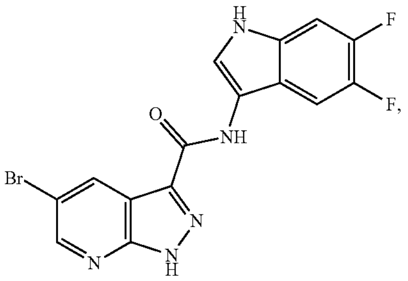
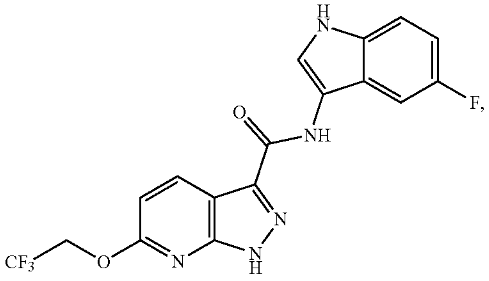
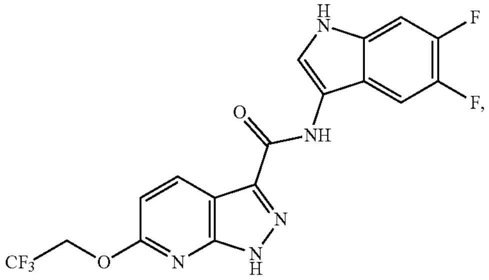
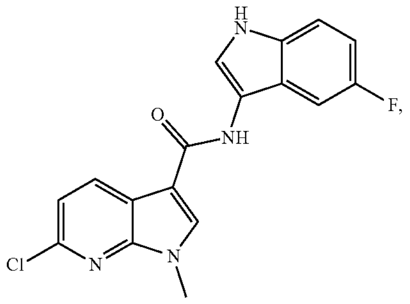
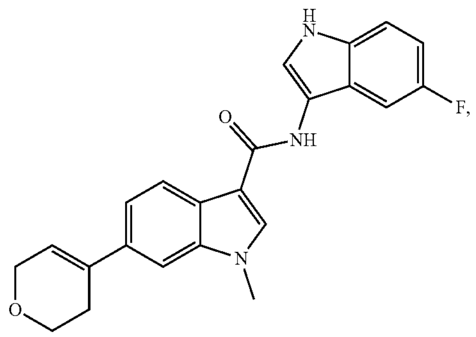
-continued
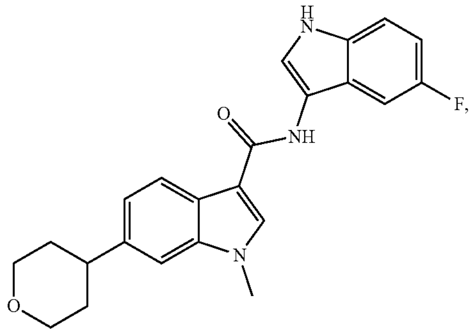
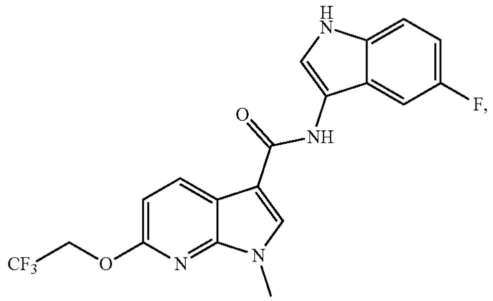
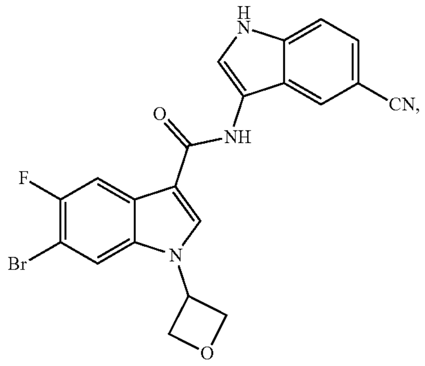
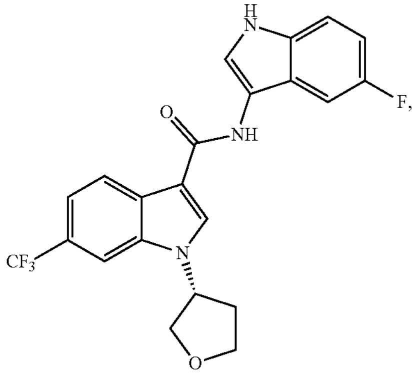

-continued
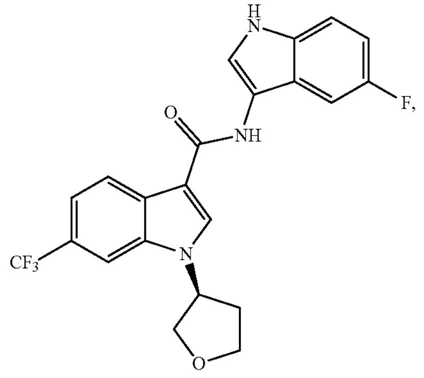
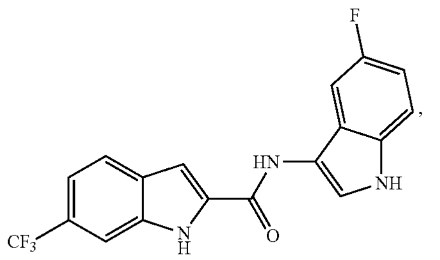
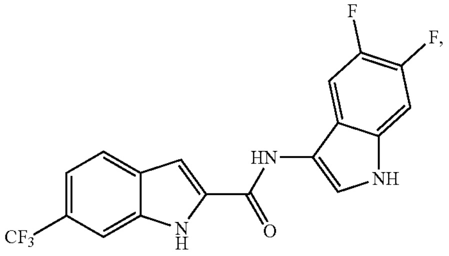
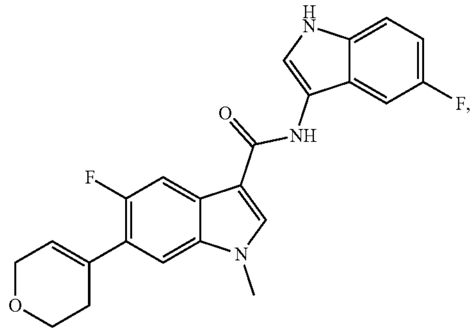
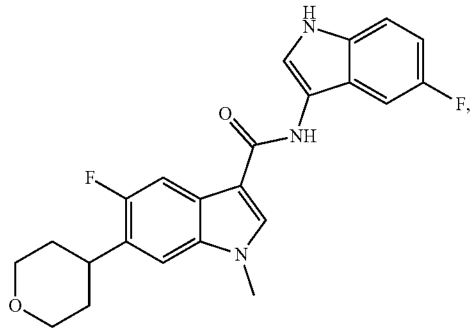
-continued
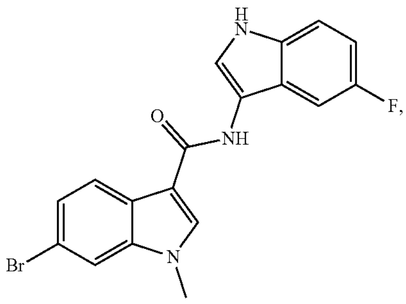
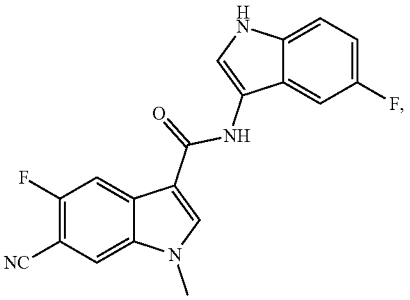
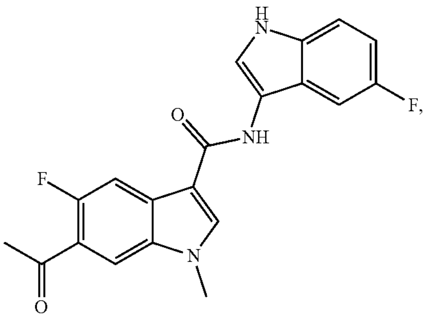
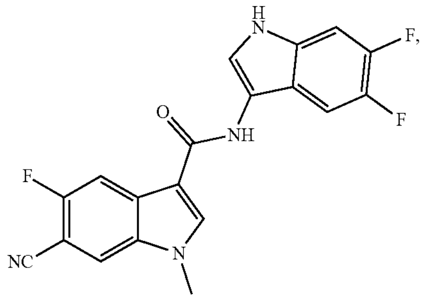
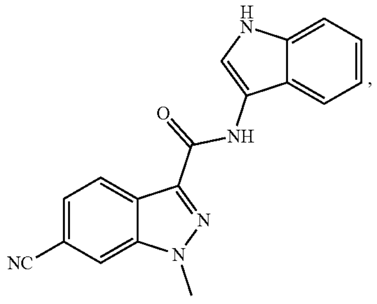

-continued
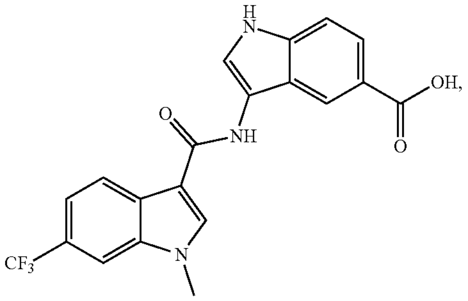
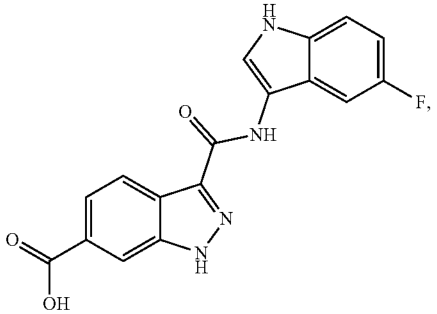
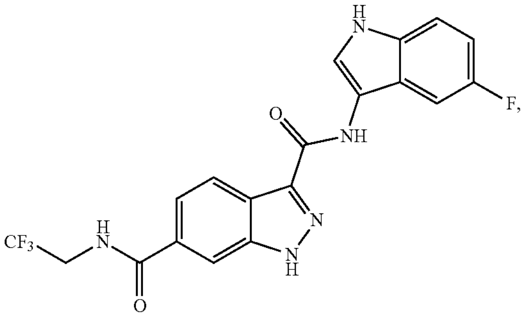
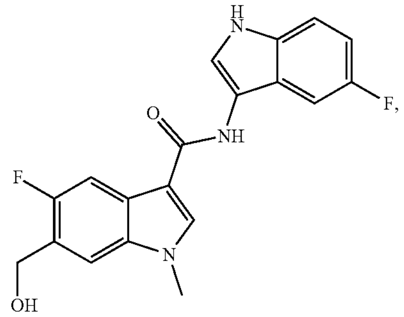
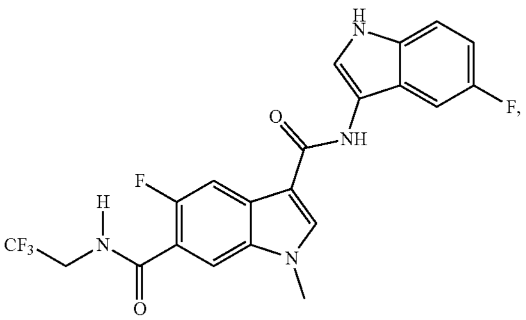
-continued
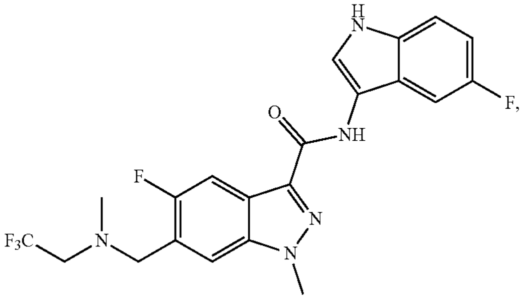
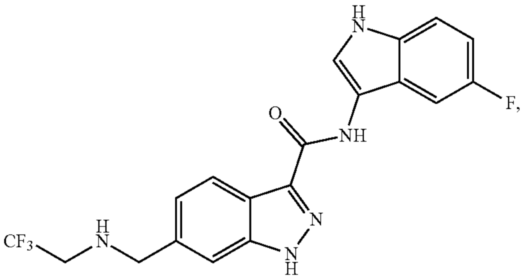
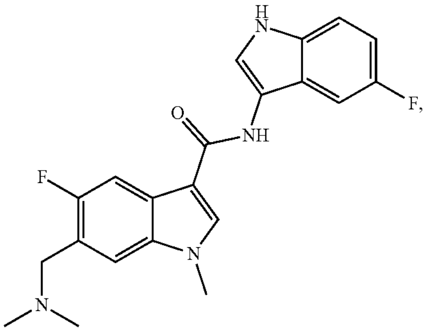
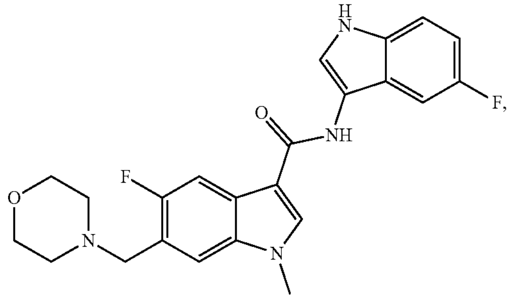
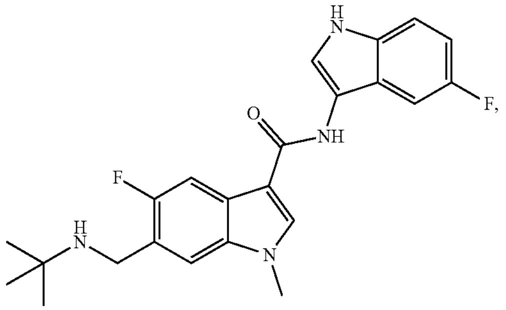

-continued
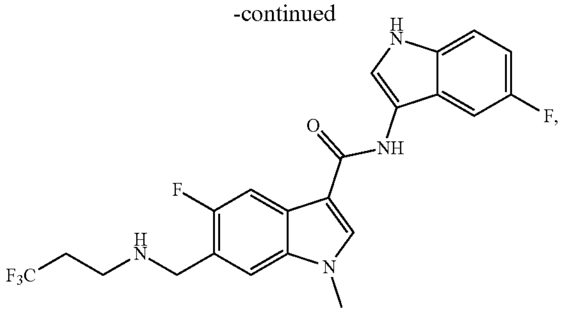
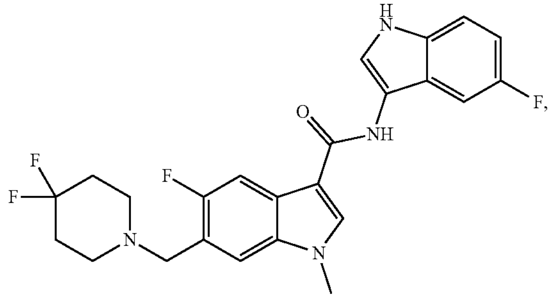
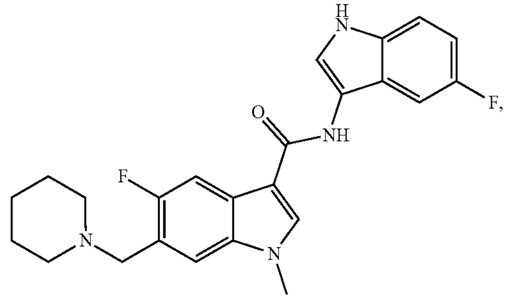
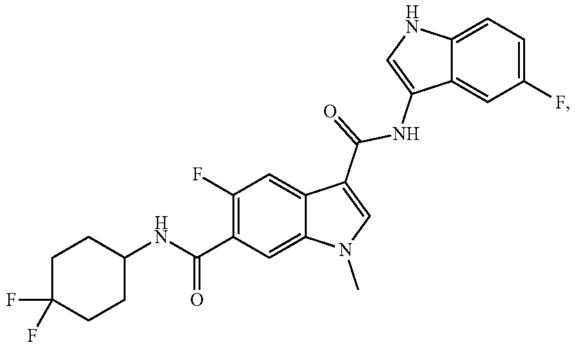
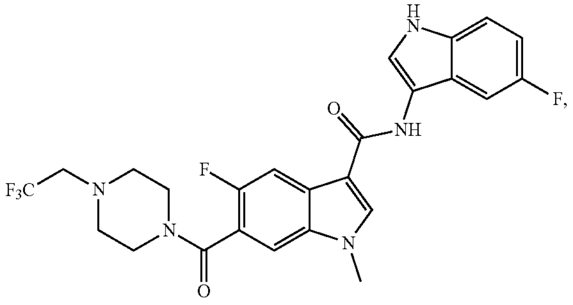
-continued
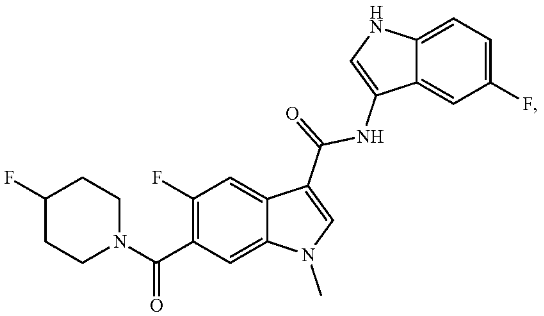
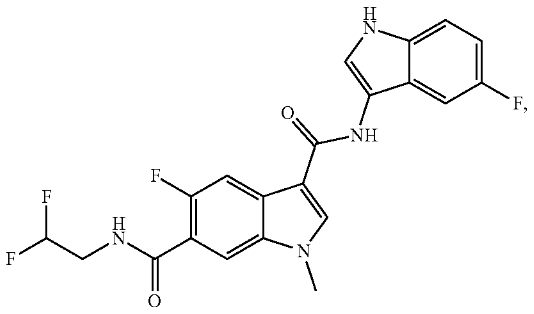
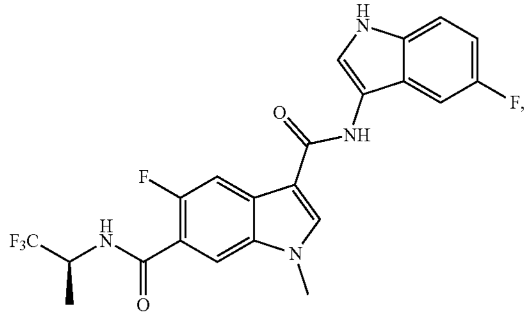
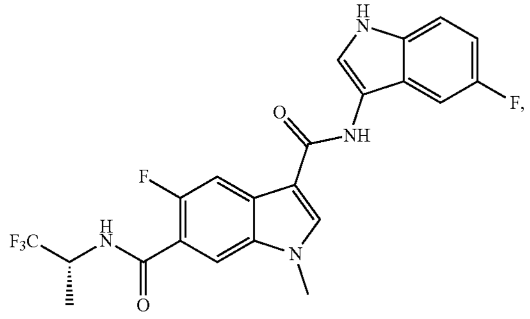
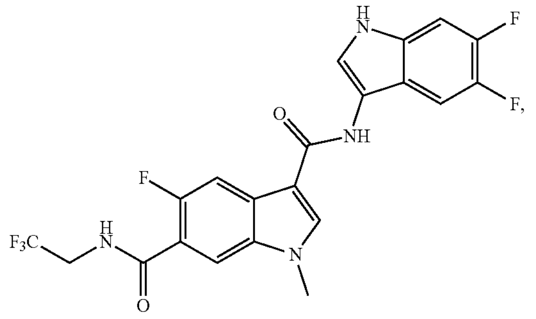

-continued
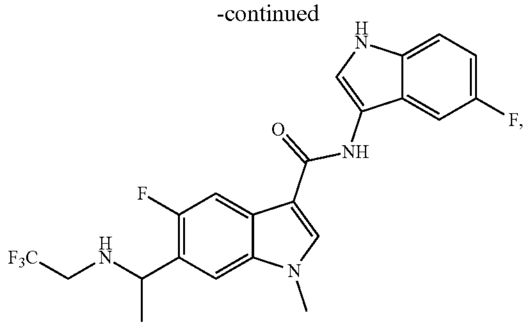
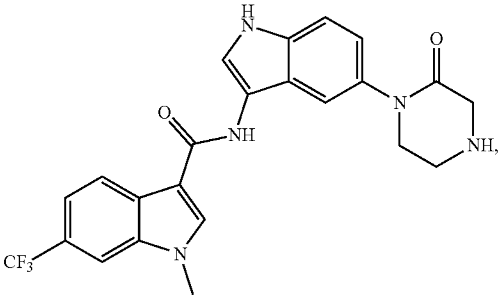
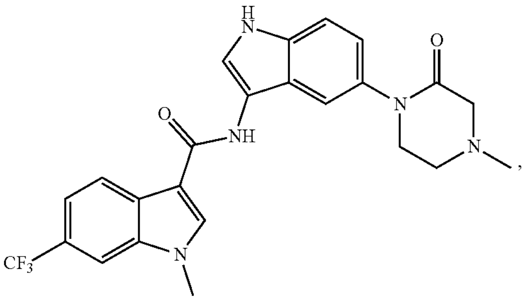
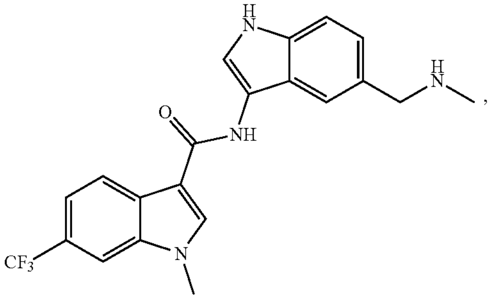
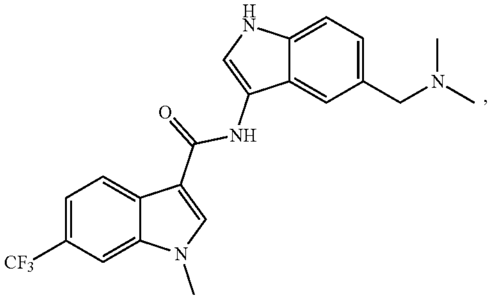
-continued
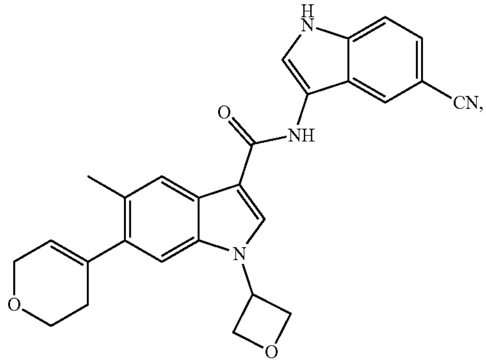
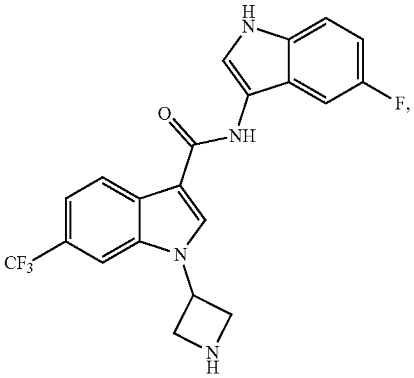
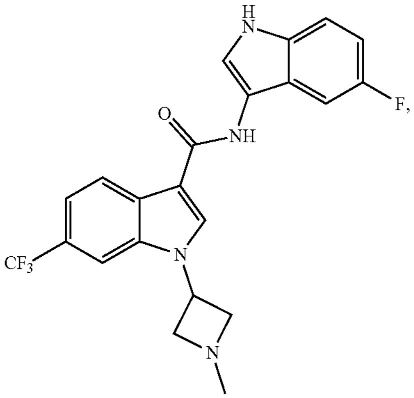
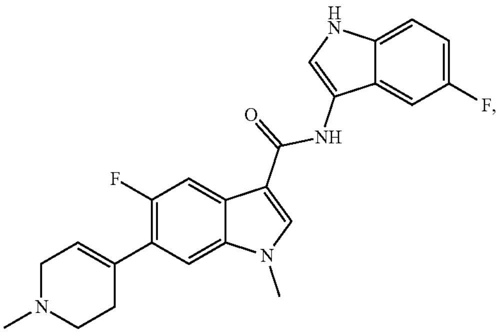

-continued

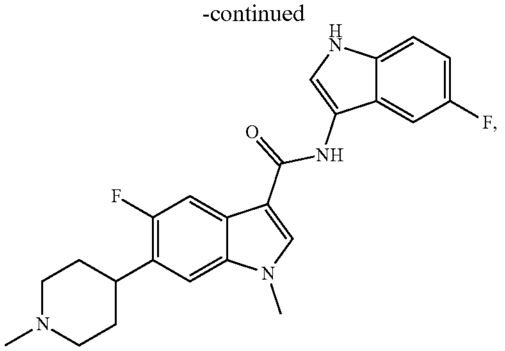

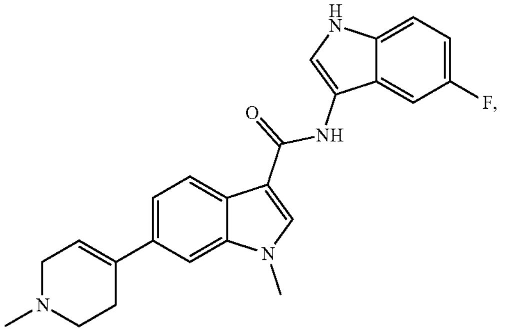

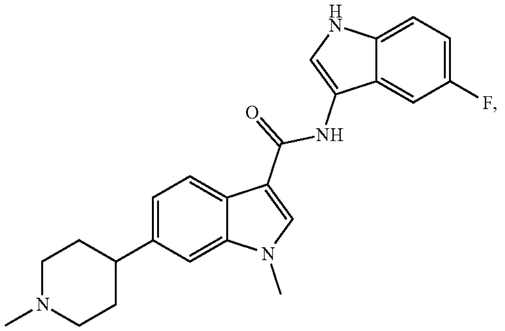

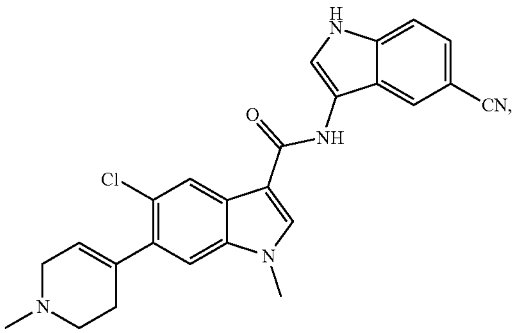

or

-continued

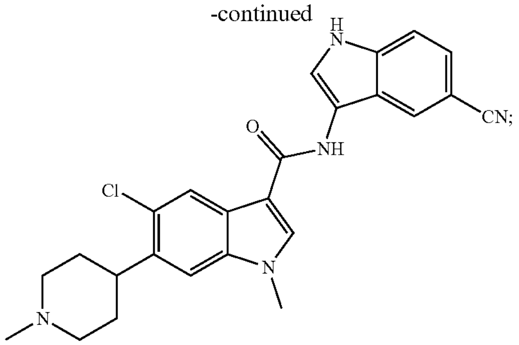

a pharmaceutically acceptable salt, a stereoisomer, or a tautomer thereof.

16. A pharmaceutical composition comprising an effective amount of the compound of claim 1, a pharmaceutically acceptable salt, a stereoisomer, or a tautomer thereof, and a pharmaceutically acceptable carrier.

17. A method of treating a subject with an autoimmune disease, inflammation-associated disorder or infectious disease, comprising administering to the subject an effective amount of the compound of claim 1, a pharmaceutically acceptable salt, a stereoisomer, or a tautomer thereof, wherein the autoimmune disease, inflammation-associated disorder or infectious disease is associated with increased STING signaling.

18. A method of treating a subject with cancer associated with increased STING signaling, comprising administering to the subject an effective amount of the compound of claim 1, a pharmaceutically acceptable salt, a stereoisomer, or a tautomer thereof.

19. A compound, wherein the compound is

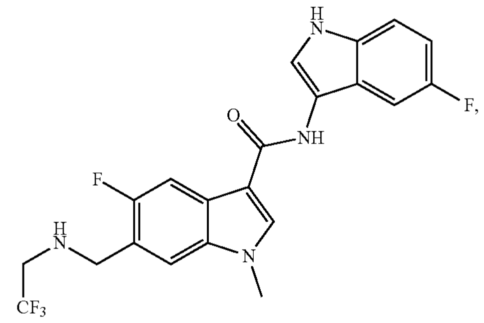 [SMILES: Cn1cc(C(=O)Nc2c[nH]c3ccc(F)cc23)c2cc(F)c(CNCC(F)(F)F)cc21]

or a pharmaceutically acceptable salt thereof.

20. A pharmaceutical composition comprising an effective amount of the compound of claim 19, or a pharmaceutically acceptable salt thereof, and a pharmaceutically acceptable carrier.

* * * * *